(12) United States Patent
Jannes et al.

(10) Patent No.: US 7,390,623 B2
(45) Date of Patent: Jun. 24, 2008

(54) **DETECTION AND IDENTIFICATION OF *STAPHYLOCOCCUS AUREUS* AND *EPIDERMIDIS* USING THE 16S-23S RRNA SPACER**

(75) Inventors: Geert Jannes, Kessel-Lo (BE); Rudi Rossau, Ekeren (BE); Hugo Van Heuverswyn, Kalken (BE)

(73) Assignee: Innogenetics N.V., Ghent (BE)

( * ) Notice: Subject to any disclaimer, the term of this patent is extended or adjusted under 35 U.S.C. 154(b) by 9 days.

(21) Appl. No.: 10/895,114

(22) Filed: Jul. 21, 2004

(65) Prior Publication Data

US 2005/0142575 A1 Jun. 30, 2005

Related U.S. Application Data

(62) Division of application No. 09/931,486, filed on Aug. 17, 2001, now Pat. No. 6,811,978, which is a division of application No. 09/448,894, filed on Nov. 29, 1999, now Pat. No. 6,312,903, which is a division of application No. 08/765,332, filed as application No. PCT/EP95/02452 on Jun. 23, 1995, now Pat. No. 6,025,132.

(30) Foreign Application Priority Data

| Jun. 24, 1994 | (EP) | ................................ 94 870 106 |
| Apr. 7, 1995 | (EP) | ................................ 95 870 032 |

(51) Int. Cl.
*C12Q 1/68* (2006.01)
*C07H 21/04* (2006.01)
(52) U.S. Cl. .......................................... 435/6; 536/24.32
(58) Field of Classification Search .................... 435/6; 536/24.32, 24.33
See application file for complete search history.

(56) References Cited

U.S. PATENT DOCUMENTS

| 4,508,823 | A | 4/1985 | Olsen |
| 5,212,059 | A | 5/1993 | Schwartz et al. |
| 5,298,392 | A | 3/1994 | Atlas et al. |
| 5,358,846 | A | 10/1994 | Ohno et al. |
| 5,521,300 | A | 5/1996 | Shah et al. |
| 5,536,638 | A | 7/1996 | Rossau et al. |
| 5,545,541 | A | 8/1996 | Molin et al. |
| 5,574,145 | A | 11/1996 | Barry et al. |
| 5,627,032 | A * | 5/1997 | Ulanovsky ....................... 435/6 |
| 5,631,130 | A | 5/1997 | Leckie et al. |
| 5,712,095 | A | 1/1998 | Britschgi et al. |
| 5,726,021 | A | 3/1998 | Britschgi et al. |
| 5,849,488 | A * | 12/1998 | Alatossava et al. ............. 435/6 |
| 6,025,132 | A | 2/2000 | Jannes et al. |
| 6,312,903 | B1 | 11/2001 | Jannes et al. |
| 6,593,114 | B1 * | 7/2003 | Kunsch et al. ............ 435/91.41 |
| 6,737,248 | B2 * | 5/2004 | Kunsch et al. ............. 435/69.1 |

FOREIGN PATENT DOCUMENTS

| EP | A-0395292 | 10/1990 |
| EP | A-0452596 | 10/1991 |
| EP | 0 497 464 A1 | 8/1992 |
| FR | A2651505 | 3/1991 |
| FR | A-2683227 | 5/1993 |
| WO | WO93/04201 | 3/1993 |
| WO | WO 93/11264 | 6/1993 |
| WO | WO95/34574 | 12/1995 |
| WO | WO96/19585 | 6/1996 |

OTHER PUBLICATIONS

Gurtler et al., Microbiology 141, 1255-1265 (May 1995).*
Accession No. L36472, Nov. 11, 1994.*
Jensen et al, Applied and Environmental Microbilogy, Apr. 1993, vol. 59, No. 4, pp. 945-952.
Microbiology, vol. 140, No. 5, May 1994, Reading GB pp. 1103-1108, J.W. Van Der Giessen et al.
Journal of Bacteriology, vol. 175, No. 10, May 1993, Baltimore US, pp. 2818-2825, R. Frothingham et al.
Microbiology, vol. 140, No. 1, 4, Reading GB, pp. 123-132, Y.Ji et al., (1993).
Journal of Infectious Diseases, vol. 169, No. 2, Chicago US, pp. 305-312, R. Frothingham et al., (1993).
Journal of Bacteriology, vol. 170, No. 6, Baltimore US, pp. 2886-2889, Y. Suzuki et al., (1994).
Journal of General Microbiology, vol. 138, No. 8., London GB, pp. 1717-1727, K.E. Kempsell et al., (1994).
Methods in Molecular and Cellular Biology, vol. 5, No. 1, 4, New York US, pp. 3-12, T.M. Schmidt., (1993).
Emond et al, "A Ribosomal DNA Fragment of *Listeria monocytogenes* and its Use as Genus-Specific Probe . . . ", Applied and Environmental Microbiology, Aug. 1993, p. 2690-2697.

(Continued)

*Primary Examiner*—Kenneth R. Horlick
(74) *Attorney, Agent, or Firm*—Nixon & Vanderhye P.C.

(57) ABSTRACT

The present invention relates to 16S-23S rRNA spacer sequences from *Staphylococcus aureus* and their use in a method for detection and/or identification of *Staphylococcus aureus*. The invention further relates to a method for detection and identification of *Staphylococcus aureus* in a sample, involving the steps of: (i) optionally releasing, isolating and/or concentrating the polynucleic acids present in the sample; (ii) optionally amplifying the 16S-23S rRNA spacer region, or a part thereof, with at least one primer pair; (iii) detecting the presence of a 16S-23S rRNA spacer sequence; and (iv) identifying the *Staphylococcus aureus* present in the sample from the nucleic acid(s) detected in the sample.

32 Claims, 103 Drawing Sheets

OTHER PUBLICATIONS

Tyler et al, "Oligonucleotide Primers . . . Transcribed Spacers", Clinical and Diagnostic Laboratory Immunology, Jul. 1995, p. 448-453; XP 000604143.

Kostman et al, "Molecular Epidemiology . . . Ribotyping", Journal of Clinical Microbiology, Aug. 1992; p. 2084-2087; XP-000926225.

Gill et al, "Identification of . . . soil isolates", Can. J. Microbiol., vol. 40, 1994.

* cited by examiner

Figure 1

```
AAGGAGCACC ACGAAAACGC CCCAACTGGT GGGGCGTAGG CCGTGAGGGG TTCTTGTCTG TAGTGGGCGA
GAGCCGGGTG CATGACAACA AAGTTGGCCA CCAACACACT GTTGGGTCCT GAGGCAACAC TCGGACTTGT
TCCAGGTGTT GTCCCACCGC CTTGGTGGTG GGGTGTGGTG TTTGAGAACT GGATAGTGGT TGCGAGCATC
AATGGATACG CTGCCGGCTA GCGGTGGCGT GTTCTTTGTG CAATATTCTT TGGTTTTTGT TGTGT
```

(SEQ ID NO 76)

Figure 2

AAGGAGCACC ACGAAAAGCA CCCCAACTGG TGGGGTGCGA GCCGTGAGGG GTTCCCGTCT GTAGTGGACG
GGGGCCGGNT GCGCAACAGC AAATGATTGC CAGACACACT ATTGGGCCCT GAGACAACAC TCGGTCCGTC
CGTGTGGAGT CCCTCCATCT TGGTGGGTGG GTGTGGTGTT TGAGTATTGG ATAGTGGTTG CGAGCATCTA
GATGAGCGCA TGGTCTTCGT GGCCGGGCGTT CATCGAAATG TGTAATTTCT TCCTTAACTC TTGTGTGT (SEQ ID NO 77)

Figure 3

AAGGAGCACC ACGAAAAGCA CCCCAACTGG TGGGGTGCGA GCCGTGAGGG GTTCCCGTCT GTAGTGGACG
GGGGCCGGGT GCGCAACAGC AAATGATTGC CAGACACACT ATTGGGCCCT GAGACAACAC TCGGTCCGTC
CGTGTGGAGT CCCTCCATCT TGGTGGTGGG GTGTGGTGTT TGAGTATTGG ATAGTGGTTG CGAGCATCTA
GATGAGCGCA TGGTCTTCGT GGCCGGGCTT CATCGAAATG TGTAATTTCT TTTTTAACTC TTGTGTGT (SEQ ID NO 78)

Figure 4

AAGGAGCACC ACGAAAAGCA CTCCAATTGG TGGGGTGCGA GCCGTGAGGG GTTCCCGTCT GTAGTGGACG
GGGGCCGGNT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTGT GGCTGATGCG CTCGTCGAAA TGTGTAATTT CTTCTTTGGT GTNTGTGTGT (SEQ ID NO 79)

Figure 5

AAGGAGCACC ACGAAAAGCA TCCCAATTGG TGGGGTGCGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCG TAGTCCTTTG TGGCTGATGC GTTCATCAAA ATGTGTAATT TCTTTTTTGG TTTNTGTGTG
T (SEQ ID NO 80)

Figure 6

```
AAGGAGCACC ACGAAAAGCA CTCCAATTGG TGGGGTGCGA GCCGTGAGGG GTTCCCGTCT GTAGTGGACG
GGGGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGCCCTTGC GGCTGATCCG TTCGNCGAAA TGTGTAATTT CTTCTCTGGT TTCTGTGTGT
```

(SEQ ID NO 81)

Figure 7

AAGGAGCACC ACGAAAAGCA CTCCAATTGG TGGGGTGCGA GCCGTGAGGG GTTCTCGTCT GTAGTGGACG
GNAGCCGGGT GCACAACAGC AAATGATTGC CAGACACACT ATTGGGCCCT GAGACAAACAC TCGGTCGATC
CGTGTGGAGT CCCTCCATCT TGGTGGGG GTGTGGTGTT TGAGTATTGG ATAGTGGTTG CGAGCATCTA
GATGAGCGCG TAGTCCTTCG TGGCTGATGC GTTCATCGAA ATGTGTAATT TCTTCTTTGG TTTTGGGTGT
GT (SEQ ID NO 82)

Figure 8

AAGGAGCACC ACGAAAAGCA CTCCAATTGG TGGGGTGCGA GCCGTGAGGG GTTCCCGTCT GTAGTGGACG
GGGGCCGGGT GCACAACAGC AAATGATCGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTTG GGGCTGATGT GTTTCATCAA AATGTGTAAT TTCTTTTTNG GTTTTNGTGT
GT (SEQ ID NO 83)

Figure 9

AAGGAGCACC ACGAAAAGCA CTCCAATTGG TGGGGTGCGA GCCGTGAGGG GTTCTCGTCT GTAGTGGACG
GGAGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGGTGTT TGAGTATTGG ATAGTGGTTG CGAGCATCTA
GATGAGCGGCG TAGTCCTTCG TGGCTGATGC GTTCATTGAA ATGTGTAATT TCTTCTCTGG TTTTGTGTG
T (SEQ ID NO 84)

Figure 10

AAGGAGCACC ACGAAAAGCA CTCCAATTGG TGGGGTGCGA GCCGTGAGGG GTTCCCGTCT GTAGTGGACG
GGGGCCGGGT GCACAACAGC AAATGATTGC CAGACACACT ATTGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTGT GGCTGATGCG CTCGTCGAAA TGTGTAATT CTTCTTTGGT TTTGTGTGT (SEQ ID NO 85)

Figure 11

AAGGAGCACC ACGAAAAGCA CTCCAATTGG TGGGGTGCGA GCCGTGAGGG GTTCCCGTCT GTAGTGGACG
GGGGCCGGGT GCGCAACAGC AAATGATTGC CAGACACACT ATTGGGCCCT GAGACAACAC TCGGTCGATC
CGTGTGGAGT CCCTCCATCT TGGTGGTGGG GTGTTGGTGT TTGAGTATTG GATAGTGGTT GCGAGCATCT
AGATGAGCGC GTAGTCCTTG TGGCTGATGC GTTCGTCGAA ATGTGTAATT TCTTCTTTGG GTTTTTGTGT
GT (SEQ ID NO 86)

Figure 12

AAGGAGCACC ACGAAAAGCA CCCCAATTGG TGGGGTGCGA GCCGTGAGGG GTTCTCGTCT GTAGTGGACG
GNAGCCGGNT GCGCAACAGC AAATGATTGC CAGACACACT ATTGGGCCCT GAGACAACAC TCGGNCGATC
CGTGTGGAGT CCCTCCATCT TGGTGGTGGG GTGTNGTGTT TGAGTATTGG ATAGTGGTTG CGAGCATCTA
GATGGGGCGCG TAGTCCTTTG TGACTGATGC GTTCATCAAA ATGTGTAATT TCTTTTTTGN NTTTNGTGTG
T (SEQ ID NO 87)

Figure 13

AAGGAGCACC ACGAAAAGCA CTCCAATTGG TGGGGTGCGA GCCGTGAGGG GTTCTCGTCT GTAGTGGACG
GGAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTTG TGGCTGACGC GTTCATCGAA ATGTGTAATT TCTTCTTTGG TTTTTGTGTG
T (SEQ ID NO 88)

Figure 14

AAGGAGCACC ACGAAAAGCA CTCCAAATTGG TGGGGTGCGA GCCGTGANGG GTTCCCGTCT GTAGTGGACG
GGGCCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTAG GGCTGATGCG TTCGTCGNAA TGTGTAATTT CTTCTTTGGT TTTTGTGTGT (SEQ ID NO 89)

Figure 15

AAGGAGCACC ACGAAAAGCA TCCCAATTGG TGGGGTGCGA GCCCGTGAGGG GTTCTCGTCT GTAGTGGACG
AAACCGGGT GCACAACAGC AAATAATTGC CAGACACACT ATTGGGCCCT GAGACAACAC TCGGTCGATC
CGTGTGGTGT CCCTCCATCT TGGTGGTGGG GTGTGGTGTT TGAGTATTGG ATAGTGGTTG CGAGCATCTA
GATGAACGCG TAGTCCTTCG TGGCTGACGT GTTCATCGAA ATGTGTAATT TCTTNTNTTA ACTCTTGTGT
GT (SEQ ID NO 90)

Figure 16

AAGGAGCACC ACGAAAAGCA CCCCAATTGG TGGGGTGCGA GCCGTGAGGG GTTCTCGTCT GTAGTGGACG
GGAGCCGGGT GCACAACAGC AAATGATTGC CAGACACACT ATTGGGCCCT GAGACAACAC TCGGTCAGTC
CGTGTGGTGT CCCTCCATCT TGGTGGTGGG GTGTGGTGTT TGAGTATTGG ATAGTGGTTG CGAGCATCTA
GATGAACGCG TAGTCCTTGT GACTGACGTG TTCATCGAAA TGTGTAATTT CTTTTCTAAC TCTTGTGTGT (SEQ ID NO 91)

Figure 17

AAGGAGCACC ACGAAAAGCA CTTCAATTGG TGAAGTGCGA GCCGTGAGGG GTTCTCGTCT GTAGTGGACG
AAAGCCGGGT GCACAACAGC AAATGATTGC CAGACACACT ATTGGGCCCT GAGACAACAC TCGGTCGAAC
CGTGTGGAGT CCCTCCATCT TGGTGGTCGG GTGTGGTGTT TGAGTATTGG ATAGTGGTTG CGAGCATCTA
GATGAACGCG TGGTCTTCAT GGCCGGGCGTG TTCATCGAAA TGTGTAATAT CTTCTCTGT TTTCGGTGTG
T (SEQ ID NO 92)

Figure 18

AAGGAGCACC ACGAAAAGCA CTTCAATTGG TGAAGTGCGA GCCGTGAGGG GTTCTCGTCT GTAGTGGACG
AAAACCGGNT GCACAACAGC AAATGATTGC CAGACACACT ATTGGGCCCT GAGACAACAC TCGGTCGATC
CGTGTGGAGT CCCTCCATCT TGGTGGGTGG GTGTGGGTGTT TGAGTATTGG ATAGTGGTTG CGAGCATCTA
GATGAACGCG TGGTCTTCAT GGCCGGGCGTG TTCATCGAAA TGTGTAATTT CTTTTTNNAC TCTTGTGTGT (SEQ ID NO 93)

Figure 19

AAGGAGCACC ACGAAAAGCA CTTCAATTGG TGAAGTGCCGA GCCGTGAGGG GTTCTCGTCT GTAGTGGACG
AAAGCCGGGT GCACAACAGC AAATGATTGC CAGACACACT ATTGGGCCCT GAGACAACAC TCGGTCGAAC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCGGCGTG TTCATCGAAA TGTGTAATTT CTTCTTTGGT TTTNGTGTGT (SEQ ID NO 94)

Figure 20

```
AAGGAGCACC ACGAAAAGCA CTTCAATTGG TGAAGTGCGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TAGTCCTTCG NGGNCNGCGT GTTCATCGAA ATGTGTAATT TCTNTNTNTAA CTCTNGTGTG
T
```

(SEQ ID NO 95)

Figure 21

AAGGAGCACC ACGAAAAGCA TCCCAATTGG TGGGGTGTGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGGTGTT TGAGTATTGG ATAGTGGTTG CGAGCATCTA
GATGAACGCG TAGTCCTTCG GGGCCGGCGT GTTCATCGAA ATGTGTAATT TCTTTTTAA CTCTTGTGTG
T (SEQ ID NO 96)

Figure 22

AAGGAGCACC ACGAAAAGCA CTTCANTTGG TGAAGTGCGA GCCGTGAGGG GTTCTCGTCT GTAGTGGACG
AAACCGGGT GCACAACAGC AAATGATTGC CAGACACACT ATTGGCCCT GAGACAACAC TCGGTCGAAC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCGGCGTG TTCATCGAAA TGTGTAATTT CTTCTTTAAC TCTTGTGTGT (SEQ ID NO 97)

Figure 23

AAGGAGCACC ACGAAAAGCA CTTCAATTGG TGAAGTGCGA GCCGTGAGGG GTTCTCGTCT GTAGTGGACG
AAAACCGGGT GCACAACAGN AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCNGGCGTG TTCATCGAAA TGTGTAATTT CTTTTTTAAC TCTTGTGTGT (SEQ ID NO 98)

Figure 24

AAGGAGCACC ACGAAAAGCA CTTCAATTGG TGAAGTGCGA GCCGTGAGGG GTTCTCGTCT GTAGTGGACG
AAAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCGGGCGTG TTCATCGAAA TGTGTAATTT CTTTTTTAAC TCTTGTGTGT (SEQ ID NO 99)

Figure 25

AAGGAGCACC ACGAAAAGCA CCCCAACTGG TGGGGTGCGA GCCGTGAGGG GTCCTCGCCT GTAGTGGGCG
GGGGCCGGGT GCACAACAGC AAATGATTGC CAGACACACT ATTGGGCCCT GAGGCAACAC TCGGCTCGTT
CTGAGTGGTG TCCCTCCATC TTGGTGGTGG GGTGGTGGTGT TTGAGTATTG GATAGTGGTT GCGAGCATCT
AAACGGATGC GTGGCCGGCA ACGGTGGCGT GTTCGTTGAA ATGTGTAATT TCTTTTTTGG TTTTTGTGTG
T (SEQ ID NO 100)

Figure 26

AAGGAGCACC ACGAAAAGCA TCCCAACAAG TGGGGTGCAA NCCGTGAGGG GTTCTCGTCT GTAGTGGACG
AAAGCCGGGT GCACGACAAC AAGCAAAGCC AGACACACTA TTGGGTCCTG AGGCAACACT CGGGCTCTGT
TCGAGAGTTG TCCCACCATC TTGGTGGTGG GGTGTGGTGT TTGAGAATTG GATAGTGGTT GCGAGCATCA
AATGGATGCG TTGCCCTACG GGTAGCGTGT TCTTTTGTGC AATTTTATTC TTTGGTTTTT GTGT (SEQ ID NO 101)

Figure 27

AAGGAGCACC ATTTCCCAGT CGATGAACTA GGGAACATAA AGTAGGCATC TGTAGTGGAT ATCTACTTGG
TGAATATGTT TTGTAAATCC TGTCCACCCC GTGGATGGGT AGTCGGCAAA ACGTCGGACT GTCATAAGAA
TTGAAACGCT GGCACACTGT TGGGTCCTGA GGCAACACGT TGTGTTGTCA CCCTGCTTGG TGGTGGGGTG
TGGACTTTGA CTTCTGAATA GTGGTTGCGA GCATCTAAAC ATAGCCCTCGC TCGTTTTCGA GTGGGGCTGG
TTTTGCAATT TTA (SEQ ID NO 102)

Figure 28

AAGGAGCACC ATTCCCAGT CGGATGAACT AGGGAACATA AAGTAGGCAT CTGTAGTGGG TATCTACTTG
GTGAATATGT TTTGTAAATC CTGTCCACCC CCGTGGATGG GTAGTCGGCA AAACGTCGGA CTGTCATAAG
AATTGAAACG CTGGCACACT GTTGGGTCCT GAGGCAACAC GTTGTGTTGT CACCCTGCTT GGTGGTGGGG
TGTGGACTTT GACTTCTGAA TAGTGGTTGC GAGCATCTAA ACATAGCCTC GCTCGTTTTC GAGTGAGGCT
GGTTTTTGCA ATTTTA (SEQ ID NO 103)

Figure 29

AAGGAGCACC ACGAAGAGCA CTCCAATTGG TGGGGTGCGA GCCGTGAGGG GTCATCGTCT GTAGTGGACG
AAGACCGGGT GCACGACAAC AAGCTAAGCC AGACACACTA TTGGGTCCTG AGGCAACACC CTCGGGTGCT
GTCCCCCCAT CTTGGTGGTG GGGTGTGGTG TTTGAGAATT GGATAGTGGT TGCGAGCATC AAAATGTATG
CGTTGTCGTT CTCGGCAACG TGTTCTTTTT GTGCAATTTA TTCTTTGGTT TTTGTAGTGT TTGT (SEQ ID NO 104)

Figure 30

AAGGAGCACC ACGAAGAGCA CTCCAATTGG TGGGGTGCGA GCCGNGAGGG GTCATCGTCT GTAGTGGACG
AAGACTGGGT GCACGACAAC AAAGCAAGCC AGACACACTA TTGGGTCCTG AGGCAACACC CTCGGGTGCT
GCCCCTCCAT CTTGGTGGTG GGGTGTGGTG TTTGAGAACT GGATAGTGGT TGCGAGCATC AAAAATGTAT
GCGTTGTCGT TCGCGACAAC GTGTTCTTTT TGTGCAATTT TAATTCTTTT GGTTTTGGTA GTGTTTGT (SEQ ID NO 105)

Figure 31

AAGGAGCACC ACGAGAAGCA CTCCAATTGG TGGGGTGCAA GCCGTGAGGG GTCATCGTCT GTAGTGGACG
AAGACCGGGT GCACGACAAC AAGCAAAGCC AGACACACTA TTGGGTCCTG AGGCAACACC CTCGGGTGCT
GTCCCCCCAT CTTGGTGGTG GGGTGTGGTG TTTGAGAACT GGATAGTGGT TGCGAGCATC AAAATGTATG
CGTTGTCGTT CGCGGCAACG TGTTCTTTTT GTGCAATTTT TATTCTTTGG TTTTTGTAGT GTTTGT (SEQ ID NO 106)

Figure 32

AAGGAGCACC ACGAAAAGCA CCCCAATTGG TGGGGTGCAA GCCCGTGAGGG GTTCCCGCCT GTAGTGGGCG
GGGCCGGGTG CGCAACAGCA AATGATTGCC AGACACACTA TTGGGCCCTG AGGCAACACT CGGATCGATT
GAGTGCTTGT CCCCCCATCT TGGTGGTGGG GTGTGGTGTT TGAGAACTGG ATAGTGGTTG CGAGCATCTA
AATGAACGCA CTGCCGATGG TGGTGTGTTC GTTTTGTGTA ATTTTATTCT TTGGTTTTTG TGTTTGT (SEQ ID NO 107)

Figure 33

AAGGAGCACC ACGAAAAGCA CTCCAATTGG TGGGGTGCGA GCCGTNAGGG GTTCTCGTCT GTAGTGGATG
GCAGCCGGGT GCACANCAGC AAATGATTGC CAGACACACT ATTGGGCCCT GAGACAACAC TCGGTCAGTC
CGTGTGGAGT CCCTCCATCT TGGTGGTGGG GTGTGGGNGTT TGAGTATTGG ATAGTGGTTG CGANCATCTA
GATGAACGCG TAGTCCTCNG TGGCTGACGT GTTCATCAAA ATGTGTAATT TCTTTTANGG GTTTNGGTGT
CT (SEQ ID NO 108)

Figure 34

AAGGAGCACC ACGAAAAGCA CTCCAATTGG TGGGGTGCGA GCCGNGAGGG GTTCTCGCCT GTAGTGGNCG
AGGGCCGGAT GCACAACAAC ACATGATTGC CAGACACACT ATTGGGCCCT GANACAACAC TCGGCCAGTC
CGTGGTGT CCCTCCATCT TGGTGGTGGG GTGTGGTGTT TGAGTATNGG ATAGTNGTTG NGANCATCTA
AACGGCTGCG TNGNCNNGAA CGGTGGCGTG TTCGNTAAAA TGTGTAATTT CTTTTNNGGT TTGGGTGTNT (SEQ ID NO 109)

Figure 35

```
AAGGAGCACC ACGAAAAGCA CTCCAATTGG TGGGGTGCGA GCCGTGAGGG GTTCTCGCCT GTAGTGGGCG
ANGGCCGGGT GCACAACAAC AAATGATTGC CAGACACACT ATTGGGCCCT GAGACAACAC TCGGCCAGTC
CGTGTGGTGT CCCNCCATCT TGGTGGGTGGG GTGTGGTGTT TGAGTATTGG ATAGTGGTTG CGAGCATCTA
AANGGNTGCG TTGCCGNNAN CNGTGGCGTN TTCGNTAAAA TGTGTAANTT CTTTTNGGT TTGTGTGTGT
```

(SEQ ID NO 110)

Figure 36

ATCGAAGATC CCGGCTTCTT CATAAGCTCC CACACGAATT GCTTGATTCA CTGGTTAGAC GATTGGGTCT
GTAGCTCAGT TGGTTAGAGC GCACCCCTGA TAAGGGTGAG GTCGGCAGTT CGAATCTGCC CAGACCCACC
AATTGTTGGT GTGCTGCGTG ATCCGATACG GGGCCATAGC TCAGCTGGGA GAGCGCCTGC TTTGCACGCA
GGAGGTCAGG AGTTCGATCC TCCTTGGCTC CACCATCTAA AACAATCGTC GAAAGCTCAG AAATGAATGT
TCGTGGATGA ACATTGATTT CTGGTCTTTG CACCAGAACT GTTCTTTAAA AATTCGGGTA TGTGATAGAA
GTAAGACTGA ATGATCTCTT TCACTGGTGA TCATTCAAGT CAAGGTAAAA TTTGCGAGTT CAAGCGCGAA
TTTCGGCGA ATGTCGTCTT CACAGTATAA CCAGATTGCT TGGGGTTATA T (SEQ ID NO 111)

Figure 37

ATCGAAGACA TCAGCTTCTT CATAAGTATC CACACGAATT GCTTGATTCA TAGTCGAACG AATGCTGTAA
CGCGACCCGT GTTATAGGTC TGTAGCTCAG TTGGTTAGAG CGCACCCCTG ATAAGGGTGA GGTCGGCAGT
TCAAATCTGC CCAGACCTAC CAATTGCTTG GTCGAGAAGA ATACGGGGCC ATAGCTCAGC TGGGAGAGCG
CCTGCCTTGC ACGCAGGAGG TCAGCGGTTC GATCCCGCTT GGCTCCACCA CTCTCTCGTG TTGCGGTGAG
TGTTAAAGAG TTCAGAAATG ATGCCGCTTC AGGTTTGTCC TGTTGAGTGC TGATTTCTGG TCTTTTGACC
GGTACGAAAA TCGTTCTTTA AAAATTTGGA TATGTGATAG AAGTGACTGA TTAATTGCTT TCACTGGCAA
TTGATCTGGT CAAGGTAAAA TTTGTAGTTC TCAAGACGCA AATTTTCGGC GAATGTCGTC TTCACGATTG
AGACAGTAAC CAGATTGCTT GGGGTTATAT (SEQ ID NO 112)

Figure 38

```
ATCGAAGACA CCGGCTTCGT CATAAGCTCC CACACGAATT GCTTGATTCA CTTGCGAAAG GCGATTGGGT
TTAGACCCGA GAGTAACGAT TGGGTCTGTA GCTCAGTTGG TTAGAGCGCA CCCCTGATAA GGGTGAGGTC
GGCAGTTCGA ATCTGCCCAG ACCCACCAAT CGAAGGGGCC ATAGCTCAGC TGGGAGAGCG CCTGCTTTGC
ACGCAGGAGG TCAGCGGTTC GATCCCGCTT GGCTCCACCA TTAACTCTAG TCGCCGAAAG CTCAGAAATG
AGTGTTTACC AGGATGAGGT TGATTGCCTG GGTTGAACAT TGATTTCTGG ACTTTGCGCC AGAACTGTTC
TTTAAAAATT TGGGTATGTG ATAGAAGTAG ACCGATGTGT TGCTTTCACT GGCAGCATGT CGCGTCAAGG
TAAATTTGC GTGTTCTCTA TGCAAATTTT CGGCGAATGT CGTCTTCACG TTATAGACAG TAACCAGATT
GCTTGGGGTT ATAT
```

(SEQ ID NO 113)

Figure 39

```
ATCGAAGACT TCAGCTTCTT CATAAGTTCC CACACGAATT GCTTGATTCA CTTGCGAAAA GCGATTGGGT
TGAGACCCGA GAGTGACGAT TGGGTCTGTA GCTCAGTTGG TTAGAGCGCA CCCCTGATAA GGGTGAGGTC
GGCAGTTCGA ATCTGCCCAG ACCCACCAAT TGTCGGGATG GCCAGTGTCA AATGGGGCCA TAGCTCAGCT
GGGAGAGCGC CTGCTTTGCA CGCAGGAGGT CAGGAGTTCG ATCCTCCTTG GCTCCACCAT CAACTCACGA
TCGCTGAAAG CTCAGAAATG AACATTGGTA GTTCAATGTT GATTTCTGGT CTTTGCGCCA GAACTGTTCT
TTAAAAATTT GGGTATGTGA TAGAAGTGAC TAACAGCCGTG TTTCACTGCA CGTTGTTAAT CAAGGCAAAA
TTTGCGAGTT CAAGCGCGAA TTTTCGGGCGA ATGTCGTCTT CACGTTACGA ATCTATAACC AGATTGCTTG
GGGTTATAT
```

(SEQ ID NO 114)

Figure 40

ATCGACGACA TCAGCTGTCT CATAAGCTCC CACACGAATT GCTTGATTCA TTGAAGAAGA CGATTAGGTT
AGCAACCTTC GATTGGGTCT GTAGCTCAGT TGGTTAGAGC GCACCCCTGA TAAGGGTGAG GTCGGCAGTT
CGAATCTGCC CAGACCCACC AATTTGCTGG GGCCATAGCT CAGCTGGGAG AGCGCCTGCC TTGCACGCAG
GAGGTCAGCG GTTCGATCCC GCTTGGCTCC ACCACCCCGC TTGCCAGTTT GTCAAAGCTT AGAAATGAAT
ATTCGCGTCG AATATTGATT TCTGAACTTT ATCAGAATCG TTCTTTAAAA ATTTGGGTAT GTGATAGAAA
GATAGACTGG ACAGCACTTT CACTGGTGTG TGTTCAGGCT AAGGTAAAAT TTGTGAGTAA TTACAAGTTT
TCGGCGAATG TTGTCTTCAC AGTATAACCA GATTGCTTGG GGTTATAT (SEQ ID NO 115)

Figure 41

TAAGGAAAAG GAAACCTGTG AGTTTTCGTT CTTCTCTGTT TGTTCAGTTT TGAGAGGTTA ATTCTTCTCT
ATACTGTTTG TTCTTTGAAA ACTAGATAAG AAAGTTAGTA AAGTTAGCAT AAATAGGTAA CTATTTATGA
CACAAGTAAC CGAGAATCAT CTGAAAGTGA ATCTTTCATC TGATTGGAAG TATCATCGCT GATACGAAAA
ATCAGAAAAA CAACCTTTAC TTCATCGAAG TAAATT (SEQ ID NO 116)

Figure 42

CTAAGGAAAA GGAAACCTGT GAGTTTTCGT TCTTCTCTAT TTGTTCAGTT TTGAGAGGTT AGTACTTCTC
AGTATGTTTG TTCTTTGAAA ACTAGATAAG AAAGTTAGTA AAGTTAGCAT AGATAATTTA TTATTTATGA
CACAAGTAAC CGAGAATCAT CTGAAAGTGA ATCTTTCATC TGATTGGAAG TATCATCGCT GATACGGAAA
ATCAGAAAAA CAACCTTTAC TTCGTAGAAG TAAATT (SEQ ID NO 117)

Figure 43

TAAGGAAAAG GAAACCTGTG AGTTTTCGTT CTTCTCTGTT TGTTCAGTTT TGAGAGGTTA TTACTTCTCT
GTATGTTTGT TCTTTGAAAA CTAGATAAGA AAGTTAGTAA AGTTAGCATA AGTAGTGTAA CTATTTATGA
CACAAGTAAC CGAGAATCAT CTGAAAGTGA ATCTTTCATC TAATTCGACG TATCATCGCT GATACAGACA
ATTAGAAAAA CAACCTTTAC TTCGACGAAG TAAATT (SEQ ID NO 118)

Figure 44

GGCCTATAGC TCAGCTGGTT AGAGCGCACG CCTGATAAGC GTGAGGTCGA TGGTTCGAGT CCATTTAGGC
CCACTTTTTC TTTCTGACAG AAGAAACACT GTATAACCTA TTTAAGGGGC CTTAGCTCAG CTGGGAGAGC
GCCTGCTTTG CACGCAGGAG GTCAGCGGTT CGATCCCGCT AGGCTCCACC AAAATTGTTC TTTGAAAACT
AGATAAGAAA GTTAGTAAAG TTAGCATAAA TAGGTAACTA TTTATGACAC AAGTAACCGA GAATCATCTG
AAAGTGAATC TTTCATCTGA TGGAAGTAT CATCGCTGAT ACGAAAAATC AGAAAAACAA CCTTTACTTC
ATCGAAGTAA ATT (SEQ ID NO 119)

Figure 45

TAAGGAAAAG GAAACCTGTG AGTTTTCGTT CTTCTCTATT TGTTCAGTTT TGAGAGGTTA CTCTCTTTTA
TGTCAGATAA AGTATGCAAG GCACTATGCT TGAAGCATCG CGCCACTACA TTTTGACGG GCCTATAGCT
CAGCTGGTTA GAGCGCACGC CTGATAAGCG TGAGGTCGAT GGTTCGAGTC CATTAGGCC CACTTTTCT
TTCTGACATA AGAAATACAA ATAATCATAC CCTTTTACGG GGCCTTAGCT CAGCTGGGAG AGCGCCTGCT
TTGCACGCAG GAGGTCAGCG GTTCGATCCC GCTAGGCTCC ACCAAAATTG TTCTTTGAAA ACTAGATAAG
AAGTTAGTA AAGTTAGCAT AGATAATTTA TTATTTATGA CACAAGTAAC CGAGAATCAT CTGAAAGTGA
ATCTTTCATC TGATTGGAAG TATCATCGCT GATACGGAAA ATCAGAAAAA CAACCTTTAC TTCGTAGAAG
TAAATT (SEQ ID NO 120)

Figure 46

TAAGGAAAAG GAAACCTGTN AGTTTNCGTN CTTCTCTGTT TGTNCAGTTT TNAGAGGTTA CTCTCTTTNA
TGTCAGATAA AGTACGCCACG GCACGTTGCC TTGGGCAAAG AGCCACTACA TTATTGACGG GCCTATAGCT
CAGCTGGTTA GAGCGCACGC CTGATAAGCG TGAGGTCGAT GGTTCGAGTC CATTTAGGCC CACTTTTCT
TTCTGACAGA AGAAATCATT TGCACATCCT ATTAATAAGG GNCCTTAGCT CAGCTGGGAG AGCGCCTGCT
TTGCACGCAG GAGGTCAGCG GTTCGATCCC GCTAGGCTCC ACCCAAAATT GTTCTTTGAA AACTAGATAA
GAAAGTTAGT AAAGTTAGCA TAAGTAGTAT AACTATTTAT GACACAAGTA ACCGAGAATC ATCTGAAAGT
GAATCTTTCA TCTAATTCGA CGTATCATCG CTGATACAGA CAATTNGAAA AACAACCTTT ACTTCGACGA
AGTAAATT (SEQ ID NO 121)

Figure 47

TAAGGATAAG GATAACTGTC TTAGGACGGT TTGACTAGGT TGGGCAAGCG TTTTTTTAAT CTTGTATTCT
ATTCCTTTTG CATTGTTAAG CGTTGTTTCC AAAACATTTA GTTACGATC AAGTATGTTA TGTAAATAAT
ATGGTAACAA GTAAATTCAC ATATAATAAT AGACGTTTAA GAATATATGT CTTTAGGTGA TGTTAACTTG
CATGGATCAA TAATTTACA (SEQ ID NO 122)

Figure 48

TAAGGATAAG GAAGAAGCCT GAGAAGGTTT CTGACTAGGT TGGGCAAGCA TTTATATGTA AGAGCAAGCA
TTCTATTTCA TTTGTGTTGT TAAGAGTAGC GTGGTGAGGA CGAGACATAT AGTTTGTGAT CAAGTATGTT
ATTGTAAAGA AATAATCATG GTAACAAGTA TATTCACGC ATAATAATAG ACGTTAAGA GTATTTGTCT
TTTAGGTGAA GTGCTTGCAT GGATCTATAG AAATTACA (SEQ ID NO 123)

Figure 49

CAAATGGAGT TTTTATTTTT TATTTATCTT AAACACCCAT TAATTTTTTC GGTGTTAAAA CCCAAATCAA
TGTTTGGTCT CACAACTAAC ACATTGGTC AGTTTGTATC CAGTTCTGAA AGAATGTTTT TGAACAGTTC
TTTCAAAACT GAAAACGACA ATCTTTCTAG TTCCAAAAAT AAATACCAAA GGATCAATAC AATAAGTTAC
TAAGGGCTTA TGGT (SEQ ID NO 124)

Figure 50

```
CTAATGAAAGT TTTTTACTTT TTCTTTTCAT CTTTAATAAA GATAAATACT AAACAAAACA TCAAAATCCA
TTTATTTATC GGTGGTAAAT TAAACCCAAA TCCCTGTTTG GTCTCACAAC TAACATATTT GGTCAGATTG
TATCCAGTTC TGAAAGAACA TTTCCGCTTC TTTCAAAACT GAAAACGACA ATCTTTCTAG TTCCAAATAA
ATACCAAAGG ATCAATACAA TAAGTTACTA AGGGCTTATG GT
```

(SEQ ID NO 125)

Figure 51

AACGAAAGAT TGACGATTGG TAAGAATCCA CAACAAGTTG TTCTTCATAG ATGTATCTGA GGGTCTGTAG
CTCAGTTGGT TAGAGCACAC GCTTGATAAG CGTGGGGTCA CAAGTTCAAG TCTTGTCAGA CCCACCATGA
CTTTGACTGG TTGAAGTTAT AGATAAAAGA TACATGATTG ATGATGTAAG CTGGGGACTT AGCTTAGTTG
GTAGAGCGCC TGCTTTGCAC GCAGGAGGTC AGGAGTTCGA CTCTCCCTAGT CTCCACCAGA ACTTAAGATA
AGTTCGGATT ACAGAAATTA GTAAATAAAG ATTGAGATCT TGGTTTATTA ACTTCTGTGA TTTCATTATC
ACGTAATTA GTGTGATCTG ACGAAGACAC ATTAACTCAT TAACAGATTG GCAAAATTGA GTCTGAAATA
AATTGTTCAC TCAAGAGTTT AGGTTAAGCA ATTAATCTAG ATGAATTGAG AACTAGCAAA TTAACTGAAT
CAAGCGTTTT GGTATGTGAA TTTAGATTGA AGCTGTACAG TGCTTAAGTG CACAGTGCTC TAAACTGAAA
TGTTGAAGTT ACTAACTTGT AGGTAACATC GACTGTTTGG GGTTGTAT (SEQ ID NO 126)

Figure 52

AACGAAAGAT TGACGATTGG TAAGAATCCA CGACAAGTTG TTCTTCATAG ATGTATCTGA GGGTCTGTAG
CTCAGTTGGT TAGAGCACAC GCTTGATAAG CGTGGGGTCA CAAGTTCAAG TCTTGTCAGA CCCACCATGA
CTTTGACTGG TTGAAGTTAT AGAAAAGAAG ATACATAACT GATGATGTAA GCTGGGACT TAGCTTAGTT
GGTAGAGCGC CTGCTTTGCA CGCAGGAGGT CAGGAGTTCG ACTCTCCTAG TCTCCACCA (SEQ ID NO 127)

Figure 53

AACGAAAGAT TGATGGCCGG TAAGAATCCA CAACAAGTTG TTCTTCGAAG ATGTATCTGA GGGTCTGTAG
CTCAGTTGGT TAGAGCACAC GCTTGATAAG CGTGGGGTCA CAAGTTCAAG TCTTGTCAGA CCCACCAAAT
CTGAAAGATA TGTCGTTCAT TATGATTAAA GCTGGGGACT TAGCTTAGTT GGTAGAGCGC CTGCTTTGCA
CGCAGGAGGT CAGGAGTTCG ACTCTCCCTAG TCTCCACCA (SEQ ID NO 128)

Figure 54

AACGAAAGAT TGACGATTGG TAAGAATCCA CAACAAGTTG TTCTTCATGA CGATGTATCT GAGGGTCTGT
AGCTCAGTTG GTTAGAGCAC AGCCTTGATA AGCGTGGGGT CACAAGTTCA AGTCTTGTCA GACCCACCAA
ATCTGACTAA CAAGCATTAT TAAATGCTGA ATACAGAAAA ACAGAGACAT TGACTTATTG ATAAGCTGGG
GACTTAGCTT AGTTGGTAGA GCGCCTGCTT TGCACGCAGG AGGTCAGGAG TTCGACTCTC CTAGTCTCCA
CCA (SEQ ID NO 129)

Figure 55

AACGAAAGAT TGGTGACCGG TAAGAATCCA CAACAAGTTG TTCTTCGAAG ATGTATCTGA GGGTCTGTAG
CTCAGTTGGT TAGAGCACAC GCTTGATAAG CGTGGGGTCA CAAGTTCAAG TCTTGTCAGA CCCACCACTA
CTGACGAAGT GATGAATAAT CACAAGCTGC TAGATGAAAA GATATGTCGT TCATTATGAT TAAAGCTGGG
GACTTAGCTT AGTTGGTAGA GCGCCTGCTT TGCACGCAGG AGGTCAGGAG TTCGACTCTC CTAGTCTCCA
CCA (SEQ ID NO 130)

Figure 56

```
TAAGGAAGAT CGAGAATTGG AAAGAGGTCG GATTTATCCG GATGATCCTT CTCCATCTTA TTAGAACATA
GATCGCAGGC CAGTCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GCCCATCAGG GCCGACGCC
GGTCGGCCTT GCNAAGCTTC GCTTCGGGGT GGATCTGTGG ATCGCGTAGT AGCCGTTTGCG TCGGTATCTG
GGCTTGTAGC TCAGTTGGTT AGAGCACACG CTTGATAAGC GTGGGGTCGG AGGTTCAAGT CCTCCCAGGC
CCACCAAGTT ACTTGATGAG GGGCCCGTAGC TCAGCTGGGA GAGCACCTGC TTTGCAAGCA GGGGGTCGTC
GGTTCGATCC CGTCCGGCTC CACCATCATG TTGGTGTTGA GACGGATATT GGCAATCAAC AAAAGAAAGA
AACAAGTTTG CGGACTNTTA CGAAAGTCTG CCTGTTCTGT ATGAAATCGT GAAGAGAAGA TGTAATCGGA
TCAACTGAAG AGTTGATGTC GCAAGAAGCT TGCTCAAGCC TTGCATAATG ATTGATGTGT TTAACCGCCA
TCACCGATTG TATCTCGAGA AGCTGGTCTT TCTGCTGATA CTGTTGAAAC GAGCATTGC AGTCGAATGG
CAACATTCGG CGTCGCATAA TGCGGCTTTA AGAGCTGAGT TTTGATGGAT ATTGGCAATG AGAGTGATCA
AGTGTCTTAA GGGCATTGGT GGATGCCCTTG GCATGCAC
```

(SEQ ID NO 131)

Figure 57

```
TAAGGAGGAT CGAGAATTGG AAAGAGGCCG GATTTATCCG GATGATCCTT CTCCATCTTA TTAGAACATA
GATCGCAGNC CAGTCCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GNCCATCAGG GCCGACGGCC
GGTCGGCCTT GCGAAGCTTC GCTTCGGGGT GGATCTGTGG ATCGCGTAGT AGCGTTTGCG TCGGTATCTG
GGCTTGTAGC TCAGTTGGTT AGAGCACACG CTTGATAAGC GTGGGGTCGG AGGTTCAAGT CCTCCCAGGC
CCACCAAGTT ACTTGATGAG GGGCCGTAGC TCAGCTGGGA GAGCACCTGC TTTGCAAGCA GGGGTCGTC
GGTTCGATCC CGTCCGGCTC CACCATCATG TTGGTGTTGA GACGGATATT GGCAATCAAC AAAAGAAAGA
AACAAGTTTG CGGACTNTTA CGAAAGTCTG CCTGTTCTGT ATGAAATCGT GAAGAGAAGA TGTAATCGGA
TCAACTGAAG AGTTGATGTC GCAAGAAGCT TGCTCAAGCC TTGCATAATG ATTGATGTGT TTAACCGCCA
TCACCGATTG TATCTCGAGA AGCTGGTCTT TCTGCTGATA CTGTTGAAAC GAGCATTTGC AGTCGAATGG
CAACATTCGG CGTCGCATAA TGCGGCTTTA AGAGCTGAGT TTTGATGGAT ATTGGCAATG AGAGTGATCA
AGTGTCTTAA GGGCATTGGT GGATGCCTTG GCATGCAC
```

(SEQ ID NO 132)

Figure 58

CCTTAAAGAA CTGTTCTTTG CAGTGCTCAC ACAGATTGTC TGATGAAAAG TAAATAGCAA GGCGTCTTGC
GAAGCAGACT GATACGTCCC CTTCGTCTAG AGGCCCAGGA CACCGCCCTT TCACGGCGGT AACAGGGGTT
CGAATCCCCT AGGGACGCC ACTTGCGCGG TAATGTGTGA AAGCGTTGCC ATCAGTATCT CAAAACTGAC
TTACGAGTCA CGTTTGAGAT ATTTGCTCTT TAAAAATCTG GATCAAGCTG AAAATTGAAA CACAGAACAA
CGAAAGTTGT TCGTGAGTCT CTCAAATTTT CGCAACACGA TGATGAATCG TAAGAAACAT CTTCGGGTTG
TGA (SEQ ID NO 133)

Figure 59

CCTTAAAGAA CTGTTCTTTG CAGTGCTCAC ACAGATTGTC TGATGAAAAA CGAGCAGTAA AACCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATATCGTG AGTGTTTACG
AAAAATACT TCAGAGTGTA CCTGAAAGGG TTCACTGCGA AGTTTTGCTC TTTAAAAATC TGGATCAAGC
TGAAATTGA AACACAGAAC AACGAAAGTT GTTCGTGAGT CTCTCAAATT TTCGCAACAC GATGATGAAT
CGTAAGAAAC ATCTTCGGGT TGTGA (SEQ ID NO 134)

Figure 60

CCTTAAAGAA GCGTACTTTG CAGTGCTCAC ACAGATTGTC TGATGAAAAG TAAATAGCAA GGCGTCTTGC
GAAGCAGACT GATACGTCCC CTTCGTCTAG AGGCCCAGGA CACCGCCCTT TCACGGCGGT AACAGGGTT
CGAATCCCCT AGGGGACGCC ACTTGCGCGG TAATGTGTGA AGCCGTTGCC ATCAGTATCT CAAAACTGAC
TTACGAGTCA CGTTTGAGAT ATTTGCTCTT TAAAAATCTG GATCAAGCTG AAAATTGAAA CACAGAACAA
CGAAAGTTGT TCGTGAGTCT CTCAAATTTT CGCAACACGA TGATGAATCG TAAGAAACAT CTTCGGGTTG
TGA (SEQ ID NO 135)

Figure 61

CCTTAAAGAA CTGTTCTTTG AAGTGCTCAC ACAGATTGTC TGATGAAAAA CGAGCAGTAA AACCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATCTCGTG AGTGTTTACG
AAAAAATACT TCAGAGTGTA CCTGAAAGGG TTCACTGCGA AGTTTTGCTC TTTAAAAATC TGGATCAAGC
TGAAAATTGA AACACAGAAC AACGAAAGTT GTTCGTGAGT CTCTCAAATT TTCGCAACAC G (SEQ ID NO 136)

Figure 62

```
CCTTAAAGAA GCGTACTTTG AAGTGCTCAC ACAGATTGTC TGATGAAAAG TGAATAGCAA GGCGTCTTGC
GATTGAGACT TCAGTGTCCC CTTCGTCTAG AGGCCCAGGA CACCGCCCTT TCACGGCGGT AACAGGGGTT
CGAATCCCCT AGGGGACGCC AGCGTTCAAA CTGATGAGGT CAAACCTCCA GGGACGCCAC TTGCTGGTTT
GTGAGTGAAA GTCACCTGCC TTAATATCTC AAAACTGACT TACGAGTCAC GTTTGAGATA TTTGCTCTTT
AAAAATCTGG ATCAAGCTGA AAATTGAAAC ACAGAACAAC GAAAGTTGTT CGTGAGTCTC TCAAATTTTC
GCAACACGAT GATGAATCGT AAGAAACATC TTCGGGTTGT GA
```

(SEQ ID NO 137)

Figure 63

CCTTAAAGAA ACGGTCTTTG AAGTGCTCAC ACAGATTGTC TGATGAAAAA CGAGCAGTAA AACCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATCTCGTG AGTGTTTACG
AAAAATACT TCAGAGTGTA CCTGAAAGGG TTCACTGCGA AGTTTTGCTC TTTAAAAATC TGGATCAAGC
TGAAATTGA AACACAGAAC AACGAAAGTT GTTCGTGAGT CTCTCAAATT TTCGCAACAC GATGATGAAT
CGTAAGAAAC ATCTTCGGGT TGTGA (SEQ ID NO 138)

Figure 64

CTAAGGATAT ATTCGGAACA TCTTCTTCGG AAGATGCGGA ATAACGTGAC ATATTGTATT CAGTTTTGAA
TGTTTATTTA ACATTCAAAT ATTTTTTGGT TAAAGTGATA TTGCTTTTGA AAATAAAGCA GTATGCGAGC
GCTTGACTAA AAAAAATTGT ACATTGAAAA CTAGATAAGT AAGTAAAATA TAGATTTTAC CAAGCAAAAC
CGAGTGAATA AAGAGTTTTA AATAAGCTTG AATTCATAAG AAATAATCGC TAGTGTTCGA AAGAACACTC
ACAAGATTAA TAACGCGTTT AAATCTTTTT ATAAAAGAAC GTAACTTCAT GTTAACGTTT GACTTATAAA
AATGGTGGAA ACATA (SEQ ID NO 139)

Figure 65

```
CTAAGGATAT ATTCGGAACA TCTTCTTCAG AAGATGCGGA ATAACGTGAC ATATTGTATT CAGTTTTGAA
TGTTTATTTA ACATTCAAAT ATTTTTGGT TAAAGTGATA TTGCTTATGC GAGCNCTTGA CAATCTATTC
TTTTAAAGA AAGCGGTTGT CAGACAATGC ATTAAAGAAA ATTAAAGCGG AGTTTACTTT TGTAAATGAG
CATTTGATTT TTTGAAAATA AAGCAGTATG CGAGCGCTTG ACTAAAAAGA AATTGTACAT TGAAAACTAG
ATAAGTAAGT AAAATATAGA TTTTACCAAG CAAAACCGAG TGAATAAAGA GTTTTAAATA AGCTTGAATT
CATAAGAAAT AATCGCTAGT GTTCGAAAGA ACACTCACAA GATTAATAAC GCGTTTAAAT CTTTTTATAA
AAGAAAACGT TTAGCAGACA ATGAGTTAAA TTATTTTAAA GCAGAGTTTA CTTATGTAAA TGAGCATTTA
AAATAATGAA AACGAAGCCG TATGTGAGCA TTTGACTTAT AAAAATGGTG GAAACATA
```

(SEQ ID NO 140)

Figure 66

CTAAGGATAT ATTCGGAACA TCTTCTTCAG AAGATGCGGA ATAACGTGAC ATATTGTATT CAGTTTTGAA
TGTTTATTTA ACATTCAAAT ATTTTTGGT TAAAGTGATA TTGCTTATGC GAGCGCTTGA CAATCTATTC
TTTTTAAAGA AAGCGGTTGT CAGACAATGC ATTAAAGCGG AGTTTACTTT TGTAAATGAG
CATTTGATTT TTTGAAAATA AAGCAGTATG CGAGCGCTTG ACTAAAANGA AATTGTACAT TGAAAACTAG
ATAAGTAAGT AAAATATAGA TTTTACCAAG CAAAACCGAG TGAATAAAGA GTTTTGAATA AGCTTGAATT
CATAAGAAAT AATCGCTAGT GTTCGAAAGA ACACTCACAA GATTAATAAC GCGTTTAAAT CTTTTTATAA
AAGAACGTTA CTTCATGTTA ACGTTTGACT TATAAAAATG GTGGAAACAT A (SEQ ID NO 141)

Figure 67

CTAAGGATAT ATTCGGAACA TCTTCTTCAG AAGATGCGGA ATAACGTGAC ATATTGTATT CAGNTTTGAA
TGTTTATTTA ACATTCAAAA AATGGGCCTA TAGCTCAGCT GGTTAGAGCG CACGCCTGAT AAGCGTGAGG
TCGGTGGTTC GAGTCCACTT AGGCCCACCA TTATTGTAC ATTGAAAACT AGATAAGTAA GTAAAATATA
GATTTACCA AGCAAAACCG AGTGAATAAA GAGTTTAAA TAAGCTTGAA TTCATAAGAA ATAATCGCTA
GTGTTCGAAA GAACACTCAC AAGATTAATA ACGCGTTTAA ATCTTTTTAT AAAAGAACGT AACTTCATGT
TAACGTTTGA CTTATAAAAA TGGTGGAAAC ATA (SEQ ID NO 142)

Figure 68

CTAAGGATAT ATTCGGAACA TCTTCYTCAG AAGATGCGGA ATAATGTGAC ATATTGTATT CAGTTTTGAA
TGTTTATTTA ACATTCAAAT ATTTTTTGGT TAAAGTGATA TTGCTTATGC GAGCGGCTTGA CTAAAAAGAA
ATTGTACATT GAAAACTAGA TAAGTAAGTA AAANTATAGA TTTTACCAAG CAAAACCGAG TGAATAAAGA
GTTTTAAATA AGCTTGAATT CATAAGAAAT AATCGCTAGT GTTCGAAAGA ACACTCACAA GATTAATAAC
GCGTTTAAAT CTTTTTATAA AAGAACGTAA CTTCATGTTA ACGTTTGACT TATAAAAATG GTGGAAACAT
A (SEQ ID NO 143)

Figure 69

CTAAGGATAT ATTCGGAACA TCTTCTACGA AGATGAGGGA ATAACGTGAC ATATTGTATT CAGTTTTGAA
TGTTTATTAA CATTCATTTG TACATTGAAA ACTAGATAAG TAAGTAAGAT TTTACCAAGC AAAACCGAGT
GAATAGAGTT TTAAATAAGC TTGAATTCAT AAATAATCGC TAGTGTTCGA AAGACNTCCA CAAGATTAAT
AACTAGTTTT AGCTATTTAT TTTGAATAAC AATTCAAAAT ATGGTGGGAC ATA (SEQ ID NO 144)

Figure 70

AAGGATAAGG AACTGCACAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAAGA GTTTATGACT GAAAGGTCAA AAAATAA (SEQ ID NO 145)

Figure 71

AAGGAAATGG AACACGTTTA TCGTCTTATT TAGTTTTGAG AGGTCTTGTG GGGCCTTAGC TCAGCTGGGA
GAGCGCCTGC TTNGCACGCA GGAGGTCAGC GGTTCGATCC CGCTAGGCTC CATCAGGATA CANTCCTACT
AAACTTAATA CAAGTGAAGT TGAACACGCA ACTCACTTCC TAGGAAAATA GACAATCTTC GCTTGTGTGC
AAGGCACACA TGGTCAGATT CCTAATTTTC TACAGAAGTT TCGCTAAAGC GAGCGTTGCT TAGTATCCTA
TATAATAGTC CATNGAAAAT TGAATATCTA TATCAAATTC CACGATCTAG AAATAGATTG TGGAAACGTA
ACAAGAAATT AACCCGNAAA CGCTG (SEQ ID NO 146)

Figure 72

AAGGATAAGG AACTGCACAT TGGTCTTGTT TAGTCTTGAG AGGTCTTGTG GGGCCTTAGC TCAGCTGGGA
GAGCGCCTGC TTTGCACGCA GGAGGTCAGC GGTTCCGATCC CGCTAGGCTC CATTGGTGAG AGATCACCAA
GTAATGCACA TTGAAAATTG AATATCTATA TCAAATAGTA ACAAGAAAAT AAACCGAAAC GCTGTAGTAT
TAAAAGAGTT TATGACTGAA AGGTCAGAAA ATAA (SEQ ID NO 147)

Figure 73

CTAAGGATAT ATTCGGAACA TCTTCTTACG AAGATGCAGG AATAACATTG ACATATTGTA TTCAGNTGTG
AATGCTCATT GGAGNATTCA TNGCATNATT TGGTNCATTG ACANCTAGAT AAGNAAGTAA AATTTATGAT
TTTACCAAGC AAAACCGAGT GAATTAGAGT TNTNNAACAA GCTTTGATTT CAAAAAGAAA TAATCGCTAG
TGTTCGAAAG AACACTCACA GATTANTAAC ATCTTGGGTT TTCACCCGAC TTGTTCGTNT CGAAAGTCAA
AAAA (SEQ ID NO 148)

Figure 74

AAGGATAAGG AACTGCGCAT TGGTCTTGTT TAGTCTTGAG AGGTCTTGTG GGGCCTTAGC TCAGCTGGGA
GAGCGGCCTGC TTTGCACGCA GGAGGTCAGC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAAA AAATAA (SEQ ID NO 149)

Figure 75

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC CGCTAGGCTC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAGA AAAATAA (SEQ ID NO 150)

Figure 76

AAGGAAAAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAGA AAAATAA (SEQ ID NO 151)

Figure 77

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAC GCTGTAGTAT
TAAAAGAGTT TATGACTGAA AGGTCAGAAA ATAA (SEQ ID NO 152)

Figure 78

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAC GCTGTAGTAT
TAAAAGAGTT TATGACTGAA AGGTCAAAAA TAA (SEQ ID NO 153)

Figure 79

TAAGGAAGAT CGAGAATTGG AAAGAGGTCG GATTTATCCG GATGATCCTT CTCCATCTTA TTAGAACATA
GATCGCAGGC CAGTCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GCCCATCAGG GCCGAACGGC
CGGTCGGCCT TGCNAAGCTT CGCTTCGGGG TGGATCTGTG GATCGCGTAG TAGCGTTTGC GTCGGTATCT
GGGCTTGTAG CTCAGTTGGT TAGAGCACAC GCTTGATAAG CGTGGGGTCG GAGGTTCAAG TCCTCCCAGG
CCCACCAAGT TACTTGATGA GGGGCCGTAG CTCAGCTGGG AGAGCACCTG CTTTGCAAGC AGGGGTCGT
CGGTTCGATC CCGTCCGGCT CCACCATCAT GTTGGGTGTTG AGACGGATAT TGGCAATCAA CAAAAGAAAG
AAACAAGTTT GCGGACTNTT ACGAAAAGTCT GCCTGTTCTG TATGAAATCG TGAAGAGAAG ATGTAATCGG
ATCAACTGAA GAGTTGATGT CGCAAGAAGC TTGCTCAAGC CTTGCATAAT GATTGATGTG TTTAACCGCC
ATCACCGATT GTATCTCGAG AAGCTGGTCT TTCTGCTGAT ACTGTTGAAA CGAGCATTTG CAGTCGAATG
GCAACATTCG GCGTCGCATA ATGCGGCTTT AAGAGCTGAG TATTGGCAAT GAGAGTGATC
AAGTGTCTTA AGGGCATTGG TGGATGCCTT GGCATGCAC (SEQ ID NO 154)

Figure 80

```
AAGGAGCACC ACGAGAAACA CTCCAATTGG TGGGGTGTAA GCCGTGAGGG GTTCTCGTCT GTAGTGGACG
GAAGCCGGGT GCACAACAAC AAGCAAGCCA GACACACTAT TGGGTCCTGA GGCAACATCT CTGTTGGTTT
CGGGATGTTG TCCCACCATC TTGGTGGTGG GGTGTGGTGT TTGAGAATTG GATAGTGGTT GCGAGCATCA
ATTGGATGCG CTGCCTTTTG GTGGCGTGTT CTGTTGTGCA ATTTTATTCT TTGGTTTTTG TGTTTAT
```

(SEQ ID NO 157)

Figure 81

AAGGAGCACC ACGAGAAACA CCCCAATTGG TGGGGTGTGA GCCCGTGAGGG GTTCTCGTCT GTAGTGGACG
AGGGCCGGGT GCACAACAAC AGGCAATCGC CGGACACACT ATTGGGCCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGCCG GATGCGTTCC CCAGTGGTGC GCGTTCGTCA AAAATGTGTA ATTTTTCTTT TGGTTTTTGT
GTTCGT (SEQ ID NO 158)

Figure 82

AAGGAGCACC ACGAGAAACA CCCCAATTGG TGGGGTGTGA GCCGTGAGGG GTTCTCGTCT GTAGTGGACG
AGGGCCGGGT GCACAACAAC AGGCAATCGC CGGACACACT ATTGGGCCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGACG GATGCGTTCC CCAGTGGTGC GCGTTCGTCA AAAATGTGTA ATTTTTCTTT TGGTTTTTGT
GTTCGT (SEQ ID NO 159)

Figure 83

```
AAGGAGCACC ACGAGAAACA CCCCAATTGG TGGGGTGTGA GCCGTGAGGG GTTCTCGTCT GTAGTGGACG
AGGNNCGGGT NNACAACAAC NGCCAATCGC CGGACACACT ATTGGGNCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGCCG GATGCGTTCC CCAGTGGTGC GCGTTCGTCA AAAATGTGTA ATTTTTCTNT TGGTTTTTGT
GTTCGT
```

(SEQ ID NO 160)

Figure 84

AAGGAGCACC ACGAGAAACA CTCCAATTGG TGGAGTGTGA GCCGTGAGGG GTTCTCGTCT GTAGTGGACG
AGGGCCGGGT GCACAACAGC AGACAATCGC CAGACACACT ATTGGGCCCT GAGACAACAC TCGGCCGACT
TTGGTCGACG TGGTGTCCCT CCATCTTGGT GGTGGGGTGT GGTGTTTGAG CATTGAATAG TGGTTGCGAG
CATCTAGACG GATGCGTTGC CCTCGGGCCG CGTGTTCGTC AAAAATGTGT AATTTTTTCT TTTGGTTTTT
GTGTTCGT (SEQ ID NO 161)

Figure 85

AAGGAGCACC ACGAGAAACA CTCCAATTGG TGGAGTGTGA GCCGTGAGGG GTTCTCGTCT GTAGTGGACG
GGAGCCGGGT GCACAACAAC AGGCAATCGC CAGACACACT ATTGGCCCT GAGACAACAC TCGGCCGGCT
TTGAGTCGAA GTGGTGTCCC TCCATCTTGG TGGTGGGGTG TGGTGTTTGA GCATTGAATA GTGGTTGCGA
GCATCTAGAC GGATGCGTTG CCTTCGGGCC GCGTGTTCGT CAAAAATGTG TAATTTTTC TTTTGGTTTT
TGTGTTCGT (SEQ ID NO 162)

Figure 86

AGGGAGCACC GNAAACGCAT CCCGCGTGGG GTGTGGGTTC GGCGTGTGTT GGCGTCGGNC CGAGGTGTTG
GGCAGCAGGC AGTAACCNCC GGAACACTGT TGGGTTTTGA GNNAACACCC GTGGTGGTGT TGTGCTCCCC
GTGGTGNCGG GGTGTGGTGT TTGAGTGTTG GATAGTGGTT GCGAGCATCT GGCAAAGACT GTGGTAAGCG
GTTTTTGTTG ANTGTTTTCT GGTGTTTGT (SEQ ID NO 163)

Figure 87

```
AAGGAGCACC ACGAGAAACA CTCCAATTGG TGGGGTGTGA GCCGTGAGGG GTTCTCGTCT GTAGTGGACG
AGGGNCGGGT GCACAACAAC AGNCAATCGC CAGACACACT ATTGGNCCCT GAGACAACAC TCGGCCGACT
TNGGTTGAAG TGGTGTCCCT CCATCTTGGT GGTGGGGTGT GGTGTTTGAG TATTGGATAG TGGTTGCGAG
CATCTAANTG AACGCGTCGC CGNCAACGGT TACGTGTTCG TTTTGTGTAA TTNTTTCTAT TGGTTTTTGT
GTTCGT
```

(SEQ ID NO 164)

Figure 88

AAGGAGCACC ACGAGAAACA CTCCAATTGG TGGGGTGTGA GCCGTGAGGG GTTCTCGTCT GTAGTGGACG
AGGGCCGGGT GCACAACAAC AGGCAATCGC CAGACACACT ATTGGNCCCT GAGACAACAC TCGGCCGACT
TTGGTCGAAG TGGTGTCCCC CCATCTTGGT GGTGGGGTGT GGTGTTTGAG TATTGGATAG TGGTTGCGAA
CATCTAAATG AACGCGTTGC CGGCAACGGT TACGTGTTCG TTTTAGTGTA ATTNTTTCTA ATGGTTTTTG
TGTTCGT (SEQ ID NO 165)

Figure 89

AAGGAGCACC ACGAGACCTG GGCCGGCCCC GCAGATCGCG GGATCAGCTG AGCTTTCAGG CGATTCGTTG
GATGGCCTCG CACCTGTAGT GGGTGGGGGT CTGGTGCACT CAACAAACTT GGCGTGGGAT GCGGGAAAGC
ATCTGCGGAA AATCATCAGA CACACTATTG GGCTTTGAGA CAACAGGCCC GCAGNCCTGN CCCGTTGGGG
GCAGNGGGTG TGTTGTTGCC TCACTTTGGT GGTGGGGGTG GTGTTTGATT TGTGGATAGT GGTTGCGAGC
ATCTAGCGCG CAGAATGTGT GGTCTCACTC CTTGTGGGTG GGGCCTGGTT TTGTGTGCGA TTGATGTGCA
ATTTCTTTTG AAACTCATTT TTTGGTTTTT GTGTTGT (SEQ ID NO 166)

Figure 90

AAGGAGCACC ACGAAAAACT CCCCAATTGG TGGGGTGTAA GCCGTGAGGG GTTCCCGTCT GTAGTGGACG
GGGGCCGGGT GCGCAACAGC AAGCGAAACG CCGGACACAC TATTGGGTCC TGAGGCAACA CTCGGGTTTG
TCCCCTCAG GGATTTTCTG GGTGTTGTCC CACCATCTTG GTGGTGGGT GTGGTGTTG AGAATTGGAT
AGTGGTTGCG AGCATCAAAT GGATGCGTTG CCCCTACGGG TAGCGTGTTC TTTGTGCAA TTTTATTCNT
TGGTTTTTGT GTTTGT (SEQ ID NO 167)

Figure 91

AAGGAGCACC ACGAGAAGCA CTCCAACTGG TGGGGTGCAA GCCGTGAGGG GTTCTCGTCT GTAGTGGACG
AGAGCCGGGT GCGCGACAAC GAACGAGCCA GACACACTAT TGGGTCCTGA GGCAACACTC GGGCTTGGCC
AGAGCTGTTG TCCCACCATC TTGGTGGTGG GGTGTGGTGT TTGAGAATTG GATAGTGGTT GCGAGCATCA
AATGGATGCG TTGCCCCTAC GGGTGGGCGTG TTCTTTTGTG CAATTTTATT CTTTGGTTTT TGTGTTTGT (SEQ ID NO 168)

Figure 92

AAGGAGCACC ACGAAAAACA CCCCAACTGG TGGGGTGTAA GCCCGTGAGGG GCTCCCGTCT GTAGTAGACG
GGCGCCGGGT GCGCAACAGC AAGCGAGCCA TGGGTCCTGA GACACACTAT TGGGTCCTGA GGCAACACTC GGGCTTGTCT
TGGACTCGTC CAAGAGTGTT GTCCCACCAT CTTGGTGGTG GGGTGTGGTG TTTGAGAATT GGATAGTGGT
TGCGAGCATC ANCTGGATGC GTTGCCCCCA GGGGTAGCGT GTTCTTTTGT GCAATTNTAT TCNNTGGTTT
TTGTGTTAGT (SEQ ID NO 169)

Figure 93

AAGGAGCACC ACGAAAAACA CTCCGCATCC GGTGGGGTGT GAGCCCGTGAG GGAGCCCGTG CCTGTAGTGG
GTGTGGGGTTG GGTGCGCGAC AACAAATGGG AAAAATCGCT GGGCACACTA TTGGGCTTTG AGGCAACACC
TGGTTTGTTT TGGGTGGTGT CGCTCCATCT TGGTGGTGGG GTGTGGTGTT TGAGTTGTGG ATAGTGGTTG
CGAGCATCTA AGCAAAAGCT GTTGTTTGAC GGTTTTTGTC GAGTGTTGTG TGTGT (SEQ ID NO 170)

Figure 94

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGGT GTGGTGTTTG AGTATTGGAT
AGTGGTTGCG AGCATCTAAA TGGATACGTT GCCAGTAATG GTGGCGTATT CATTGAAAAT GTGTAATTTT
CTTCTTTGGT TTTGTGTGT (SEQ ID NO 171)

Figure 95

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGT GTGGTGTTTG AGTATTGGAT
AGTGGTTGCG AGCATCTAAA TGGATACGTT GCCAGTAATG GTGGCGTGTT CATTGAAAAT GTGTAATTTT
CTTCTTTGGT TTTGTGTGT (SEQ ID NO 172)

Figure 96

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGT GTGGTGTTTG AGTATTGGAT
AGTGGTTGCG AGCATCTAAA TGGANACGTT GCCAGTAATG GTGGCGTGTT CATTGAAAAT GTGTAATTTT
CTTCTTTGGT TTTGTGTGT (SEQ ID NO 173)

Figure 97

AAGGAGCACC ATTTCTCAGT CGAATGAACT GAGAACATAA AGCGAGTATC TGTAGTGGAT ACATGCTTGG
TGAATATGTT TTATAAATCC TGTCCACCCC GTGGATAGGT AGTCGGCAAA ACGTCGGACT GTCATAAGAA
TTGAAACGCT GGCACACTGT TGGGTCCTGA GGCAACACAT TGTGTTGTCA CCCTGCTTGG TGGTGGGGTG
TGGTCCTTGA CTTATGGATA GTGGTTGCGA GCATCTAAAC ATAGCCTCGC TCGTTTTCGA GTGAGGCTGG
TTTTTGCAAT TTTATTAGCT (SEQ ID NO 174)

Figure 98

CCTAATGATA TTGATTCGCG TGAAGTGCTC ACACAGATTG TCTGATGAAA AAGTAACGAG CAGAAATACC
TTTATAGGCT TGTAGCTCAG GTGGTTAGAG CGCACCCCTG ATAAGGGTGA GGTCGGTGGT TCAAGTCCAC
TCAGGCCTAC CACTTCTCGA AGTGGAAAAG GTACTGCACG TGACTGTATG GGGCTATAGC TCAGCTGGGA
GAGCGCCTGC CTTGCACGCA GGAGGTCAGC GGTTCGATCC CGCTTAGCTC CACCATATAG TCCTGTATTT
CAATACTTCA GAGTGTACTG GCAACAGTAT GCTGCGAAGT ATTTGCTCT TTAACAATCT GGAACAAGCT
GAAAATTGAA ACATGACAGC CCCTCCGTAG AAGTATTGGG GTAAGGATTA ACCTGTCATA
GAGTCTCTCA AATGTAGCAG CACGAAAGTG GAAACACCTT CGGGTTGTGA (SEQ ID NO 195)

Figure 99

CCTAATGATA TTGATTCGCG TGAAGTGCTC ACACAGATTG TTTGATAGAA ACGTAATGAG CAAAAGCGCT
ACCTGTTGAT GTAATGAGTC ACTGACTCAT GCTGATACGA ACCGATTAAG ACAGTCAGTT TAATCGGATT
TTCGTGTCCC CATCGTCTAG AGGCCTAGGA CACTGCCCTT TCACGGCTGT AACAGGGGTT CGAATCCCCT
TGGGACGCC ATTCGATAAT GAGTGAAAGA CATTATCACC GGTTCTTGGA ACCGAAAACA TCTTAAAGAT
GACTCTTGCG AGTCGTGTTT AAGATATTGC TCTTTAACAA TCTGGAACAA GCTGAAAATT GAAACATGAC
AGCTGAAACT TATCCCTCCG TAGAAGTATT GGGGTAAGGA TTAACCTGTC ATAGAGTCTC TCAAATGTAG
CAGCACGAAA GTGGAAACAC CTTCGGGTTG TGA (SEQ ID NO 196)

Figure 100

TAAGGATAAG GAAGAAGCCT GAGAAGGTTT CTGACTAGGT TGGGCAAGCA TTTATATGTA AGAGCAAGCA
TTCTATTTCA TTTGTGTTGT TAAGAGTAGC GCGGTGAGGA CGAGACATAT AGTTTGTGAT CAAGTATGTT
ATTGTAAAGA AATAATCATG GTAACAAGTA TATTTCACGC ATAATAAATAG ACGTTTAAGA GTATTGTCT
TTTAGGTGAA GTGCTTGCAT GGATCTATAG AAATTACA (SEQ ID NO 197)

Figure 101

TAAGGATAAG GAAACCTGTG AATCTTTTTC CCTTCTTTTG TTCAGTTTTG AGAGGTTCAT CTCTCAAAAC
GTGTTCTTTG AAAACTAGAT AAGAAAAGTT AGTGTAAAAA GACGAAGAGA AACCGTAGGT TTTTCTTCAA
CCAAAACCGA GAATCAAACC GAGAAAGAAT CTTTCCGTTT TCATAAGCGA TCGCACGTTT ATGAAAACAC
AACAACACCT TCGTAAGAAG GATGA (SEQ ID NO 213)

Figure 102

TAAGGATAAG GAAACCTGTG AATCTTTTTC CCTTCTTTTG TTCAGTTTTG AGAGGTCAAT GACGCTCATA
CTGAGTACCA GGTGACACGT TTTGAGGTG TCTCTTCCGTA TGAGGGGCCT ATAGCTCAGC TGGTTAGAGC
GCACGCCTGA TAAGCGTGAG GTCGGTGGTT CGAGTCCACT TAGGCCCACT TTTTTGAATA AACCTTTCTT
TTTTATATGT TAATAAGGGG CCTTAGCTCA GCTGGGAGAG CGCCTGCTTT GCACGCAGGA GGTCAGCGGT
TCGATCCCGC TAGGCTCCAC CAAAGATAGT TTGTTCTTTG AAAACTAGAT AAGAAAAGTT AGTGTAAAAA
GACGAAGAGA AACCGTAGGT TTTTCTTCAA CCAAAACCGA GAATCAAACC GAGAAAGAAT CTTTCCGTTT
TCATAAGCGA TCGCACGTTT ATGAAAAACAC AACAACACCT TCGTAAGAAG GATGA (SEQ ID NO 214)

Figure 103

TAAGGATAAG GAAACCTGTG AATCTTTTTC CCTTCTTTTG TTCAGTTTTG AGAGGTCAAT GACGCTCATA
CTGAGTACCA GGTGACACGT TTTTGAGGTG TCTCTTCGTA TGAGGGGCCT ATAGCTCAGC TGGTTAGAGC
GCACGCCTGA TAAGCGTGAG GTCGGTGGTT CGAGTCCACT TAGGCCCACT TTTTGAATA AACCTTTCTT
TTTTATATGT TAATAAGGGG CCTTAGCTCA GCTGGGAGAG CGCCTGCTTT GCACGCAGGA GGTCAGCGGT
TCGATCCCGC TAGGCTCCAC CAAAGATAGT TTGTTCTTTG AAAACTAGAT AAGAAAAGTT AGTGTAAAAA
GACGAAGAGA AACCGTAGGT TTTTCTTCAA CCAAAACCGA GAAAGAATCT TTCCGTTTTC ATAAGCGATC
GCACGTTTAT GAAAACACAA CAACACCTTC GTAAGAAGGA TGA (SEQ ID NO 215)

SEQUENCE LISTING (1) GENERAL INFORMATION:

(iii) NUMBER OF SEQUENCES: 216

(2) INFORMATION FOR SEQ ID NO: 1:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

ACTGGATAGT GGTTGCGAGC ATCTA                                              25

(2) INFORMATION FOR SEQ ID NO: 2:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

CTTCTGAATA GTGGTTGCGA GCATCT                                             26

(2) INFORMATION FOR SEQ ID NO: 3:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

GGGTGCATGA CAACAAAGTT GGCCA                                              25

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

GACTTGTTCC AGGTGTTGTC CCAC                                               24

(2) INFORMATION FOR SEQ ID NO: 5:

(i) SEQUENCE CHARACTERISTICS:
            (A) LENGTH: 21 base pairs
            (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

CGGCTAGCGG TGGCGTGTTC T                                              21

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

CAACAGCAAA TGATTGCCAG ACACAC                                         26

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

GAGGGGTTCC CGTCTGTAGT G                                              21

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

TGAGGGGTTC TCGTCTGTAG TG                                             22

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

-continued (ii) MOLECULE TYPE: cDNA (iii) HYPOTHETICAL: NO (iv) ANTI-SENSE: NO (xi) SEQUENCE DESCRIPTION: SEQ ID NO: 9:

CACTCGGTCG ATCCGTGTGG A                                          21

(2) INFORMATION FOR SEQ ID NO: 10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

TCGGTCCGTC CGTGTGGAGT C                                          21

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

GTGGCCGGCG TTCATCGAAA                                            20

(2) INFORMATION FOR SEQ ID NO: 12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

GCATAGTCCT TAGGGCTGAT GCGTT                                      25

(2) INFORMATION FOR SEQ ID NO: 13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

GCTGATGCGT TCGTCGAAAT GTGTA                                              25

(2) INFORMATION FOR SEQ ID NO: 14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

CTGATGCGTT CGTCGAAATG TGT                                                23

(2) INFORMATION FOR SEQ ID NO: 15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

TGATGCGTTC GTCGAAATGT GT                                                 22

(2) INFORMATION FOR SEQ ID NO: 16:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

GGCTGATGCG TTCGTCGAAA TGTGTAA                                            27

(2) INFORMATION FOR SEQ ID NO: 17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO

```
    (xi) SEQUENCE DESCRIPTION: SEQ ID NO: 17:

ACTAGATGAA CGCGTAGTCC TTGT                                              24

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

TGGACGAAAA CCGGGTGCAC AA                                                22

(2) INFORMATION FOR SEQ ID NO: 19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

GTGTAATTTC TTTTTTAACT CTTGTGTGTA AGTAAGTG                                38

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

TGGCCGGCGT GTTCATCGAA A                                                 21

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

GCACTTCAAT TGGTGAAGTG CGAGCC                                            26
```

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

```
GCGTGGTCTT CATGGCCGG                                                19
```

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 23:

```
ACGCGTGGTC CTTCGTGG                                                 18
```

(2) INFORMATION FOR SEQ ID NO: 24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 24:

```
TCGGCTCGTT CTGAGTGGTG TC                                            22
```

(2) INFORMATION FOR SEQ ID NO: 25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 25:

```
GATGCGTTTG CTACGGGTAG CGT                                           23
```

(2) INFORMATION FOR SEQ ID NO: 26:

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 26:

GATGCGTTGC CTACGGGTAG CGT                                           23

(2) INFORMATION FOR SEQ ID NO: 27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 27:

ATGCGTTGCC CTACGGGTAG CGT                                           23

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 28:

CGGGCTCTGT TCGAGAGTTG TC                                            22

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

GGTGTGGACT TTGACTTCTG AATAG                                         25

(2) INFORMATION FOR SEQ ID NO: 30:

(i) SEQUENCE CHARACTERISTICS:
        (A) LENGTH: 21 base pairs
```

(B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 30:

CGGCAAAACG TCGGACTGTC A                                              21

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 31:

AACACCCTCG GGTGCTGTCC                                                20

(2) INFORMATION FOR SEQ ID NO: 32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 32:

GTATGCGTTG TCGTTCGCGG C                                              21

(2) INFORMATION FOR SEQ ID NO: 33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

CGTGAGGGGT CATCGTCTGT AG                                             22

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued

```
    (ii) MOLECULE TYPE: cDNA (iii) HYPOTHETICAL: NO (iv) ANTI-SENSE: NO (xi) SEQUENCE DESCRIPTION: SEQ ID NO: 34:

TGGTGTGCTG CGTGATCCGA T                                         21

(2) INFORMATION FOR SEQ ID NO: 35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 35:

TGAATGTTCG TGGATGAACA TTGATT                                    26

(2) INFORMATION FOR SEQ ID NO: 36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 36:

CACTGGTGAT CATTCAAGTC AAG                                       23

(2) INFORMATION FOR SEQ ID NO: 37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 37:

TGAATGTTCG TVVATGAACA TTGATTTCTG GTC                            33

(2) INFORMATION FOR SEQ ID NO: 38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 38:

CTCTTTCACT GGTGATCATT CAAGTCAAG                                                29

(2) INFORMATION FOR SEQ ID NO: 39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 39:

CAAGTAACCG AGAATCATCT GAAAGTGAAT C                                             31

(2) INFORMATION FOR SEQ ID NO: 40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 40:

AAACAACCTT TACTTCGTAG AAGTAAATTG GTTAAG                                        36

(2) INFORMATION FOR SEQ ID NO: 41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

TGAGAGGTTA GTACTTCTCA GTATGTTTGT TC                                            32

(2) INFORMATION FOR SEQ ID NO: 42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 42:

AGGCACTATG CTTGAAGCAT CGC                                                    23

(2) INFORMATION FOR SEQ ID NO: 43:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 43:

GTTAGCATAA ATAGGTAACT ATTTATGACA CAAGTAAC                                     38

(2) INFORMATION FOR SEQ ID NO: 44:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 44:

AGTTAGCATA AGTAGTGTAA CTATTTATGA CACAAG                                       36

(2) INFORMATION FOR SEQ ID NO: 45:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 45:

GGAAGAAGCC TGAGAAGGTT TCTGAC                                                  26

(2) INFORMATION FOR SEQ ID NO: 46:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 46:

GCATTTATAT GTAAGAGCAA GCATTCTATT TCA                      33

(2) INFORMATION FOR SEQ ID NO: 47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

GAGTAGCGTG GTGAGGACGA GA                                  22

(2) INFORMATION FOR SEQ ID NO: 48:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 48:

GGATAACTGT CTTAGGACGG TTTGAC                              26

(2) INFORMATION FOR SEQ ID NO: 49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 49:

ATCGGTGGTA AATTAAACCC AAATCCCTGT                          30

(2) INFORMATION FOR SEQ ID NO: 50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 50:

CAGTTCTGAA AGAACATTTC CGCTTCTTTC                          30

-continued (2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 51:

```
CACCCATTAA TTTTTTCGGT GTTAAAACCC                                    30
```

(2) INFORMATION FOR SEQ ID NO: 52:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 52:

```
CAAAACTGAA AACGACAATC TTTCTAGTTC C                                  31
```

(2) INFORMATION FOR SEQ ID NO: 53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

```
TACCAAGCAA AACCGAGTGA ATAAAGAGTT                                    30
```

(2) INFORMATION FOR SEQ ID NO: 54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 54:

```
CAGAAGATGC GGAATAACGT GAC                                           23
```

(2) INFORMATION FOR SEQ ID NO: 55:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 55:

AACGAAGCCG TATGTGAGCA TTTGAC                                      26

(2) INFORMATION FOR SEQ ID NO: 56:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 56:

GAACGTAACT TCATGTTAAC GTTTGACTTA T                                31

(2) INFORMATION FOR SEQ ID NO: 57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 57:

GCTTAAGTGC ACAGTGCTCT AAACTGA                                     27

(2) INFORMATION FOR SEQ ID NO: 58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 58:

CACGGTAATT AGTGTGATCT GACGAAG                                     27

(2) INFORMATION FOR SEQ ID NO: 59:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 59:

CGTGCCGCCT TCGTTTCTCT TT                                                    22

(2) INFORMATION FOR SEQ ID NO: 60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

TTCGCTTCGG GGTGGATCTG TG                                                    22

(2) INFORMATION FOR SEQ ID NO: 61:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 61:

CAAAACTGAC TTACGAGTCA CGTTTGAG                                              28

(2) INFORMATION FOR SEQ ID NO: 62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 62:

GATGTATGCT TCGTTATTCC ACGCC                                                 25

(2) INFORMATION FOR SEQ ID NO: 63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA

```
    (iii) HYPOTHETICAL: NO (iv) ANTI-SENSE: NO (xi) SEQUENCE DESCRIPTION: SEQ ID NO: 63:

GGTCAAACCT CCAGGGACGC C                                              21

(2) INFORMATION FOR SEQ ID NO: 64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 64:

GCGGTAATGT GTGAAAGCGT TGCC                                           24

(2) INFORMATION FOR SEQ ID NO: 65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 65:

TCCCTTGTGG CCTGTGTG                                                  18

(2) INFORMATION FOR SEQ ID NO: 66:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 66:

TCCTTCATCG GCTCTTCGA                                                 19

(2) INFORMATION FOR SEQ ID NO: 67:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

-continued (iv) ANTI-SENSE: NO (xi) SEQUENCE DESCRIPTION: SEQ ID NO: 67:

GATGCCAAGG CATCCACC                                                  18

(2) INFORMATION FOR SEQ ID NO: 68:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 68:

CCTCCCACGT CCTTCATCG                                                 19

(2) INFORMATION FOR SEQ ID NO: 69:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 69:

AAGGTTTCTG ACTAGGTTGG GC                                             22

(2) INFORMATION FOR SEQ ID NO: 70:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 70:

GGTGAAGTGC TTGCATGGAT CT                                             22

(2) INFORMATION FOR SEQ ID NO: 71:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 71:

ACCTGTGAGT TTTCGTTCTT CTC                                              23

(2) INFORMATION FOR SEQ ID NO: 72:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 72:

CTATTTGTTC AGTTTTGAGA GGTT                                             24

(2) INFORMATION FOR SEQ ID NO: 73:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 73:

ATTTTCCGTA TCAGCGATGA TAC                                              23

(2) INFORMATION FOR SEQ ID NO: 74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 74:

ACGAAGTAAA GGTTGTTTTT CT                                               22

(2) INFORMATION FOR SEQ ID NO: 75:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 75:

GAGAGGTTAC TCTCTTTTAT GTCAG                                            25

(2) INFORMATION FOR SEQ ID NO: 76:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 76:

```
AAGGAGCACC ACGAAAACGC CCCAACTGGT GGGGCGTAGG CCGTGAGGGG TTCTTGTCTG      60
TAGTGGGCGA GAGCCGGGTG CATGACAACA AAGTTGGCCA CCAACACACT GTTGGGTCCT     120
GAGGCAACAC TCGGACTTGT TCCAGGTGTT GTCCCACCGC CTTGGTGGTG GGGTGTGGTG     180
TTTGAGAACT GGATAGTGGT TGCGAGCATC AATGGATACG CTGCCGGCTA GCGGTGGCGT     240
GTTCTTTGTG CAATATTCTT TGGTTTTTGT TGTGT                                275
```

(2) INFORMATION FOR SEQ ID NO: 77:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 77:

```
AAGGAGCACC ACGAAAAGCA CCCCAACTGG TGGGGTGCGA GCCGTGAGGG GTTCCCGTCT      60
GTAGTGGACG GGGGCCGGNT GCGCAACAGC AAATGATTGC CAGACACACT ATTGGGCCCT     120
GAGACAACAC TCGGTCCGTC CGTGTGGAGT CCCTCCATCT TGGTGGTGGG GTGTGGTGTT     180
TGAGTATTGG ATAGTGGTTG CGAGCATCTA GATGAGCGCA TGGTCTTCGT GGCCGGCGTT     240
CATCGAAATG TGTAATTTCT TCCTTAACTC TTGTGTGT                             278
```

(2) INFORMATION FOR SEQ ID NO: 78:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 78:

```
AAGGAGCACC ACGAAAAGCA CCCCAACTGG TGGGGTGCGA GCCGTGAGGG GTTCCCGTCT      60
GTAGTGGACG GGGGCCGGGT GCGCAACAGC AAATGATTGC CAGACACACT ATTGGGCCCT     120
GAGACAACAC TCGGTCCGTC CGTGTGGAGT CCCTCCATCT TGGTGGTGGG GTGTGGTGTT     180
TGAGTATTGG ATAGTGGTTG CGAGCATCTA GATGAGCGCA TGGTCTTCGT GGCCGGCGTT     240
```

-continued

```
CATCGAAATG TGTAATTTCT TTTTTAACTC TTGTGTGT                                    278
```

(2) INFORMATION FOR SEQ ID NO: 79:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 79:

```
AAGGAGCACC ACGAAAAGCA CTCCAATTGG TGGGGTGCGA GCCGTGAGGG GTTCCCGTCT              60
GTAGTGGACG GGGGCCGGNT GCACAACAGC AAATGATTGC CAGACACACT ATTGGGCCCT             120
GAGACAACAC TCGGTCGATC CGTGTGGAGT CCCTCCATCT TGGTGGTGGG GTGTGGTGTT             180
TGAGTATTGG ATAGTGGTTG CGAGCATCTA GATGAGCGCA TAGTCCTTGT GGCTGATGCG             240
CTCGTCGAAA TGTGTAATTT CTTCTTTGGT GTNTGTGTGT                                   280
```

(2) INFORMATION FOR SEQ ID NO: 80:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 80:

```
AAGGAGCACC ACGAAAAGCA TCCCAATTGG TGGGGTGCGA GCCGTGAGGG GTTCTCGTCT              60
GTAGTGGACG AAAACCGGGT GCACAACAGC AAATGATTGC CAGACACACT ATTGGGCCCT             120
GAGACAACAC TCGGTCGATC CGTGTGGAGT CCCTCCATCT TGGTGGTGGG GTGTGGTGTT             180
TGAGTATTGG ATAGTGGTTG CGAGCATCTA GATGAGCGCG TAGTCCTTTG TGGCTGATGC             240
GTTCATCAAA ATGTGTAATT TCTTTTTTGG TTTNTGTGTG T                                 281
```

(2) INFORMATION FOR SEQ ID NO: 81:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 81:

```
AAGGAGCACC ACGAAAAGCA CTCCAATTGG TGGGGTGCGA GCCGTGAGGG GTTCCCGTCT              60
GTAGTGGACG GGGGCCGGGT GCACAACAGC AAATGATTGC CAGACACACT ATTGGGCCCT             120
GAGACAACAC TCGGTCGATC CGTGTGGAGT CCCTCCATCT TGGTGGTGGG GTGTGGTGTT             180
```

```
TGAGTATTGG ATAGTGGTTG CGAGCATCTA GATGAGCGCA TAGCCCTTGC GGCTGATGCG        240

TTCGNCGAAA TGTGTAATTT CTTCTCTGGT TTCTGTGTGT                              280

(2) INFORMATION FOR SEQ ID NO: 82:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 82:

AAGGAGCACC ACGAAAAGCA CTCCAATTGG TGGGGTGCGA GCCGTGAGGG GTTCTCGTCT         60

GTAGTGGACG GNAGCCGGGT GCACAACAGC AAATGATTGC CAGACACACT ATTGGGCCCT        120

GAGACAACAC TCGGTCGATC CGTGTGGAGT CCCTCCATCT TGGTGGTGGG GTGTGGTGTT        180

TGAGTATTGG ATAGTGGTTG CGAGCATCTA GATGAGCGCG TAGTCCTTCG TGGCTGATGC        240

GTTCATCGAA ATGTGTAATT TCTTCTTTGG TTTTGGGTGT GT                           282

(2) INFORMATION FOR SEQ ID NO: 83:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 83:

AAGGAGCACC ACGAAAAGCA CTCCAATTGG TGGGGTGCGA GCCGTGAGGG GTTCCCGTCT         60

GTAGTGGACG GGGGCCGGGT GCACAACAGC AAATGATCGC CAGACACACT ATTGGGCCCT        120

GAGACAACAC TCGGTCGATC CGTGTGGAGT CCCTCCATCT TGGTGGTGGG GTGTGGTGTT        180

TGAGTATTGG ATAGTGGTTG CGAGCATCTA GATGAGCGCA TAGTCCTTTG GGGCTGATGT        240

GTTTCATCAA AATGTGTAAT TTCTTTTTNG GTTTTNGTGT GT                           282

(2) INFORMATION FOR SEQ ID NO: 84:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 84:

AAGGAGCACC ACGAAAAGCA CTCCAATTGG TGGGGTGCGA GCCGTGAGGG GTTCTCGTCT         60

GTAGTGGACG GGAGCCGGGT GCACAACAGC AAATGATTGC CAGACACACT ATTGGGCCCT        120
```

```
GAGACAACAC TCGGTCGATC CGTGTGGAGT CCCTCCATCT TGGTGGTGGG GTGTGGTGTT      180

TGAGTATTGG ATAGTGGTTG CGAGCATCTA GATGAGCGCG TAGTCCTTCG TGGCTGATGC      240

GTTCATTGAA ATGTGTAATT TCTTCTCTGG TTTTTGTGTG T                         281

(2) INFORMATION FOR SEQ ID NO: 85:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 85:

AAGGAGCACC ACGAAAAGCA CTCCAATTGG TGGGGTGCGA GCCGTGAGGG GTTCCCGTCT       60

GTAGTGGACG GGGGCCGGGT GCACAACAGC AAATGATTGC CAGACACACT ATTGGGCCCT      120

GAGACAACAC TCGGTCGATC CGTGTGGAGT CCCTCCATCT TGGTGGTGGG GTGTGGTGTT      180

TGAGTATTGG ATAGTGGTTG CGAGCATCTA GATGAGCGCA TAGTCCTTGT GGCTGATGCG      240

CTCGTCGAAA TGTGTAATTT CTTCTTTGGT TTTTGTGTGT                           280

(2) INFORMATION FOR SEQ ID NO: 86:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 86:

AAGGAGCACC ACGAAAAGCA CTCCAATTGG TGGGGTGCGA GCCGTGAGGG GTTCCCGTCT       60

GTAGTGGACG GGGGCCGGGT GCGCAACAGC AAATGATTGC CAGACACACT ATTGGGCCCT      120

GAGACAACAC TCGGTCGATC CGTGTGGAGT CCCTCCATCT TGGTGGTGGG GTGTTGGTGT      180

TTGAGTATTG GATAGTGGTT GCGAGCATCT AGATGAGCGC GTAGTCCTTG TGGCTGATGC      240

GTTCGTCGAA ATGTGTAATT TCTTCTTTGG GTTTTTGTGT GT                        282

(2) INFORMATION FOR SEQ ID NO: 87:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 87:

AAGGAGCACC ACGAAAAGCA CCCCAATTGG TGGGGTGCGA GCCGTGAGGG GTTCTCGTCT       60
```

```
GTAGTGGACG GNAGCCGGNT GCGCAACAGC AAATGATTGC CAGACACACT ATTGGGCCCT    120

GAGACAACAC TCGGNCGATC CGTGTGGAGT CCCTCCATCT TGGTGGTGGG GTGTNGTGTT    180

TGAGTATTGG ATAGTGGTTG CGAGCATCTA GATGGGCGCG TAGTCCTTTG TGACTGATGC    240

GTTCATCAAA ATGTGTAATT TCTTTTTTGN NTTTNGTGTG T                       281
```

(2) INFORMATION FOR SEQ ID NO: 88:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 88:

```
AAGGAGCACC ACGAAAAGCA CTCCAATTGG TGGGGTGCGA GCCGTGAGGG GTTCTCGTCT    60

GTAGTGGACG GGAACCGGGT GCACAACAGC AAATGATTGC CAGACACACT ATTGGGCCCT    120

GAGACAACAC TCGGTCGATC CGTGTGGAGT CCCTCCATCT TGGTGGTGGG GTGTGGTGTT    180

TGAGTATTGG ATAGTGGTTG CGAGCATCTA GATGAGCGCA TAGTCCTTTG TGGCTGACGC    240

GTTCATCGAA ATGTGTAATT TCTTCTTTGG TTTTTGTGTG T                       281
```

(2) INFORMATION FOR SEQ ID NO: 89:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 89:

```
AAGGAGCACC ACGAAAAGCA CTCCAATTGG TGGGGTGCGA GCCGTGANGG GTTCCCGTCT    60

GTAGTGGACG GGGGCCGGGT GCACAACAGC AAATGATTGC CAGACACACT ATTGGGCCCT    120

GAGACAACAC TCGGTCGATC CGTGTGGAGT CCCTCCATCT TGGTGGTGGG GTGTGGTGTT    180

TGAGTATTGG ATAGTGGTTG CGAGCATCTA GATGAGCGCA TAGTCCTTAG GGCTGATGCG    240

TTCGTCGNAA TGTGTAATTT CTTCTTTGGT TTTTGTGTGT                         280
```

(2) INFORMATION FOR SEQ ID NO: 90:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 90:

```
AAGGAGCACC ACGAAAAGCA TCCCAATTGG TGGGGTGCGA GCCGTGAGGG GTTCTCGTCT      60

GTAGTGGACG AAAACCGGGT GCACAACAGC AAATAATTGC CAGACACACT ATTGGGCCCT     120

GAGACAACAC TCGGTCGATC CGTGTGGTGT CCCTCCATCT TGGTGGTGGG GTGTGGTGTT     180

TGAGTATTGG ATAGTGGTTG CGAGCATCTA GATGAACGCG TAGTCCTTCG TGGCTGACGT     240

GTTCATCGAA ATGTGTAATT TCTTNTNTTA ACTCTTGTGT GT                        282

(2) INFORMATION FOR SEQ ID NO: 91:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 91:

AAGGAGCACC ACGAAAAGCA CCCCAATTGG TGGGGTGCGA GCCGTGAGGG GTTCTCGTCT      60

GTAGTGGACG GGAGCCGGGT GCACAACAGC AAATGATTGC CAGACACACT ATTGGGCCCT     120

GAGACAACAC TCGGTCAGTC CGTGTGGTGT CCCTCCATCT TGGTGGTGGG GTGTGGTGTT     180

TGAGTATTGG ATAGTGGTTG CGAGCATCTA GATGAACGCG TAGTCCTTGT GACTGACGTG     240

TTCATCGAAA TGTGTAATTT CTTTTCTAAC TCTTGTGTGT                            280

(2) INFORMATION FOR SEQ ID NO: 92:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 92:

AAGGAGCACC ACGAAAAGCA CTTCAATTGG TGAAGTGCGA GCCGTGAGGG GTTCTCGTCT      60

GTAGTGGACG AAAGCCGGGT GCACAACAGC AAATGATTGC CAGACACACT ATTGGGCCCT     120

GAGACAACAC TCGGTCGAAC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCGGCGTG     240

TTCATCGAAA TGTGTAATAT CTTCTCTGGT TTTCGGTGTG T                         281

(2) INFORMATION FOR SEQ ID NO: 93:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(xi) SEQUENCE DESCRIPTION: SEQ ID NO: 93:

AAGGAGCACC ACGAAAAGCA CTTCAATTGG TGAAGTGCGA GCCGTGAGGG GTTCTCGTCT        60

GTAGTGGACG AAAACCGGNT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCGGCGTG       240

TTCATCGAAA TGTGTAATTT CTTTTTNNAC TCTTGTGTGT                             280

(2) INFORMATION FOR SEQ ID NO: 94:

(i) SEQUENCE CHARACTERISTICS:
            (A) LENGTH: 280 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 94:

AAGGAGCACC ACGAAAAGCA CTTCAATTGG TGAAGTGCGA GCCGTGAGGG GTTCTCGTCT        60

GTAGTGGACG AAAGCCGGGT GCACAACAGC AAATGATTGC CAGACACACT ATTGGGCCCT       120

GAGACAACAC TCGGTCGAAC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCGGCGTG       240

TTCATCGAAA TGTGTAATTT CTTCTTTGGT TTTNGTGTGT                             280

(2) INFORMATION FOR SEQ ID NO: 95:

(i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 95:

AAGGAGCACC ACGAAAAGCA CTTCAATTGG TGAAGTGCGA GCCGTGAGGG GTTCTCGTCT        60

GTAGTGGACG AAAACCGGGT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAACGCG TAGTCCTTCG NGGNCNGCGT       240

GTTCATCGAA ATGTGTAATT TCTNTTNTAA CTCTNGTGTG T                           281

(2) INFORMATION FOR SEQ ID NO: 96:

(i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 96:

AAGGAGCACC ACGAAAAGCA TCCCAATTGG TGGGGTGTGA GCCGTGAGGG GTTCTCGTCT        60

GTAGTGGACG AAAACCGGGT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAACGCG TAGTCCTTCG GGGCCGGCGT       240

GTTCATCGAA ATGTGTAATT TCTTTTTTAA CTCTTGTGTG T                          281

(2) INFORMATION FOR SEQ ID NO: 97:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 97:

AAGGAGCACC ACGAAAAGCA CTTCANTTGG TGAAGTGCGA GCCGTGAGGG GTTCTCGTCT        60

GTAGTGGACG AAAACCGGGT GCACAACAGC AAATGATTGC CAGACACACT ATTGGGCCCT       120

GAGACAACAC TCGGTCGAAC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCGGCGTG       240

TTCATCGAAA TGTGTAATTT CTTCTTTAAC TCTTGTGTGT                            280

(2) INFORMATION FOR SEQ ID NO: 98:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 98:

AAGGAGCACC ACGAAAAGCA CTTCAATTGG TGAAGTGCGA GCCGTGAGGG GTTCTCGTCT        60

GTAGTGGACG AAAACCGGGT GCACAACAGN AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCNGCGTG       240

TTCATCGAAA TGTGTAATTT CTTTTTTAAC TCTTGTGTGT                            280

(2) INFORMATION FOR SEQ ID NO: 99:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 99:

AAGGAGCACC ACGAAAAGCA CTTCAATTGG TGAAGTGCGA GCCGTGAGGG GTTCTCGTCT      60

GTAGTGGACG AAAACCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCGGCGTG     240

TTCATCGAAA TGTGTAATTT CTTTTTTAAC TCTTGTGTGT                           280

(2) INFORMATION FOR SEQ ID NO: 100:

(i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 100:

AAGGAGCACC ACGAAAAGCA CCCCAACTGG TGGGGTGCGA GCCGTGAGGG GTCCTCGCCT      60

GTAGTGGGCG GGGGCCGGGT GCACAACAGC AAATGATTGC CAGACACACT ATTGGGCCCT     120

GAGGCAACAC TCGGCTCGTT CTGAGTGGTG TCCCTCCATC TTGGTGGTGG GGTGTGGTGT     180

TTGAGTATTG GATAGTGGTT GCGAGCATCT AAACGGATGC GTGGCCGGCA ACGGTGGCGT     240

GTTCGTTGAA ATGTGTAATT TCTTTTTTGG TTTTTGTGTG T                         281

(2) INFORMATION FOR SEQ ID NO: 101:

(i) SEQUENCE CHARACTERISTICS:
            (A) LENGTH: 274 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 101:

AAGGAGCACC ACGAAAAGCA TCCCAACAAG TGGGGTGCAA NCCGTGAGGG GTTCTCGTCT      60

GTAGTGGACG AAAGCCGGGT GCACGACAAC AAGCAAAGCC AGACACACTA TTGGGTCCTG     120

AGGCAACACT CGGGCTCTGT TCGAGAGTTG TCCCACCATC TTGGTGGTGG GGTGTGGTGT     180

TTGAGAATTG GATAGTGGTT GCGAGCATCA AATGGATGCG TTGCCCTACG GGTAGCGTGT     240

TCTTTTGTGC AATTTTATTC TTTGGTTTTT GTGT                                 274

(2) INFORMATION FOR SEQ ID NO: 102:

(i) SEQUENCE CHARACTERISTICS:
            (A) LENGTH: 293 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 102:

AAGGAGCACC ATTTCCCAGT CGATGAACTA GGGAACATAA AGTAGGCATC TGTAGTGGAT    60

ATCTACTTGG TGAATATGTT TTGTAAATCC TGTCCACCCC GTGGATGGGT AGTCGGCAAA   120

ACGTCGGACT GTCATAAGAA TTGAAACGCT GGCACACTGT TGGGTCCTGA GGCAACACGT   180

TGTGTTGTCA CCCTGCTTGG TGGTGGGGTG TGGACTTTGA CTTCTGAATA GTGGTTGCGA   240

GCATCTAAAC ATAGCCTCGC TCGTTTTCGA GTGGGGCTGG TTTTGCAATT TTA          293

(2) INFORMATION FOR SEQ ID NO: 103:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 103:

AAGGAGCACC ATTTCCCAGT CGGATGAACT AGGGAACATA AGTAGGCAT CTGTAGTGGG     60

TATCTACTTG GTGAATATGT TTTGTAAATC CTGTCCACCC CGTGGATGG GTAGTCGGCA    120

AAACGTCGGA CTGTCATAAG AATTGAAACG CTGGCACACT GTTGGGTCCT GAGGCAACAC   180

GTTGTGTTGT CACCCTGCTT GGTGGTGGGG TGTGGACTTT GACTTCTGAA TAGTGGTTGC   240

GAGCATCTAA ACATAGCCTC GCTCGTTTTC GAGTGAGGCT GGTTTTTGCA ATTTTA       296

(2) INFORMATION FOR SEQ ID NO: 104:

(i) SEQUENCE CHARACTERISTICS:
        (A) LENGTH: 274 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 104:

AAGGAGCACC ACGAAGAGCA CTCCAATTGG TGGGGTGCGA GCCGTGAGGG GTCATCGTCT    60

GTAGTGGACG AAGACCGGGT GCACGACAAC AAGCTAAGCC AGACACACTA TTGGGTCCTG   120

AGGCAACACC CTCGGGTGCT GTCCCCCCAT CTTGGTGGTG GGGTGTGGTG TTTGAGAATT   180

GGATAGTGGT TGCGAGCATC AAAATGTATG CGTTGTCGTT CTCGGCAACG TGTTCTTTTT   240

GTGCAATTTA TTCTTTGGTT TTTGTAGTGT TTGT                               274

(2) INFORMATION FOR SEQ ID NO: 105:

(i) SEQUENCE CHARACTERISTICS:
        (A) LENGTH: 278 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 105:

```
AAGGAGCACC ACGAAGAGCA CTCCAATTGG TGGGGTGCGA GCCGNGAGGG GTCATCGTCT      60
GTAGTGGACG AAGACTGGGT GCACGACAAC AAAGCAAGCC AGACACACTA TTGGGTCCTG     120
AGGCAACACC CTCGGGTGCT GCCCCTCCAT CTTGGTGGTG GGGTGTGGTG TTTGAGAACT     180
GGATAGTGGT TGCGAGCATC AAAAATGTAT GCGTTGTCGT TCGCGACAAC GTGTTCTTTT     240
TGTGCAATTT TAATTCTTTT GGTTTTGGTA GTGTTTGT                             278
```

(2) INFORMATION FOR SEQ ID NO: 106:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 106:

```
AAGGAGCACC ACGAGAAGCA CTCCAATTGG TGGGGTGCAA GCCGTGAGGG GTCATCGTCT      60
GTAGTGGACG AAGACCGGGT GCACGACAAC AAGCAAAGCC AGACACACTA TTGGGTCCTG     120
AGGCAACACC CTCGGGTGCT GTCCCCCCAT CTTGGTGGTG GGGTGTGGTG TTTGAGAACT     180
GGATAGTGGT TGCGAGCATC AAAATGTATG CGTTGTCGTT CGCGGCAACG TGTTCTTTTT     240
GTGCAATTTT TATTCTTTGG TTTTTGTAGT GTTTGT                               276
```

(2) INFORMATION FOR SEQ ID NO: 107:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 107:

```
AAGGAGCACC ACGAAAAGCA CCCCAATTGG TGGGGTGCAA GCCGTGAGGG GTTCCCGCCT      60
GTAGTGGGCG GGGCCGGGTG CGCAACAGCA AATGATTGCC AGACACACTA TTGGGCCCTG     120
AGGCAACACT CGGATCGATT GAGTGCTTGT CCCCCCATCT TGGTGGTGGG GTGTGGTGTT     180
TGAGAACTGG ATAGTGGTTG CGAGCATCTA AATGAACGCA CTGCCGATGG TGGTGTGTTC     240
GTTTTGTGTA ATTTTATTCT TTGGTTTTTG TGTTTGT                              277
```

(2) INFORMATION FOR SEQ ID NO: 108:

(i) SEQUENCE CHARACTERISTICS:
        (A) LENGTH: 282 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 108:

AAGGAGCACC ACGAAAAGCA CTCCAATTGG TGGGGTGCGA GCCGTNAGGG GTTCTCGTCT      60

GTAGTGGATG GCAGCCGGGT GCACANCAGC AAATGATTGC CAGACACACT ATTGGGCCCT     120

GAGACAACAC TCGGTCAGTC CGTGTGGAGT CCCTCCATCT TGGTGGTGGG GTGTGGNGTT     180

TGAGTATTGG ATAGTGGTTG CGANCATCTA GATGAACGCG TAGTCCTCNG TGGCTGACGT     240

GTTCATCAAA ATGTGTAATT TCTTTTTANGG GTTTNGGTGT CT                       282

(2) INFORMATION FOR SEQ ID NO: 109:

(i) SEQUENCE CHARACTERISTICS:
         (A) LENGTH: 280 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 109:

AAGGAGCACC ACGAAAAGCA CTCCAATTGG TGGGGTGCGA GCCGNGAGGG GTTCTCGCCT      60

GTAGTGGNCG AGGGCCGGAT GCACAACAAC ACATGATTGC CAGACACACT ATTGGGCCCT     120

GANACAACAC TCGGCCAGTC CGTGTGGTGT CCCTCCATCT TGGTGGTGGG GTGTGGTGTT     180

TGAGTATNGG ATAGTNGTTG NGANCATCTA AACGGCTGCG TNGNCNNGAA CGGTGGCGTG     240

TTCGNTAAAA TGTGTAATTT CTTTTNNGGT TTGGGTGTNT                           280

(2) INFORMATION FOR SEQ ID NO: 110:

(i) SEQUENCE CHARACTERISTICS:
         (A) LENGTH: 280 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 110:

AAGGAGCACC ACGAAAAGCA CTCCAATTGG TGGGGTGCGA GCCGTGAGGG GTTCTCGCCT      60

GTAGTGGGCG ANGGCCGGGT GCACAACAAC AAATGATTGC CAGACACACT ATTGGGCCCT     120

GAGACAACAC TCGGCCAGTC CGTGTGGTGT CCCNCCATCT TGGTGGTGGG GTGTGGTGTT     180

TGAGTATTGG ATAGTGGTTG CGAGCATCTA AANGGNTGCG TTGCCGNNAN CNGTGGCGTN     240

TTCGNTAAAA TGTGTAANTT CTTTTTNGGT TTGTGTGTGT                           280

(2) INFORMATION FOR SEQ ID NO: 111:
```

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 111:

ATCGAAGATC CCGGCTTCTT CATAAGCTCC CACACGAATT GCTTGATTCA CTGGTTAGAC      60

GATTGGGTCT GTAGCTCAGT TGGTTAGAGC GCACCCCTGA TAAGGGTGAG GTCGGCAGTT     120

CGAATCTGCC CAGACCCACC AATTGTTGGT GTGCTGCGTG ATCCGATACG GGGCCATAGC     180

TCAGCTGGGA GAGCGCCTGC TTTGCACGCA GGAGGTCAGG AGTTCGATCC TCCTTGGCTC     240

CACCATCTAA ACAATCGTC GAAAGCTCAG AAATGAATGT TCGTGGATGA ACATTGATTT      300

CTGGTCTTTG CACCAGAACT GTTCTTTAAA AATTCGGGTA TGTGATAGAA GTAAGACTGA     360

ATGATCTCTT TCACTGGTGA TCATTCAAGT CAAGGTAAAA TTTGCGAGTT CAAGCGCGAA     420

TTTTCGGCGA ATGTCGTCTT CACAGTATAA CCAGATTGCT TGGGGTTATA T              471

(2) INFORMATION FOR SEQ ID NO: 112:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 112:

ATCGAAGACA TCAGCTTCTT CATAAGTATC CACACGAATT GCTTGATTCA TAGTCGAACG      60

AATGCTGTAA CGCGACCCGT GTTATAGGTC TGTAGCTCAG TTGGTTAGAG CGCACCCCTG     120

ATAAGGGTGA GGTCGGCAGT TCAAATCTGC CCAGACCTAC CAATTGCTTG GTCGAGAAGA     180

ATACGGGGCC ATAGCTCAGC TGGGAGAGCG CCTGCCTTGC ACGCAGGAGG TCAGCGGTTC     240

GATCCCGCTT GGCTCCACCA CTCTCTCGTG TTGCGGTGAG TGTTAAAGAG TTCAGAAATG     300

ATGCCGCTTC AGGTTTGTCC TGTTGAGTGC TGATTTCTGG TCTTTTGACC GGTACGAAAA     360

TCGTTCTTTA AAAATTTGGA TATGTGATAG AAGTGACTGA TTAATTGCTT TCACTGGCAA     420

TTGATCTGGT CAAGGTAAAA TTTGTAGTTC TCAAGACGCA AATTTTCGGC GAATGTCGTC     480

TTCACGATTG AGACAGTAAC CAGATTGCTT GGGGTTATAT                           520

(2) INFORMATION FOR SEQ ID NO: 113:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 113:

```
ATCGAAGACA CCGGCTTCGT CATAAGCTCC CACACGAATT GCTTGATTCA CTTGCGAAAG      60
GCGATTGGGT TTAGACCCGA GAGTAACGAT TGGGTCTGTA GCTCAGTTGG TTAGAGCGCA     120
CCCCTGATAA GGGTGAGGTC GGCAGTTCGA ATCTGCCCAG ACCCACCAAT CGAAGGGGCC     180
ATAGCTCAGC TGGGAGAGCG CCTGCTTTGC ACGCAGGAGG TCAGCGGTTC GATCCCGCTT     240
GGCTCCACCA TTAACTCTAG TCGCCGAAAG CTCAGAAATG AGTGTTTACC AGGATGAGGT     300
TGATTGCCTG GGTTGAACAT TGATTTCTGG ACTTTGCGCC AGAACTGTTC TTTAAAAATT     360
TGGGTATGTG ATAGAAGTAG ACCGATGTGT TGCTTTCACT GGCAGCATGT CGCGTCAAGG     420
TAAAATTTGC GTGTTCTCTA TGCAAATTTT CGGCGAATGT CGTCTTCACG TTATAGACAG     480
TAACCAGATT GCTTGGGGTT ATAT                                            504
```

(2) INFORMATION FOR SEQ ID NO: 114:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 114:

```
ATCGAAGACT TCAGCTTCTT CATAAGTTCC CACACGAATT GCTTGATTCA CTTGCGAAAA      60
GCGATTGGGT TGAGACCCGA GAGTGACGAT TGGGTCTGTA GCTCAGTTGG TTAGAGCGCA     120
CCCCTGATAA GGGTGAGGTC GGCAGTTCGA ATCTGCCCAG ACCCACCAAT TGTCGGGATG     180
GCCAGTGTCA AATGGGGCCA TAGCTCAGCT GGGAGAGCGC CTGCTTTGCA CGCAGGAGGT     240
CAGGAGTTCG ATCCTCCTTG GCTCCACCAT CAACTCACGA TCGCTGAAAG CTCAGAAATG     300
AACATTGGTA GTTCAATGTT GATTTCTGGT CTTTGCGCCA GAACTGTTCT TTAAAAATTT     360
GGGTATGTGA TAGAAGTGAC TAACAGCGTG TTTCACTGCA CGTTGTTAAT CAAGGCAAAA     420
TTTGCGAGTT CAAGCGCGAA TTTTCGGCGA ATGTCGTCTT CACGTTACGA ATCTATAACC     480
AGATTGCTTG GGGTTATAT                                                  499
```

(2) INFORMATION FOR SEQ ID NO: 115:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 115:

```
ATCGACGACA TCAGCTGTCT CATAAGCTCC CACACGAATT GCTTGATTCA TTGAAGAAGA      60
CGATTAGGTT AGCAACCTTC GATTGGGTCT GTAGCTCAGT TGGTTAGAGC GCACCCCTGA     120
TAAGGGTGAG GTCGGCAGTT CGAATCTGCC CAGACCCACC AATTTGCTGG GGCCATAGCT     180
```

```
CAGCTGGGAG AGCGCCTGCC TTGCACGCAG GAGGTCAGCG GTTCGATCCC GCTTGGCTCC    240

ACCACCCCGC TTGCCAGTTT GTCAAAGCTT AGAAATGAAT ATTCGCGTCG AATATTGATT    300

TCTGAACTTT ATCAGAATCG TTCTTTAAAA ATTTGGGTAT GTGATAGAAA GATAGACTGG    360

ACAGCACTTT CACTGGTGTG TGTTCAGGCT AAGGTAAAAT TTGTGAGTAA TTACAAGTTT    420

TCGGCGAATG TTGTCTTCAC AGTATAACCA GATTGCTTGG GGTTATAT               468

(2) INFORMATION FOR SEQ ID NO: 116:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 116:

TAAGGAAAAG GAAACCTGTG AGTTTTCGTT CTTCTCTGTT TGTTCAGTTT TGAGAGGTTA     60

ATTCTTCTCT ATACTGTTTG TTCTTTGAAA ACTAGATAAG AAAGTTAGTA AAGTTAGCAT    120

AAATAGGTAA CTATTTATGA CACAAGTAAC CGAGAATCAT CTGAAAGTGA ATCTTTCATC    180

TGATTGGAAG TATCATCGCT GATACGAAAA ATCAGAAAAA CAACCTTTAC TTCATCGAAG    240

TAAATT                                                              246

(2) INFORMATION FOR SEQ ID NO: 117:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 117:

CTAAGGAAAA GGAAACCTGT GAGTTTTCGT TCTTCTCTAT TTGTTCAGTT TTGAGAGGTT     60

AGTACTTCTC AGTATGTTTG TTCTTTGAAA ACTAGATAAG AAAGTTAGTA AAGTTAGCAT    120

AGATAATTTA TTATTTATGA CACAAGTAAC CGAGAATCAT CTGAAAGTGA ATCTTTCATC    180

TGATTGGAAG TATCATCGCT GATACGGAAA ATCAGAAAAA CAACCTTTAC TTCGTAGAAG    240

TAAATT                                                              246

(2) INFORMATION FOR SEQ ID NO: 118:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(xi) SEQUENCE DESCRIPTION: SEQ ID NO: 118:

```
TAAGGAAAAG GAAACCTGTG AGTTTTCGTT CTTCTCTGTT TGTTCAGTTT TGAGAGGTTA      60

TTACTTCTCT GTATGTTTGT TCTTTGAAAA CTAGATAAGA AAGTTAGTAA AGTTAGCATA     120

AGTAGTGTAA CTATTTATGA CACAAGTAAC CGAGAATCAT CTGAAAGTGA ATCTTTCATC     180

TAATTCGACG TATCATCGCT GATACAGACA ATTAGAAAAA CAACCTTTAC TTCGACGAAG     240

TAAATT                                                                246
```

(2) INFORMATION FOR SEQ ID NO: 119:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 119:

```
GGCCTATAGC TCAGCTGGTT AGAGCGCACG CCTGATAAGC GTGAGGTCGA TGGTTCGAGT      60

CCATTTAGGC CCACTTTTTC TTTCTGACAG AAGAAACACT GTATAACCTA TTTAAGGGGC     120

CTTAGCTCAG CTGGGAGAGC GCCTGCTTTG CACGCAGGAG GTCAGCGGTT CGATCCCGCT     180

AGGCTCCACC AAAATTGTTC TTTGAAAACT AGATAAGAAA GTTAGTAAAG TTAGCATAAA     240

TAGGTAACTA TTTATGACAC AAGTAACCGA GAATCATCTG AAAGTGAATC TTTCATCTGA     300

TTGGAAGTAT CATCGCTGAT ACGAAAAATC AGAAAAACAA CCTTTACTTC ATCGAAGTAA     360

ATT                                                                   363
```

(2) INFORMATION FOR SEQ ID NO: 120:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 120:

```
TAAGGAAAAG GAAACCTGTG AGTTTTCGTT CTTCTCTATT TGTTCAGTTT TGAGAGGTTA      60

CTCTCTTTTA TGTCAGATAA AGTATGCAAG GCACTATGCT TGAAGCATCG CGCCACTACA     120

TTTTTGACGG GCCTATAGCT CAGCTGGTTA GAGCGCACGC CTGATAAGCG TGAGGTCGAT     180

GGTTCGAGTC CATTTAGGCC CACTTTTTCT TCTGACATA AGAAATACAA ATAATCATAC      240

CCTTTTACGG GGCCTTAGCT CAGCTGGGAG AGCGCCTGCT TGCACGCAG GAGGTCAGCG      300

GTTCGATCCC GCTAGGCTCC ACCAAAATTG TCTTTGAAA ACTAGATAAG AAAGTTAGTA      360

AAGTTAGCAT AGATAATTTA TTATTATGA CACAAGTAAC CGAGAATCAT CTGAAAGTGA      420

ATCTTTCATC TGATTGGAAG TATCATCGCT GATACGAAA ATCAGAAAAA CAACCTTTAC      480

TTCGTAGAAG TAAATT                                                     496
```

(2) INFORMATION FOR SEQ ID NO: 121:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 121:

```
TAAGGAAAAG GAAACCTGTN AGTTTNCGTN CTTCTCTGTT TGTNCAGTTT TNAGAGGTTA    60
CTCTCTTTNA TGTCAGATAA AGTACGCACG GCACGTTGCC TTGGGCAAAG AGCCACTACA   120
TTATTGACGG GCCTATAGCT CAGCTGGTTA GAGCGCACGC CTGATAAGCG TGAGGTCGAT   180
GGTTCGAGTC CATTTAGGCC CACTTTTTCT TTCTGACAGA AGAAATCATT TGCACATCCT   240
ATTAATAAGG GNCCTTAGCT CAGCTGGGAG AGCGCCTGCT TTGCACGCAG GAGGTCAGCG   300
GTTCGATCCC GCTAGGCTCC ACCCAAAATT GTTCTTTGAA AACTAGATAA GAAAGTTAGT   360
AAAGTTAGCA TAAGTAGTAT AACTATTTAT GACACAAGTA ACCGAGAATC ATCTGAAAGT   420
GAATCTTTCA TCTAATTCGA CGTATCATCG CTGATACAGA CAATTNGAAA AACAACCTTT   480
ACTTCGACGA AGTAAATT                                                 498
```

(2) INFORMATION FOR SEQ ID NO: 122:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 122:

```
TAAGGATAAG GATAACTGTC TTAGGACGGT TTGACTAGGT TGGGCAAGCG TTTTTTTAAT    60
CTTGTATTCT ATTCCTTTTG CATTGTTAAG CGTTGTTTCC AAAACATTTA GTTTACGATC   120
AAGTATGTTA TGTAAATAAT ATGGTAACAA GTAAATTCAC ATATAATAAT AGACGTTTAA   180
GAATATATGT CTTTAGGTGA TGTTAACTTG CATGGATCAA TAATTTACA               229
```

(2) INFORMATION FOR SEQ ID NO: 123:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 123:

```
TAAGGATAAG GAAGAAGCCT GAGAAGGTTT CTGACTAGGT TGGGCAAGCA TTTATATGTA    60
AGAGCAAGCA TTCTATTTCA TTTGTGTTGT TAAGAGTAGC GTGGTGAGGA CGAGACATAT   120
```

-continued

```
AGTTTGTGAT CAAGTATGTT ATTGTAAAGA AATAATCATG GTAACAAGTA TATTTCACGC      180

ATAATAATAG ACGTTTAAGA GTATTTGTCT TTTAGGTGAA GTGCTTGCAT GGATCTATAG      240

AAATTACA                                                              248
```

(2) INFORMATION FOR SEQ ID NO: 124:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 124:

```
CAAATGGAGT TTTTATTTTT TATTTATCTT AAACACCCAT TAATTTTTTC GGTGTTAAAA       60

CCCAAATCAA TGTTTGGTCT CACAACTAAC ACATTTGGTC AGTTTGTATC CAGTTCTGAA      120

AGAATGTTTT TGAACAGTTC TTTCAAAACT GAAAACGACA ATCTTTCTAG TTCCAAAAAT      180

AAATACCAAA GGATCAATAC AATAAGTTAC TAAGGGCTTA TGGT                       224
```

(2) INFORMATION FOR SEQ ID NO: 125:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 125:

```
CTAATGAAGT TTTTTACTTT TTCTTTTCAT CTTTAATAAA GATAAATACT AAACAAAACA       60

TCAAAATCCA TTTATTTATC GGTGGTAAAT TAAACCCAAA TCCCTGTTTG GTCTCACAAC      120

TAACATATTT GGTCAGATTG TATCCAGTTC TGAAAGAACA TTTCCGCTTC TTTCAAAACT      180

GAAAACGACA ATCTTTCTAG TTCCAAATAA ATACCAAAGG ATCAATACAA TAAGTTACTA      240

AGGGCTTATG GT                                                         252
```

(2) INFORMATION FOR SEQ ID NO: 126:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 126:

```
AACGAAAGAT TGACGATTGG TAAGAATCCA CAACAAGTTG TTCTTCATAG ATGTATCTGA       60

GGGTCTGTAG CTCAGTTGGT TAGAGCACAC GCTTGATAAG CGTGGGGTCA CAAGTTCAAG      120
```

```
TCTTGTCAGA CCCACCATGA CTTTGACTGG TTGAAGTTAT AGATAAAAGA TACATGATTG      180

ATGATGTAAG CTGGGGACTT AGCTTAGTTG GTAGAGCGCC TGCTTTGCAC GCAGGAGGTC      240

AGGAGTTCGA CTCTCCTAGT CTCCACCAGA ACTTAAGATA AGTTCGGATT ACAGAAATTA      300

GTAAATAAAG ATTGAGATCT TGGTTTATTA ACTTCTGTGA TTTCATTATC ACGGTAATTA      360

GTGTGATCTG ACGAAGACAC ATTAACTCAT TAACAGATTG GCAAAATTGA GTCTGAAATA      420

AATTGTTCAC TCAAGAGTTT AGGTTAAGCA ATTAATCTAG ATGAATTGAG AACTAGCAAA      480

TTAACTGAAT CAAGCGTTTT GGTATGTGAA TTTAGATTGA AGCTGTACAG TGCTTAAGTG      540

CACAGTGCTC TAAACTGAAA TGTTGAAGTT ACTAACTTGT AGGTAACATC GACTGTTTGG      600

GGTTGTAT                                                              608

(2) INFORMATION FOR SEQ ID NO: 127:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 127:

AACGAAAGAT TGACGATTGG TAAGAATCCA CGACAAGTTG TTCTTCATAG ATGTATCTGA       60

GGGTCTGTAG CTCAGTTGGT TAGAGCACAC GCTTGATAAG CGTGGGGTCA CAAGTTCAAG      120

TCTTGTCAGA CCCACCATGA CTTTGACTGG TTGAAGTTAT AGAAAGAAG ATACATAACT      180

GATGATGTAA GCTGGGGACT TAGCTTAGTT GGTAGAGCGC TGCTTTGCA CGCAGGAGGT      240

CAGGAGTTCG ACTCTCCTAG TCTCCACCA                                       269

(2) INFORMATION FOR SEQ ID NO: 128:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 128:

AACGAAAGAT TGATGGCCGG TAAGAATCCA CAACAAGTTG TTCTTCGAAG ATGTATCTGA       60

GGGTCTGTAG CTCAGTTGGT TAGAGCACAC GCTTGATAAG CGTGGGGTCA CAAGTTCAAG      120

TCTTGTCAGA CCCACCAAAT CTGAAAGATA TGTCGTTCAT TATGATTAAA GCTGGGGACT      180

TAGCTTAGTT GGTAGAGCGC TGCTTTGCA CGCAGGAGGT CAGGAGTTCG ACTCTCCTAG      240

TCTCCACCA                                                             249

(2) INFORMATION FOR SEQ ID NO: 129:

(i) SEQUENCE CHARACTERISTICS:
        (A) LENGTH: 283 base pairs
        (B) TYPE: nucleic acid
```

(C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 129:

```
AACGAAAGAT TGACGATTGG TAAGAATCCA CAACAAGTTG TTCTTCATGA CGATGTATCT      60
GAGGGTCTGT AGCTCAGTTG GTTAGAGCAC ACGCTTGATA AGCGTGGGGT CACAAGTTCA     120
AGTCTTGTCA GACCCACCAA ATCTGACTAA CAAGCATTAT TAAATGCTGA ATACAGAAAA     180
ACAGAGACAT TGACTTATTG ATAAGCTGGG GACTTAGCTT AGTTGGTAGA GCGCCTGCTT     240
TGCACGCAGG AGGTCAGGAG TTCGACTCTC CTAGTCTCCA CCA                       283
```

(2) INFORMATION FOR SEQ ID NO: 130:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 130:

```
AACGAAAGAT TGGTGACCGG TAAGAATCCA CAACAAGTTG TTCTTCGAAG ATGTATCTGA      60
GGGTCTGTAG CTCAGTTGGT TAGAGCACAC GCTTGATAAG CGTGGGGTCA CAAGTTCAAG     120
TCTTGTCAGA CCCACCACTA CTGACGAAGT GATGAATAAT CACAAGCTGC TAGATGAAAA     180
GATATGTCGT TCATTATGAT TAAAGCTGGG GACTTAGCTT AGTTGGTAGA GCGCCTGCTT     240
TGCACGCAGG AGGTCAGGAG TTCGACTCTC CTAGTCTCCA CCA                       283
```

(2) INFORMATION FOR SEQ ID NO: 131:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 131:

```
TAAGGAAGAT CGAGAATTGG AAAGAGGTCG GATTTATCCG GATGATCCTT CTCCATCTTA      60
TTAGAACATA GATCGCAGGC CAGTCAGCCT GACGATCGCT TGCAGGCGTG CCGCCTTCGT     120
TTCTCTTTCT TCATTGTTGA TTGCTCACGG GCCGTACCGC AGCTGACGCT GCTGGCCCTG     180
CGCAGGCGCG GCCCATCAGG GCCGACGGCC GGTCGGCCTT GCNAAGCTTC GCTTCGGGGT     240
GGATCTGTGG ATCGCGTAGT AGCGTTTGCG TCGGTATCTG GGCTTGTAGC TCAGTTGGTT     300
AGAGCACACG CTTGATAAGC GTGGGGTCGG AGGTTCAAGT CCTCCCAGGC CCACCAAGTT     360
ACTTGATGAG GGGCCGTAGC TCAGCTGGGA GAGCACCTGC TTTGCAAGCA GGGGGTCGTC     420
```

```
GGTTCGATCC CGTCCGGCTC CACCATCATG TTGGTGTTGA GACGGATATT GGCAATCAAC      480

AAAAGAAAGA AACAAGTTTG CGGACTNTTA CGAAAGTCTG CCTGTTCTGT ATGAAATCGT      540

GAAGAGAAGA TGTAATCGGA TCAACTGAAG AGTTGATGTC GCAAGAAGCT TGCTCAAGCC      600

TTGCATAATG ATTGATGTGT TTAACCGCCA TCACCGATTG TATCTCGAGA AGCTGGTCTT      660

TCTGCTGATA CTGTTGAAAC GAGCATTTGC AGTCGAATGG CAACATTCGG CGTCGCATAA      720

TGCGGCTTTA AGAGCTGAGT TTTGATGGAT ATTGGCAATG AGAGTGATCA AGTGTCTTAA      780

GGGCATTGGT GGATGCCTTG GCATGCAC                                        808
```

(2) INFORMATION FOR SEQ ID NO: 132:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 132:

```
TAAGGAGGAT CGAGAATTGG AAAGAGGCCG GATTTATCCG GATGATCCTT CTCCATCTTA       60

TTAGAACATA GATCGCAGNC CAGTCAGCCT GACGATCGCT TGCAGGCGTG CCGCCTTCGT      120

TTCTCTTTCT TCATTGTTGA TTGCTCACGG GCCGTACCGC AGCTGACGCT GCTGGCCCTG      180

CGCAGGCGCG GNCCATCAGG GCCGACGGCC GGTCGGCCTT GCGAAGCTTC GCTTCGGGGT      240

GGATCTGTGG ATCGCGTAGT AGCGTTTGCG TCGGTATCTG GCTTGTAGC TCAGTTGGTT       300

AGAGCACACG CTTGATAAGC GTGGGGTCGG AGGTTCAAGT CCTCCCAGGC CCACCAAGTT      360

ACTTGATGAG GGGCCGTAGC TCAGCTGGGA GAGCACCTGC TTTGCAAGCA GGGGGTCGTC      420

GGTTCGATCC CGTCCGGCTC CACCATCATG TTGGTGTTGA GACGGATATT GGCAATCAAC      480

AAAAGAAAGA AACAAGTTTG CGGACTNTTA CGAAAGTCTG CCTGTTCTGT ATGAAATCGT      540

GAAGAGAAGA TGTAATCGGA TCAACTGAAG AGTTGATGTC GCAAGAAGCT TGCTCAAGCC      600

TTGCATAATG ATTGATGTGT TTAACCGCCA TCACCGATTG TATCTCGAGA AGCTGGTCTC      660

TCTGCTGATA CTGTTGAAAC GAGCATTTGC AGTCGAATGG CAACATTCGG CGTCGCATAA      720

TGCGGCTTTA AGAGCTGAGT TTTGATGGAT ATTGGCAATG AGAGTGATCA AGTGTCTTAA      780

GGGCATTGGT GGATGCCTTG GCATGCAC                                        808
```

(2) INFORMATION FOR SEQ ID NO: 133:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 133:

```
CCTTAAAGAA CTGTTCTTTG CAGTGCTCAC ACAGATTGTC TGATGAAAAG TAAATAGCAA       60

GGCGTCTTGC GAAGCAGACT GATACGTCCC CTTCGTCTAG AGGCCCAGGA CACCGCCCTT      120
```

```
TCACGGCGGT AACAGGGGTT CGAATCCCCT AGGGGACGCC ACTTGCGCGG TAATGTGTGA      180

AAGCGTTGCC ATCAGTATCT CAAAACTGAC TTACGAGTCA CGTTTGAGAT ATTTGCTCTT      240

TAAAAATCTG GATCAAGCTG AAAATTGAAA CACAGAACAA CGAAAGTTGT TCGTGAGTCT      300

CTCAAATTTT CGCAACACGA TGATGAATCG TAAGAAACAT CTTCGGGTTG TGA             353
```

(2) INFORMATION FOR SEQ ID NO: 134:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 134:

```
CCTTAAAGAA CTGTTCTTTG CAGTGCTCAC ACAGATTGTC TGATGAAAAA CGAGCAGTAA      60

AACCTCTACA GGCTTGTAGC TCAGGTGGTT AGAGCGCACC CCTGATAAGG GTGAGGTCGG      120

TGGTTCAAGT CCACTCAGGC CTACCAAATT TTCCCTGAAT ACTGCGTTGT GAATAACTC       180

ACATACTGAT GTATGCTTCG TTATTCCACG CCTTGTCTCA GGAAAAATTA TCGGTAAAGA      240

GGTTCTGACT ACACGATGGG GCTATAGCTC AGCTGGGAGA GCGCCTGCTT TGCACGCAGG      300

AGGTCTGCGG TTCGATCCCG CATAGCTCCA CCATATCGTG AGTGTTTACG AAAAAATACT      360

TCAGAGTGTA CCTGAAAGGG TTCACTGCGA AGTTTTGCTC TTTAAAAATC TGGATCAAGC      420

TGAAAATTGA ACACAGAAC AACGAAAGTT GTTCGTGAGT CTCTCAAATT TTCGCAACAC       480

GATGATGAAT CGTAAGAAAC ATCTTCGGGT TGTGA                                515
```

(2) INFORMATION FOR SEQ ID NO: 135:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 135:

```
CCTTAAAGAA GCGTACTTTG CAGTGCTCAC ACAGATTGTC TGATGAAAAG TAAATAGCAA      60

GGCGTCTTGC GAAGCAGACT GATACGTCCC CTTCGTCTAG AGGCCCAGGA CACCGCCCTT      120

TCACGGCGGT AACAGGGGTT CGAATCCCCT AGGGGACGCC ACTTGCGCGG TAATGTGTGA      180

AAGCGTTGCC ATCAGTATCT CAAAACTGAC TTACGAGTCA CGTTTGAGAT ATTTGCTCTT      240

TAAAAATCTG GATCAAGCTG AAAATTGAAA CACAGAACAA CGAAAGTTGT TCGTGAGTCT      300

CTCAAATTTT CGCAACACGA TGATGAATCG TAAGAAACAT CTTCGGGTTG TGA             353
```

(2) INFORMATION FOR SEQ ID NO: 136:

(i) SEQUENCE CHARACTERISTICS:
        (A) LENGTH: 481 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 136:

CCTTAAAGAA CTGTTCTTTG AAGTGCTCAC ACAGATTGTC TGATGAAAAA CGAGCAGTAA      60

AACCTCTACA GGCTTGTAGC TCAGGTGGTT AGAGCGCACC CCTGATAAGG GTGAGGTCGG     120

TGGTTCAAGT CCACTCAGGC CTACCAAATT TTCCCTGAAT ACTGCGTTGT GAAATAACTC     180

ACATACTGAT GTATGCTTCG TTATTCCACG CCTTGTCTCA GGAAAAATTA TCGGTAAAGA     240

GGTTCTGACT ACACGATGGG CTATAGCTC AGCTGGGAGA GCGCCTGCTT TGCACGCAGG      300

AGGTCTGCGG TTCGATCCCG CATAGCTCCA CCATCTCGTG AGTGTTTACG AAAAAATACT     360

TCAGAGTGTA CCTGAAAGGG TTCACTGCGA AGTTTTGCTC TTTAAAAATC TGGATCAAGC     420

TGAAAATTGA ACACAGAAC AACGAAAGTT GTTCGTGAGT CTCTCAAATT TTCGCAACAC     480

G                                                                    481

(2) INFORMATION FOR SEQ ID NO: 137:

(i) SEQUENCE CHARACTERISTICS:
         (A) LENGTH: 392 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 137:

CCTTAAAGAA GCGTACTTTG AAGTGCTCAC ACAGATTGTC TGATGAAAAG TGAATAGCAA      60

GGCGTCTTGC GATTGAGACT TCAGTGTCCC CTTCGTCTAG AGGCCCAGGA CACCGCCCTT     120

TCACGGCGGT AACAGGGGTT CGAATCCCCT AGGGGACGCC AGCGTTCAAA CTGATGAGGT     180

CAAACCTCCA GGGACGCCAC TTGCTGGTTT GTGAGTGAAA GTCACCTGCC TTAATATCTC     240

AAAACTGACT TACGAGTCAC GTTTGAGATA TTTGCTCTTT AAAAATCTGG ATCAAGCTGA     300

AAATTGAAAC ACAGAACAAC GAAAGTTGTT CGTGAGTCTC TCAAATTTTC GCAACACGAT     360

GATGAATCGT AAGAAACATC TTCGGGTTGT GA                                   392

(2) INFORMATION FOR SEQ ID NO: 138:

(i) SEQUENCE CHARACTERISTICS:
         (A) LENGTH: 515 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 138:

CCTTAAAGAA ACGGTCTTTG AAGTGCTCAC ACAGATTGTC TGATGAAAAA CGAGCAGTAA      60
```

```
AACCTCTACA GGCTTGTAGC TCAGGTGGTT AGAGCGCACC CCTGATAAGG GTGAGGTCGG      120

TGGTTCAAGT CCACTCAGGC CTACCAAATT TTCCCTGAAT ACTGCGTTGT GAAATAACTC      180

ACATACTGAT GTATGCTTCG TTATTCCACG CCTTGTCTCA GGAAAAATTA TCGGTAAAGA      240

GGTTCTGACT ACACGATGGG GCTATAGCTC AGCTGGGAGA GCGCCTGCTT TGCACGCAGG      300

AGGTCTGCGG TTCGATCCCG CATAGCTCCA CCATCTCGTG AGTGTTTACG AAAAAATACT      360

TCAGAGTGTA CCTGAAAGGG TTCACTGCGA AGTTTTGCTC TTTAAAAATC TGGATCAAGC      420

TGAAAATTGA ACACAGAAC AACGAAAGTT GTTCGTGAGT CTCTCAAATT TTCGCAACAC       480

GATGATGAAT CGTAAGAAAC ATCTTCGGGT TGTGA                                 515
```

(2) INFORMATION FOR SEQ ID NO: 139:

(i) SEQUENCE CHARACTERISTICS:
        (A) LENGTH: 365 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 139:

```
CTAAGGATAT ATTCGGAACA TCTTCTTCGG AAGATGCGGA ATAACGTGAC ATATTGTATT       60

CAGTTTTGAA TGTTTATTTA ACATTCAAAT ATTTTTTGGT TAAAGTGATA TTGCTTTTGA      120

AAATAAAGCA GTATGCGAGC GCTTGACTAA AAAAAATTGT ACATTGAAAA CTAGATAAGT      180

AAGTAAAATA TAGATTTTAC CAAGCAAAAC CGAGTGAATA AAGAGTTTTA ATAAGCTTG       240

AATTCATAAG AAATAATCGC TAGTGTTCGA AGAACACTC ACAAGATTAA TAACGCGTTT       300

AAATCTTTTT ATAAAAGAAC GTAACTTCAT GTTAACGTTT GACTTATAAA AATGGTGGAA      360

ACATA                                                                 365
```

(2) INFORMATION FOR SEQ ID NO: 140:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 140:

```
CTAAGGATAT ATTCGGAACA TCTTCTTCAG AAGATGCGGA ATAACGTGAC ATATTGTATT       60

CAGTTTTGAA TGTTTATTTA ACATTCAAAT ATTTTTTGGT TAAAGTGATA TTGCTTATGC      120

GAGCNCTTGA CAATCTATTC TTTTTAAAGA AAGCGGTTGT CAGACAATGC ATTAAGAAAA      180

ATTAAAGCGG AGTTTACTTT TGTAAATGAG CATTTGATTT TTTGAAAATA AAGCAGTATG      240

CGAGCGCTTG ACTAAAAAGA AATTGTACAT TGAAACTAG ATAAGTAAGT AAAATATAGA       300

TTTTACCAAG CAAAACCGAG TGAATAAAGA GTTTTAAATA AGCTTGAATT CATAAGAAAT      360

AATCGCTAGT GTTCGAAAGA ACACTCACAA GATTAATAAC GCGTTTAAAT CTTTTTATAA      420

AAGAAAACGT TTAGCAGACA ATGAGTTAAA TTATTTTAAA GCAGAGTTTA CTTATGTAAA      480
```

TGAGCATTTA AAATAATGAA AACGAAGCCG TATGTGAGCA TTTGACTTAT AAAAATGGTG        540

GAAACATA                                                                548

(2) INFORMATION FOR SEQ ID NO: 141:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 141:

CTAAGGATAT ATTCGGAACA TCTTCTTCAG AAGATGCGGA ATAACGTGAC ATATTGTATT         60

CAGTTTTGAA TGTTTATTTA ACATTCAAAT ATTTTTTGGT TAAAGTGATA TTGCTTATGC        120

GAGCGCTTGA CAATCTATTC TTTTTAAAGA AAGCGGTTGT CAGACAATGC ATTAAGAAAA        180

ATTAAAGCGG AGTTTACTTT TGTAAATGAG CATTTGATTT TTTGAAAATA AAGCAGTATG        240

CGAGCGCTTG ACTAAAANGA AATTGTACAT TGAAAACTAG ATAAGTAAGT AAAATATAGA        300

TTTTACCAAG CAAAACCGAG TGAATAAAGA GTTTTGAATA AGCTTGAATT CATAAGAAAT        360

AATCGCTAGT GTTCGAAAGA ACACTCACAA GATTAATAAC GCGTTTAAAT CTTTTTATAA        420

AAGAACGTAA CTTCATGTTA ACGTTTGACT TATAAAAATG GTGGAAACAT A                471

(2) INFORMATION FOR SEQ ID NO: 142:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 142:

CTAAGGATAT ATTCGGAACA TCTTCTTCAG AAGATGCGGA ATAACGTGAC ATATTGTATT         60

CAGNTTTGAA TGTTTATTTA ACATTCAAAA AATGGGCCTA TAGCTCAGCT GGTTAGAGCG        120

CACGCCTGAT AAGCGTGAGG TCGGTGGTTC GAGTCCACTT AGGCCCACCA TTATTTGTAC        180

ATTGAAAACT AGATAAGTAA GTAAAATATA GATTTTACCA AGCAAAACCG AGTGAATAAA        240

GAGTTTTAAA TAAGCTTGAA TTCATAAGAA ATAATCGCTA GTGTTCGAAA GAACACTCAC        300

AAGATTAATA ACGCGTTTAA ATCTTTTTAT AAAAGAACGT AACTTCATGT TAACGTTTGA        360

CTTATAAAAA TGGTGGAAAC ATA                                               383

(2) INFORMATION FOR SEQ ID NO: 143:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 143:

CTAAGGATAT ATTCGGAACA TCTTCYTCAG AAGATGCGGA ATAATGTGAC ATATTGTATT      60

CAGTTTTGAA TGTTTATTTA ACATTCAAAT ATTTTTTGGT TAAAGTGATA TTGCTTATGC     120

GAGCGCTTGA CTAAAAAGAA ATTGTACATT GAAAACTAGA TAAGTAAGTA AAANTATAGA    180

TTTTACCAAG CAAAACCGAG TGAATAAAGA GTTTTAAATA AGCTTGAATT CATAAGAAAT    240

AATCGCTAGT GTTCGAAAGA ACACTCACAA GATTAATAAC GCGTTTAAAT CTTTTTATAA    300

AAGAACGTAA CTTCATGTTA ACGTTTGACT TATAAAAATG GTGGAAACAT A            351

(2) INFORMATION FOR SEQ ID NO: 144:

(i) SEQUENCE CHARACTERISTICS:
            (A) LENGTH: 263 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 144:

CTAAGGATAT ATTCGGAACA TCTTCTACGA AGATGAGGGA ATAACGTGAC ATATTGTATT     60

CAGTTTTGAA TGTTTATTAA CATTCATTTG TACATTGAAA ACTAGATAAG TAAGTAAGAT    120

TTTACCAAGC AAAACCGAGT GAATAGAGTT TTAAATAAGC TTGAATTCAT AAATAATCGC    180

TAGTGTTCGA AGACNTCCA CAAGATTAAT AACTAGTTTT AGCTATTTAT TTGAATAAC     240

AATTCAAAAT ATGGTGGGAC ATA                                           263

(2) INFORMATION FOR SEQ ID NO: 145:

(i) SEQUENCE CHARACTERISTICS:
            (A) LENGTH: 247 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 145:

AAGGATAAGG AACTGCACAT TGGTCTTGTT TAGTCTTGAG AGGTCTTGTG GGGCCTTAGC     60

TCAGCTGGGA GAGCGCCTGC TTTGCACGCA GGAGGTCAGC GGTTCGATCC CGCTAGGCTC    120

CATTGGTGAG AGATCACCAA GTAATGCACA TTGAAAATTG AATATCTATA TCAAATAGTA    180

ACAAGAAAAT AAACCGAAAA CGCTGTAGTA TTAATAAAGA GTTTATGACT GAAAGGTCAA    240

AAAATAA                                                             247

(2) INFORMATION FOR SEQ ID NO: 146:

(i) SEQUENCE CHARACTERISTICS:
            (A) LENGTH: 375 base pairs
            (B) TYPE: nucleic acid (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 146:

AAGGAAATGG AACACGTTTA TCGTCTTATT TAGTTTTGAG AGGTCTTGTG GGGCCTTAGC      60

TCAGCTGGGA GAGCGCCTGC TTNGCACGCA GGAGGTCAGC GGTTCGATCC CGCTAGGCTC     120

CATCAGGATA CANTCCTACT AAACTTAATA CAAGTGAAGT TGAACACGCA ACTCACTTCC     180

TAGGAAAATA GACAATCTTC GCTTGTGTGC AAGGCACACA TGGTCAGATT CCTAATTTTC     240

TACAGAAGTT TCGCTAAAGC GAGCGTTGCT TAGTATCCTA TATAATAGTC CATNGAAAAT     300

TGAATATCTA TATCAAATTC CACGATCTAG AAATAGATTG TGGAAACGTA ACAAGAAATT     360

AACCCGNAAA CGCTG                                                     375

(2) INFORMATION FOR SEQ ID NO: 147:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 147:

AAGGATAAGG AACTGCACAT TGGTCTTGTT TAGTCTTGAG AGGTCTTGTG GGGCCTTAGC      60

TCAGCTGGGA GAGCGCCTGC TTTGCACGCA GGAGGTCAGC GGTTCGATCC CGCTAGGCTC     120

CATTGGTGAG AGATCACCAA GTAATGCACA TTGAAAATTG AATATCTATA TCAAATAGTA     180

ACAAGAAAAT AAACCGAAAC GCTGTAGTAT TAAAAGAGTT TATGACTGAA AGGTCAGAAA     240

ATAA                                                                 244

(2) INFORMATION FOR SEQ ID NO: 148:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 148:

CTAAGGATAT ATTCGGAACA TCTTCTTACG AAGATGCAGG AATAACATTG ACATATTGTA      60

TTCAGNTGTG AATGCTCATT GGAGNATTCA TNGCATNATT TGGTNCATTG ACANCTAGAT     120

AAGNAAGTAA AATTTATGAT TTTACCAAGC AAAACCGAGT GAATTAGAGT TNTNNAACAA     180

GCTTTGATTT CAAAAGAAA TAATCGCTAG TGTTCGAAAG AACACTCACA GATTANTAAC     240

ATCTTGGGTT TTCACCCGAC TTGTTCGTNT CGAAAGTCAA AAAA                     284

(2) INFORMATION FOR SEQ ID NO: 149:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 149:

```
AAGGATAAGG AACTGCGCAT TGGTCTTGTT TAGTCTTGAG AGGTCTTGTG GGGCCTTAGC      60
TCAGCTGGGA GAGCGCCTGC TTTGCACGCA GGAGGTCAGC GGTTCGATCC CGCTAGGCTC     120
CATTGGTGAG AGATCACCAA GTAATGCACA TTGAAAATTG AATATCTATA TCAAATAGTA     180
ACAAGAAAAT AAACCGAAAA CGCTGTAGTA TTAATAAGAG TTTATGACTG AAAGGTCAAA     240
AAATAA                                                                246
```

(2) INFORMATION FOR SEQ ID NO: 150:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 150:

```
AAGGATAAGG AACTGCGCAT TGGTCTTGTT TAGTCTTGAG AGGTCTTGTG GGGCCTTAGC      60
TCAGCTGGGA GAGCGCCTGC TTTGCACGCA GGAGGTCAGC GGTTCGATCC CGCTAGGCTC     120
CATTGGTGAG AGATCACCAA GTAATGCACA TTGAAAATTG AATATCTATA TCAAATAGTA     180
ACAAGAAAAT AAACCGAAAA CGCTGTAGTA TTAATAAGAG TTTATGACTG AAAGGTCAGA     240
AAAATAA                                                               247
```

(2) INFORMATION FOR SEQ ID NO: 151:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 151:

```
AAGGAAAAGG AACTGCGCAT TGGTCTTGTT TAGTCTTGAG AGGTCTTGTG GGGCCTTAGC      60
TCAGCTGGGA GAGCGCCTGC TTTGCACGCA GGAGGTCAGC GGTTCGATCC CGCTAGGCTC     120
CATTGGTGAG AGATCACCAA GTAATGCACA TTGAAAATTG AATATCTATA TCAAATAGTA     180
ACAAGAAAAT AAACCGAAAA CGCTGTAGTA TTAATAAGAG TTTATGACTG AAAGGTCAGA     240
```

```
AAAATAA                                                                         247

(2) INFORMATION FOR SEQ ID NO: 152:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 152:

AAGGATAAGG AACTGCGCAT TGGTCTTGTT TAGTCTTGAG AGGTCTTGTG GGGCCTTAGC    60

TCAGCTGGGA GAGCGCCTGC TTTGCACGCA GGAGGTCAGC GGTTCGATCC CGCTAGGCTC   120

CATTGGTGAG AGATCACCAA GTAATGCACA TTGAAAATTG AATATCTATA TCAAATAGTA   180

ACAAGAAAAT AAACCGAAAC GCTGTAGTAT TAAAAGAGTT TATGACTGAA AGGTCAGAAA   240

ATAA                                                                244

(2) INFORMATION FOR SEQ ID NO: 153:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 153:

AAGGATAAGG AACTGCGCAT TGGTCTTGTT TAGTCTTGAG AGGTCTTGTG GGGCCTTAGC    60

TCAGCTGGGA GAGCGCCTGC TTTGCACGCA GGAGGTCAGC GGTTCGATCC CGCTAGGCTC   120

CATTGGTGAG AGATCACCAA GTAATGCACA TTGAAAATTG AATATCTATA TCAAATAGTA   180

ACAAGAAAAT AAACCGAAAC GCTGTAGTAT TAAAAGAGTT TATGACTGAA AGGTCAAAAA   240

TAA                                                                 243

(2) INFORMATION FOR SEQ ID NO: 154:

(i) SEQUENCE CHARACTERISTICS:
        (A) LENGTH: 809 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 154:

TAAGGAAGAT CGAGAATTGG AAAGAGGTCG GATTTATCCG GATGATCCTT CTCCATCTTA    60

TTAGAACATA GATCGCAGGC CAGTCAGCCT GACGATCGCT TGCAGGCGTG CCGCCTTCGT   120

TTCTCTTTCT TCATTGTTGA TTGCTCACGG GCCGTACCGC AGCTGACGCT GCTGGCCCTG   180
```

```
CGCAGGCGCG GCCCATCAGG GCCGAACGGC CGGTCGGCCT TGCNAAGCTT CGCTTCGGGG      240

TGGATCTGTG GATCGCGTAG TAGCGTTTGC GTCGGTATCT GGGCTTGTAG CTCAGTTGGT      300

TAGAGCACAC GCTTGATAAG CGTGGGGTCG GAGGTTCAAG TCCTCCCAGG CCCACCAAGT      360

TACTTGATGA GGGGCCGTAG CTCAGCTGGG AGAGCACCTG CTTTGCAAGC AGGGGGTCGT      420

CGGTTCGATC CCGTCCGGCT CCACCATCAT GTTGGTGTTG AGACGGATAT TGGCAATCAA      480

CAAAAGAAAG AAACAAGTTT GCGGACTNTT ACGAAAGTCT GCCTGTTCTG TATGAAATCG      540

TGAAGAGAAG ATGTAATCGG ATCAACTGAA GAGTTGATGT CGCAAGAAGC TTGCTCAAGC      600

CTTGCATAAT GATTGATGTG TTTAACCGCC ATCACCGATT GTATCTCGAG AAGCTGGTCT      660

TTCTGCTGAT ACTGTTGAAA CGAGCATTTG CAGTCGAATG GCAACATTCG GCGTCGCATA      720

ATGCGGCTTT AAGAGCTGAG TTTTGATGGA TATTGGCAAT GAGAGTGATC AAGTGTCTTA      780

AGGGCATTGG TGGATGCCTT GGCATGCAC                                       809

(2) INFORMATION FOR SEQ ID NO: 155:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 155:

TGGGGTGAAG TCGTAACAAG GTA                                              23

(2) INFORMATION FOR SEQ ID NO: 156:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 156:

CCTTTCCCTC ACGGTACTGG T                                                21

(2) INFORMATION FOR SEQ ID NO: 157:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 157:

AAGGAGCACC ACGAGAAACA CTCCAATTGG TGGGGTGTAA GCCGTGAGGG GTTCTCGTCT       60
```

```
GTAGTGGACG GAAGCCGGGT GCACAACAAC AAGCAAGCCA GACACACTAT TGGGTCCTGA    120

GGCAACATCT CTGTTGGTTT CGGGATGTTG TCCCACCATC TTGGTGGTGG GGTGTGGTGT    180

TTGAGAATTG GATAGTGGTT GCGAGCATCA ATTGGATGCG CTGCCTTTTG GTGGCGTGTT    240

CTGTTGTGCA ATTTTATTCT TTGGTTTTTG TGTTTAT                             277
```

(2) INFORMATION FOR SEQ ID NO: 158:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 158:

```
AAGGAGCACC ACGAGAAACA CCCCAATTGG TGGGGTGTGA GCCGTGAGGG GTTCTCGTCT     60

GTAGTGGACG AGGGCCGGGT GCACAACAAC AGGCAATCGC CGGACACACT ATTGGGCCCT    120

GAGACAACAC TCGGCCGACT GAGGTCGACG TGGTGTCCCT CCATCTTGGT GGTGGGGTGT    180

GGTGTTTGAG CATTGAATAG TGGTTGCGAG CATCTAGCCG GATGCGTTCC CCAGTGGTGC    240

GCGTTCGTCA AAATGTGTA ATTTTTCTTT TGGTTTTTGT GTTCGT                    286
```

(2) INFORMATION FOR SEQ ID NO: 159:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 159:

```
AAGGAGCACC ACGAGAAACA CCCCAATTGG TGGGGTGTGA GCCGTGAGGG GTTCTCGTCT     60

GTAGTGGACG AGGGCCGGGT GCACAACAAC AGGCAATCGC CGGACACACT ATTGGGCCCT    120

GAGACAACAC TCGGCCGACT GAGGTCGACG TGGTGTCCCT CCATCTTGGT GGTGGGGTGT    180

GGTGTTTGAG CATTGAATAG TGGTTGCGAG CATCTAGACG GATGCGTTCC CCAGTGGTGC    240

GCGTTCGTCA AAATGTGTA ATTTTTCTTT TGGTTTTTGT GTTCGT                    286
```

(2) INFORMATION FOR SEQ ID NO: 160:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 160:

```
AAGGAGCACC ACGAGAAACA CCCCAATTGG TGGGGTGTGA GCCGTGAGGG GTTCTCGTCT         60

GTAGTGGACG AGGCGGGTAC AACAACGCCA ATCGCCGGAC ACACTATTGG GCCTGAGACA        120

ACACTCGGCC GACTGAGGTC GACGTGGTGT CCCTCCATCT TGGTGGTGGG GTGTGGTGTT        180

TGAGCATTGA ATAGTGGTTG CGAGCATCTA GCCGGATGCG TTCCCCAGTG GTGCGCGTTC        240

GTCAAAAATG TGTAATTTTT CTTTGGTTTT TGTGTTCGT                              279
```

(2) INFORMATION FOR SEQ ID NO: 161:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 161:

```
AAGGAGCACC ACGAGAAACA CTCCAATTGG TGGAGTGTGA GCCGTGAGGG GTTCTCGTCT         60

GTAGTGGACG AGGGCCGGGT GCACAACAGC AGACAATCGC CAGACACACT ATTGGGCCCT        120

GAGACAACAC TCGGCCGACT TTGGTCGACG TGGTGTCCCT CCATCTTGGT GGTGGGGTGT        180

GGTGTTTGAG CATTGAATAG TGGTTGCGAG CATCTAGACG GATGCGTTGC CCTCGGGCCG        240

CGTGTTCGTC AAAAATGTGT AATTTTTCT TTTGGTTTTT GTGTTCGT                     288
```

(2) INFORMATION FOR SEQ ID NO: 162:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 162:

```
AAGGAGCACC ACGAGAAACA CTCCAATTGG TGGAGTGTGA GCCGTGAGGG GTTCTCGTCT         60

GTAGTGGACG GGAGCCGGGT GCACAACAAC AGGCAATCGC CAGACACACT ATTGGGCCCT        120

GAGACAACAC TCGGCCGGCT TTGAGTCGAA GTGGTGTCCC TCCATCTTGG TGGTGGGGTG        180

TGGTGTTTGA GCATTGAATA GTGGTTGCGA GCATCTAGAC GGATGCGTTG CCTTCGGGCC        240

GCGTGTTCGT CAAAAATGTG TAATTTTTTC TTTTGGTTTT TGTGTTCGT                   289
```

(2) INFORMATION FOR SEQ ID NO: 163:

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 163:

AGGGAGCACC GAAACGCATC CCGCGTGGGG TGTGGGTTCG GCGTGTTGTG GCGTCGGCCG    60

AGGTGTTGGG CAGCAGGCAG TAACCCCGGA ACACTGTTGG GTTTTGAGAA CACCCGTGGT   120

GGTGTTGTGC TCCCCGTGGT GCGGGGTGTG GTGTTTGAGT GTTGGATAGT GGTTGCGAGC   180

ATCTGGCAAA GACTGTGGTA AGCGGTTTTT GTTGATGTTT TCTGGTGTTT GT           232

(2) INFORMATION FOR SEQ ID NO: 164:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 164:

AAGGAGCACC ACGAGAAACA CTCCAATTGG TGGGGTGTGA GCCGTGAGGG GTTCTCGTCT    60

GTAGTGGACG AGGGCGGGTG CACAACAACA GCAATCGCCA GACACACTAT TGGCCCTGAG   120

ACAACACTCG GCCGACTTGG TTGAAGTGGT GTCCCTCCAT CTTGGTGGTG GGTGTGGTG    180

TTTGAGTATT GGATAGTGGT TGCGAGCATC TAATGAACGC GTCGCCGCAA CGGTTACGTG   240

TTCGTTTTGT GTAATTTTTC TATTGGTTTT TGTGTTCGT                          279

(2) INFORMATION FOR SEQ ID NO: 165:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 165:

AAGGAGCACC ACGAGAAACA CTCCAATTGG TGGGGTGTGA GCCGTGAGGG GTTCTCGTCT    60

GTAGTGGACG AGGGCCGGGT GCACAACAAC AGGCAATCGC CAGACACACT ATTGGCCCTG   120

AGACAACACT CGGCCGACTT TGGTCGAAGT GGTGTCCCCC CATCTTGGTG GTGGGGTGTG   180

GTGTTTGAGT ATTGGATAGT GGTTGCGAAC ATCTAAATGA ACGCGTTGCC GGCAACGGTT   240

ACGTGTTCGT TTTAGTGTAA TTTTTCTAAT GGTTTTTGTG TTCGT                   285

(2) INFORMATION FOR SEQ ID NO: 166:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 166:

```
AAGGAGCACC ACGAGACCTG GGCCGGCCCC GCAGATCGCG GGATCAGCTG AGCTTTCAGG        60

CGATTCGTTG GATGGCCTCG CACCTGTAGT GGGTGGGGGT CTGGTGCACT CAACAAACTT       120

GGCGTGGGAT GCGGGAAAGC ATCTGCGGAA AATCATCAGA CACACTATTG GGCTTTGAGA       180

CAACAGGCCC GCAGCCTGCC CGTTGGGGGC AGGGGTGTGT TGTTGCCTCA CTTTGGTGGT       240

GGGGGTGGTG TTTGATTTGT GGATAGTGGT TGCGAGCATC TAGCGCGCAG AATGTGTGGT       300

CTCACTCCTT GTGGGTGGGG CCTGGTTTTG TGTGCGATTG ATGTGCAATT TCTTTTGAAA       360

CTCATTTTTT GGTTTTTGTG TTGT                                             384
```

(2) INFORMATION FOR SEQ ID NO: 167:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 167:

```
AAGGAGCACC ACGAAAAACT CCCCAATTGG TGGGGTGTAA GCCGTGAGGG GTTCCCGTCT        60

GTAGTGGACG GGGGCCGGGT GCGCAACAGC AAGCGAAACG CCGGACACAC TATTGGGTCC       120

TGAGGCAACA CTCGGGTTTG TCCCCCTCAG GGATTTTCTG GGTGTTGTCC CACCATCTTG       180

GTGGTGGGGT GTGGTGTTTG AGAATTGGAT AGTGGTTGCG AGCATCAAAT GGATGCGTTG       240

CCCCTACGGG TAGCGTGTTC TTTTGTGCAA TTTTATTCTT GGTTTTTGTG TTTGT            295
```

(2) INFORMATION FOR SEQ ID NO: 168:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 168:

```
AAGGAGCACC ACGAGAAGCA CTCCAACTGG TGGGGTGCAA GCCGTGAGGG GTTCTCGTCT        60

GTAGTGGACG AGAGCCGGGT GCGCGACAAC GAACGAGCCA GACACACTAT TGGGTCCTGA       120

GGCAACACTC GGGCTTGGCC AGAGCTGTTG TCCCACCATC TTGGTGGTGG GGTGTGGTGT       180

TTGAGAATTG GATAGTGGTT GCGAGCATCA AATGGATGCG TTGCCCCTAC GGGTGGCGTG       240

TTCTTTTGTG CAATTTTATT CTTTGGTTTT TGTGTTTGT                              279
```

(2) INFORMATION FOR SEQ ID NO: 169:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 169:

AAGGAGCACC ACGAAAAACA CCCCAACTGG TGGGGTGTAA GCCGTGAGGG GCTCCCGTCT      60

GTAGTAGACG GGCGCCGGGT GCGCAACAGC AAGCGAGCCA GACACACTAT TGGGTCCTGA     120

GGCAACACTC GGGCTTGTCT TGGACTCGTC CAAGAGTGTT GTCCCACCAT CTTGGTGGTG     180

GGGTGTGGTG TTTGAGAATT GGATAGTGGT TGCGAGCATC ACTGGATGCG TTGCCCCCAG     240

GGGTAGCGTG TTCTTTTGTG CAATTTATTC TGGTTTTTGT GTTAGT                    286

(2) INFORMATION FOR SEQ ID NO: 170:

(i) SEQUENCE CHARACTERISTICS:
            (A) LENGTH: 265 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 170:

AAGGAGCACC ACGAAAAACA CTCCGCATCC GGTGGGGTGT GAGCCGTGAG GGAGCCCGTG      60

CCTGTAGTGG GTGTGGGTTG GGTGCGCGAC AACAAATGGG AAAAATCGCT GGGCACACTA     120

TTGGGCTTTG AGGCAACACC TGGTTTGTTT TGGGTGGTGT CGCTCCATCT TGGTGGTGGG     180

GTGTGGTGTT TGAGTTGTGG ATAGTGGTTG CGAGCATCTA AGCAAAAGCT GTTGTTTGAC     240

GGTTTTTGTC GAGTGTTGTG TGTGT                                          265

(2) INFORMATION FOR SEQ ID NO: 171:

(i) SEQUENCE CHARACTERISTICS:
            (A) LENGTH: 299 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 171:

AAGGAGCACC ACGAAAAACA CTCCAATTGG TGGGGTGTAA GCCGTGAGGG GTTCTCATCT      60

GTAGTGGACG AGAGCCGGGT GCACAACAGC AAATGAATCG CCAGACACAC TGTTGGGTCC     120

TGAGGCAACA CTCAGGCTTG TCCCATGTTG GGCTTGATCG GGTGCTGTCC CCCCATCTTG     180

GTGGTGGGGT GTGGTGTTTG AGTATTGGAT AGTGGTTGCG AGCATCTAAA TGGATACGTT     240

GCCAGTAATG GTGGCGTATT CATTGAAAAT GTGTAATTTT CTTCTTTGGT TTTGTGTGT     299

(2) INFORMATION FOR SEQ ID NO: 172:

(i) SEQUENCE CHARACTERISTICS:
            (A) LENGTH: 299 base pairs
            (B) TYPE: nucleic acid
            (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 172:

AAGGAGCACC ACGAAAAACA CTCCAATTGG TGGGGTGTAA GCCGTGAGGG GTTCTCATCT        60

GTAGTGGACG AGAGCCGGGT GCACAACAGC AAATGAATCG CCAGACACAC TGTTGGGTCC       120

TGAGGCAACA CTCAGGCTTG TCCCATGTTG GGCTTGATCG GGTGCTGTCC CCCCATCTTG       180

GTGGTGGGGT GTGGTGTTTG AGTATTGGAT AGTGGTTGCG AGCATCTAAA TGGATACGTT       240

GCCAGTAATG GTGGCGTGTT CATTGAAAAT GTGTAATTTT CTTCTTTGGT TTTGTGTGT        299

(2) INFORMATION FOR SEQ ID NO: 173:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 173:

AAGGAGCACC ACGAAAAACA CTCCAATTGG TGGGGTGTAA GCCGTGAGGG GTTCTCATCT        60

GTAGTGGACG AGAGCCGGGT GCACAACAGC AAATGAATCG CCAGACACAC TGTTGGGTCC       120

TGAGGCAACA CTCAGGCTTG TCCCATGTTG GGCTTGATCG GGTGCTGTCC CCCCATCTTG       180

GTGGTGGGGT GTGGTGTTTG AGTATTGGAT AGTGGTTGCG AGCATCTAAA TGGAACGTTG       240

CCAGTAATGG TGGCGTGTTC ATTGAAAATG TGTAATTTTC TTCTTTGGTT TTGTGTGT         298

(2) INFORMATION FOR SEQ ID NO: 174:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 174:

AAGGAGCACC ATTTCTCAGT CGAATGAACT GAGAACATAA AGCGAGTATC TGTAGTGGAT        60

ACATGCTTGG TGAATATGTT TTATAAATCC TGTCCACCCC GTGGATAGGT AGTCGGCAAA       120

ACGTCGGACT GTCATAAGAA TTGAAACGCT GGCACACTGT TGGGTCCTGA GGCAACACAT       180

TGTGTTGTCA CCCTGCTTGG TGGTGGGGTG TGGTCCTTGA CTTATGGATA GTGGTTGCGA       240

GCATCTAAAC ATAGCCTCGC TCGTTTTCGA GTGAGGCTGG TTTTTGCAAT TTTATTAGCT       300

(2) INFORMATION FOR SEQ ID NO: 175:

(i) SEQUENCE CHARACTERISTICS:
        (A) LENGTH: 22 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 175:

GGTTTCGGGA TGTTGTCCCA CC                                             22

(2) INFORMATION FOR SEQ ID NO: 176:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 176:

CGACTGAGGT CGACGTGGTG T                                              21

(2) INFORMATION FOR SEQ ID NO: 177:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 177:

GGTGTTTGAG CATTGAATAG TGGTTGC                                        27

(2) INFORMATION FOR SEQ ID NO: 178:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 178:

GTTGGGCAGC AGGCAGTAAC C                                              21

(2) INFORMATION FOR SEQ ID NO: 179:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 179:

CCGGCAACGG TTACGTGTTC                                                                20

(2) INFORMATION FOR SEQ ID NO: 180:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 180:

TCGTTGGATG GCCTCGCACC T                                                              21

(2) INFORMATION FOR SEQ ID NO: 181:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 181:

ACTTGGCGTG GGATGCGGGA A                                                              21

(2) INFORMATION FOR SEQ ID NO: 182:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 182:

CCCTCAGGGA TTTTCTGGGT GTTG                                                           24

(2) INFORMATION FOR SEQ ID NO: 183:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 183:

GGACTCGTCC AAGAGTGTTG TCC                                           23

(2) INFORMATION FOR SEQ ID NO: 184:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 184:

TCGGGCTTGG CCAGAGCTGT T                                             21

(2) INFORMATION FOR SEQ ID NO: 185:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 185:

GGGTGCGCAA CAGCAAGCGA                                               20

(2) INFORMATION FOR SEQ ID NO: 186:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 186:

GATGCGTTGC CCCTACGGG                                                19

(2) INFORMATION FOR SEQ ID NO: 187:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 187:

CCCTACGGGT AGCGTGTTCT TTTG                                          24

(2) INFORMATION FOR SEQ ID NO: 188:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 188:

CGGATCGATT GAGTGCTTGT CCC                                           23

(2) INFORMATION FOR SEQ ID NO: 189:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 189:

TCTAAATGAA CGCACTGCCG ATG                                           23

(2) INFORMATION FOR SEQ ID NO: 190:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 190:

TGAGGGAGCC CGTGCCTGTA                                               20

(2) INFORMATION FOR SEQ ID NO: 191:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 191:

```
CATGTTGGGC TTGATCGGGT GC                                            22

(2) INFORMATION FOR SEQ ID NO: 192:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 192:

CCTGGGTTTG ACATGCACAG                                               20

(2) INFORMATION FOR SEQ ID NO: 193:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 193:

GCGTAGTAGC GTTTGCGTCG G                                             21

(2) INFORMATION FOR SEQ ID NO: 194:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 194:

CGCAAGAAGC TTGCTCAAGC C                                             21

(2) INFORMATION FOR SEQ ID NO: 195:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 195:

CCTAATGATA TTGATTCGCG TGAAGTGCTC ACACAGATTG TCTGATGAAA AGTAACGAG    60

CAGAAATACC TTTATAGGCT TGTAGCTCAG GTGGTTAGAG CGCACCCCTG ATAAGGGTGA   120
```

```
GGTCGGTGGT TCAAGTCCAC TCAGGCCTAC CACTTCTCGA AGTGGAAAAG GTACTGCACG        180

TGACTGTATG GGGCTATAGC TCAGCTGGGA GAGCGCCTGC CTTGCACGCA GGAGGTCAGC        240

GGTTCGATCC CGCTTAGCTC CACCATATAG TCCTGTATTT CAATACTTCA GAGTGTACTG        300

GCAACAGTAT GCTGCGAAGT ATTTTGCTCT TTAACAATCT GGAACAAGCT GAAAATTGAA        360

ACATGACAGC TGAAACTTAT CCCTCCGTAG AAGTATTGGG GTAAGGATTA ACCTGTCATA        420

GAGTCTCTCA AATGTAGCAG CACGAAAGTG GAAACACCTT CGGGTTGTGA                   470

(2) INFORMATION FOR SEQ ID NO: 196:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 196:

CCTAATGATA TTGATTCGCG TGAAGTGCTC ACACAGATTG TTTGATAGAA ACGTAATGAG         60

CAAAAGCGCT ACCTGTTGAT GTAATGAGTC ACTGACTCAT GCTGATACGA ACCGATTAAG        120

ACAGTCAGTT TAATCGGATT TTCGTGTCCC CATCGTCTAG AGGCCTAGGA CACTGCCCTT        180

TCACGGCTGT AACAGGGGTT CGAATCCCCT TGGGGACGCC ATTCGATAAT GAGTGAAAGA        240

CATTATCACC GGTTCTTGGA ACCGAAAACA TCTTAAAGAT GACTCTTGCG AGTCGTGTTT        300

AAGATATTGC TCTTTAACAA TCTGGAACAA GCTGAAAATT GAAACATGAC AGCTGAAACT        360

TATCCCTCCG TAGAAGTATT GGGGTAAGGA TTAACCTGTC ATAGAGTCTC TCAAATGTAG        420

CAGCACGAAA GTGGAAACAC CTTCGGGTTG TGA                                    453

(2) INFORMATION FOR SEQ ID NO: 197:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 197:

TAAGGATAAG GAAGAAGCCT GAGAAGGTTT CTGACTAGGT TGGGCAAGCA TTTATATGTA         60

AGAGCAAGCA TTCTATTTCA TTTGTGTTGT TAAGAGTAGC GCGGTGAGGA CGAGACATAT        120

AGTTTGTGAT CAAGTATGTT ATTGTAAAGA AATAATCATG GTAACAAGTA TATTTCACGC        180

ATAATAATAG ACGTTAAGA GTATTTGTCT TTTAGGTGAA GTGCTTGCAT GGATCTATAG        240

AAATTACA                                                                 248

(2) INFORMATION FOR SEQ ID NO: 198:

(i) SEQUENCE CHARACTERISTICS:
        (A) LENGTH: 23 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 198:

GGAAAAGGTA CTGCACGTGA CTG                                         23

(2) INFORMATION FOR SEQ ID NO: 199:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 199:

GACAGCTGAA ACTTATCCCT CCG                                         23

(2) INFORMATION FOR SEQ ID NO: 200:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 200:

GCTACCTGTT GATGTAATGA GTCAC                                       25

(2) INFORMATION FOR SEQ ID NO: 201:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 201:

GAGTAGCGCG GTGAGGACGA GA                                          22

(2) INFORMATION FOR SEQ ID NO: 202:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

(iv) ANTI-SENSE: NO (xi) SEQUENCE DESCRIPTION: SEQ ID NO: 202:

CTTTTATGTC AGATAAAGTA TGCAA                                              25

(2) INFORMATION FOR SEQ ID NO: 203:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 203:

CGTAAAAGGG TATGATTATT TG                                                 22

(2) INFORMATION FOR SEQ ID NO: 204:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 204:

TCGAGAATTG GAAAGAGGTC                                                    20

(2) INFORMATION FOR SEQ ID NO: 205:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 205:

AAGAGGTCGG ATTTATCCG                                                     19

(2) INFORMATION FOR SEQ ID NO: 206:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 206:

```
TTCGACTGCA AATGCTCG                                                        18

(2) INFORMATION FOR SEQ ID NO: 207:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 207:

TCTTAAAGCC GCATTATGC                                                       19

(2) INFORMATION FOR SEQ ID NO: 208:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 208:

CCTAATGATA TTGATTCGCG                                                      20

(2) INFORMATION FOR SEQ ID NO: 209:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 209:

ATGACAGGTT AATCCTTACC CC                                                   22

(2) INFORMATION FOR SEQ ID NO: 210:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 210:

GGTGTGGTCC TTGACTTATG GATAG                                                25
```

(2) INFORMATION FOR SEQ ID NO: 211:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 211:

TCGGGCCGCG TGTTCGTCAA A                                            21

(2) INFORMATION FOR SEQ ID NO: 212:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 212:

CGTTTTCATA AGCGATCGCA CGTT                                         24

(2) INFORMATION FOR SEQ ID NO: 213:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 213:

TAAGGATAAG GAAACCTGTG AATCTTTTTC CCTTCTTTTG TTCAGTTTTG AGAGGTTCAT    60

CTCTCAAAAC GTGTTCTTTG AAAACTAGAT AAGAAAAGTT AGTGTAAAAA GACGAAGAGA   120

AACCGTAGGT TTTTCTTCAA CCAAAACCGA GAATCAAACC GAGAAAGAAT CTTTCCGTTT   180

TCATAAGCGA TCGCACGTTT ATGAAAACAC AACAACACCT TCGTAAGAAG GATGA        235

(2) INFORMATION FOR SEQ ID NO: 214:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 214:

```
TAAGGATAAG GAAACCTGTG AATCTTTTTC CCTTCTTTTG TTCAGTTTTG AGAGGTCAAT     60

GACGCTCATA CTGAGTACCA GGTGACACGT TTTTGAGGTG TCTCTTCGTA TGAGGGGCCT    120

ATAGCTCAGC TGGTTAGAGC GCACGCCTGA TAAGCGTGAG GTCGGTGGTT CGAGTCCACT    180

TAGGCCCACT TTTTTGAATA AACCTTTCTT TTTTATATGT TAATAAGGGG CCTTAGCTCA    240

GCTGGGAGAG CGCCTGCTTT GCACGCAGGA GGTCAGCGGT TCGATCCCGC TAGGCTCCAC    300

CAAAGATAGT TTGTTCTTTG AAAACTAGAT AAGAAAAGTT AGTGTAAAAA GACGAAGAGA    360

AACCGTAGGT TTTTCTTCAA CCAAAACCGA GAATCAAACC GAGAAAGAAT CTTTCCGTTT    420

TCATAAGCGA TCGCACGTTT ATGAAAACAC AACAACACCT TCGTAAGAAG GATGA         475
```

(2) INFORMATION FOR SEQ ID NO: 215:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 215:

```
TAAGGATAAG GAAACCTGTG AATCTTTTTC CCTTCTTTTG TTCAGTTTTG AGAGGTCAAT     60

GACGCTCATA CTGAGTACCA GGTGACACGT TTTTGAGGTG TCTCTTCGTA TGAGGGGCCT    120

ATAGCTCAGC TGGTTAGAGC GCACGCCTGA TAAGCGTGAG GTCGGTGGTT CGAGTCCACT    180

TAGGCCCACT TTTTTGAATA AACCTTTCTT TTTTATATGT TAATAAGGGG CCTTAGCTCA    240

GCTGGGAGAG CGCCTGCTTT GCACGCAGGA GGTCAGCGGT TCGATCCCGC TAGGCTCCAC    300

CAAAGATAGT TTGTTCTTTG AAAACTAGAT AAGAAAAGTT AGTGTAAAAA GACGAAGAGA    360

AACCGTAGGT TTTTCTTCAA CCAAAACCGA GAAAGAATCT TCCGTTTTC ATAAGCGATC     420

GCACGTTTAT GAAAACACAA CAACACCTTC GTAAGAAGGA TGA                      463
```

(2) INFORMATION FOR SEQ ID NO: 216:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 216:

```
TGGCCGGTGC AAAGGGCTG                                                  19
```

DETECTION AND IDENTIFICATION OF *STAPHYLOCOCCUS AUREUS* AND *EPIDERMIDIS* USING THE 16S-23S RRNA SPACER

The present application is divisional of application Ser. No. 09/931,486, filed Aug. 17, 2001 (now U.S. Pat. No. 6,811, 978) which is a divisional of application Ser. No. 09/448,894, filed Nov. 29, 1999 (now U.S. Pat. No. 6,312,903), which in turn is a divisional application of Ser. No. 08/765,332, filed Dec. 23,1996 (now U.S. Pat. No. 6,025,132), which is a 371 U.S. national phase of PCT/EP95/02452, filed Jun. 23, 1995, and claims benefit of EP 94870106, filed Jun. 24, 1994, and EP 95870032, filed Apr. 7, 1995, the entire contents of each of which are incorporated herein by reference.

The present invention relates to nucleic acid probes derived from the spacer region between the 16S and 23S ribosomal ribonucleic acid (rRNA) genes to be used for the specific detection of eubacterial organisms in a biological sample by a hybridization procedure, as well as to nucleic acid primers to be used for the amplification of said spacer region of eubacterial organisms in a biological sample. The present invention also relates to new spacer region sequences from which said probes or primers may be derived.

Since the advent of the polymerase chain reaction and some other nucleic acid amplification techniques the impact of DNA-probe technology in the diagnosis of micro-organisms in biological samples of all sorts is increasing. Being often more specific and potentially more sensitive—if an adequate amplification and/or detection system is used—the DNA probe approach may eventually replace the conventional identification techniques.

The reliability of nucleic acid based tests essentially depends on the sensitivity and specificaty of the probes and/or primers used. Thus the corner stone of this type of assay is the identification of nucleic acid sequences which are unique to the group of organisms of interest.

Most of the nucleic acid based tests either described in literature and/or commercially available aim at the detection of just one particular organism in a biological sample. Since most biological samples usually may contain a great variety of clinically relevant micro-organisms, a multitude of separate assays have to be performed to detect all relevant organisms possibly present. This approach would be very expensive, laborious and time-consuming. Consequently, the number of tests actually performed in most routine diagnostic labs on a particular sample is restricted to the detection of just a few of the most relevant organisms. Therefore it would be extremely convenient to have access to a system which enables the fast, easy and simultaneous detection of a multitude of different organisms. The more organisms that can be screened for in the same assay the more cost-effective the procedure would be.

As put forward in earlier published documents the spacer region situated between the 16S rRNA and the 23S rRNA gene, also referred to as the internal transcribed spacer (ITS), is an advantageous target region for probe development for detection of pathogens of bacterial origin (International application WO 91/16454; Rossau et al. 1992; EP-A-0 395 292).

One of its most appreciated advantages is that sequences unique to a great variety of bacterial taxa can be found in a very limited area of the bacterial genome. This characteristic allows for an advantageous design of "probe-panels" enabling the simultaneous detection of a set of organisms possibly present in a particular type of a biological sample. Moreover, being flanked by quasi-universally conserved nucleotide sequences—more particularly located in the 3'-part of the 16S rRNA gene and the 5'-part of the 23S rRNA gene respectively—almost all spacers can be simultaneously amplified with a limited set of amplification primers. Alternatively, specific primer sets can be derived from the spacer sequences themselves, thereby allowing species- or group-specific amplifications.

The 16S-23S rRNA spacer region is a relatively short (about 200 to 1000 base pairs) stretch of DNA present in one or multiple copies in the genome of almost all eubacterial organisms. If multiple copies are present in the genome of one bacterium these copies can either be identical (as is most probably the case in some *Neisseria* species) or may differ from each other (as is the case for *E. coli*). This difference can be limited to a few nucleotides but also deletions and insertions of considerable length may be present.

Until now, spacer probes are only described and made publicly available for a limited number of organisms many of which were disclosed in international application WO 91/16454. As described above, it would be very advantageous to be able to detect simultaneously a panel of pathogens: e.g. a panel of pathogens possibly present in the same type of biological sample, or a panel of pathogens possibly causing the same type of disease symptoms, which are difficult to differentiate clinically and/or biochemically, or a panel of organisms belonging to the same taxon. In order to make the different panels as complete as possible, additional probes or sets of probes located in the spacer region and enabling the identification of at least the following bacterial groups or species are required:

*Mycobacterium* species
*Listeria* species
*Chlamydia* species
*Acinetobacter* species
*Mycoplasma* species
*Streptococcus* species
*Staphylococcus* species
*Salmonella* species
*Brucella* species
*Yersinia* species
*Pseudomonas* species These additional spacer probes need to be meticulously designed such that they can be used simultaneously with at least one other probe, under the same hybridization and wash conditions, allowing the detection of a particular panel of organisms.

It is thus the aim of the present invention to select probes or sets of probes which have as target the 16S-23S rRNA spacer region, and which allow the detection and identification of at least one, and preferably more than one of the above mentioned micro-organisms. The probes or probe sets are selected in such a way that they can be used in combination with at least one other probe, preferably also originating from the 16S-23S rRNA spacer region, under the same hybridisation and wash conditions, to allow possibly the simultaneous detection of several micro-organisms in a sample.

It is also an aim of the present invention to provide for a selection method for use in the selection of said spacer probes or probe sets.

It is also an aim of the present invention to provide a rapid and reliable hybridization method for detection and identification of at least one micro-organism in a sample, or for the simultaneous detection and identification of several micro-organisms in a sample.

It is more particularly an aim of the present invention to provide a hybridization method allowing simultaneous detection and identification of a set of micro-organisms, liable to be present in a particular type of sample.

It is more particularly an aim of the present invention to provide probes or sets of probes for the possible simultaneous detection of micro-organisms in a sample originating from respiratory tract.

It is another particular aim of the present invention to provide probes or sets of probes for the possible simultaneous detection of micro-organisms in a sample originating from cerebrospinal fluid.

It is still another particular aim of the present invention to provide probes or sets of probes for the possible simultaneous detection of micro-organisms in a sample originating from urogenital tract.

It is still another particular aim of the present invention to provide probes or sets of probes for the possible simultaneous detection of micro-organisms in a sample taken from the gastro-intestinal tract of a patient.

It is still another particular aim of the present invention to provide probes or sets of probes for the possible simultaneous detection of micro-organisms in a sample originating from food or environmental samples.

It is moreover an aim of the present invention to provide a method for detection and identification of a particular taxon in a sample, or a set of particular taxa, said taxon being either a complete genus, or a subgroup within a genus, a species or even subtypes within a species (subspecies, serovars, sequevars, biovars . . . ).

It is more particularly an aim of the present invention to provide probes or sets of probes for the detection of *Mycobacterium* species and subspecies, more particularly for the detection of *M. tuberculosis* complex strains, *Mycobacterium* strains from the MAIS-complex, *M. avium* and *M. paratuberculosis*, *M. intracellulare* and *M. intracellulare*-like strains, *M. scrofulaceum, M. kansasii, M. chelonae, M. gordonae, M. ulcerans, M. genavense, M. xenopi, M. simiae, M. fortuitum, M. malmoense, M. celatum* and *M. haemophilum*.

It is also an aim of the present invention to provide probes or sets of probes for the detection of *Mycoplasma* strains, more particularly of *M. pneumoniae* and *M. genitalium*.

It is also an aim of the present invention to provide probes or sets of probes for the detection of *Pseudomonas* strains, more particularly *P. aeruginosa*.

It is also an aim of the present invention to provide probes or sets of probes for detection of *Staphylococcus* species, more particularly *S. aureus* and *S. epidermidis*.

It is also an aim of the present invention to provide probes or sets of probes for the detection of *Acinetobacter* strains, more particularly *A. baumanii*.

It is also an aim of the present invention to provide probes or sets of probes for the detection of *Listeria* strains, more particularly *Listeria monocytogenes*.

It is also an aim of the present invention to provide probes or sets of probes for the detection of *Brucella* strains.

It is also an aim of the present invention to provide probes or sets of probes for the detection of *Salmonella* strains.

It is also an aim of the present invention to provide probes or sets of probes for the detection of *Chlamydia* strains, more particularly *C. trachomatis* and *C. psittaci*.

It is also an aim of the present invention to provide probes or sets of probes for the detection of *Streptococcus* strains.

It is also an aim of the present invention to provide probes or sets of probes for the detection of *Yersinia enterolitica* strains.

It is also an aim of the present invention to provide primers allowing specific amplification of the 16S-23S rRNA spacer region for certain organisms. More particularly, it is an aim of the present invention to provide primers for the specific amplification of the spacer region of *Mycobacterium, Chlamydia, Listeria, Brucella* and *Yersinia enterolitica* strains.

It is also an aim of the present invention to provide new sequences of 16S-23S rRNA spacer regions from which useful spacer probes or primers can be derived.

It is also an aim of the present invention to provide for kits for detection of at least one organism in a sample in which said probes and/or primers are used.

It is noted that for a few of the above-mentioned organisms spacer sequences have already been published in literature or in publicly accessible data-banks.

However, it should be made clear that the spacer region sequences disclosed in the current invention (FIGS. 1-103) are new and, in case they originate from the same species as those of which a spacer sequence was already described in the prior art, they differ to some extent from the already described sequences.

Moreover it is the principal aim of the present invention to select from the compilation of sequence data on spacer regions, specific probes and sets of probes enabling the detection and identification of a particular panel of organisms, be it the organisms belonging to a common taxon, or the organisms possibly present in the same type of sample.

The selection procedure usually consists of a theoretical and an experimental part. First of all, the different spacer sequences need to be aligned to those of the 'closest neighbours' or to the spacer sequences of other micro-organisms liable to be present in the same sample. This requires of course the sequence determination of the spacer region, as described in the examples. From the alignment, regions of divergence can be defined, from which probes with desired hybridization characteristics are designed according to guidelines known to the man skilled in the art and specified in more detail below.

Secondly the designed probes need to be tested experimentally and evaluated for their usefulness under specific hybridization conditions and/or in combination with other probes. Experimental testing can be done according to any hybridization method known in the art but a preferred assay for the simultaneous testing of different probes under the same conditions is the reverse hybridization assay. A specific format for reverse hybridization of different probes simultaneously used in the current invention is the LiPA (Line Probe Assay) as described below.

Upon experimental testing unexpected hybridization behaviour may show up when the probes are hybridized to the target nucleic acid and specific probe adaptations may be required.

Moreover, specificity and sensitivity of the probes need to be tested with a large collection of strains, both belonging to the taxon to be detected and belonging to other taxa. Due to genome heterogeneity in the spacer region, or the existence of multiple spacer regions with different sequences in the same organism, it is quite often necessary to sequence spacer regions of additional strains, or to sequence additional spacer regions in the same strain and redesign the probes according to the new sequence data in order to obtain a better sensitivity and/or specificity (see e.g. example 3). In some cases it may be necessary or preferable to use several probes for the same organism (see e.g. example 2 and 7). Also, upon sequencing the spacer region, some organisms may show unexpected (un)relatedness, which may lead to a revision of strain classification contrary to classical taxonomic criteria (see e.g. examples 2 and 7).

In conclusion the experimental part of the probe selection procedure is indispensable and complementary to the theoretical part. Probe design, especially under the fixed conditions of reverse hybridization (the same conditions for each probe) is not straightforward and probes have to be evaluated meticulously before they can be used in a reverse hybridization format. Therefor, probes cannot always be simply derived on a theoretical basis from a known gene sequence.

For designing probes with desired characteristics the following useful guidelines may be followed.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions explained further herein, are known to those skilled in the art.

First, the stability of the [probe:target] nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and % GC result in a Tm about 2-10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strenght of the reaction mixture increases, and that the thermal stability of the hybrids will increase with increasing ionic strenght. On the other hand chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid. In some examples of the current invention, e.g. when highly related organisms need to be differentiated, it may be necessary to detect single base pair changes. In those cases, conditions of very high stringency are needed.

Second, probes should be positioned so as to minimize the stability of the [probe:nontarget] nucleic acid hybrid. This may be accomplished by minimizing the length of perfect complementarity to non-target organisms, avoiding GC rich regions of homology to non-target sequences, and by positioning the probe to span as many destabilizing mismatches as possible. Whether a probe sequence is useful to detect only a specific type of organism depends largely on the thermal stability difference between [probe:target] hybrids and [probe:nontarget] hybrids. In designing probes, the differences in these Tm values should be as large as possible (e.g. at least 2° C. and preferably 5° C.).

The length of the target nucleic acid sequence and, accordingly the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions in the target DNA or RNA which are known to form strong internal structures inhibitory to hybridization are less preferred. Likewise, probes with extensive self-complementarity should be avoided. As explained above hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded the rate and extent of hybridization may be greatly increased. Computer programs are available to search for this type of interaction. However, in certain instances, it may not be possible to avoid this type of interaction.

The probes of the present invention are designed for attaining optimal performance under the same hybridization conditions so that they can be used in sets for simultaneous hybridization; this highly increases the usability of these probes and results in a significant gain in time and labour. Evidently, when other hybridization conditions should be preferred all probes should be adapted accordingly by adding or deleting a number of nucleotides at their extremities. It should be understood that these concommitant adaptations should give rise to essentially the same result, namely that the respective probes still hybridize specifically with the defined target. Such adaptations might also be necessary if the amplified material should be RNA in nature and not DNA as in the case for the NASBA system.

The hybridization conditions can be monitored relying upon several parameters, such as the nature and concentration of the components of the media, and the temperatures under which the hybrids are formed and washed.

The hybridization and wash temperature is limited in upper value depending on the sequence of the probe (its nucleic acid composition, kind and length). The maximum hybridization or wash temperature of the probes described in the present invention ranges from 40° C. to 60° C., more preferably from 45° C. to 55° C., in the specific hybridization and wash media as described in the Examples section. At higher temperatures duplexing (=formation of the hybrids) competes with the dissociation (or denaturation) of the hybrid formed between the probe and the target.

In a preferred hybridization medium of the invention, containing 3× SSC and 20% formamide, hybridization temperatures can range from 45° C. to 55° C., with a preferred hybridization temperature of 50° C. A preferred wash medium contains 3× SSC and 20% formamide, and preferred wash temperatures are the same as the preferred hybridization temperatures, i.e. preferably between 45° C. and 55° C., and most preferably 50° C.

However, when modifications are introduced, be it either in the probes or in the media, the temperatures at which the probes can be used to obtain the required specificity should be changed according to known relationships, such as those described in the following reference: Hames B and Higgins S (eds.). Nucleic acid hybridization. A practical approach, IRL Press, Oxford, U.K., 1985.

The selected nucleic acid probes derived from the 16S-23S rRNA spacer region and described by the present invention are listed in Table 1a (SEQ ID NO 1 to 64, 175 to 191, 193 to 201, and 210 to 212). As described in the examples section, some of these probes show a better sensitivity and/or specificity than others, and the better probes are therefore preferentially used in methods to detect the organism of interest in a biological sample. However, it is possible that for certain applications (e.g. epidemiology, substrain typing, . . . ) a set of probes including the less specific and/or less sensitive probes may be very informative (see e.g. example 7).

The following definitions serve to illustrate the terms and expressions used in the different embodiments of the present invention as set out below.

The term "spacer" is an abbreviated term referring to the 16S-23S rRNA internal transcribed spacer region.

The term "probe" refers to single stranded sequence-specific oligonucleotides which have a sequence which is sufficiently complementary to hybridize to the target sequence to be detected.

The more specific term "spacer probe" refers to a probe as defined above having a sequence which is sufficiently complementary to hybridize to a target sequence which is located in the spacer region(s) of the organism (or group of organisms) to be detected.

Preferably said probes are 70%, 80%, 90%, or more than 95% homologous to the exact complement of the target sequence to be detected. These target sequences are either genomic DNA or precursor RNA, or amplified versions thereof.

Preferably, these probes are about 5 to 50 nucleotides long, more preferably from about 10 to 25 nucleotides. The nucleotides as used in the present invention may be ribonucleotides, deoxyribonucleotides and modified nucleotides such as inosine or nucleotides containing modified groups which do not essentially alter their hybridization characteristics. Moreover, it is obvious to the man skilled in the art that any of the below-specified probes can be used as such, or in their complementary form, or in their RNA form (wherein T is replaced by U).

The probes according to the invention can be formed by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

The term "complementary" nucleic acids as used herein means that the nucleic acid sequences can form a perfect base-paired double helix with each other.

The term "homologous" as used in the current application is synonymous for identical: this means that polynucleic acids which are said to be e.g. 80% homologous show 80% identical base pairs in the same position upon alignment of the sequences.

The term "polynucleic acid" corresponds to either double-stranded or single-stranded cDNA or genomic DNA or RNA, containing at least 10, 20, 30, 40 or 50 contiguous nucleotides. A polynucleic acid which is smaller than 100 nucleotides in length is often also referred to as an oligonucleotide. Single stranded polynucleic acid sequences are always represented in the current invention from the 5' end to the 3' end.

The term 'closest neighbour' means the taxon which is known or expected to be most closely related in terms of DNA homology and which has to be differentiated from the organism of interest.

The expression 'desired hybridization characteristics' means that the probe only hybridizes to the DNA or RNA from organisms for which it was designed, and not to DNA or RNA from other organisms (closest neighbours or organisms liable to be present in the same sample) in practice, this means that the intensity of the hybridization signal is at least two, three, four, five, ten or more times stronger with the target DNA or RNA from the organisms for which the probes were designed, as compared to non-target sequences.

These desired hybridization characteristics correspond to what is called later in the text "specific hybridization".

The expression "taxon-specific hybridization" or "taxon-specific probe" means that the probe only hybridizes to the DNA or RNA from the taxon for which it was designed and not to DNA or RNA from other taxa.

The term taxon can refer to a complete genus or a subgroup within a genus, a species or even subtype within a species (subspecies, serovars, sequevars, biovars . . . ).

The term "specific amplification" or "specific primers" refers to the fact that said primers only amplify the spacer region from these organisms for which they were designed, and not from other organisms.

The term "sensitivity" refers to the number of false negatives: i.e. if 1 of the 100 strains to be detected is missed out, the test shows a sensitivity of (100-1/100)%=99%.

The term "specificity" refers to the number of false positives: i.e. if on 100 strains detected, 2 seem to belong to organisms for which the test is not designed, the specificity of the test is (100-2/100)%=98%.

The probes selected as being "preferential" show a sensitivity and specificity of more than 80%, preferably more than 90% and most preferably more than 95%.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides long. Specific length and sequence will depend on the complexity of the required DNA or RNA targets, as well as on the conditions of primer use such as temperature and ionic strength. The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton. 1991), transcription-based amplification system C(AS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The oligonucleotides used as primers or probes may also comprise nucleotide analogues such as phosphorothioates (Matsukura et al., 1987), alkylphosphorothioates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or by the use of labelled primers, or by any other method known to the person skilled in the art. The nature of the label may be isotopic ($^{32}P$, $^{35}S$, etc.) or non-isotopic (biotin, digoxigenin, etc.).

The "sample" may be any biological material taken either directly from the infected human being (or animal), or after culturing (enrichment), or a sample taken from food or feed. Biological material may be e.g. expectorations of any kind, broncheolavages, blood, ski tissue, biopsies, lymphocyte blood culture material, colonies, etc. Said samples may be prepared or extracted according to any of the techniques known in the art.

The "target" material in these samples may be either genomic DNA or precursor RNA of the organism to be detected (=target organism), or amplified versions thereof as set out above. More specifically, the nucleic acid sequence of the target material is localized in the spacer region of the target organism(s).

Detection and identification of the target material can be performed by using one of the many electrophoresis methods, hybridization methods or sequencing methods described in literature and currently known by men skilled in the art. However, a very convenient and advantageous technique for the simultaneous detection of nucleic acids possibly present in biological samples is the Line Probe Assay technique. The Line Probe Assay (LiPA) is a reverse hybridization format (Saiki et al., 1989) using membrane strips onto which several oligonucleotide probes (including negative or positive control oligonucleotides) can be conveniently applied as parallel lines.

The LiPA technique, as described by Stuyver et al. (1993) and in international application WO 94/12670, provides a very rapid and user-friendly hybridization test. Results can be read within 4 h. after the start of the amplification. After amplification during which usually a non-isotopic label is incorporated in the amplified product, and alkaline denaturation, the amplified product is contacted with the probes on the membrane and the hybridization is carried out for about 1 to 1.5 h. Consequently, the hybrids formed are detected by an enzymatic procedure resulting in a visual purple-brown precipitate. The LiPA format is completely compatible with commercially availabe scanning devices, thus rendering automatic interpretation of the results possible. All those advantages make the LiPA format liable for use in a routine setting.

The LiPA format is not only an advantageous tool for identification and detection of pathogens at the species level but also at higher or lower taxonomical levels. For instance, probe-configurations on LiPA strips can be selected in such a manner that they can detect a complete genus (e.g. *Neisseria, Listeria*, etc.) or can identify subgroups within a genus (e.g. subgroups in the *Mycobacterium avium-intracellulare-scrofulaceum* complex) or can in some cases even detect subtypes (subspecies, serovars, sequevars, biovars, etc. whatever is clinically relevant) within a species.

It should be stressed that the ability to simultaneously generate hybridization results with a number of probes is an outstanding benefit of the LiPA technology. In many cases the amount of information which can be obtained by a particular combination of probes greatly outnumbers the data obtained by using single probe assays. Therefor the selection of probes on the membrane strip is of utmost importance since an optimized set of probes will generate the maximum of information possible. This is more particularly exemplified further herein.

The fact that different probes can be combined on one strip also offers the possibility to conveniently cope with a lack of sensitivity due to sequence heterogeneity in the target region of the group of organisms to be detected. Due to this heterogenity, two or more probes may be required to positively identify all organisms of the particular group. These probes can be applied to membrane strips at different locations and the result is interpreted as positive if at least one of these probes is positive. Alternatively these probes can be applied as a mixture at the same location, hereby reducing the number of lines on a strip. This reduction may be convenient in order to make the strip more concise or to be able to extend the total number of probes on one strip. Another alternative approach, in view of its practical benefits, is the synthesis of oligonucleotides harbouring the sequences of two (or more) different probes (=degenerate probes) which then can be further processed and applied to the strip as one oligonucleotide molecule. This approach would considerably simplify the manufacturing procedures of the LiPA-strips. For example, probes with nucleotide sequences A and B are both required to detect all strains of taxon X. In the latter alternative a probe can be synthesized having the nucleotide sequence AB. This probe will have the combined characteristics of probes A and B.

By virtue of the above-mentioned properties the LiPA system can be considered as a preferential format for a hybridization method wherein several organisms need to be detected simultaneously in a sample. Moreover, as described in the examples section, the LiPA system is a preferred format for a selection method for the experimental evaluation and selection of theoretically designed probes.

However, it should be clear that any other hybridization assay, whereby different probes are used under the same hybridization and wash conditions can be used for the above-mentioned detection and/or selection methods. For example, it may be possible to immobilize the target nucleic acid to a solid support, and use mixtures of different probes, all differently labeled, resulting in a different detection signal for each of the probes hybridized to the target.

As an example, the procedure to be followed for the detection of one or more organisms in a sample using the LiPA format is outlined below:

First, the nucleic acids of the organism(s) to be detected in the sample, is made available for amplification and/or hybridization.

Secondly, the nucleic acids, if present, are amplified with one or another target amplification system, as specified below. Usually, amplification is needed to enhance the subsequent hybridization signal. However for some samples or some organisms amplification might not be necessary. This might also be the case if, for the detection of the hybrids formed, highly sensitive signal-amplification systems are used.

Thirdly, eventually after a denaturation step, the nucleic acids present in the sample or the resulting amplified product are contacted with LiPA strips onto which one or more DNA-probes, allowing the detection of the organisms of interest, are immobilized, and hybridization is allowed to proceed.

Finally, eventually after having performed a wash step, the hybrids are detected using a convenient and compatible detection system. From the hybridization signals or patterns observed the presence or absence of one or several organisms screened for in that particular biological sample can be deduced.

The amplification system used may be more or less universal, depending on the specific application needed.

By using universal primers located in the conserved flanking regions (16S and 23S gene) of the rRNA spacer, the spacer region of most if not all organisms of eubacterial origin will be amplified. The same result may be obtained by using a combination of different sets of primers with reduced universality (multiplex amplification, i.e. an amplification procedure in which two or more primer sets are used simultaneously in one and the same reaction mixture).

For some applications it may be appropriate to amplify not all organisms present in the sample but more specifically, beforehand defined taxa. This may be achieved using specific primers located either in less conserved parts of the flanking genes of the spacers (e.g. MYCP1-5 for amplification of the spacer region of mycobacteria) or located in the spacers themselves (e.g. LIS-P1-P7, BRU-P14, CHTR-P1-2 and YEC-P1-2 for specific amplification of the spacer region(s) of *Listeria* species, *Brucella* species, *Chlamydia trachomatis*, and *Yersinia enterocolitica* respectively).

The present invention thus provides a method for detection and identification of at least one micro-organism, or for the simultaneous detection of several micro-organisms in a sample, comprising the steps of:
(i) if need be releasing, isolating and/or concentrating the polynucleic acids from the micro-organism(s) to be detected in the sample;
(ii) if need be amplifying the 16S-23S rRNA spacer region, or a part of it, from the micro-organism(s) to be detected, with at least one suitable primer pair;
(iii) hybridizing the polynucleic acids of step (i) or (ii) with a set of probes comprising at least two probes, under the same hybridization and wash conditions, with said probes being selected from the sequences of table 1a or equivalents thereof and/or from taxon-specific probes derived from any of the spacer sequences represented in FIGS. 1-103, with said taxon-specific probe being selected such that it is capable of hybridizing under the same hybridization and wash conditions as at least one of the probes of table 1a;
(iv) detecting the hybrids formed in step (iii);
(v) identification of the micro-organism(s) present in the sample from the differential hybridization signals obtained in step (iv).

The probes as mentioned in table 1a are all selected in such a way that they show the desired hybridization characteristics at a hybridization and wash temperature of 50° C. in a preferred hybridization and wash medium of 3× SSC and 20% formanmide.

The term "equivalents" of a probe, also called "variants" or "homologues" or "obvious derivatives", refers to probes differing in sequence from any of the probes specified in table 1 either by addition to or removal from any of their respective extremities of one or several nucleotides, or by changing one or more nucleotides within said sequences, or a combination of both, provided that said equivalents still hybridize with the same RNA or DNA target as the corresponding unmodified probe sequence. Said equivalents share at least 75 % homology, preferably more than 80%, most preferably more than 85 % homology with the corresponding unmodified probe sequence. It should be noted that, when using an equivalent of a probe, it may be necessary to modify the hybridization conditions to obtain the same specificity as the corresponding unmodified probe. As a consequence, since it is the aim of this invention to use a set of probes which work under the same hybridization and wash conditions, it will also be necessary to modify accordingly the sequence of the other probes, belonging to the same set as the original unmodified probe. These modifications can be done according to principles known in the art, e.g. such as those described in Hames B and Higgins S (Eds): Nucleic acid hybridization. Practical approach. IRL Press, Oxford, UK, 1985.

The invention also provides for a method to select taxon-specific probes from the spacer region sequence(s) of said taxon, said probes being selected such that they show their desired hybridization characteristics under unified hybridization and wash conditions.

The term "unified" conditions means that these conditions are the same for the different probes enabling the detection of different taxa.

Preferentially, the present invention provides for a method as described above wherein at least 2 micro-organisms are detected simultaneously.

In a preferred embodiment, the set of probes as described in step (iii) is comprising at least two probes being selected from the sequences of table 1a, or equivalents thereof.

In another embodiment, the set of probes as described in step (iii) is comprising at least one probe being selected from the sequences of table 1a, or equivalents thereof, and at least one taxon-specific probe derived from any of the spacer sequences as represented in FIGS. 1-103.

In still another embodiment, the set of probes as described in step (iii) is comprising at least two taxon-specific probes derived from any of the spacer sequences as represented in FIGS. 1-103.

The present invention also provides for a method as described above, wherein the probes as specified in step (iii) are combined with at least one other probe, preferentially also from the 16S-23S rRNA spacer region, enabling the simultaneous detection of different pathogenic bacteria liable to be present in the same sample.

The organisms of clinical relevance present in biological samples may vary considerably depending on the origin of the sample. The most common pathogenic bacteria which may be found in sputum samples, or in samples originating from the respiratory tract, are:
- Moraxella catarrhalis
- Streptococcus pneumomiae
- Haemophilus influenzae
- Pseudomonas aeruginosa
- Mycoplasma pneumomiae
- Acinetobacter species
- Mycobacterium species
- Staphylococcus aureus
- Legionella pneumophila A LiPA-strip harbouring spacer-probes enabling the detection of most if not all of these organisms would be extremely beneficial for reasons explained above.

Evidently, this also applies for other biological samples, as there are cerebrospinal fluid, urogenital samples, gastrointestinal samples, blood, urine, food products, soil, etc. For example, a preferred panel for cerebrospinal fluid would contain probe combinations enabling the detection and differentiation of the following organisms
- Neisseria meningitidis
- Streptococcus pneumoniae
- Streptococcus agalactiae
- Listeria monocytogenes
- Mycobacterium tuberculosis For some of the above mentioned organisms, spacer probes were already designed in a previous patent application (WO 91/16454). In order to be able to detect most pathogens possibly present in a sample in a single test, the probes of the present invention may be combined with at least one of the probes of WO 91/16454, or their obvious derivatives as specified in WO 91/16454. For clarity, these probes are listed hereafter:

```
Neisseria gonorrheoae:
NGI1:
CGATGCGTCGTTATTCTACTTCGC

NGI2:
TTCGTTTACCTACCCGTTGACTAAGTAAGCAAAC

Neisseria meningitidis:
NMI1:
GGTCAAGTGTGACGTCGCCCTG

NMI2:
GTTCTTGGTCAAGTGTGACGTC

NMI3:
GCGTTCGTTATAGCTATCTACTGTGC

NMI4:
TGCGTTCGATATTGCTATCTACTGTGCA

NMI5:
TTTTGTTCTTGGTCAAGTGTGACGTCGCCCTGAA
TGGATTCTGTTCCATT

NMI6:
TTTGCCTAACATTCCGTTGACTAGAACATCAGAC

Haemophilus ducrevi
HDI1:
TTATTATGCGCGAGGCATATTG

Branharnella catharralis
BCI1:
TTAAACATCTTACCAAAG

BCI2:
TTGATGTTTAAACTTGCTTGGTGGA

Bordetella pertussis
BPI1:
CCACACCCATCCTCTGGACAGGCTT

Haemophilus influenzae
HII1:
ACGCATCAAATTGACCGCACTT

HII2:
ACTTTGAAGTGAAAACTTAAAG

Streptococcus agalactiae
SAI1:
AATCGAAAGGTTCAAATTGTT

SAI2:
GGAAACCTGCCATTTGCGTCTT

SAI3:
TCCACGATCTAGAAATAGATTGTAGAA

SAI4:
TCTAGTTTTAAAGAAACTAGGTT

Streptococcus pneumoniae
SPI1:
GTGAGAGATCACCAAGTAATGCA

SPI2:
AGGAACTGCGCATTGGTCTT

SPI3:
GAGTTTATGACTGAAAGGTCAGAA
```

The invention thus provides for a method as described above, wherein said sample is originating from the respiratory tract, and wherein the set of probes as defined in step (iii) comprises at least one probe chosen from the following spacer probes:

| | | |
|---|---|---|
| MYC-ICG-1: | ACTGGATAGTGGTTGCGAGCATCTA | (SEQ ID NO 1) |
| MYC-ICG-22: | CTTCTGAATAGTGGTTGCGAGCATCT | (SEQ ID NO 2) |
| MTB-ICG-1: | GGGTGCATGACAACAAAGTTGGCCA | (SEQ ID NO 3) |
| MTB-ICG-2: | GACTTGTTCCAGGTGTTGTCCCAC | (SEQ ID NO 4) |
| MTB-ICG-3: | CGGCTAGCGGTGGCGTGTTCT | (SEQ ID NO 5) |
| MAI-ICG-1: | CAACAGCAAATGATTGCCAGACACAC | (SEQ ID NO 6) |
| MIL-ICG-11: | GAGGGGTTCCCGTCTGTAGTG | (SEQ ID NO 7) |
| MIL-ICG-22: | TGAGGGGTTCTCGTCTGTAGTG | (SEQ ID NO 8) |
| MAC-ICG-1: | CACTCGGTCGATCCGTGTGGA | (SEQ ID NO 9) |
| MAV-ICG-1: | TCGGTCCGTCCGTGTGGAGTC | (SEQ ID NO 10) |
| MAV-ICG-22: | GTGGCCGGCGTTCATCGAAA | (SEQ ID NO 11) |

```
MIN-ICG-1:
GCATAGTCCTTAGGGCTGATGCGTT              (SEQ ID NO 12)

MIN-ICG-2:
GCTGATGCGTTCGTCGAAATGTGTA              (SEQ ID NO 13)

MIN-ICG-22:
CTGATGCGTTCGTCGAAATGTGT                (SEQ ID NO 14)

MIN-ICG-222:
TGATGCGTTCGTCGAAATGTGT                 (SEQ ID NO 15)

MIN-ICG-2222:
GGCTGATGCGTTCGTCGAAATGTGTAA            (SEQ ID NO 16)

MAL-ICG-1:
ACTAGATGAACGCGTAGTCCTTGT               (SEQ ID NO 17)

MHEF-ICG-1:
TGGACGAAAACCGGGTGCACAA                 (SEQ ID NO 18)

MAH-ICG-1:
GTGTAATTTCTTTTTTAACTCTTGTGTGTAAGTA     (SEQ ID NO 19)
AGTG

MCO-ICG-11:
TGGCCGGCGTGTTCATCGAAA                  (SEQ ID NO 20)

MTH-ICG-11:
GCACTTCAATTGGTGAAGTGCGAGCC             (SEQ ID NO 21)

MTH-ICG-2:
GCGTGGTCTTCATGGCCGG                    (SEQ ID NO 22)

MEF-ICG-11:
ACGCGTGGTCCTTCGTGG                     (SEQ ID NO 23)

MSC-ICG-1:
TCGGCTCGTTCTGAGTGGTGTC                 (SEQ ID NO 24)

MKA-ICG-1:
GATGCGTTTGCTACGGGTAGCGT                (SEQ ID NO 25)

MKA-ICG-2:
GATGCGTTGCCTACGGGTAGCGT                (SEQ ID NO 26)

MKA-ICG-3:
ATGCGTTGCCCTACGGGTAGCGT                (SEQ ID NO 27)

MKA-ICG-4:
CGGGCTCTGTTCGAGAGTTGTC                 (SEQ ID NO 28)

MKA-ICG-5:
CCCTCAGGGATTTTCTGGGTGTTG               (SEQ ID NO 182)

MKA-IGG-6:
GGACTCGTCCAAGAGTGTTGTCC                (SEQ ID NO 183)

MKA-ICG-7:
TCGGGCTTGGCCAGAGCTGTT                  (SEQ ID NO 184)

MKA-ICG-8:
GGGTGCGCAACAGCAAGCGA                   (SEQ ID NO 185)

MKA-ICG-9:
GATGCGTTGCCCCTACGGG                    (SEQ ID NO 186)

MKA-ICG-10:
CCCTACGGGTAGCGTGTTCTTTTG               (SEQ ID NO 187)

MCH-ICG-1:
GGTGTGGACTTTGACTTCTGAATAG              (SEQ ID NO 29)

MCH-ICG-2:
CGGCAAAACGTCGGACTGTCA                  (SEQ ID NO 30)

MCH-ICG-3:
GGTGTGGTCCTTGACTTATGGATAG              (SEQ ID NO 210)

MGO-ICG-1:
AACACCCTCGGGTGCTGTCC                   (SEQ ID NO 31)

MGO-ICG-2:
GTATGCGTTGTCGTTCGCGGC                  (SEQ ID NO 32)

MGO-ICG-5:
CGTGAGGGGTCATCGTCTGTAG                 (SEQ ID NO 33)

MUL-ICG-1:
GGTTTCGGATGTTGTCCCACC                  (SEQ ID NO 175)

MGV-ICG-1:
CGACTGAGGTCGACGTGGTGT                  (SEQ ID NO 176)

MGV-ICG-2:
GGTGTTTGAGCATTGAATAGTGGTTGC            (SEQ ID NO 177)

MGV-ICG-3:
TCGGGCCGCGTGTTCGTCAAA                  (SEQ ID NO 211)

MXE-ICG-1:
GTTGGGCAGCAGGCAGTAACC                  (SEQ ID NO 178)

MSI-ICG-1:
CCGGCAACGGTTACGTGTTC                   (SEQ ID NO 179)

MFO-ICG-1:
TCGTTGGATGGCCTCGCACCT                  (SEQ ID NO 180)

MFO-ICG-2:
ACTTGGCGTGGGATGCGGAA                   (SEQ ID NO 181)

MML-ICG-1:
CGGATCGATTGAGTGCTTGTCCC                (SEQ ID NO 188)

MML-ICG-2:
TCTAAATGAACGCACTGCCGATGG               (SEQ ID NO 189)

MCE-ICG-1:
TGAGGGAGCCCGTGCCTGTA                   (SEQ ID NO 190)

MHP-ICG-1:
CATGTTGGGCTTGATCGGGTGC                 (SEQ ID NO 191)

PA-ICG 1:
TGGTGTGCTGCGTGATCCGAT                  (SEQ ID NO 34)

PA-ICG 2:
TGAATGTTCGTGGATGAACATTGATT             (SEQ ID NO 35)

PA-ICG 3:
CACTGGTGATCATTCAAGTCAAG                (SEQ ID NO 36)

PA-ICG 4:
TGAATGTTCGT(G/A)(G/A)ATGAACATTGATT     (SEQ ID NO 37)
TCTGGTC

PA-ICG 5:
CTCTTTCACTGGTGATCATTCAAGTCAAG          (SEQ ID NO 38)

MPN-ICG 1:
ATCGGTGGTAATTAAACCCAAATCCCTGT          (SEQ ID NO 49)

MPN-ICG 2:
CAGTTCTGAAAGAACATTTCCGCTTCTTTC         (SEQ ID NO 50)

MGE-ICG 1:
CACCCATTAATTTTTCGGTGTTAAAACCC          (SEQ ID NO 51)

Mycoplasma-ICG:
CAAAACTGAAAACGACAATCTTTCTAGTTCC        (SEQ ID NO 52)

STAU-ICG 1:
TACCAAGCAAAACCGAGTGAATAAAGAGTT         (SEQ ID NO 53)

STAU-ICG 2:
CAGAAGATGCGGAATAACGTGAC                (SEQ ID NO 54)
```

-continued

```
STAU-ICG 3:
AACGAAGCCGTATGTGAGCATTTGAC              (SEQ ID NO 55)

STAU-ICG 4:
GAACGTAACTTCATGTTAACGTTTGACTTAT         (SEQ ID NO 56)

ACI-ICG 1:
GCTTAAGTGCACAGTGCTCTAAACTGA             (SEQ ID NO 57)

ACI-ICG 2:
CACGGTAATTAGTGTGATCTGACGAAG             (SEQ ID NO 58)
``` and more preferably from the following spacer probes:

```
MYC-ICG-1:
ACTGGATAGTGGTTGCGAGCATCTA               (SEQ ID NO 1)

MYC-ICG-22:
CTTCTGAATAGTGGTTGCGAGCATCT              (SEQ ID NO 2)

MTB-ICG-1:
GGGTGCATGACAACAAAGTTGGCCA               (SEQ ID NO 3)

MTB-ICG-2:
GACTTGTTCCAGGTGTTGTCCCAC                (SEQ ID NO 4)

MTB-ICG-3:
CGGCTAGCGGTGGCGTGTTCT                   (SEQ ID NO 5)

MAI-ICG-1:
CAACAGCAAATGATTGCCAGACACAC              (SEQ ID NO 6)

MIL-ICG-11:
GAGGGGTTCCCGTCTGTAGTG                   (SEQ ID NO 7)

MIL-ICG-22:
TGAGGGGTTCTCGTCTGTAGTG                  (SEQ ID NO 8)

MAC-ICG-1:
CACTCGGTCGATCCGTGTGGA                   (SEQ ID NO 9)

MAV-ICG-1:
TCGGTCCGTCCGTGTGGAGTC                   (SEQ ID NO 10)

MAV-ICG-22:
GTGGCCGGCGTTCATCGAAA                    (SEQ ID NO 11)

MIN-ICG-1:
GCATAGTCCTTAGGGCTGATGCGTT               (SEQ ID NO 12)

MAL-ICG-1:
ACTAGATGAACGCGTAGTCCTTGT                (SEQ ID NO 17)

MCO-ICG-11:
TGGCCGGCGTGTTCATCGAAA                   (SEQ ID NO 20)

MTH-ICG-11:
GCACTTCAATTGGTGAAGTGCGAGCC              (SEQ ID NO 21)

MTH-ICG-2:
GCGTGGTCTTCATGGCCGG                     (SEQ ID NO 22)

MEF-ICG-11:
ACGCGTGGTCCTTCGTGG                      (SEQ ID NO 23)

MSC-ICG-1:
TCGGCTCGTTCTGAGTGGTGTC                  (SEQ ID NO 24)

MKA-ICG-3:
ATGCGTTGCCCTACGGGTAGCGT                 (SEQ ID NO 27)

MKA-ICG-4:
CGGGCTCTGTTCGAGAGTTGTC                  (SEQ ID NO 28)

MKA-ICG-5:
CCCTCAGGGATTTTCTGGGTGTTG                (SEQ ID NO 182)

MKA-ICG-6:
GGACTCGTCCAAGAGTGTTGTCC                 (SEQ ID NO 183)

MKA-ICG-7:
TCGGGCTTGGCCAGAGCTGTT                   (SEQ ID NO 184)

MKA-ICG-8:
GGGTGCGCAACAGCAAGCGA                    (SEQ ID NO 185)

MKA-ICG-9:
GATGCGTTGCCCCTACGGG                     (SEQ ID NO 186)

MKA-ICG-10:
CCCTACGGGTAGCGTGTTCTTTTG                (SEQ ID NO 187)

MCH-ICG-1:
GGTGTGGACTTTGACTTCTGAATAG               (SEQ ID NO 29)

MCH-ICG-2:
CGGCAAAACGTCGGACTGTCA                   (SEQ ID NO 30)

MCH-ICG-3:
GGTGTGGTCCTTGACTTATGGATAG               (SEQ ID NO 210)

MGO-ICG-5:
CGTGAGGGGTCATCGTCTGTAG                  (SEQ ID NO 33)

MUL-ICG-1:
GGTTTCGGGATGTTGTCCCACC                  (SEQ ID NO 175)

MGV-ICG-1:
CGACTGAGGTCGACGTGGTGT                   (SEQ ID NO 176)

MGV-ICG-2:
GGTGTTTGAGCATTGAATAGTGGTTGC             (SEQ ID NO 177)

MGV-ICG-3:
TCGGGCCGCGTGTTCGTCAAA                   (SEQ ID NO 211)

MXE-ICG-1:
GTTGGGCAGCAGGCAGTAACC                   (SEQ ID NO 178)

MSI-ICG-1:
CCGGCAACGGTTACGTGTTC                    (SEQ ID NO 179)

MFO-ICG-1:
TCGTTGGATGGCCTCGCACCT                   (SEQ ID NO 180)

MFO-ICG-2:
ACTTGGCGTGGGATGCGGGAA                   (SEQ ID NO 181)

MML-ICG-1:
CGGATCGATTGAGTGCTTGTCCC                 (SEQ ID NO 188)

MML-ICG-2:
TCTAAATGAACGCACTGCCGATGG                (SEQ ID NO 189)

MCE-ICG-1:
TGAGGGAGCCCGTGCCTGTA                    (SEQ ID NO 190)

MHP-ICG-1:
CATGTTGGGCTTGATCGGGTGC                  (SEQ ID NO 191)

PA-ICG 1:
TGGTGTGCTGCGTGATCCGAT                   (SEQ ID NO 34)

PA-ICG 4:
TGAATGTTCGT(G/A)(G/A)ATGAACATTGATT      (SEQ ID NO 37)
TCTGGTC

PA-ICG 5:
CTCTTTCACTGGTGATCATTCAAGTCAAG           (SEQ ID NO 38)

MPN-ICG 1:
ATCGGTGGTAAATTAAACCCAAATCCCTGT          (SEQ ID NO 49)

MPN-ICG 2:
CAGTTCTGAAAGAACATTTCCGCTTCTTTC          (SEQ ID NO 50)
```

```
MGE-ICG 1:
CACCCATTAATTTTTTCGGTGTTAAAACCC          (SEQ ID NO 51)

Mycoplasma-ICG:
CAAAACTGAAAACGACAATCTTTCTAGTTCC         (SEQ ID NO 52)

STAU-ICG 1:
TACCAAGCAAAACCGAGTGAATAAAGAGTT          (SEQ ID NO 53)

STAU-ICG 2:
CAGAAGATGCGGAATAACGTGAC                 (SEQ ID NO 54)

STAU-ICG 3:
AACGAAGCCGTATGTGAGCATTTGAC              (SEQ ID NO 55)

STAU-ICG 4:
GAACGTAACTTCATGTTAACGTTTGACTTAT         (SEQ ID NO 56)

ACI-ICG 1:
GCTTAAGTGCACAGTGCTCTAAACTGA             (SEQ ID NO 57)

ACI-ICG 2:
CACGGTAATTAGTGTGATCTGACGAAG             (SEQ ID NO 58)
``` or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 76 to 106, 157 to 174, 124, 125, 111 to 115, 139 to 144, or 126 to 130, and with said probes or equivalents being possibly used in combination with any probe detecting at least one of the following organisms: *Haemophilus influenzae, Streptococcus pneumoniae, Moraxella catarrhalis* or *Bordetella pertussis*.

The above mentioned probes of the invention are designed for the detection of *Mycobacterium* species (SEQ ID NO 1 to 33 and 175 to 191), of *Pseudomonas aeruginosa* (SEQ ID NO 34 to 38), of *Mycoplasma* species (SEQ ID NO 49 to 52), of *Staphylococcus aureus* (SEQ ID NO 53 to 56) and of *Acinetobacter baumanii* (SEQ ID NO 57 and 58).

Preferentially, at least two, three, four, five, six, seven, eight or more of said probes are used simultaneously.

The invention also relates to a method as described above, wherein said sample is a sample taken from the cerebrospinal fluid, and wherein the set of probes as described in step (iii) comprises at least one probe chosen from the following spacer probes:

```
MYC-ICG-1:
ACTGGATAGTGGTTGCGAGCATCTA               (SEQ ID NO 1)

MYC-ICG-22:
CTTCTGAATAGTGGTTGCGAGCATCT              (SEQ ID NO 2)

MTB-ICG-1:
GGGTGCATGACAACAAAGTTGGCCA               (SEQ ID NO 3)

MTB-ICG-2:
GACTTGTTCCAGGTGTTGTCCCAC                (SEQ ID NO 4)

MTB-ICG-3:
CGGCTAGCGGTGGCGTGTTCT                   (SEQ ID NO 5)

LIS-ICG 1:
CAAGTAACCGAGAATCATCTGAAAGTGAATC         (SEQ ID NO 39)

LMO-ICG 1:
AAACAACCTTTACTTCGTAGAAGTAAATTGGT        (SEQ ID NO 40)

TAAG

LMO-ICG 2:
TGAGAGGTTAGTACTTCTCAGTATGTTTGTTC        (SEQ ID NO 41)

LMO-ICG 3:
AGGCACTATGCTTGAAGCATCGC                 (SEQ ID NO 42)

LISP-ICG 1:
CGTTTTCATAAGCGATCGCACGTT                (SEQ ID NO 212)
``` and preferably from the following spacer probes:

```
MYC-ICG-1:
ACTGGATAGTGGTTGCGAGCATCTA               (SEQ ID NO 1)

MYC-ICG-22:
CTTCTGAATAGTGGTTGCGAGCATCT              (SEQ ID NO 2)

MTB-ICG-1:
GGGTGCATGACAACAAAGTTGGCCA               (SEQ ID NO 3)

MTB-ICG-2:
GACTTGTTCCAGGTGTTGTCCCAC                (SEQ ID NO 4)

MTB-ICG-3:
CGGCTAGCGGTGGCGTGTTCT                   (SEQ ID NO 5)

LIS-ICG 1:
CAAGTAACCGAGAATCATCTGAAAGTGAATC         (SEQ ID NO 39)

LMO-ICG 3:
AGGCACTATGCTTGAAGCATCGC                 (SEQ ID NO 42)

LISP-ICG 1:
CGTTTTCATAAGCGATCGCACGTT                (SEQ ID NO 212)
``` or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 116, 118-121, or 213-215, and with said probes or equivalents being possibly used in combination with any probe detecting at least one of the following organisms: *Neisseria meningitidis, Haemophilus influenzae* or *Streptococcus pneumoniae*.

The above mentioned probes of the invention are designed for the detection of *Mycobacterium* species, and more particularly *Mycobacterium tuberculosis* (SEQ ID NO 1 to 5), and of *Listeria* species, more particularly *Listeria monocytogenes* (SEQ ID NO 39 to 42).

Preferentially, at least two, three, four, five, six, seven, eight or more of said probes are used simultaneously.

The invention also relates to a method as described above, wherein said sample is a sample taken from the urogenital tract, and wherein the set of probes as described in step (iii) comprises at least one probe chosen from the following spacer probes:

```
CHTR-ICG 1:
GGAAGAAGCCTGAGAAGGTTTCTGAC              (SEQ ID NO 45)

CHTR-ICG 2:
GCATTTATATGTAAGAGCAAGCATTCTATTTCA       (SEQ ID NO 46)

CHTR-ICG 3:
GAGTAGCGTGGTGAGGACGAGA                  (SEQ ID NO 47)
```

```
CHTR-ICG 4:
GAGTAGCGCGGTGAGGACGAGA            (SEQ ID NO 201)

CHPS-ICG 1:
GGATAACTGTCTTAGGACGGTTTGAC        (SEQ ID NO 48)

MGE-ICG 1:
CACCCATTAATTTTTTCGGTGTTAAAACCC    (SEQ ID NO 51)

Mycoplasma-ICG:
CAAAACTGAAAACGACAATCTTTCTAGTTCC   (SEQ ID NO 52)
``` or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 122, 123, 197, 124 or 125, with said probes or equivalents being possibly used in combination with any probe detecting at least one of the following organisms: *Neisseria gonorrhoeae, Haemophilus ducreyi* or *Streptococcus agalactiae*.

The above mentioned probes of the invention are designed for the detection of *Chlamydia* species (SEQ ID NO 45 to 48 and 201) and of *Mycoplasma* species (SEQ ID NO 51 and 52).

Preferentially, at least two, three, four, five, six or seven of said probes are used simultaneously.

The invention also relates to a method as described above, wherein said sample is a sample taken from food, and wherein the set of probes as defined in step (iii) comprises at least one probe chosen from the following spacer probes:

```
LIS-ICG 1:
CAAGTAACCGAGAATCATCTGAAAGTGAATC   (SEQ ID NO 39)

LMO-ICG 1:
AAACAACCTTTACTTCGTAGAAGTAAATTGGTT (SEQ ID NO 40)
AAG

LMO-ICG 2:
TGAGAGGTTAGTACTTCTCAGTATGTTTGTTC  (SEQ ID NO 41)

LMO-ICG 3:
AGGCACTATGCTTGAAGCATCGC           (SEQ ID NO 42)

LIV-ICG 1:
GTTAGCATAAATAGGTAACTATTTATGACACAA (SEQ ID NO 43)
GTAAC

LSE-ICG 1:
AGTTAGCATAAGTAGTGTAACTATTTATGACAC (SEQ ID NO 44)
AAG

LISP-ICG 1:
CGTTTTCATAAGCGATCGCACGTT          (SEQ ID NO 212)

STAU-ICG 1:
TACCAAGCAAAACCGAGTGAATAAAGAGTT    (SEQ ID NO 53)

STAU-ICG 2:
CAGAAGATGCGGAATAACGTGAC           (SEQ ID NO 54)

STAU-ICG 3:
AACGAAGCCGTATGTGAGCATTTGAC        (SEQ ID NO 55)

STAU-ICG 4:
GAACGTAACTTCATGTTAACGTTTGACTTAT   (SEQ ID NO 56)

BRU-ICG 1:
CGTGCCGCCTTCGTTTCTCTTT            (SEQ ID NO 59)

BRU-ICG 2:
TTCGCTTCGGGGTGGATCTGTG            (SEQ ID NO 60)

BRU-ICG 3:
GCGTAGTAGCGTTTGCGTCGG             (SEQ ID NO 193)

BRU-ICG 4:
CGCAAGAAGCTTGCTCAAGCC             (SEQ ID NO 194)

SALM-ICG 1:
CAAAACTGACTTACGAGTCACGTTTGAG      (SEQ ID NO 61)

SALM-ICG 2:
GATGTATGCTTCGTTATTCCACGCC         (SEQ ID NO 62)

STY-ICG 1:
GGTCAAACCTCCAGGGACGCC             (SEQ ID NO 63)

SED-ICG 1:
GCGGTAATGTGTGAAAGCGTTGCC          (SEQ ID NO 64)

YEC-ICG 1:
GGAAAAGGTACTGCACGTGACTG           (SEQ ID NO 198)

YEC-ICG 2:
GACAGCTGAAACTTATCCCTCCG           (SEQ ID NO 199)

YEC-ICG 3:
GCTACCTGTTGATGTAATGAGTCAC         (SEQ ID NO 200)
``` and preferably from the following spacer probes:

```
LIS-ICG 1:
CAAGTAACCGAGAATCATCTGAAAGTGAATC   (SEQ ID NO 39)

LMO-ICG 3:
AGGCACTATGCTTGAAGCATCGC           (SEQ ID NO 42)

LISP-ICG 1:
CGTTTTCATAAGCGATCGCACGTT          (SEQ ID NO 212)

STAU-ICG 1:
TACCAAGCAAAACCGAGTGAATAAAGAGTT    (SEQ ID NO 53)

STAU-ICG 2:
CAGAAGATGCGGAATAACGTGAC           (SEQ ID NO 54)

STAU-ICG 3:
AACGAAGCCGTATGTGAGCATTTGAC        (SEQ ID NO 55)

STAU-ICG 4:
GAACGTAACTTCATGTTAACGTTTGACTTAT   (SEQ ID NO 56)

BRU-ICG 2:
TTCGCTTCGGGGTGGATCTGTG            (SEQ ID NO 60)

BRU-ICG 3:
GCGTAGTAGCGTTTGCGTCGG             (SEQ ID NO 193)

BRU-ICG 4:
CGCAAGAAGCTTGCTCAAGCC             (SEQ ID NO 194)

SALM-ICG 1:
CAAAACTGACTTACGAGTCACGTTTGAG      (SEQ ID NO 61)

YEC-ICG 1:
GGAAAAGGTACTGCACGTGACTG           (SEQ ID NO 198)

YEC-ICG 2:
GACAGCTGAAACTTATCCCTCCG           (SEQ ID NO 199)

YEC-ICG 3:
GCTACCTGTTGATGTAATGAGTCAC         (SEQ ID NO 200)
``` or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 116, 118-121, 213-215, 139-144, 131, 132, 154, 133-138, 195 or 196, with said probes or equivalents being possibly used in combination with any probe detecting strains of *Campylobacter* species.

The above mentioned probes of the invention are designed for the detection of *Listeria* species (SEQ ID NO 39 to 44), of *Staphylococcus* species (SEQ ID NO 53 to 56), of *Brucella* species (SEQ ID NO 59, 60, 193 and 194), of *Salmonella* species (SEQ ID NO 61 to 64) and of *Yersinia enterocolitica* (SEQ ID NO 198 to 200).

Preferentially, at least two, three, four, five, six, seven, eight or more of said probes are used simultaneously.

The invention also relates to a method as described above, wherein said sample is a sample taken from the gastrointestinal tract of a patient, and wherein the set of probes as defined in step (iii) comprises at least one probe chosen from the following spacer probes:

```
SALM-ICG 1:
CAAAACTGACTTACGAGTCACGTTTGAG      (SEQ ID NO 61)

SALM-ICG 2:
GATGTATGCTTCGTTATTCCACGCC         (SEQ ID NO 62)

STY-ICG 1:
GGTCAAACCTCCAGGGACGCC             (SEQ ID NO 63)

SED-ICG 1:
GCGGTAATGTGTGAAAGCGTTGCC          (SEQ ID NO 64)

YEC-ICG 1:
GGAAAAGGTACTGCACGTGACTG           (SEQ ID NO 198)

YEC-ICG 2:
GACAGCTGAAACTTATCCCTCCG           (SEQ ID NO 199)

YEC-ICG 3:
GCTACCTGTTGATGTAATGAGTCAC         (SEQ ID NO 200)
``` and preferably from the following spacer probes:

```
SALM-ICG 1:
CAAAACTGACTTACGAGTCACGTTTGAG      (SEQ ID NO 61)

YEC-ICG 1:
GGAAAAGGTACTGCACGTGACTG           (SEQ ID NO 198)

YEC-ICG 2:
GACAGCTGAAACTTATCCCTCCG           (SEQ ID NO 199)

YEC-ICG 3:
GCTACCTGTTGATGTAATGAGTCAC         (SEQ ID NO 200)
``` or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 133-138 or 195-196, with said probes or equivalents being possibly used in combination with any probe detecting *Campylobacter* species.

The above mentioned probes of the invention are designed to detect *Salmonella* species (SEQ ID NO 61 to 64) and *Yersinia enterocolitica* (SEQ ID NO 198 to 200).

Preferentially, at least two, three, four, five, six or seven of said probes are used simultaneously.

The invention also relates to the use of the selected probes or their equivalents for the detection of specific bacterial taxa, said taxa being either a complete genus, or a subgroup within a genus, a species, or even a subtype within a species.

The invention thus provides for a method as described above to detect and identify one or more strains of *Mycobacterium* species and subspecies in a sample, wherein step (iii) comprises hybridizing to at least one of the following probes:

```
MYC-ICG-1:
ACTGGATAGTGGTTGCGAGCATCTA         (SEQ ID NO 1)

MYC-ICG-22:
CTTCTGAATAGTGGTTGCGAGCATCT        (SEQ ID NO 2)

MTB-ICG-1:
GGGTGCATGACAACAAAGTTGGCCA         (SEQ ID NO 3)

MTB-ICG-2:
GACTTGTTCCAGGTGTTGTCCCAC          (SEQ ID NO 4)

MTB-ICG-3:
CGGCTAGCGGTGGCGTGTTCT             (SEQ ID NO 5)

MAI-ICG-1:
CAACAGCAAATGATTGCCAGACACAC        (SEQ ID NO 6)

MIL-ICG-11:
GAGGGGTTCCCGTCTGTAGTG             (SEQ ID NO 7)

MIL-ICG-22:
TGAGGGGTTCTCGTCTGTAGTG            (SEQ ID NO 8)

MAC-ICG-1:
CACTCGGTCGATCCGTGTGGA             (SEQ ID NO 9)

MAV-ICG-1:
TCGGTCCGTCCGTGTGGAGTC             (SEQ ID NO 10)

MAV-ICG-22:
GTGGCCGGCGTTCATCGAAA              (SEQ ID NO 11)

MIN-ICG-1:
GCATAGTCCTTAGGGCTGATGCGTT         (SEQ ID NO 12)

MIN-ICG-2:
GCTGATGCGTTCGTCGAAATGTGTA         (SEQ ID NO 13)

MIN-ICG-22:
CTGATGCGTTCGTCGAAATGTGT           (SEQ ID NO 14)

MIN-ICG-222:
TGATGCGTTCGTCGAAATGTGT            (SEQ ID NO 15)

MIN-ICG-2222:
GGCTGATGCGTTCGTCGAAATGTGTAA       (SEQ ID NO 16)

MAL-ICG-1:
ACTAGATGAACGCGTAGTCCTTGT          (SEQ ID NO 17)

MHEF-ICG-1:
TGGACGAAAACCGGGTGCACAA            (SEQ ID NO 18)

MAH-ICG-1:
GTGTAATTTCTTTTTTAACTCTTGTGTGTAAGTA (SEQ ID NO 19)
AGTG

MCO-ICG-11:
TGGCCGGCGTGTTCATCGAAA             (SEQ ID NO 20)

MTH-ICG-11:
GCACTTCAATTGGTGAAGTGCGAGCC        (SEQ ID NO 21)
```

-continued

```
MTH-ICG-2:
GCGTGGTCTTCATGGCCGG          (SEQ ID NO 22)

MEF-ICG-11:
ACGCGTGGTCCTTCGTGG           (SEQ ID NO 23)

MSC-ICG-1:
TCGGCTCGTTCTGAGTGGTGTC       (SEQ ID NO 24)

MKA-ICG-1:
GATGCGTTTGCTACGGGTAGCGT      (SEQ ID NO 25)

MKA-ICG-2:
GATGCGTTGCCTACGGGTAGCGT      (SEQ ID NO 26)

MKA-ICG-3:
ATGCGTTGCCCTACGGGTAGCGT      (SEQ ID NO 27)

MKA-ICG-4:
CGGGCTCTGTTCGAGAGTTGTC       (SEQ ID NO 28)

MKA-ICG-5:
CCCTCAGGGATTTTCTGGGTGTTG     (SEQ ID NO 182)

MKA-ICG-6:
GGACTCGTCCAAGAGTGTTGTCC      (SEQ ID NO 183)

MKA-ICG-7:
TCGGGCTTGGCCAGAGCTGTT        (SEQ ID NO 184)

MKA-ICG-8:
GGGTGCGCAACAGCAAGCGA         (SEQ ID NO 185)

MKA-ICG-9:
GATGCGTTGCCCCTACGGG          (SEQ ID NO 186)

MKA-ICG-10:
CCCTACGGGTAGCGTGTTCTTTTG     (SEQ ID NO 187)

MCH-ICG-1:
GGTGTGGACTTTGACTTCTGAATAG    (SEQ ID NO 29)

MCH-ICG-2:
CGGCAAAACGTCGGACTGTCA        (SEQ ID NO 30)

MGO-ICG-1:
AACACCCTCGGGTGCTGTCC         (SEQ ID NO 31)

MGO-ICG-2:
GTATGCGTTGTCGTTCGCGGC        (SEQ ID NO 32)

MGO-ICG-5:
CGTGAGGGGTCATCGTCTGTAG       (SEQ ID NO 33)

MUL-ICG-1:
GGTTTCGGGATGTTGTCCCACC       (SEQ ID NO 175)

MGV-ICG-1:
CGACTGAGGTCGACGTGGTGT        (SEQ ID NO 176)

MGV-ICG-2:
GGTGTTTGAGCATTGAATAGTGGTTGC  (SEQ ID NO 177)

MXE-ICG-1:
GTTGGGCAGCAGGCAGTAACC        (SEQ ID NO 178)

MSI-ICG-1:
CCGGCAACGGTTACGTGTTC         (SEQ ID NO 179)

MFO-ICG-1:
TCGTTGGATGGCCTCGCACCT        (SEQ ID NO 180)

MFO-ICG-2:
ACTTGGCGTGGGATGCGGGAA        (SEQ ID NO 181)

MML-ICG-1:
CGGATCGATTGAGTGCTTGTCCC      (SEQ ID NO 188)

MML-ICG-2:
TCTAAATGAACGCACTGCCGATGG     (SEQ ID NO 189)

MCE-ICG-1:
TGAGGGAGCCCGTGCCTGTA         (SEQ ID NO 190)

MHP-ICG-1:
CATGTTGGGCTTGATCGGGTGC       (SEQ ID NO 191)
``` and more preferably to at least one probe of the following restricted group of spacer probes:

```
MYC-ICG-1:
ACTGGATAGTGGTTGCGAGCATCTA    (SEQ ID NO 1)

MYC-ICG-22:
CTTCTGAATAGTGGTTGCGAGCATCT   (SEQ ID NO 2)

MTB-ICG-1:
GGGTGCATGACAACAAAGTTGGCCA    (SEQ ID NO 3)

MTB-ICG-2:
GACTTGTTCCAGGTGTTGTCCCAC     (SEQ ID NO 4)

MTB-ICG-3:
CGGCTAGCGGTGGCGTGTTCT        (SEQ ID NO 5)

MAI-ICG-1:
CAACAGCAAATGATTGCCAGACACAC   (SEQ ID NO 6)

MIL-ICG-11:
GAGGGGTTCCCGTCTGTAGTG        (SEQ ID NO 7)

MIL-ICG-22:
TGAGGGGTTCTCGTCTGTAGTG       (SEQ ID NO 8)

MAC-ICG-1:
CACTCGGTCGATCCGTGTGGA        (SEQ ID NO 9)

MAV-ICG-1:
TCGGTCCGTCCGTGTGGAGTC        (SEQ ID NO 10)

MAV-ICG-22:
GTGGCCGGCGTTCATCGAAA         (SEQ ID NO 11)

MIN-ICG-1:
GCATAGTCCTTAGGGCTGATGCGTT    (SEQ ID NO 12)

MAL-ICG-1:
ACTAGATGAACGCGTAGTCCTTGT     (SEQ ID NO 17)

MCO-ICG-11:
TGGCCGGCGTTCATCGAAA          (SEQ ID NO 20)

MTH-ICG-11:
GCACTTCAATTGGTGAAGTGCGAGCC   (SEQ ID NO 21)

MTH-ICG-2:
GCGTGGTCTTCATGGCCGG          (SEQ ID NO 22)

MEF-ICG-11:
ACGCGTGGTCCTTCGTGG           (SEQ ID NO 23)

MSC-ICG-1:
TCGGCTCGTTCTGAGTGGTGTC       (SEQ ID NO 24)

MKA-ICG-3:
ATGCGTTGCCCTACGGGTAGCGT      (SEQ ID NO 27)

MKA-ICG-4:
CGGGCTCTGTTCGAGAGTTGTC       (SEQ ID NO 28)

MKA-ICG-5:
CCCTCAGGGATTTTCTGGGTGTTG     (SEQ ID NO 182)
```

```
                        -continued

MKA-ICG-6:
GGACTCGTCCAAGAGTGTTGTCC          (SEQ ID NO 183)

MKA-ICG-7:
TCGGGCTTGGCCAGAGCTGTT            (SEQ ID NO 184)

MKA-ICG-8:
GGGTGCGCAACAGCAAGCGA             (SEQ ID NO 185)

MKA-ICG-9:
GATGCGTTGCCCCTACGGG              (SEQ ID NO 186)

MKA-ICG-10:
CCCTACGGGTAGCGTGTTCTTTTG         (SEQ ID NO 187)

MCH-ICG-1:
GGTGTGGACTTTGACTTCTGAATAG        (SEQ ID NO 29)

MCH-ICG-2:
CGGCAAAACGTCGGACTGTCA            (SEQ ID NO 30)

MCH-ICG-3:
GGTGTGGTCCTTGACTTATGGATAG        (SEQ ID NO 210)

MGO-ICG-5:
CGTGAGGGGTCATCGTCTGTAG           (SEQ ID NO 33)

MUL-ICG-1:
GGTTTCGGGATGTTGTCCCACC           (SEQ ID NO 175)

MGV-ICG-1:
CGACTGAGGTCGACGTGGTGT            (SEQ ID NO 176)

MGV-ICG-2:
GGTGTTTGAGCATTGAATAGTGGTTGC      (SEQ ID NO 177)

MGV-ICG-3:
TCGGGCCGCGTGTTCGTCAAA            (SEQ ID NO 211)

MXE-ICG-1:
GTTGGGCAGCAGGCAGTAACC            (SEQ ID NO 178)

MSI-ICG-1:
CCGGCAACGGTTACGTGTTC             (SEQ ID NO 179)

MFO-ICG-1:
TCGTTGGATGGCCTCGCACCT            (SEQ ID NO 180)

MFO-ICG-2:
ACTTGGCGTGGGATGCGGGAA            (SEQ ID NO 181)

MML-ICG-1:
CGGATCGATTGAGTGCTTGTCCC          (SEQ TD NO 188)

MML-ICG-2:
TCTAAATGAACGCACTGCCGATGG         (SEQ ID NO 189)

MCE-ICG-1:
TGAGGGAGCCCGTGCCTGTA             (SEQ ID NO 190)

MHP-ICG-1:
CATGTTGGGCTTGATCGGGTGC           (SEQ ID NO 191)
``` or to equivalents of said probes,
and/or to any probe derived from SEQ ID NO 76-110, or 157-174 provided said probe hybridizes specifically to a *Mycobacterium* species.

The sequences represented by SEQ ID NO 761-110 and 157-174 are new.

Preferentially, at least two, three, four, five, six, seven, eight or more of said probes are used simultaneously.

As described above, the preferred restricted set of probes are those probes which showed a sensitivity and specificity of more than 80%, preferably more than 90%, most preferably more than 95%, under the specific hybridization conditions as described in the examples section.

In one specific embodiment, the invention provides for a method as described above to detect and identify one or more *Mycobacterium tuberculosis* complex strains in a sample, wherein step (iii) comprises hybridizing to at least one of the following probes:

```
MTB-ICG-1:  GGGTGCATGACAACAAAGTTGGCCA   (SEQ ID NO 3)
MTB-ICG-2:  GACTTGTTCCAGGTGTTGTCCCAC    (SEQ ID NO 4)
MTB-ICG-3:  CGGCTAGCGGTGGCGTGTTCT       (SEQ ID NO 5)
``` or to equivalents of said probes,
and/or to any probe derived from SEQ ID NO 76 provided said probe hybridizes specifically to the *M. tuberculosis* complex. The *M. tuberculosis* complex comprises *M. tuberculosis*, *M. bovis*, *M. bovis* BCG, *M. africanum* and *M. microti* strains.

The sequence represented in SEQ ID NO 76 is new.

Preferentially, at least two, or three of said probes are used simultaneously.

In another specific embodiment, the invention provides for a method as described above to detect and identify one or more *Mycobacterium* strains from the MAIS-complex, wherein step (iii) comprises hybridizing to at least one of the following probes:

```
MAI-ICG-1:
CAACAGCAAATGATTGCCAGACACAC       (SEQ ID NO 6)

MIL-ICG-11:
GAGGGGTTCCCGTCTGTAGTG            (SEQ ID NO 7)

MIL-ICG-22:
TGAGGGGTTCTCGTCTGTAGTG           (SEQ ID NO 8)

MAC-ICG-1:
CACTCGGTCGATCCGTGTGGA            (SEQ ID NO 9)

MAV-ICG-1:
TCGGTCCGTCCGTGTGGAGTC            (SEQ ID NO 10)

MAV-ICG-22:
GTGGCCGGCGTTCATCGAAA             (SEQ ID NO 11)

MIN-ICG-1:
GCATAGTCCTTAGGGCTGATGCGTT        (SEQ ID NO 12)

MIN-ICG-2:
GCTGATGCGTTCGTCGAAATGTGTA        (SEQ ID NO 13)

MIN-ICG-22:
CTGATGCGTTCGTCGAAATGTGT          (SEQ ID NO 14)

MIN-ICG-222:
TGATGCGTTCGTCGAAATGTGT           (SEQ ID NO 15)

MIN-ICG-2222:
GGCTGATGCGTTCGTCGAAATGTGTAA      (SEQ ID NO 16)

MAL-ICG-1:
ACTAGATGAACGCGTAGTCCTTGT         (SEQ ID NO 17)

MHEF-ICG-1:
TGGACGAAAACCGGGTGCACAA           (SEQ ID NO 18)

MAH-ICG-1:
GTGTAATTTCTTTTTTAACTCTTGTGTGTAAGT    (SEQ ID NO 19)
AAGTG

MCO-ICG-11:
TGGCCGGCGTGTTCATCGAAA            (SEQ ID NO 20)
```

```
MTH-ICG-11:
GCACTTCAATTGGTGAAGTGCGAGCC        (SEQ ID NO 21)

MTH-ICG-2:
GCGTGGTCTTCATGGCCGG               (SEQ ID NO 22)

MEF-ICG-11:
ACGCGTGGTCCTTCGTGG                (SEQ ID NO 23)

MSC-ICG-1:
TCGGCTCGTTCTGAGTGGTGTC            (SEQ ID NO 24)
``` or to equivalents of said probes, and/or to any probe derived from SEQ ID NO 77-100 or 108-110, provided said probe hybridizes specifically to strains from the MAIS complex. The MAIS complex as defined in this invention comprises all strains of *M. avium, M. intracellulare* and *M. scrofulaceum* and all strains closely related to the above mentioned species and not clearly belonging to another defined *Mycobacterium* species. The latter group of strains are defined in this invention as "MIC strains" (*M. intracellulare* complex).

Preferentially, at least two, three, four, five, six, seven, eight or more of said probes are used simultaneously.

In still another specific embodiment, the invention provides for a method as described above, to detect and identify one or more *M. avium* and *M. paratuberculosis* strains in a sample, wherein step (iii) comprises hybridizing to at least one of the following probes:

```
MAV-ICG-1:    TCGGTCCGTCCGTGTGGAGTC  (SEQ ID NO 10)

MAV-ICG-22:   GTGGCCGGCGTTCATCGAAA   (SEQ ID NO 11)
``` or to equivalents of said probes, and/or to any probe derived from SEQ ID NO 77 and 78 provided said probe hybridizes specifically to *M. avium* or *M. paratuberculosis*.

The sequences as represented in SEQ ID NO 77 and 78 are new.

Preferentially, this embodiment uses both probes in combination.

In still another specific embodiment, the invention provides for a method as described above to detect and identify one or more *Mycobacterium intracellulare* strains and MIC-strains in a sample, wherein step (iii) comprises hybridizing to at least one of the following probes:

```
MAI-ICG-1:
CAACAGCAAATGATTGCCAGACACAC        (SEQ ID NO 6)

MIL-ICG-11:
GAGGGGTTCCCGTCTGTAGTG             (SEQ ID NO 7)

MIL-ICG-22:
TGAGGGGTTCTCGTCTGTAGTG            (SEQ ID NO 8)

MAC-ICG-1:
CACTCGGTCGATCCGTGTGGA             (SEQ ID NO 9)

MIN-ICG-1:
GCATAGTCCTTAGGGCTGATGCGTT         (SEQ ID NO 12)

MIN-ICG-2:
GCTGATGCGTTCGTCGAAATGTA           (SEQ ID NO 13)

MIN-ICG-22:
CTGATGCGTTCGTCGAAATGTGT           (SEQ ID NO 14)

MIN-ICG-222:
TGATGCGTTCGTCGAAATGTGT            (SEQ ID NO 15)

MIN-ICG-2222:
GGCTGATGCGTTCGTCGAAATGTGTAA       (SEQ ID NO 16)

MAL-ICG-1:
ACTAGATGAACGCGTAGTCCTTGT          (SEQ ID NO 17)

MHEF-ICG-1:
TGGACGAAAACCGGGTGCACAA            (SEQ ID NO 18)

MAH-ICG-1:
GTGTAATTTCTTTTTTAACTCTTGTGTGTAAGT (SEQ ID NO 19)
AAGTG

MCO-ICG-11:
TGGCCGGCGTGTTCATCGAAA             (SEQ ID NO 20)

MTH-ICG-11:
GCACTTCAATTGGTGAAGTGCGAGCC        (SEQ ID NO 21)

MTH-ICG-2:
GCGTGGTCTTCATGGCCGG               (SEQ ID NO 22)

MEF-ICG-11:
ACGCGTGGTCCTTCGTGG                (SEQ ID NO 23)
``` or to equivalents of said probes, and/or to any probe derived from SEQ ID NO 79, 80, 81, 82, 83, 84, 85, 86, 87, 88, 89, 90, 91, 92, 93, 94, 95, 96, 97, 98 or 99 provided said probe hybridizes specifically to *M. intracellulare* strains and MIC-strains.

The sequences as represented in SEQ ID NO 79, 80, 81, 82, 83, 84, 85, 86, 87, 88, 89, 90, 91, 92, 93, 94, 95, 96, 97, 98 or 99 are new.

Preferentially, at least two, three, four, five, six, seven, eight or more of said probes are used simultaneously.

In still another specific embodiment, the invention provides for a method as described above, to detect and identify one or more *Mycobacterium intracellulare* strains in a sample, wherein step (iii) comprises hybridizing to at least the following probes:

```
MIN-ICG-1:
  GCATAGTCCTTAGGGCTGATGCGTT       (SEQ ID NO 12)
``` or to equivalents of said probe, and/or to any probe derived from SEQ ID NO 89 provided said probe hybridizes specifically to *M. intracellulare* strains.

In still another specific embodiment, the invention provides for a method as described above, to detect and identify one or more *Mycobacterium scrofulaceum* strains in a sample, wherein step (iii) comprises hybridizing to the following probe:

```
MSC-ICG-1:   TCGGCTCGTTCTGAGTGGTGTC  (SEQ ID NO 24)
``` or to equivalents of said probes, and/or to any probe derived from SEQ ID NO 100 provided said probe hybridizes specifically to *M. scrofulaceum*.

The sequence as represented in SEQ ID NO 100 is new.

In still another specific embodiment, the invention provides for a method as described above to detect and identify one or more *Mycobacterium kansasii* strains in a sample, wherein step (iii) comprises hybridizing to at least one of the following probes:

```
MKA-ICG-1:
GATGCGTTTGCTACGGGTAGCGT       (SEQ ID NO 25)

MKA-ICG-2:
GATGCGTTGCCTACGGGTAGCGT       (SEQ ID NO 26)

MKA-ICG-3:
ATGCGTTGCCCTACGGGTAGCGT       (SEQ ID NO 27)

MKA-ICG-4:
CGGGCTCTGTTCGAGAGTTGTC        (SEQ ID NO 28)

MKA-ICG-5:
CCCTCAGGGATTTTCTGGGTGTTG      (SEQ ID NO 182)

MKA-ICG-6:
GGACTCGTCCAAGAGTGTTGTCC       (SEQ ID NO 183)

MKA-ICG-7:
TCGGGCTTGGCCAGAGCTGTT         (SEQ ID NO 184)

MKA-ICG-8:
GGGTGCGCAACAGCAAGCGA          (SEQ ID NO 185)

MKA-ICG-9:
GATGCGTTGCCCCTACGGG           (SEQ ID NO 186)

MKA-ICG-10:
CCCTACGGGTAGCGTGTTCTTTTG      (SEQ ID NO 187)
``` and more preferably to:

```
MKA-ICG-3:
ATGCGTTGCCCTACGGGTAGCGT       (SEQ ID NO 27)

MKA-ICG-4:
CGGGCTCTGTTCGAGAGTTGTC        (SEQ ID NO 28)

MKA-ICG-5:
CCCTCAGGGATTTTCTGGGTGTTG      (SEQ ID NO 182)

MKA-ICG-6:
GGACTCGTCCAAGAGTGTTGTCC       (SEQ ID NO 183)

MKA-ICG-7:
TCGGGCTTGGCCAGAGCTGTT         (SEQ ID NO 184)

MKA-ICG-8:
GGGTGCGCAACAGCAAGCGA          (SEQ ID NO 185)

MKA-ICG-9:
GATGCGTTGCCCCTACGGG           (SEQ ID NO 186)

MKA-ICG-10:
CCCTACGGGTAGCGTGTTCTTTTG      (SEQ ID NO 187)
``` or to equivalents of said probes, and/or to any probe derived from SEQ ID NO 101, 167, 168 or 169 provided said probe hybridizes specifically to *M. kansasii*.

The sequences as represented in SEQ ID NO 101, 167, 168 and 169 are new.

Preferentially, at least two, three or four of said probes are used simultaneously.

In still another specific embodiment, the invention provides for a method as described above to detect and identify one or more *Mycobacterium chelonae* strains in a sample, wherein step (iii) comprises hybridizing to at least one of the following probes:

```
MCH-ICG-1:
GGTGTGGACTTTGACTTCTGAATAG     (SEQ ID NO 29)

MCH-ICG-2:
CGGCAAAACGTCGGACTGTCA         (SEQ ID NO 30)

MCH-ICG-3:
GGTGTGGTCCTTGACTTATGGATAG     (SEQ ID NO 210)
``` or to equivalents of said probes, and/or to any probe derived from SEQ ID NO 102, 103 or 174 provided said probe hybridizes specifically to *M. chelonae*. According to another preferential embodiment, these three probes are used in combination.

The sequences as represented in SEQ ID NO 102, 103 and 174 are new.

In still another specific embodiment, the invention provides for a method as described above to detect and identify one or more *Mycobacterium gordonae* strains in a sample, wherein step (iii) comprises hybridizing to at least one of the following probes:

```
MGO-ICG-1:  AACACCCTCGGGTGCTGTCC    (SEQ ID NO 31)

MGO-IGG-2:  GTATGCGTTGTCGTTCGCGGC   (SEQ ID NO 32)

MGO-ICG-5:  CGTGAGGGGTCATCGTCTGTAG  (SEQ ID NO 33)
``` and more preferably to:

```
MGO-ICG-5:  CGTGAGGGGTCATCGTCTGTAG  (SEQ ID NO 33)
``` or to equivalents of said probes, and/or to any probe derived from SEQ ID NO 104, 105 or 106 provided said probe hybridizes specifically to *M. gordonae*.

The sequences as represented in SEQ ID NO 104 to 106 are new.

Preferentially, at least two or three of said probes are used simultaneously.

In still another specific embodiment, the invention provides for a method as described above to detect and identify one or more *Mycobacterium ulcerans* strains or *Mycobacterium marinum* strains in a sample, wherein step (iii) comprises hybridizing to the following probe:

```
MUL-ICG-1:  GGTTTCGGGATGTTGTCCCACC  (SEQ ID NO 175)
``` or to equivalents of said probe, and/or to any probe derived from SEQ ID NO 157 provided said probe hybridizes specifically to *M. ulcerans* and *M. marinum*.

The sequence as represented in SEQ ID NO 157 is new.

In still another specific embodiment, the invention provides for a method as described above to detect and identify one or more *Mycobacterium genavense* strains in a sample, wherein step (iii) comprises hybridizing to at least one of the following probes:

```
MGV-ICG-1:
CGACTGAGGTCGACGTGGTGT         (SEQ ID NO 176)
```

```
MGV-ICG-2:
GGTGTTTGAGCATTGAATAGTGGTTGC     (SEQ ID NO 177)

MGV-ICG-3:
TCGGGCCGCGTGTTCGTCAAA           (SEQ ID NO 211)
``` or to equivalents of said probes, and/or to any probe derived from SEQ ID NO 158, 159, 160, 161 or 162 provided said probe hybridizes specifically to *M. genavense*.

The sequences as represented in SEQ ID NO 158 to 162 are new.

As described in the examples, *M. genavense* includes *M. genavense* strains sensu strictu and a group of closely related strains called *M. simiae*-like. The former group of strains can be detected specifically with probe MGV-ICG-1 while the latter group hybridizes specifically with probe MGV-ICG-3. Probe MGV-ICG-2 detects both groups.

In still another specific embodiment, the invention provides for a method as described above to detect and identify one or more *Mycobacterium xenopi* strains in a sample, wherein step (iii) comprises hybridizing to the following probe:

```
MXE-ICG-1:   GTTGGGCAGCAGGCAGTAACC (SEQ ID NO 178)
``` or to equivalents of said probe, and/or to any probe derived from SEQ ID NO 163 provided said probe hybridizes specifically to *M. xenopi*.

The sequence as represented in SEQ ID NO 163 is new.

In still another specific embodiment, the invention provides for a method as described above to detect and identify one or more *Mycobacterium simiae* strains in a sample, wherein step (iii) comprises hybridizing to the following probe:

```
MSI-ICG-1: CCGGCAACGGTTACGTGTTC  (SEQ ID NO 179)
``` or to equivalents of said probe, and/or to any probe derived from SEQ ID NO 164 or 165 provided said probe hybridizes specifically to *M. simiae*.

The sequence as represented in SEQ ID NO 164 or 165 is new.

In still another specific embodiment, the invention provides for a method as described above to detect and identify one or more *Mycobacterium fortuitum* strains in a sample, wherein step (iii) comprises hybridizing to at least one of the following probes:

```
MFO-ICG-1:   TCGTTGGATGGCCTCGCACCT (SEQ ID NO 180)

MFO-ICG-2:   ACTTGGCGTGGGATGCGGGAA (SEQ ID NO 181)
``` or to equivalents of said probes or to any probe derived from SEQ ID NO 166 provided said probe hybridizes specifically to *M. fortuitum*.

The sequence as represented in SEQ ID NO 166 is new.

In still another specific embodiment, the invention provides for a method as described above to detect and identify one or more *Mycobacterium celatum* strains in a sample, wherein step (iii) comprises hybridizing to the following probe:

```
MCE-ICG-1:   TGAGGGAGCCCGTGCCTGTA  (SEQ ID NO 190)
``` or to equivalents of said probe, and/or to any probe derived from SEQ ID NO 170 provided said probe hybridizes specifically to *M. celatum*.

The sequence as represented in SEQ ID NO 170 is new.

In still another specific embodiment, the invention provides for a method as described above to detect and identify one or more *Mycobacterium haemophilum* strains in a sample, wherein step (iii) comprises hybridizing to the following probe:

```
MHP-ICG-1:   CATGTTGGGCTTGATCGGGTGC (SEQ ID NO 191)
``` or to equivalents of said probe, and/or to any probe derived from SEQ ID NO 171, 172 or 173 provided said probe hybridizes specifically to *M. haemophilum*.

The sequences as represented in SEQ ID NO 171 to 173 are new.

In still another specific embodiment, the invention provides for a method as described above to detect and identify one or more *Mycobacterium malmoense* skins in a sample, wherein step (iii) comprises hybridizing to at least one of the following probes:

```
MML-ICG-1:
CGGATCGATTGAGTGCTTGTCCC         (SEQ ID NO 188)

MML-ICG-2:
TCTAAATGAACGCACTGCCGATGG        (SEQ ID NO 189)
``` or to equivalents of said probes, and/or to any probe derived from SEQ ID NO 107 provided said probe hybridizes specifically to *M. malmoense*.

The sequence as represented in SEQ ID NO 107 is new.

In still another specific embodiment, the invention provides for a method as described above to detect and identify one or more *Mycobacterium* strains in a sample, wherein step (iii) comprises hybridizing to at least one of the following probes:

```
MYC-ICG-1:   ACTGGATAGTGGTTGCGAGCATCTA (SEQ ID NO 1)

MYC-ICG-22:  CTTCTGAATAGTGGTTGCGAGCATCT (SEQ ID NO 2)
``` or to equivalents of said probes.

According to a preferred embodiment, both probes are used in combination.

The invention also provides for a method as described above to detect and identify one or more *Mycoplasma* strains in a sample, wherein step (iii) comprises hybridizing to at least one of the following probes:

```
MPN-ICG 1:
ATCGGTGGTAAATTAAACCCAAATCCCTGT  (SEQ ID NO 49)

MPN-ICG 2:
CAGTTCTGAAAGAACATTTCCGCTTCTTTC  (SEQ ID NO 50)
```

```
MGE-ICG 1:
CACCCATTAATTTTTTCGGTGTTAAAACCC      (SEQ ID NO 51)

Mycoplasma-ICG:
CAAAACTGAAAACGACAATCTTTCTAGTTCC     (SEQ ID NO 52)
``` or to equivalents of said probes, and/or to any probe derived from SEQ ID NO 124 or 125 provided said probe hybridizes specifically with *Mycoplasma* species.

Preferentially, at least two, three or four of said probes are used simultaneously.

More particularly, the invention provides for a method as described above to detect and identify one or more *Mycoplasma pneumoniae* strains in a sample, wherein step (iii) comprises hybridizing to at least one of the following probes:

```
MPN-ICG 1:
ATCGGTGGTAAATTAAACCCAAATCCCTGT      (SEQ ID NO 49)

MPN-ICG 2:
CAGTTCTGAAAGAACATTTCCGCTTCTTTC      (SEQ ID NO 50)
``` or to equivalents of said probes, and/or to any probe derived from SEQ ID NO 125 provided said probe hybridizes specifically to *Mycoplasma pneumoniae*. According to a preferred embodiment, both these probes are used in combination.

The sequence as represented in SEQ ID NO 125 is new.

In another particular embodiment, the invention provides for a method as described above to detect and identify one or more *Mycoplasma genitalium* strains in a sample, wherein step (iii) comprises hybridizing to the following probe:

```
MGE-ICG 1:
CACCCATTAATTTTTTCGGTGTTAAAACCC      (SEQ ID NO 51)
``` or to equivalents of said probes, and/or to any probe derived from SEQ ID NO 124 provided said probe hybridizes specifically to *Mycoplasma genitalium*.

The sequence as represented in SEQ ID NO 124 is new.

The invention also provides for a method as described above to detect and identify one or more *Pseudomonas* strains in a sample, wherein step (iii) comprises hybridizing to at least one of the following probes:

```
PA-ICG 1:
TGGTGTGCTGCGTGATCCGAT               (SEQ ID NO 34)

PA-ICG 2:
TGAATGTTCGTGGATGAACATTGATT          (SEQ ID NO 35)

PA-ICG 3:
CACTGGTGATCATTCAAGTCAAG             (SEQ ID NO 36)

PA-ICG 4:
TGAATGTTCGT(G/A)(G/A)ATGAACATTGATT  (SEQ ID NO 37)
TCTGGTC

PA-ICG 5:
CTCTTTCACTGGTGATCATTCAAGTCAAG       (SEQ ID NO 38)
``` or to equivalents of said probes, and/or to any probe derived from SEQ ID NO 111, 112, 113, 114 or 115 provided said probe hybridizes specifically to *Pseudomonas* strains.

The sequences as represented in SEQ ID NO 111 to 115 are new.

Preferentially, at least two, three or four of said probes are used simultaneously.

More particularly, the invention provides for a method as described above to detect and identify one or more *Pseudomonas aeruginosa* strains in a sample, wherein step (iii) comprises hybridizing to at least one of the following probes:

```
PA-ICG 1:
TGGTGTGCTGCGTGATCCGAT               (SEQ ID NO 34)

PA-ICG 2:
TGAATGTTCGTGGATGAACATTGATT          (SEQ ID NO 35)

PA-ICG 3:
CACTGGTGATCATTCAAGTCAAG             (SEQ ID NO 36)

PA-IGG 4:
TGAATGTTCGT(G/A)(G/A)ATGAACATTGATTTC (SEQ ID NO 37)
TGGTC

PA-ICG 5:
CTCTTTCACTGGTGATCATTCAAGTCAAG       (SEQ ID NO 38)
``` and most preferably to at least one of the following probes:

```
PA-ICG 1:
TGGTGTGCTGCGTGATCCGAT               (SEQ ID NO 34)

PA-ICG 4:
TGAATGTTCGT(G/A)(G/A)ATGAACATTGATTTC (SEQ ID NO 37)
TGGTC

PA-ICG 5:
CTCTTTCACTGGTGATCATTCAAGTCAAG       (SEQ ID NO 38)
``` or to equivalents of said probes, and/or to any probe derived from SEQ ID NO 111 provided said probe hybridizes specifically to *Pseudomonas aeruginosa*.

The sequence as represented in SEQ ID NO 111 is new.

Preferentially, at least two, three, four or five of said probes are used simultaneously.

The invention also provides for a method as described above to detect and identify one or more *Staphylococcus* species in a sample, wherein step (iii) comprises hybridizing to at least one of the following probes:

```
STAU-ICG 1:
TACCAAGCAAAACCGAGTGAATAAAGAGTT      (SEQ ID NO 53)

STAU-ICG 2:
CAGAAGATGCGGAATAACGTGAC             (SEQ ID NO 54)

STAU-ICG 3:
AACGAAGCCGTATGTGAGCATTTGAC          (SEQ ID NO 55)

STAU-ICG 4:
GAACGTAACTTCATGTTAACGTTTGACTTAT     (SEQ ID NO 56)
``` or to equivalents of said probes, and/or to any probe derived from SEQ ID NO 139, 140, 141, 142, 143 or 144 provided said probe hybridizes specifically to *Staphylococcus* species.

The sequences as represented in SEQ ID NO 139 to 144 are new.

Preferentially, at least two, three or four of said probes are used simultaneously.

More particularly, the invention provides for a method as described above to detect and identify one or more *Staphylococcus aureus* strains in a sample, wherein step (iii) comprises hybridizing to at least one, and preferably both of the following probes:

```
STAU-ICG 3:
AACGAAGCCGTATGTGAGCATTTGAC            (SEQ ID NO 55)

STAU-ICG 4:
GAACGTAACTTCATGTTAACGTTTGACTTAT       (SEQ ID NO 56)
``` or to equivalents of said probes, and/or to any probe derived from SEQ ID NO 139, 140, 141, 142 or 143 provided said probe hybridizes specifically to *Staphylococcus aureus*. According to a preferred embodiment, both these probes are used in combination.

In another specific embodiment the invention provides for a method as described above to detect and identify one or more *Staphylococcus epidermidis* strains in a sample, wherein step (iii) comprises hybridizing to any probe derived from SEQ ID NO 144 as long as this probe can be caused to hybridize specifically to *Staphylococcus epidermidis*.

The invention also provides for a method as described above to detect and identify one or more *Acinetobacter* strains in a sample, wherein step (iii) comprises hybridizing to at least one of the following probes:

```
ACI-ICG 1:
GCTTAAGTGCACAGTGCTCTAAACTGA           (SEQ ID NO 57)

ACI-ICG 2:
CACGGTAATTAGTGTGATCTGACGAAG           (SEQ ID NO 58)
``` or to equivalents of said probes, and/or to any probe derived from SEQ ID NO 126, 127, 128, 129 or 130 provided said probe hybridizes specifically to *Acinetobacter* sp. According to a preferred embodiment, both these probes are used in combination.

The sequences as represented in SEQ ID NO 126 to 130 are new.

More particularly, the invention provides for a method as described above to detect and identify one or more *Acinetobacter baumanii* strains in a sample, wherein step (iii) comprises hybridizing to at least one of the following probes:

```
ACI-ICG 1:
GCTTAAGTGCACAGTGCTCTAAACTGA           (SEQ ID NO 57)

ACI-ICG 2:
CACGGTAATTAGTGTGATCTGACGAAG           (SEQ ID NO 58)
``` or to equivalents of said probes, and/or to any probe derived from SEQ ID NO 126 provided said probe hybridizes specifically to *Acinetobacter baumanii*. According to a preferred embodiment, both these probes are used in combination.

The invention also provides for a method as described above, to detect and identify one or more *Listeria* strains in a sample, wherein step (iii) comprises hybridizing to at least one of the following probes:

```
LIS-ICG 1:
CAAGTAACCGAGAATCATCTGAAAGTGAATC       (SEQ ID NO 39)

LMO-ICG 1:
AAACAACCTTTACTTCGTAGAAGTAAATTGGT      (SEQ ID NO 40)
TAAG

LMO-ICG 2:
TGAGAGGTTAGTACTTCTCAGTATGTTTGTTC      (SEQ ID NO 41)

LMO-ICG 3:
AGGCACTATGCTTGAAGCATCGC               (SEQ ID NO 42)

LIV-ICG 1:
GTTAGCATAAATAGGTAACTATTTATGACACA      (SEQ ID NO 43)
AGTAAC

LSE-ICG 1:
AGTTAGCATAAGTAGTGTAACTATTTATGACA
CAAG

LISP-ICG 1:
CGTTTTCATAAGCGATCGCACGTT              (SEQ ID NO 212)
``` and most preferably to at least one of the following probes:

```
LIS-ICG 1:
CAAGTAACCGAGAATCATCTGAAAGTGAATC       (SEQ ID NO 39)

LMO-ICG 3:
AGGCACTATGCTTGAAGCATCGC               (SEQ ID NO 42)

LISP-ICG 1:
CGTTTTCATAAGCGATCGCACGTT              (SEQ ID NO 212)
``` or to equivalents of said probes, and/or to any probe derived from SEQ ID NO 116, 118, 119, 120, 121, 213, 214 or 215 provided said probe hybridizes specifically to *Listeria* species.

As described in the examples section, *Listeria* species encompass *Listeria* species sensu strictu, and a group of closely related organisms referred to as "*Listeria*-like organisms". The latter group can be specifically recognized by probe LISP-ICG 1.

The sequences as represented in SEQ ID NO 116, 118 to 121 and 213 to 215 are new.

Preferentially, at least two, three, four, five or six of said probes are used simultaneously.

More particularly, the invention provides for a method as described above, to detect and identify one or more *Listeria monocytogenes* strains in a sample, wherein step (iii) comprises hybridizing to at least one of the following probes:

```
LMO-ICG 1:
AAACAACCTTTACTTCGTAGAAGTAAATTGGTTAAG  (SEQ ID NO 40)

LMO-ICG 2:
TGAGAGGTTAGTACTTCTCAGTATGTTTGTTC      (SEQ ID NO 41)

LMO-ICG 3:
AGGCACTATGCTTGAAGCATCGC               (SEQ ID NO 42)
``` and most preferably to the following probe:

```
LMO-ICG 3:  AGGCACTATGCTTGAAGCATCGC   (SEQ ID NO 42)
``` or to equivalents of said probes, and/or to any probe derived from SEQ ID NO 120 provided said probe hybridizes specifically to *Listeria monocytogenes*.

Preferentially, at least two, or three of said probes are used simultaneously.

The invention also provides for a method as described above to detect and identify one or more *Brucella* strains in a sample, wherein step (iii) comprises hybridizing to at least one of the following probes:

```
BRU-ICG 1:  CGTGCCGCCTTCGTTTCTCTTT   (SEQ ID NO 59)
BRU-ICG 2:  TTCGCTTCGGGGTGGATCTGTG   (SEQ ID NO 60)
BRU-ICG 3:  GCGTAGTAGCGTTTGCGTCGG    (SEQ ID NO 193)
BRU-ICG 4:  CGCAAGAAGCTTGCTCAAGCC    (SEQ ID NO 194)
``` and most preferably to at least one of the following probes:

```
BRU-ICG 2:  TTCGCTTCGGGGTGGATCTGTG   (SEQ ID NO 60)
BRU-ICG 3:  GCGTAGTAGCGTTTGCGTCGG    (SEQ ID NO 193)
BRU-ICG 4:  CGCAAGAAGCTTGCTCAAGCC    (SEQ ID NO 194)
``` or to equivalents of said probes, and/or to any probe derived from SEQ ID NO 131, 132 or 154 provided said probe hybridizes specifically to *Brucella* strains.

The sequences as represented in SEQ ID NO 131, 132 and 154 are new.

The invention also provides for a method as described above to detect and identify one or more *Salmonella* strains in a sample, wherein step (iii) comprises hybridizing to at least one of the following probes:

```
SALM-ICG 1:
CAAAACTGACTTACGAGTCACGTTTGAG     (SEQ ID NO 61)

SALM-ICG 2:
GATGTATGCTTCGTTATTCCACGCC        (SEQ ID NO 62)

STY-ICG 1:
GGTCAAACCTCCAGGGACGCC            (SEQ ID NO 63)

SED-ICG 1:
GCGGTAATGTGTGAAAGCGTTGCC         (SEQ ID NO 64)
``` and most preferably to the following probe:

```
SALM-ICG 1:
CAAAACTGACTTACGAGTCACGTTTGAG     (SEQ ID NO 61)
``` or to equivalents of said probes, and/or to any probe derived from SEQ ID NO 133, 134, 135, 136, 137 or 138 provided said probe hybridizes specifically to *Salmonella* strains.

The sequences as represented in SEQ ID NO 133 to 138 are new.

Preferentially, at least two, three, or four of said probes are used simultaneously.

The invention also relates to a method as described above to detect and identify one or more *Chlamydia* strains in a sample, wherein step (iii) comprises hybridizing to at least one of the following probes:

```
CHTR-ICG 1:
GGAAGAAGCCTGAGAAGGTTTCTGAC       (SEQ ID NO 45)

CHTR-ICG 2:
GCATTTATATGTAAGAGCAAGCATTCTATTTCA (SEQ ID NO 46)

CHTR-ICG 3:
GAGTAGCGTGGTGAGGACGAGA           (SEQ ID NO 47)

CHTR-ICG 4:
GAGTAGCGCGGTGAGGACGAGA           (SEQ ID NO 201)

CHPS-ICG 1:
GGATAACTGTCTTAGGACGGTTTGAC       (SEQ ID NO 48)
``` or to equivalents of said probes, and/or to any probe derived from SEQ ID NO 122, 123 or 197 provided that said probe hybridizes specifically to *Chlamydia* strain.

Preferentially, at least two, three, four or five of said probes are used simultaneously.

More particularly, the invention relates to a method as described above to detect and identify one or more *Chlamydia trachomatis* strains in a sample, wherein step (iii) comprises hybridizing to at least one of the following probes:

```
CHTR-ICG 1:
GGAAGAAGCCTGAGAAGGTTTCTGAC       (SEQ ID NO 45)

CHTR-ICG 2:
GCATTTATATGTAAGAGCAAGCATTCTATTTCA (SEQ ID NO 46)

CHTR-ICG 3:
GAGTAGCGTGGTGAGGACGAGA           (SEQ ID NO 47)

CHTR-ICG 4:
GAGTAGCGCGGTGAGGACGAGA           (SEQ ID NO 201)
``` or to equivalents of said probes, and/or to any probe derived from SEQ ID NO 123 or 197 provided said probe hybridizes specifically to *Chlamydia trachomatis*.

The sequences as represented in SEQ ID NO 123 and 197 are new.

Preferentially, at least two, three or four of said probes are used simultaneously.

In another particular embodiment, the invention provides for a method as described above to detect and identify one or more *Chlamydia psittaci* strains in a sample, wherein step (iii) comprises hybridizing to at least the following probe:

```
CHPS-ICG 1:
GGATAACTGTCTTAGGACGGTTTGAC       (SEQ ID NO 48)
``` or to equivalents of said probe, and/or to any probe derived from SEQ ID NO 122 provided said probe hybridizes specifically to *Chlamydia psittaci*.

The sequence of SEQ ID NO 122 is new.

The invention also provides for a method as described above, to detect one or more *Streptococcus* stains in a sample, wherein step (iii) comprises hybridizing to any probe derived from SEQ ID NO 145, 146, 147, 148, 149, 150, 151, 152 or 153 provided said probe hybridizes specifically to *Streptococcus* strains, or equivalents of these probes.

The sequences as represented in SEQ ID NO 145, 146, 147, 148, 149, 150, 151, 152 or 153 are new.

The invention also provides for a method as described above, to detect one or more *Yersinia enterocolitica* strains in a sample, wherein step (iii) comprises hybridizing to at least one of the following probes:

```
YEC-ICG 1:
GGAAAAGGTACTGCACGTGACTG       (SEQ ID NO 198)

YEC-ICG 2:
GACAGCTGAAACTTATCCCTCCG       (SEQ ID NO 199)

YEC-ICG 3:
GCTACCTGTTGATGTAATGAGTCAC     (SEQ ID NO 200)
``` or to equivalents of said probes, and/or to any probe derived from SEQ ID NO 195 or 196, provided said probe hybridizes specifically to *Yersinia enterocolitica*.

The sequences as represented in SEQ ID NO 195 and 196 are new.

In some cases it may be advantageous to amplify not all organisms present in a sample, but only more specific taxa, which are considered to be relevant. In these cases the invention provides for primers allowing the specific amplification of the spacer region for only those beforehand defined taxa.

The invention thus provides for a method as described above to detect and identify specifically *Chlamydia trachomatis* in a sample, wherein step (ii) comprises amplification of the 16S-23S rRNA spacer region or a part of it, using at least one of the following primers:

```
CHTR-P1:   AAGGTTTCTGACTAGGTTGGGC    (SEQ ID NO 69)

CHTR-P2:   GGTGAAGTGCTTGCATGGATCT    (SEQ ID NO 70)
``` or equivalents of these primers, said equivalents differing in sequence from the above mentioned primers by changing one or more nucleotides, provided that said equivalents still amplify specifically the spacer region or part of it from *Chlamydia trachomatis*.

Preferably both primers are used.

The invention also provides for a method as described above to detect and identify specifically *Listeria* species in a sample, wherein step (ii) comprises amplification of the 16S-23S rRNA spacer region or a part of it, using at least one of the following primers:

```
LIS-P1:   ACCTGTGAGTTTTCGTTCTTCTC    (SEQ ID NO 71)

LIS-P2:   CTATTTGTTCAGTTTTGAGAGGTT   (SEQ ID NO 72)

LIS-P3:   ATTTTCCGTATCAGCGATGATAC    (SEQ ID NO 73)

LIS-P4:   ACGAAGTAAAGGTTGTTTTTCT     (SEQ ID NO 74)

LIS-P5:   GAGAGGTTACTCTCTTTTATGTCAG  (SEQ ID NO 75)

LIS-P6:   CTTTTATGTCAGATAAAGTATGCAA  (SEQ ID NO 202)

LIS-P7:   CGTAAAAGGGTATGATTATTTG     (SEQ ID NO 203)
``` or equivalents of these primers, said equivalents differing in sequence from the above mentioned primers by changing one or more nucleotides, provided that said equivalents still amplify specifically the spacer region or part of it from *Listeria* species.

The invention also relates to a method as described above to detect and identify specifically *Mycobacterium* species in a sample, wherein step (ii) comprises amplification of the 16S-23S rRNA spacer region or a part of it, using at least one of the following primers:

```
MYC-P1:   TCCCTTGTGGCCTGTGTG        (SEQ ID NO 65)

MYC-P2:   TCCTTCATCGGCTCTCGA        (SEQ ID NO 66)

MYC-P3:   GATGCCAAGGCATCCACC        (SEQ ID NO 67)

MYC-P4:   CCTCCCACGTCCTTCATCG       (SEQ ID NO 68)

MYC-P5:   CCTGGGTTTGACATGCACAG      (SEQ ID NO 192)
``` or equivalents of these primers, said equivalents differing in sequence from the above mentioned primers by changing one or more nucleotides, provided that said equivalents still amplify specifically the spacer region or part of it from *Mycobacterium* species.

The invention also provides for a method as described above to detect and identify specifically *Brucella* species in a sample, wherein step (ii) comprises amplification of the 16S-23S rRNA spacer region or part of it, using at least one of the following primers:

```
BRU-P1:   TCGAGAATTGGAAAGAGGTC      (SEQ ID NO 204)

BRU-P2:   AAGAGGTCGGATTTATCCG       (SEQ ID NO 205)

BRU-P3:   TTCGACTGCAAATGCTCG        (SEQ ID NO 206)

BRU-P4:   TCTTAAAGCCGCATTATGC       (SEQ ID NO 207)
``` or equivalents of these primers, said equivalents differing in sequence from the above-mentioned primers by changing one or more nucleotides, provided that said equivalents still amplify specifically the spacer region of part of it from *Brucella* species.

The invention also provides for a method as described above to detect and identify specifically *Yersinia enterocolitica* species in a sample, wherein step (ii) comprises amplification of the 16S-23S rRNA spacer region or part of it, using at least one of the following primers:

```
YEC-P1:   CCTAATGATATTGATTCGCG      (SEQ ID NO 208)

YEC-P2:   ATGACAGGTTAATCCTTACCCC    (SEQ ID NO 209)
``` or equivalents of these primers, said equivalents differing in sequence from the above-mentioned primers by changing one or more nucleotides, provided that said equivalents still amplify specifically the spacer region of part of it from *Yersinia enterocolitica* species.

The invention also provides for a composition comprising at least one of the probes and/or primers as defined above.

Said composition may comprise any carrier, support, label or diluent known in the art for probes or primers, more particularly any of the labels or supports detailed in the definitions section.

The invention relates more particularly to isolated probes and primers as defined above, more particularly any of the probes as specified in Table 1a or any of the primers as specified in Table 1b.

According to another embodiment, the present invention relates also to new spacer region sequences as defined above and as set out in FIGS. 1-103 (SEQ ID NO 76 to 154, SEQ ID NO 157 to 174, SEQ ID NO 195 to 197 and SEQ ID NO 213 to 215).

In another embodiment the invention provides for a reverse hybridization method comprising any of the probes as defined above, wherein said probes are immobilized on a known location on a solid support, more preferably on a membrane strip.

In yet another embodiment the invention provides for a kit for the detection and identification of at least one microorganism, or the simultaneous detection and identification of several micro-organisms in a sample, comprising the following components:

(i) when appropriate, at least one suitable primer pair to allow amplification of the intercistronic 16S-23S rRNA spacer region, or a part of it;
(ii) at least one of the probes as defined above;
(iii) a buffer, or components necessary to produce the buffer, enabling a hybridization reaction between said probes and the polynucleic acids present in the sample, or the amplified products thereof;
(iv) a solution, or components necessary to produce the solution, enabling washing of the hybrids formed under the appropriate wash conditions;
(v) when appropriate, a means for detecting the hybrids resulting from the preceding hybridization.

BRIEF DESCRIPTION OF THE DRAWINGS

FIG. 1: represents the DNA sequence of die 16S-23S rRNA spacer region from *Mycobacterium tuberculosis* strain H37RV ATCC 27294 (SEQ ID NO 76)

FIG. 2: represents the DNA sequence of the 16S-23S rRNA spacer region from *Mycobacterium avium* ATCC 151.769 (ITG 4991) (SEQ ID NO 77)

FIG. 3: represents the DNA sequence of tie 16S-23S rRNA spacer region from *Mycobacterium paratuberculosis* strains 316F and 2E (SEQ ID NO 78)

FIG. 4: represents the DNA sequence of the 16S-23S rRNA spacer region from *Mycobacterium* strain ITG 5513 (SEQ ID NO 79)

FIG. 5: represents the DNA sequence of the 16S-23S rRNA spacer region from *Mycobacterium* strain ITG 8695 (SEQ ID NO 80)

FIG. 6: represents the DNA sequence of the 16S-23S rRNA spacer region from *Mycobacterium* strain ITG 8708 (SEQ ID NO 81)

FIG. 7: represents the DNA sequence of the 16S-23S rRNA spacer region from *Mycobacterium* strain ITG 8715 (SEQ ID NO 82)

FIG. 8: represents the DNA sequence of the 16S-23S rRNA spacer region from *Mycobacterium* strain ITG 8054 (SEQ ID NO 83)

FIG. 9: represents the DNA sequence of the 16S-23S rRNA spacer region from *Mycobacterium* strain ITG 8737 (SEQ ID NO 84)

FIG. 10: represents the DNA sequence of the 16S-23S rRNA spacer region from *Mycobacterium* strain ITG 8743 (SEQ ID NO 85)

FIG. 11: represents the DNA sequence of die 16S-23S rRNA spacer region from *Mycobacterium* strain ITG 8745 (SEQ ID NO 86)

FIG. 12: represents the DNA sequence of the 16S-23S rRNA spacer region from *Mycobacterium* strain ITG 8748 (SEQ ID NO 87)

FIG. 13: represents the DNA sequence of the 16S-23S rRNA spacer region from *Mycobacterium* strain ITG 8752 (SEQ ID NO 88)

FIG. 14: represents the DNA sequence of the 16S-23S rRNA spacer region from *Mycobacterium intracellulare* serovar 12 ITG 5915 (SEQ ID NO 89)

FIG. 15: represents the DNA sequence of the 16S-23S rRNA spacer region from *Mycobacterium lufu* ITG 4755 (SEQ ID NO 90)

FIG. 16: represents the DNA sequence of the 16S-23S rRNA spacer region from *Mycobacterium* strain ITG 5922 (SEQ ID NO 91)

FIG. 17: represents the DNA sequence of the 16S-23S rRNA spacer region from *Mycobacterium* strain ITG 1329 (SEQ ID NO 92)

FIG. 18: represents the DNA sequence of the 16S-23S rRNA spacer region from *Mycobacterium* strain ITG 1812 (SEQ ID NO 93)

FIG. 19: represents the DNA sequence of the 16S-23S rRNA spacer region from *Mycobacterium* strain ITG 5280 (SEQ ID NO 94)

FIG. 20: represents the DNA sequence of the 16S-23S rRNA spacer region from *Mycobacterium* strain ITG 5620 (SEQ ID NO 95)

FIG. 21: represents the DNA sequence of the 16S-23S rRNA spacer region from *Mycobacterium* strain ITG 5765 (SEQ ID NO 96)

FIG. 22: represents the DNA sequence of the 16S-23S rRNA spacer region from *Mycobacterium* ITG 7395 (SEQ ID NO 97)

FIG. 23: represents the DNA sequence of the 16S-23S rRNA spacer region from *Mycobacterium* ITG 8738 (SEQ ID NO 98)

FIG. 24: represents the DNA sequence of the 16S-23S rRNA spacer region from *Mycobacterium* ITG 926 (SEQ ID NO 99)

FIG. 25: represents the DNA sequence of the 16S-23S spacer region from *Mycobacterium scrofulaceum* ITG 4988 (SEQ ID NO 100)

FIG. 26: represents the DNA sequence of the 16S-23S spacer region from *Mycobacterium kansasii* ATCC 22478 (=ITG 4987) (SEQ ID NO 101)

FIG. 27: represents the DNA sequence of the 16S-23S spacer region from *Mycobacterium chelonae abcessus* ITG 4975 (SEQ ID NO 102)

FIG. 28: represents the DNA sequence of the 16S-23S spacer region from *Mycobacterium chelonae chelonae* ITG 9855 (SEQ ID NO 103)

FIG. 29: represents the DNA sequence of the 16S-23S spacer region from *Mycobacterium gordonae* ITG 7703 (SEQ ID NO 104)

FIG. 30: represents the DNA sequence of the 16S-23S spacer region from *Mycobacterium gordonae* ITG 7836 (SEQ ID NO 105)

FIG. 31: represents the DNA sequence of the 16S-23S spacer region from *Mycobacterium gordonae* ITG 8059 (SEQ ID NO 106)

FIG. 32: represents the DNA sequence of the 16S-23S spacer region from *Mycobacterium malmoense* ITG 4842 and ITG 4832 (SEQ ID NO 107)

FIG. 33: represents the DNA sequence of the 16S-23S spacer region from *Mycobacterium* strain 8757 (SEQ ID NO 108)

FIG. 34: represents the DNA sequence of the 16S-23S spacer region from *Mycobacterium* ITG 8723 (SEQ ID NO 109)

FIG. 35: represents the DNA sequence of the 16S-23S spacer region from *Mycobacterium* ITG 8724 (SEQ ID NO 110)

FIG. 36: represents the DNA sequence of the 16S-23S spacer region from *Pseudomonas aeruginosa* UZG 5669 (SEQ ID NO 111)

FIG. 37: represents the DNA sequence of the 16S-23S spacer region from *Pseudomonas pseudoalcaligenes* LMG 1225 (SEQ ID NO 112)

FIG. 38: represents the DNA sequence of the 16S-23S spacer region from *Pseudomonas stutzeri* LMG 2333 (SEQ ID NO 113)

FIG. 39: represents the DNA sequence of the 16S-23S spacer region from *Pseudomonas alcaligenes* LMG 1224 (SEQ ID NO 114)

FIG. 40: represents the DNA sequence of the 16S-23S spacer region from *Pseudomonas putida* LMG 2232 (SEQ ID NO 115)

FIG. 41: represents the DNA sequence of the small 16S-23S spacer region from *Listeria ivanovii* CIP 7842 (SEQ ID NO 116)

FIG. 42: represents the DNA sequence of the small 16S-23S spacer region from *Listeria monocytogenes* (SEQ ID NO 117)

FIG. 43 represents the DNA sequence of the small 16S-23S spacer region from *Listeria seeligeri* serovar 4A nr. 4268 (SEQ ID NO 118)

FIG. 44: represents the partial DNA sequence of the large 16S-23S spacer region from partial sequence of the long spacer region of *Listeria ivanovii* CIP 7842 (SEQ ID NO 119)

FIG. 45: represents the DNA sequence of the large 16S-23S spacer region from *Listeria monocytogenes* IHE serovar 4B (SEQ ID NO 120)

FIG. 46: represents the DNA sequence of the large 16S-23S spacer region from *Listeria seeligeri* serovar 4A nr. 4268 (SEQ ID NO 121)

FIG. 47: represents the DNA sequence of the 16S-23S spacer region from *Chlamydia psittaci* 6BC (SEQ ID NO 122)

FIG. 48: represents the DNA sequence of the 16S-23S spacer region from *Chlamydia trachomatis* (SEQ ID NO 123)

FIG. 49: represents the DNA sequence of the 16S-23S spacer region from *Mycoplasma genitalium* (U. Gobel) (SEQ ID NO 124)

FIG. 50: represents the DNA sequence of the 16S-23S spacer region from *Mycoplasma pneumoniae* ATCC 29432 (SEQ ID NO 125)

FIG. 51: represents the DNA sequence of the 16S-23S spacer region from *Acinetobacter baumanii* LMG 1041 (SEQ ID NO 126)

FIG. 52: represents the DNA sequence of the 16S-23S spacer region from *Acinetobacter calcoaceticus* LMG 1046 (SEQ ID NO 127)

FIG. 53: represents the DNA sequence of the 16S-23S spacer region from *Acinetobacter haemolyticus* LMG 996 (SEQ ID NO 128)

FIG. 54: represents the DNA sequence of the 16S-23S spacer region from *Acinetobacter johnsonii* LMG 999 (SEQ ID NO 129)

FIG. 55: represents the DNA sequence of the 16S-23S spacer region from *Acinetobacter junii* LMG 998 (SEQ ID NO 130)

FIG. 56: represents the DNA sequence of the 16S-23S spacer region from *Brucella melitensis* NIDO Biovar 1 (SEQ ID NO 131)

FIG. 57: represents the DNA sequence of the 16S-23S spacer region from *Brucella suis* NIDO Biovar 1 (SEQ ID NO 132)

FIG. 58: represents the DNA sequence of one of the 16S-23S spacer region from *Salmonella dublin* (SEQ ID NO 133)

FIG. 59: represents the DNA sequence of one of the 16S-23S spacer region from *Salmonella dublin* (SEQ ID NO 134)

FIG. 60: represents the DNA sequence of one of the 16S-23S spacer region from *Salmonella enteritidis* (SEQ ID NO 135)

FIG. 61: represents the DNA sequence of one of the 16S-23S spacer region from *Salmonella enteritidis* (SEQ ID NO 136)

FIG. 62: represents the DNA sequence of one of the 16S-23S spacer region from *Salmonella typhimurium* (SEQ ID NO 137)

FIG. 63: represents the DNA sequence of one of the 16S-23S spacer region from *Salmonella typhimurium* (SEQ ID NO 138)

FIG. 64: represents the DNA sequence of one of the 16S-23S spacer region from *Staphylococcus aureus* strain UZG 5728 (SEQ ID NO 139)

FIG. 65: represents the DNA sequence of one of the 16S-23S spacer region from *Staphylococcus aureus* strain UZG 6289 (SEQ ID NO 140)

FIG. 66: represents the DNA sequence of one of the 16S-23S spacer region from *Staphylococcus aureus* strain UZG 6289 (SEQ ID NO 141)

FIG. 67: represents the DNA sequence of one of the 16S-23S spacer region from *Staphylococcus aureus* strain UZG 6289 (SEQ ID NO 142)

FIG. 68: represents the DNA sequence of one of the 16S-23S spacer region from *Staphylococcus aureus* strain UZG 6289 (SEQ ID NO 143)

FIG. 69: represents the DNA sequence of one of the 16S-23S spacer region from *Staphylococcus epidermidis* strain UZG CNS41 (SEQ ID NO 144)

FIG. 70: represents the DNA sequence of the 16S-23S spacer region from *Streptococcus mitis* UZG 2465 (SEQ ID NO 145)

FIG. 71: represents the DNA sequence of the 16S-23S spacer region from *Streptococcus pyogenes* UZG 3671 (SEQ ID NO 146)

FIG. 72: represents the DNA sequence of the 16S-23S spacer region from *Streptococcus sanguis* UZG 1042 (SEQ ID NO 147)

FIG. 73: represents the DNA sequence of the 16S-23S spacer region from *Staphylococcus saprophyticus* UZG CNS46 (SEQ ID NO 148).

FIG. 74: represents the DNA sequence of the 16S-23S spacer region from *Streptococcus* species UZG 536 (84) (SEQ ID NO 149)

FIG. 75: represents the DNA sequence of the 16S-23S spacer region from *Streptococcus* species UZG 4341 (SEQ ID NO 150)

FIG. 76: represents the DNA sequence of the 16S-23S spacer region from *Streptococcus* species UZG 457 (44B) (SEQ ID NO 151)

FIG. 77: represents the DNA sequence of the 16S-23S spacer region from *Streptococcus* species UZG 97A (SEQ ID NO 152)

FIG. 78: represents the DNA sequence of the 16S-23S spacer region from *Streptococcus* species UZG 483 (76) (SEQ ID NO 153)

FIG. 79: represents the DNA sequence of the 16S-23S spacer region from *Brucella abortus* NIDO Tulya biovar 3 (SEQ ID NO 154)

FIG. 80: represents the DNA sequence of the 16S-23S spacer region from *Mycobacterium ulcerans* ITG 1837 and *Mycobacterium marinum* ITG 7732 (SEQ ID NO 157)

FIG. 81: represents the DNA sequence of the 16S-23S spacer region from *Mycobacterium genavense* ITG 8777 (SEQ ID NO 158)

FIG. 82: represents the DNA sequence of the 16S-23S spacer region from *Mycobacterium genavense* ITG 92-742 (SEQ ID NO 159)

FIG. 83: represents the DNA sequence of the 16S-23S spacer region from *Mycobacterium genavense* ITG 9500 (SEQ ID NO 160)

FIG. 84: represents the DNA sequence of the 16S-23S spacer region from *Mycobacterium simiae*-like ITG 7379 (SEQ ID NO 161)

FIG. 85: represents the DNA sequence of the 16S-23S spacer region from *Mycobacterium simiae*-like ITG 9745 (SEQ ID NO 162)

FIG. 86: represents the DNA sequence of the 16S-23S spacer region from *Mycobacterium xenopi* ITG 4986 (SEQ ID NO 163)

FIG. 87: represents the DNA sequence of the 16S-23S spacer region from *Mycobacterium simiae* A ITG 4485 (SEQ ID NO 164)

FIG. 88: represents the DNA sequence of the 16S-23S spacer region from *Mycobacterium simiae* B ITG 4484 (SEQ ID NO 165)

FIG. 89: represents the DNA sequence of the 16S-23S spacer region from *Mycobacterium fortuitum* ITG 4304 (SEQ ID NO 166)

FIG. 90: represents the DNA sequence of the 16S-23S spacer region from *Mycobacterium kansasii* ITG 6328 (SEQ ID NO 167)

FIG. 91: represents the DNA sequence of the 16S-23S spacer region from *Mycobacterium kansasii* ITG 8698 (SEQ ID NO 168)

FIG. 92: represents the DNA sequence of the 16S-23S spacer region from *Mycobacterium kansasii* ITG 8973 (SEQ ID NO 169)

FIG. 93: represents the DNA sequence of the 16S-23S spacer region from *Mycobacterium celatum* ITG 94-123 (SEQ ID NO 170)

FIG. 94: represents the DNA sequence of the $16S_{23}S$ spacer region from *Mycobacterium haemophilum* ITG 776 (SEQ ID NO 171)

FIG. 95: represents the DNA sequence of the 16S-23S spacer region from *Mycobacterium haemophilum* ITG 778 (SEQ ID NO 172)

FIG. 96: represents the DNA sequence of the 16S-23S spacer region from *Mycobacterium haemophilum* ITG 3071 (SEQ ID NO 173)

FIG. 97: represents the DNA sequence of the 16S-23S spacer region from *Mycobacterium chelonae* ITG 94-330 and ITG 94-379 (SEQ ID NO 174)

FIG. 98: represents the DNA sequence of a 16S-23S spacer region from *Yersinia enterocolitica* strain P95 (SEQ ID NO 195)

FIG. 99: represents the DNA sequence of a 16S-23S spacer region from *Yersinia enterocolitica* strain P95 (SEQ ID NO 196)

FIG. 100: represents the DNA sequence of the 16S-23S spacer region from *Chlamydia trachomatis* strain SSDZ 94 M 1961 (SEQ ID NO 197)

FIG. 101: represents the DNA sequence of a 16S-23S spacer region from *Listeria*-like isolate MB 405 (SEQ ID NO 213)

FIG. 102: represents the DNA sequence of a 16S-23S spacer region from *Listeria*-like isolate MB 405 (SEQ ID NO 214)

FIG. 103: represents the DNA sequence of a 16S-23S spacer region from *Listeria*-like isolate MB 405 (SEQ ID NO 215)

TABLE LEGENDS

Table 1a: List of all new probes originating from the 16S-23S rRNA spacer region
Table 1b: List of possible primers to be used for taxon-specific amplification of the spacer region or part of it.
Table 2: Hybridization results for *Pseudomonas*
Table 3: Different probe patterns obtained for mycobacterial strain-types
Table 4: Mycobacteria strains tested in LiPA
Table 5: Hybridization results for *Listeria* (Probes LMO1, 2, LSE1, LIV1, LIS1)
Table 6: Hybridization results for *Listeria* (Probes LMO3, LIS1)
Table 7: Hybridization results for *Chlamydia*
Table 8: New mycobacterial probes and hybridization results
Table 9: Hybridization results for *Brucella*
Table 10: Hybridization results for *Staphylococcus*

TABLE 1a

| PROBE | SEQUENCE | SEQ ID NO |
|---|---|---|
| MYC-ICG-1 | ACTGGATAGTGGTTGCGAGCATCTA | 1 |
| MYC-ICG-22 | CTTCTGAATAGTGGTTGCGAGCATCT | 2 |
| MTB-ICG-1 | GGGTGCATGACAACAAAGTTGGCCA | 3 |
| MTB-ICG-2 | GACTTGTTCCAGGTGTTGTCCCAC | 4 |
| MTB-ICG-3 | CGGCTAGCGGTGGCGTGTTCT | 5 |
| MAI-ICG-1 | CAACAGCAAATGATTGCCAGACACAC | 6 |
| MIL-ICG-11 | GAGGGGTTCCCGTCTGTAGTG | 7 |
| MIL-ICG-22 | TGAGGGGTTCTCGTCTGTAGTG | 8 |
| MAC-ICG-1 | CACTCGGTCGATCCGTGTGGA | 9 |
| MAV-ICG-1 | TCGGTCCGTCCGTGTGGAGTC | 10 |
| MAV-ICG-22 | GTGGCCGGCGTTCATCGAAA | 11 |
| MIN-ICG-1 | GCATAGTCCTTAGGGCTGATGCGTT | 12 |
| MIN-ICG-2 | GCTGATGCGTTCGTCGAAATGTGTA | 13 |
| MIN-ICG-22 | CTGATGCGTTCGTCGAAATGTGT | 14 |
| MIN-ICG-222 | TGATGCGTTCGTCGAAATGTGT | 15 |
| MIN-ICG-2222 | GGCTGATGCGTTCGTCGAAATGTGTAA | 16 |
| MAL-ICG-1 | ACTAGATGAACGCGTAGTCCTTGT | 17 |
| MHEF-ICG-1 | TGGACGAAAACCGGGTGCACAA | 18 |
| MAH-ICG-1 | GTGTAATTTCTTTTTTAACTCTTGTGTGTAAGTAAGTG | 19 |
| MCO-ICG-11 | TGGCCGGCGTGTTCATCGAAA | 20 |
| MTH-ICG-11 | GCACTTCAATTGGTGAAGTGCGAGCC | 21 |
| MTH-ICG-2 | GCGTGGTCTTCATGGCCGG | 22 |
| MEF-ICG-11 | ACGCGTGGTCCTTCGTGG | 23 |
| MSC-ICG-1 | TCGGCTCGTTCTGAGTGGTGTC | 24 |

TABLE 1a-continued

| PROBE | SEQUENCE | SEQ ID NO |
|---|---|---|
| MKA-ICG-1 | GATGCGTTTGCTACGGGTAGCGT | 25 |
| MKA-ICG-2 | GATGCGTTGCCTACGGGTAGCGT | 26 |
| MKA-ICG-3 | ATGCGTTGCCCTACGGGTAGCGT | 27 |
| MKA-ICG-4 | CGGGCTCTGTTCGAGAGTTGTC | 28 |
| MCH-ICG-1 | GGTGTGGACTTTGACTTCTGAATAG | 29 |
| MCH-ICG-2 | CGGCAAAACGTCGGACTGTCA | 30 |
| MCH-ICG-3 | GGTGTGGTCCTTGACTTATGGATAG | 210 |
| MGO-ICG-1 | AACACCCTCGGGTGCTGTCC | 31 |
| MGO-ICG-2 | GTATGCGTTGTCGTTCGCGGC | 32 |
| MGO-ICG-5 | CGTGAGGGGTCATCGTCTGTAG | 33 |
| MUL-ICG-1 | GGTTTCGGGATGTTGTCCCACC | 175 |
| MGV-ICG-1 | CGACTGAGGTCGACGTGGTGT | 176 |
| MGV-ICG-2 | GGTGTTTGAGCATTGAATAGTGGTTGC | 177 |
| MGV-ICG-3 | TCGGGCCGCGTGTTCGTCAAA | 211 |
| MXE-ICG-1 | GTTGGGCAGCAGGCAGTAACC | 178 |
| MSI-ICG-1 | CCGGCAACGGTTACGTGTTC | 179 |
| MFO-ICG-1 | TCGTTGGATGGCCTCGCACCT | 180 |
| MFO-ICG-2 | ACTTGGCGTGGGATGCGGGAA | 181 |
| MKA-ICG-5 | CCCTCAGGGATTTTCTGGGTGTTG | 182 |
| MKA-ICG-6 | GGACTCGTCCAAGAGTGTTGTCC | 183 |
| MKA-ICG-7 | TCGGGCTTGGCCAGAGCTGTT | 184 |
| MKA-ICG-8 | GGGTGCGCAACAGCAAGCGA | 185 |
| MKA-ICG-9 | GATGCGTTGCCCCTACGGG | 186 |
| MKA-ICG-10 | CCCTACGGGTAGCGTGTTCTTTTG | 187 |
| MML-ICG-1 | CGGATCGATTGAGTGCTTGTCCC | 188 |
| MML-ICG-2 | TCTAAATGAACGCACTGCCGATGG | 189 |
| MCE-ICG-1 | TGAGGGAGCCCGTGCCTGTA | 190 |
| MHP-ICG-1 | CATGTTGGGCTTGATCGGGTGC | 191 |
| PA-ICG 1 | TGGTGTGCTGCGTGATCCGAT | 34 |
| PA-ICG 2 | TGAATGTTCGTGGATGAACATTGATT | 35 |
| PA-ICG 3 | CACTGGTGATCATTCAAGTCAAG | 36 |
| PA-ICG 4 | TGAATGTTCGT(G/A)(G/A)ATGAACATTGATTTCTGGTC | 37 |
| PA-ICG 5 | CTCTTTCACTGGTGATCATTCAAGTCAAG | 38 |
| LIS-ICG 1 | CAAGTAACCGAGAATCATCTGAAAGTGAATC | 39 |
| LMO-ICG 1 | AAACAACCTTTACTTCGTAGAAGTAAATTGGTTAAG | 40 |
| LMO-ICG 2 | TGAGAGGTTAGTACTTCTCAGTATGTTTGTTC | 41 |
| LMO-ICG 3 | AGGCACTATGCTTGAAGCATCGC | 42 |
| LIV-ICG 1 | GTTAGCATAAATAGGTAACTATTTATGACACAAGTAAC | 43 |
| LSE-ICG 1 | AGTTAGCATAAGTAGTGTAACTATTTATGACACAAG | 44 |
| LISP-ICG 1 | CGTTTTCATAAGCGATCGCACGTT | 212 |
| CHTR-ICG 1 | GGAAGAAGCCTGAGAAGGTTTCTGAC | 45 |
| CHTR-ICG 2 | GCATTTATATGTAAGAGCAAGCATTCTATTTCA | 46 |
| CHTR-ICG 3 | GAGTAGCGTGGTGAGGACGAGA | 47 |
| CHPS-ICG 1 | GGATAACTGTCTTAGGACGGTTTGAC | 48 |
| MPN-ICG 1 | ATCGGTGGTAAATTAAACCCAAATCCCTGT | 49 |
| MPN-ICG 2 | CAGTTCTGAAAGAACATTTCCGCTTCTTTC | 50 |
| MGE-ICG 1 | CACCCATTAATTTTTTCGGTGTTAAAACCC | 51 |
| Mycoplasma-ICG | CAAAACTGAAAACGACAATCTTTCTAGTTCC | 52 |
| STAU-ICG 1 | TACCAAGCAAAACCGAGTGAATAAAGAGTT | 53 |
| STAU-ICG 2 | CAGAAGATGCGGAATAACGTGAC | 54 |
| STAU-ICG 3 | AACGAAGCCGTATGTGAGCATTTGAC | 55 |
| STAU-ICG 4 | GAACGTAACTTCATGTTAACGTTTGACTTAT | 56 |
| ACI-ICG 1 | GCTTAAGTGCACAGTGCTCTAAAGTGA | 57 |
| ACI-ICG 2 | CACGGTAATTAGTGTGATCTGACGAAG | 58 |
| BRU-ICG 1 | CGTGCCGCCTTCGTTTCTCTTT | 59 |
| BRU-ICG 2 | TTCGCTTCGGGGTGGATCTGTG | 60 |
| BRU-ICG 3 | GCGTAGTAGCGTTTGCGTCGG | 193 |
| BRU-ICG 4 | CGCAAGAAGCTTGCTCAAGCC | 194 |
| SALM-ICG 1 | CAAAACTGACTTACGAGTCACGTTTGAG | 61 |
| SALM-ICG 2 | GATGTATGCTTCGTTATTCCACGCC | 62 |
| STY-ICG 1 | GGTCAAACCTCCAGGGACGCC | 63 |
| SED-ICG 1 | GCGGTAATGTGTGAAAGCGTTGCC | 64 |
| YEC-ICG 1 | GGAAAAGGTACTGCACGTGACTG | 198 |
| YEC-ICG 2 | GACAGCTGAAACTTATCCCTCCG | 199 |
| YEC-ICG 3 | GCTACCTGTTGATGTAATGAGTCAC | 200 |
| CHTR-ICG 4 | GAGTAGCGCGGTGAGGACGAGA | 201 |

TABLE 1b

| PRIMERS | SEQUENCE | SEQ ID NO |
|---|---|---|
| MYC-P1 | TCCCTTGTGGCCTGTGTG | 65 |
| MYC-P2 | TCCTTCATCGGCTCTCGA | 66 |

TABLE 1b-continued

| PRIMERS | SEQUENCE | SEQ ID NO |
|---|---|---|
| MYC-P3 | GATGCCAAGGCATCCACC | 67 |
| MYC-P4 | CCTCCCACGTCCTTCATCG | 68 |
| MYC-P5 | CCTGGGTTTGACATGCACAG | 192 |
| CHTR-P1 | AAGGTTTCTGACTAGGTTGGGC | 69 |
| CHTR-P2 | GGTGAAGTGCTTGCATGGATCT | 70 |
| LIS-P1 | ACCTGTGAGTTTTCGTTCTTCTC | 71 |
| LIS-P2 | CTATTTGTTCAGTTTTGAGAGGTT | 72 |
| LIS-P3 | ATTTTCCGTATCAGCGATGATAC | 73 |
| LIS-P4 | ACGAAGTAAAGGTTGTTTTTCT | 74 |
| LIS-P5 | GAGAGGTTACTCTCTTTTATGTCAG | 75 |
| LIS-P6 | CTTTTATGTCAGATAAAGTATGCAA | 202 |
| LIS-P7 | CGTAAAAGGGTATGATTATTTG | 203 |
| BRU-P1 | TCGAGAATTGGAAAGAGGTC | 204 |
| BRU-P2 | AAGAGGTCGGATTTATCCG | 205 |
| BRU-P3 | TTCGACTGCAAATGCTCG | 206 |
| BRU-P4 | TCTTAAAGCCGCATTATGC | 207 |
| YEC-P1 | CCTAATGATATTGATTCGCG | 208 |
| YEC-P2 | ATGACAGGTTAATCCTTACCCC | 209 |

EXAMPLE 1

*Pseudomonas aeruginosa*

*Pseudomonas aeruginosa* is a significant human pathogen usually in the context of serious underlying disease. It is also a major cause of nosocomial infections, which are characteristically prone to resistance to antimicrobial agents. This gram-negative, non-fermentative rod can be responsible for different clinical manifestations, like wound infections, bacteremia, respiratory and urinary tract infections, and is also a major cause of morbidity and mortality in patients with cystic fibrosis.

*Pseudomonas* species are currently differentiated based on growth characteristics and several biochemical features implying a time schedule of 24 h to 72 h to get a correct identification of the pathogen.

Already the development of monoclonal or polyclonal antibodies significantly improved the identification of *Pseudomonas* species. Recently however it has been shown that it is possible to detect organisms directly in clinical samples on a very sensitive and specific way using DNA probes with or without a prior amplification of the target DNA.

DNA probes to study *Pseudomonas aeruginosa* are already described and are mainly used for epidemiological typing (Ogle et al., 1987; Samadpour et al., 1988; McIntosh et al., 1992). However, none of these probes have been derived from the 16S-23S spacer.

The 16S-23S rRNA gene spacer region and a part of the 23S rRNA gene was amplified with conserved primers (upper primer: TGGGGTGAAGTCGTAACAAGGTA SEQ ID NO 155; lower primer: CCCCCTCACGGTACTGGT. SEQ ID NO 156) using the polymerase chain reaction for the following species:

*Pseudomonas aeruginosa* 5669
*Pseudomonas alcaligenes* LMG 1224$^T$
*Pseudomonas fluorescens* LMG 5167
*Pseudomonas putida* LMG 2232
*Pseudomonas stutzeri* LMG 2333$^T$
*Pseudomonas pseudoalcaligenes* LMG 1225$^T$ To facilitate cloning of the obtained amplicons a NotI recognition site was added to the lower primer. After purification and digestion of the fragment with NotI, the amplicon was cloned in a EcoRV/NotI digested pBluescript SK$^+$ plasmid vector.

Sequencing of the 16S-23S rRNA gene spacer region was performed according the dideoxy-chain terminating chemistry either using double stranded plasmid DNA combined with primers located in the plasmid vector or directly on the PCR products after purification combined with internal PCR primers.

FIGS. 36 to 40 represent the nucleotide sequence of the 16S-23S rRNA gene spacer regions from the different *Pseudomonas* species described above. For *P. fluorescens* only partial sequence information was obtained.

From the nucleic acid sequence of the spacer from *P. aeruginosa* strain 5669 five oligonucleotide-probes were chosen and chemically synthesized. The sequences of the oligonucleotides are the following:

| PA1 = PA-ICG 1: | TGGTGTGCTGCGTGATCCGATA |
|---|---|
| PA2 = PA-ICG 2: | TGAATGTTCGTGGATGAACATTGATT |
| PA3 = PA-ICG 3: | CACTGGTGATCATTCAAGTCAAG |

Specificity and sensitivity testing of the oligonucleotide-probes was carried out using a reverse hybridization assay. Genomic DNA of the different bacteria tested was amplified using biotinylated primers (idem primers as for cloning procedure, see above). The obtained amplicon, spanning the 16S-23S rRNA gene spacer region, was denatured and hybridized to a membrane-strip onto which the different oligonucleotide probes were immobilized in a line-wise fashion (LiPA). Hybridization was carried out in a mixture of 3× SSC (1× SSC=0.15 M NaCl, 0.015 M sodium citrate, pH 7.0) and 20% formamide (FA) at a temperature of 50° C. for one hour. Washing was done in the same mixture at the same temperature for 15 min.

Hybrids were detected using a streptavidine conjugate coupled to alkaline phosphatase and the probes were visualized through a precipitation reaction using NBT (nitrobluetetrazolium) and BCIP (bromo-chloro-indolylphosphate).

The hybridization results obtained with probes PA1, PA2 and PA3 are given in table 4 and show that probes PA1 and PA3 were 100% specific for *Pseudomonas aeruzinosa* and hybridized to all the strains tested. The hybridization signal with probe PA3 at 50° C. was not optimal, so the oligonucleotide-probe was improved by adding some additional nucleotides to the specific probe. This newly designed probe is PA5.

| PA5 = PA-ICG 5: | CTCTTTCACTGGTGATCATTCAAGTCAAG |
|---|---|

Hybridization experiments with probe PA5 proved that this probe also shows a 100% specificity and 100% sensitivity for *P. aeruginosa*.

Oligonucleotide-probe PA2 hybridized only to 5 out of 17 *P. aeruginosa* strains tested. Direct sequencing of the 16S-23S rRNA gene spacer region of the strains which did not hybridize to these probes, showed some heterogeneity between different strains. Two mismatches were seen in comparison to the first developed PA2 probe. To overcome this heterogeneity between different strains in the region of probe PA2 a new probe PA4 was designed. This probe is degenerated at the position of the mismatches and some additional nucleotides were added to improve the hybridization signal at 50° C.

```
PA4 = PA-ICG 4:
TGAATGTTCGT(G/A)(G/A)ATGAACATTGATTTCTGGTC
```

A 100% specificity and 100% sensitivity was obtained with this degenerated probe as is shown by the hybridization results.

TABLE 2

Hybridization results for *Pseudomonas*

| taxa tested | PA1 | PA2 | PA3 | PA4 | PA5 |
|---|---|---|---|---|---|
| Pseudomonas aeruginosa | 17/17 | 5/17 | 17/17 | 17/17 | 17/17 |
| Pseudomonas alcaligenes | 0/1 | 0/1 | 0/1 | 0/1 | 0/1 |
| Pseudomonas fluorescens | 0/1 | 0/1 | 0/1 | 0/1 | 0/1 |
| Pseudomonas putida | 0/1 | 0/1 | 0/1 | 0/1 | 0/1 |
| Pseudomonas pseudoalcaligenes | 0/1 | 0/1 | 0/1 | 0/1 | 0/1 |
| Pseudomonas stutzeri | 0/1 | 0/1 | 0/1 | 0/1 | 0/1 |
| Pseudomonas cepacia | 0/1 | 0/1 | 0/1 | ND | ND |
| Neisseria gonorrhoeae | 0/1 | 0/1 | 0/1 | ND | ND |
| Escherichia coli | 0/1 | 0/1 | 0/1 | ND | ND |
| Bordetella pertussis | 0/1 | 0/1 | 0/1 | ND | ND |
| Bordetella parapertussis | 0/1 | 0/1 | 0/1 | ND | ND |
| Bordetella bronchiseptica | 0/1 | 0/1 | 0/1 | ND | ND |
| Mycobacterium tuberculosis | 0/1 | 0/1 | 0/1 | ND | ND |
| Mycobacterium avium | 0/1 | 0/1 | 0/1 | ND | ND |
| Moraxella catarrhalis | 0/4 | 0/4 | 0/4 | ND | ND |
| Haemophilus influenzae | 0/2 | 0/2 | 0/2 | ND | ND |
| Streptococcus pneumoniae | 0/3 | 0/3 | 0/3 | ND | ND |
| Acinetobacter calcoaceticus | 0/1 | 0/1 | 0/1 | ND | ND |
| Staphylococcus aureus | 0/2 | 0/2 | 0/2 | ND | ND |

(n/m: number of strains positive/number of strains tested)
(ND: not done)

EXAMPLE 2

Mycobacterium

A variety of mycobacterial species may be involved in serious human infectious disease. Notorious examples are *Mycobacterium tuberculosis* and *Mycobacterium leprae*. Recently other species such as *M. avium*, *M. intracellulare* and *M. kansasii* have been more frequently encountered as human pathogens especially in immunocompromised hosts.

Consequently, laboratory diagnosis of mycobacterial infections should not be restricted to the *M. tuberculosis* complex but should ideally include most other clinically relevant mycobacterial species.

The identification and differentiation of pathogenic mycobacteria at the species level by conventional laboratory techniques is, in general, difficult and time-consuming.

To overcome these problems DNA-techniques were implemented. The techniques described extended from straightforward DNA-probing to automated sequence analysis. Several approaches have been recently reported (Jonas et al., 1993; Frothingham and Wilson, 1993; Tomioka et al., 1993; Saito et al., 1989; Vaneechoutte et al., 1993; Telenti et al. 1993; Böddinghaus et al., 1990).

However, these methods all have their particular disadvantages, and most of them still rely on culture. Moreover, and most importantly none of these techniques allows for a simultaneous detection of the different clinically relevant mycobacterial species in a single test run. Besides, the differentiation of particular groups within the *Mycobacterium avium-intracellulare* complex is problematic and often even impossible.

To overcome the above-mentioned disadvantages, a LiPA-test was developed which allows for the simultaneous and reliable detection and differentiation of a number of *Mycobacterium* species and groups. The sets of probes used to achieve these goals were all derived from the 16S-23S rRNA spacer region. The methods used are analogous to those mentioned in example 1.

The 16S-23S rRNA spacer region, and part of the 16S and 23S rRNA flanking genes was amplified by PCR with primers conserved for the genus *Mycobacterium*. At least one of the following primers located in the 16S gene were used as upper primers:

```
MYC-P1:   TCCCTTGTGGCCTGTGTG      (SEQ ID NO 65)

MYC-P5:   CCTGGGTTTGACATGCACAG    (SEQ ID NO 192)
```

At least one of the following primers, located in the 23S gene were used as lower primers for the amplification:

```
MYC-P2:   TCCTTCATCGGCTCTCGA      (SEQ ID NO 66)

MYC-P3:   GATGCCAAGGCATCCACC      (SEQ ID NO 67)

MYC-P4:   CCTCCCACGTCCTTCATCG     (SEQ ID NO 68)
```

All the above mentioned primers amplified the spacer region of all *Mycobacterium* strains tested, except primer MYC-P2 which was not functional for *M. chelonae*. In order to enhance the sensitivity of the detection, a nested PCR was sometimes carried out, using P5 and P4 as outer primers and P1 and P3 as inner primers.

In order to be able to design and select the probes and probe combinations which fit our purpose, the 16S-23S rRNA spacer region of a number of mycobacterial strains was sequenced. The obtained sequences were compared to each other and to those already known from literature (e.g. Frothingham et al., 1993. 1994: Kempsell et al., 1992; Suzuki et al., 1988; EP-A-0395292; Van der Giessen et al., 1994; ) or from publicly accessable data banks. The corresponding sequences are represented in FIGS. 1 to 35 (SEQ ID NO 76 to SEQ ID NO 110).

The probes derived from these data were all adjusted in such a way that the desired hybridization-behaviour was obtained using unified hybridization and wash conditions (i.e. 3× SSC, 20% deionized formamide, 50° C.). The set of adjusted probes used for hybridization to different mycobacterial strains is represented in table 1a, SEQ ID NO 1-33. Please note that the probe nomenclature used in this example is an abbreviated version of the one used in table 1a: i.e. the letters "ICG" have always been omitted. According to the specific hybridization pattern obtained, the strains tested could be assigned to one of the following species or species groups: *M. tuberculosis* complex, *M. avium*, *M. intracellulare* or *M. intracellulare* complex, *M. kansasii*, *M. chelonae* and *M. gordonae*. The strains tested which belong to each group are summarized in Table 4. All strains were obtained from the Institute of Tropical Medicine, Antwerp, Belgium. The different probe-patterns obtained for each group are illustrated in Table 3, and are discussed in more detail hereafter.

*M. tuberculosis* Complex

The *M. tuberculosis* complex harbours all strains belonging to *M. tuberculosis*. *M. bovis*, *M. africanum* and *M. microti*. The probes Mtb1, Mtb2 and Mtb3 hybridize with DNA originating from all *M. tuberculosis* complex strains tested. None of the other strains tested hybridized with these probes at the conditions used.

In addition, *M. tuberculosis* complex strains, as is the case with all other mycobacterial strains tested, hybridize with either the myc1 or the myc2 probe or both. The latter two probes are designed as general *Mycobacterium* probes, either alone or in combination with each other.

*M. avium/M. paratuberculosis*

All *M. avium* and *M. paratuberculosis* strains studied reveal an identical hybridization pattern with the set of probes. For this type of organisms positive hybridization signals are obtained with the probes myc1/myc22, mai1, mil11, mav1, mah1 and mav22. The latter two probes hybridize exclusively with *M. avium* and *M. paratuberculosis* strains, and can thus be used as species-specific probes. Since the 16S-23S spacer sequences of *M. avium* isolates and *M. paratuberculosis* isolates are identical or nearly identical these two taxa cannot be discriminated from each other. This finding supports 16S rRNA sequencing data which indicate that *M. avium* and *M. paratuberculosis* should in fact be considered as belonging to one geno-species (Rogal et al., 1990), *M. avium* ssp. avium and *M. avium* ssp. *paratuberculosis*.

*M. intracellulare* and *M. intracellulare* Complex (MIC)

MIC strains are genotypically highly related organisms which according to sequence data of the 16S-23S rRNA spacer region, belong to a distinct cluster which is separate from other *Mycobacterium* species. *M. avium* and *M. scrofulaceum* are their closest relatives. Almost all strains tested which are generally referred to as *M. avium* complex (MAC) strains (the former MAIS-complex) can be found in the MIC croup Thus, the MIC group defined in the current invention encompasses the MAC-type strains described by Frothingham and Wilson (1993) with the exception of MAC-G which appears to be *M. scrofulaceum*. Also *M. intracellulare* strains sensu stricto (*M. intracellulare* s.s.) are part of this cluster.

Because this MIC group contains a quite large group of strains with, among them, subgroups showing different hybridization characteristics to the set of probes a further subdivision into MIC-types was envisaged.

Type MIC 1 harbours *M. intracellulare* s.s., together with some other MAC-strains. All MIC 1 type isolates, without exception, hybridize to the following probes: myc1/myc22, mai1 and mac1. The following probes can be used to make further subdivisions within the MIC 1 group : mil11; min1, min2 to 2222. mil22 and mhef1.

*M. intracellulare* sensu stricto strains (type MIC 1.1.a) can be distinguished from other subtypes in this group by virtue of probe min1 which is positive only for this group of strains. All strains of type MIC 1.1.a strains are positive when tested with the *M. intracellulare* probe of the Gen-Probe Rapid Diagnostic system for MAC.

Type MIC 1.1.b and MIC 1.2 harbour strains which are highly related to *M. intracellulare*. They can be differentiated by using probes mil11 and mil22 (see Table 3). Further subdivision within these groups was not attempted although this could be achieved by using the probes: min2, min22, min222 and min2222. Further subdivision might be of value for epidemiological reasons.

Only two of our collection of strains tested group as MIC 2 strains. One of these strains is a "*Mycobacterium lufu*" strain (ITG 4755). The specific probe pattern generated by these strains is characterized by a positive hybridization signal with the following probes: myc1/myc22, mai1, mil22, mah1 and mal1. Variable hybridization results are obtained with probes min2222, mac1 and mhef1. The other probes are negative. It is not unlikely that MIC 2 would eventually prove to be a heterogeneous group when more strains of this type are being identified. The variable probes may help in a further differentiation, if this would become relevant.

Type MIC 3 groups a fairly high number of MAC-strains which are rather remotely related to *M. intracellulare* s.s. strains and most other MAC-strains. This cluster should be regarded as distinct from *M. avium* and *M. intracellulare* on genotypical grounds. All MIC 3 subtypes hybridize to probes myc1/myc22, mai1, mil22 and mco1. A positive signal with the latter probe (mco1) is characteristic for MIC 3 strains. Variable hybridization results are obtained with the following probes: mac1, mhef1 and mah1. MIC 3 can be further subdivided into four subtypes by using three probes: mth11, mth2 and mef11. Probe mth2 is specific for type MIC 3.1 which encompasses a group of highly related MAC-strains isolated from immuno-compromised human beings. Most MIC 3 strains are located in the MIC 3.1 subtype. Eventually species status may be assigned to this group of strains, as might also be the case for other groups of MAC strains, vet unnamed. In subtypes MIC 3.4. MIC 3.3 and MIC 3.2 only two, one and one strain are found respectively in our collection of strains tested.

Type MIC 4 is a collection of "MAIS" strains (including *M. malmoense*) which are remotely related to *M. intracellulare*. The only probe of the above-described set which hybridizes to MIC 4, apart from the general myc1/myc22 probes is the mai1 probe. This probe shows a broad specificity, hybridizing also with *M. avium, M. intracellulare* and other MIC strains and *M. scrofulaceum*.

*M. scrofulaceum*

All *M. scrofulaceum* strains tested reveal an identical hybrdization pattern with the set of probes. A positive signal with probe msc1 is unique to *M. scrofulaceum* strains. The only other probes with a positive signal for this species are evidently myc1/myc22 and also mai1.

*M. kansasii*

Probes mka3 and mka4 are specific for *M. kansasii*: i.e. a distinct positive signal is obtained on the LiPA strip when amplified DNA from the *M. kansasii* strains is used in the hybridization whilst with all other organisms tested the signal is absent. Although the sequences of probes mka1 and mka2 are not absolutely complementary to the target sequence (3 and 1 mismatches, respectively), these probes also proved to be useful since they hybridized exclusively to *M. kansasii* DNA and not to any other mycobacterial DNA tested under the conditions used (50° C., 3× SSC, 20% formamide). This illustrates that probes not necessarilly have to match perfectly to the target to be useful, and that modifications in sequence and length may be allowed up to a certain degree.

*M. chelonae*

The species *M. chelonae* encompasses *M. chelonae* ssp. *chelonae* and *M. chelonae* ssp. *abscessus* strains. The spacer region was sequenced for one strain of each subspecies and small differences were noticed (SEQ ID NO 103 and SEQ ID NO 102). Probes mch1 and mch2 hybridize to both strains. All other probes are negative for these 2 strains except for myc1/myc22.

Upon testing of probes mch1 and mch2 with 2 additional *M. chelonae* strains not mentioned in table 4, i.e. *M. chelonae* 94-379 and *M. chelonae* 94-330. both obtained from the Institute of Tropical Medicine in Antwerp, Belgium it appeared that they did not hybridize to probe mch1. This was confirmed by sequencing the spacer region of these two strains (SEQ ID NO 184). Cluster analysis of the spacer region with other mycobacteria revealed that *M. chelonae* strains can be subdivided in two groups. A third probe mch3 was designed to specifically detect this second group of strains, to which 94-379 and 94-330 belong.

This illustrates that the use of DNA probes derived from the 16S-23S rRNA spacer region can be helpful in differentiating different groups of strains, which belong to the same species according to the classical identification methods, and possibly can be used to detect and describe new species within the mycobacteria. In this case mch2 detects all *M. chelonae* strains, whereas mch1 and mch3 differentiate between different subgroups.

*M. gordonae*

The five *M. gordonae* strains tested all hybridize to probe mgo5. Positive hybridization signals are also obtained with probes myc1/myc22 and some *M. gordonae* strains also hybridize to probes mgo1 and mgo2.

Other Mycobacterial Species

Strains belonging to other mycobacterial species than those mentioned above only hybridize to the general probes myc1/myc22. This indicates that these strains most probably belong to the genus *Mycobacterium*, but do not belong to one of the species or groups which can be specifically identified by using one or more of the other probes described.

In conclusion we can state that, according to the particular combinations of probes of the invention used, DNA probe tests at different levels can be provided.

When all probes are used in one and the same LiPA-test, differentiation at the species level as well as subtyping of certain groups of mycobacteria can be achieved. However, the probe-assembly on one strip could be restricted to those probes which are species-specific: in that case identification is performed at the species level. A further reduction of the number of probes on the strip might lead to the specific detection of only one or just a few species. Obviously, LiPA strips can be designed which solely attempt to subtype strains, e.g. those belonging to the *M. intracellulare* complex (MIC). Depending on the particular needs of the laboratoria performing diagnosis and/or typing of mycobacteria, all these different applications might be of value. However, it is clear that by using a combination of probes in a LiPA-format the amount of information obtained as to the identity of the organisms present in the clinical sample, is considerably increased as compared to DNA probe tests using only a single probe. For some groups, or at least for further subdivision of some groups, a single probe uniquely hybridizing to this (sub)group could not be designed. In that case only probe-patterns are able to provide the information needed. For these applications the LiPA is an advantageous format.

TABLE 3

Different probe patterns obtained for mycobacterial (sub)species

| Mycobacterium | myc1 myc22 | mtb1 mtb2 mtb3 | mai1 | mil11 | mav1 mav22 | min1 | min222 | min22 | min2 | min2222 | mil22 | mac1 |
|---|---|---|---|---|---|---|---|---|---|---|---|---|
| *M. tuberculosis* | + | + | − | − | − | − | − | − | − | − | − | − |
| *M. bovis* | | | | | | | | | | | | |
| *M. avium* | + | − | + | + | + | − | − | − | − | − | − | − |
| *M. paratuberculosis* | | | | | | | | | | | | |
| MIC 1.1.a | + | − | + | + | − | + | + | + | + | + | − | + |
| MIC 1.1.b | + | − | + | + | − | − | ± | ± | ± | ± | − | + |
| MIC 1.2 | + | − | + | − | − | − | − | ± | ± | + | + | + |
| MIC 2 | + | − | + | − | − | − | − | − | − | ± | + | ± |
| MIC 3.4 | + | − | + | − | − | − | − | − | − | − | + | ± |
| MIC 3.3 | + | − | + | − | − | − | − | − | − | − | + | + |
| MIC 3.1 | + | − | + | − | − | − | − | − | − | − | + | + |
| MIC 3.2 | + | − | + | − | − | − | − | − | − | − | + | + |
| MIC 4 | + | − | + | − | − | − | − | − | − | − | − | − |
| *M. scrofulaceum* | + | − | + | − | − | − | − | − | − | − | − | − |
| *M. kansasii* | + | − | − | − | − | − | − | − | − | − | + | − |
| *M. chelonae* | + | − | − | − | − | − | − | − | − | − | − | − |
| *M. gordonae* | + | − | − | − | − | − | − | − | − | − | − | − |
| *Mycobacterium* sp. | + | − | − | − | − | − | − | − | − | − | − | − |

| Mycobacterium | mco1 | mth11 | mth2 | mef11 | mhef1 | mah1 | mal1 | msc1 | mka1, 2, 3, 4 | mch 1, 2, 3 | mgo1, 2 | mgo5 |
|---|---|---|---|---|---|---|---|---|---|---|---|---|
| *M. tuberculosis* | − | − | − | − | − | − | − | − | − | − | − | − |
| *M. bovis* | | | | | | | | | | | | |
| *M. avium* | − | − | − | − | − | + | − | − | − | − | − | − |
| *M. paratuberculosis* | | | | | | | | | | | | |
| MIC 1.1.a | − | − | − | − | − | − | − | − | − | − | − | − |
| MIC 1.1.b | − | − | − | − | − | − | − | − | − | − | − | − |
| MIC 1.2 | − | − | − | − | ± | − | − | − | − | − | − | − |
| MIC 2 | − | − | − | − | ± | + | + | − | − | − | − | − |

TABLE 3-continued

Different probe patterns obtained for mycobacterial (sub)species

| | | | | | | | | | | | | |
|---|---|---|---|---|---|---|---|---|---|---|---|---|
| MIC 3.4 | + | – | – | + | + | ± | – | – | – | – | – | – |
| MIC 3.3 | + | + | – | + | + | + | – | – | – | – | – | – |
| MIC 3.1 | + | + | + | – | ± | ± | – | – | – | – | – | – |
| MIC 3.2 | + | – | – | – | + | + | w | – | – | – | – | – |
| MIC 4 | – | – | – | – | – | – | – | – | – | – | – | – |
| M. scrofulaceum | – | – | – | – | – | – | – | + | – | – | – | – |
| M. kansasii | – | – | – | – | – | – | – | – | + | – | – | – |
| M. chelonae | – | – | – | – | – | – | – | – | – | ± | – | – |
| M. gordonae | – | – | – | – | – | – | – | – | – | – | ± | + |
| Mycobacterium sp. | – | – | – | – | – | – | – | – | – | – | – | – | w: weak/v: very weak/±: + or –, variable according to the strain tested

TABLE 4

Mycobacteria strains tested in LiPA

| species/group | strain numbers from Institute of Tropical Medecine Antwerp (except those between parentheses) |
|---|---|
| M. tuberculosis complex | 7602, 8004, 8017, 8647, 8872, 9081, 9129, 9173, 9517, (ATCC 27294), 8324, 8428 |
| M. avium/ M. paratuberculosis | 1101, 1983, 2070, 2074, 4176, 4189, 4191, 4193, 4197, 4204, 4386, 4991, 5872, 5874, 5884, 5887, 5893, 5894, 5897, 5903, 5904, 5905, 5927, 5983, 8180, 8750, (ATCC 25291), M. paratub: (316F), (2E) |
| M. intracellulare (MIC 1.1.a) | 4199, 4208, 5701, 5880, 5906, 5908, 5909, 5913, 5915, 5917, 5918, 5920, 5921, 5924, 5925, 5929, 8713, 8717, 8718, 8720, 8721, 8722, 8732, 8740, 8741, 8742, 8744, 8747, 8749 |
| MIC 1.1.b | 8694, 8745, 8754<br>8708<br>5513, 8743<br>8054, 8190 |
| MIC 1.2 | 8710, 8711, 8712, 8714, 8715, 8716, 8725, 8729, 8733, 8737, 8746, 8751, 8752<br>5919<br>8695<br>8748 |
| MIC 2 | 5922<br>4755 (M. lufu) |
| MIC 3.4 | 1815<br>8707 |
| MIC 3.3 | 5620 |
| MIC 3.1 | 925, 926, 1329, 1788, 1794, 1812, 1818, 2069, 2073, 2076, 4541, 4543, 5074, 5280, 5789, 7395, 8739, 8753<br>8738 |
| MIC 3.2 | 5765 |
| M. scrofulaceum | 4979, 4988, 5907, 8706, 8726, 8727, 8735, (MB022), (MB023), (MB024) |
| M. kansasii | 4987, (ATCC 22478) |
| M. chelonae | 4975, 9855 |
| M. gordonae | 7703, 7704, 7836, 7838, 8059 |
| MIC 4 | 8723, 8724<br>8757<br>4842 (M. malmoense) |
| other mycobacterial species | 7732 (M. marinum), 94-123 (M. celatum), 778 (M. haemophilum), 8777 (M. genavense), 4484 (M. siniae), 4986 (M. xenopi), 4304 (M. fortuitum), 1837 (M. ulcerans) |

EXAMPLE 3

Listeria

Listeria species are a group of Gram-positive rods widely spread in nature. Within this group it seems that only L. monocytogenes is pathogenic to humans and animals. L. monocytogenes is the causative agent of listeriosis, giving rise to meningitis, abortions, encephalitis and septicemia. Immunocompromised individuals, newborn infants and pregnant women are high risk groups for this foodborn disease. Most cases have been caused by the consumption of food of animal origin, particularly soft cheeses. Therefore, the presence of L. monocytogenes should be excluded from food. For safety measurements, in some countries, the absence of all Listeria species is required in food products.

The classical identification method for L. monocytogenes in dairy products involves an enrichment culture for 48 h and subsequently colony forming on selective agar medium for 48 h followed by a whole set of biochemical and morphological assays (Farber and Peterkin, 1991). This procedure could be very much simplified by the use of gene probes.

Several DNA probes are already described for the identification of L. monocytogenes. Some probes are derived from genes responsible for the pathogenicity of the organism, for instance the listeriolysin O gene (Datta et al., 1993) or the invasion-associated-protein (iap) (Bubert et al., 1992).

A commercially available identification system based on a specific 16S rRNA probe was introduced by GenProbe (Herman and De Ridder. 1993: Ninet et al. 1992).

These specific probes are used as confirmation assays on colonies obtained after enrichmnent and plating on selective agar medium.

Recently several publications reported on the use of the polymerase chain reaction to amplify the target region for the DNA probes, which can shorten the time of the assay without interfering with the specificity and the sensitivity of the assay. Different primer sets are described that can specifically amplify *L. monocytogenes* DNA. These primer sets were derived from the listeriolysin O gene (Golstein Thomas et al., 1991), and the iap gene (Jaton et al., 1992).

We used the 16S-23S rRNA gene spacer region as the target for the development of a genus-specific probe for *Listeria* and a probe specific for *Listeria monocytogenes*.

Using conserved primers derived from the 3' end of the 16S rRNA and the 5' end of the 23S rRNA (sequences are given in example 1) the spacer region was amplified using the polymerase chain reaction and subsequently -cloned in a suitable plasmid vector following the same procedures as in example 3.

Two amplicons differing in length (800 bp and 1100 bp) were obtained. Both PCR fragments were cloned for the following *Listeria* species:

*Listeria monocytogenes*, serovar 4b. IHE (Instituut voor Hygiëne en Epidermiologie, Belgium)

*Listeria ivanovii* CIP 78.42 (Collection Nationale de Cultures de Microorganisms de l'Institut Pasteur, France)

*Listeria seeligeri* serovar 4a, nr. 42.68 (Bacteriologisches Institut, Südd, Versuchs- und Forschungsanstalt für Milchwirtschaft Weihenstephan, Germany)

The sequence of the spacer region between the 16S and 23S rRNA gene was determined using the cloned material originating from the 800 bp PCR fragment and this was done for the three described *Listeria* species. FIGS. 41 to 43 show the sequences of the different short spacer regions obtained. The sequence of this short spacer region of *L. monocytogenes* was also retrieved from the EMBL databank (LMRGSPCR).

Based on this sequence information, following oligonucleotides for species-specific detection were chosen and chemically synthesized:

```
LMO-ICG-1:  AAACAACCTTTACTTCGTAGAAGTAAATTGGTTAAG

LMO-ICG-2:  TGAGAGGTTAGTACTTCTCAGTATGTTTGTTC

LSE-ICG-1:  AGTTAGCATAAGTAGTGTAACTATTTATGACACAAG

LIV-ICG-1:  GTTAGCATAAATAGGTAACTATTTATGACACAAGTAAC
```

Also, a genus specific probe for *Listeria* was designed:

```
LIS-ICG-1:  CAAGTAACCGAGAATCATCTGAAAGTGAATC
```

The oligonucleotide-probes were immobilized on a membrane strip and following reverse hybridization with biotinylated PCR fragments, the hybrids were visualized using a precipitation reaction. The hybridization results of different *Listeria* species are summarized in table 5.

TABLE 5

| Species | n | LIS1 | LMO1 | LMO2 | LSE1 | LIV1 |
|---|---|---|---|---|---|---|
| *L. monocytogenes* | 1 | + | + | + | − | − |
| *L. seeligeri* | 2 | + | + | ± | + | ± |
| *L. ivanovii* | 3 | + | ± | − | ± | + |
| *L. welshimeri* | 3 | + | + | ± | − | − |
| *L. innocua* | 2 | + | + | + | − | − |

These hybridization results show that probe LIS1 can detect all described *Listeria* species, but also that the species-specific probes cross-hybridize to each other. Hence from this short spacer region probes with sufficient specificity could not be found.

For *Listeria monocytogenes* the 16S-23S rRNA gene spacer was also determined originating from the 1100 bp fragment. FIG. 45 shows the sequence obtained for this species. This sequence information was also obtained for *L. seeligeri* (see FIG. 46) and partial sequence information of the large spacer region was obtained for *L. ivanovii* (see FIG. 44).

Based on sequence alignment with *L. seeligeri* following oligonucleotide-probe was chosen to specifically detect *L. monocytogenes*.

```
LMO-ICG-3:  AGGCACTATGCTTGAAGCATCGC
```

Initial hybridization results (not shown) indicated that no cross-hybridization with other *Listeria* species was seen with this *L. monocytogenes* probe LMO3, and that all *Listeria* strains used hybridized to the general probe LIS1.

The oligonucleotide-probes, LIS1 for detection of all *Listeria* species and LMO3 for specific detection of *L. monocytogenes*, were immobilized on a membrane strip and hybridized to labeled amplicons, containing the 16S-23S rRNA spacer region, derived from different organisms. The hybridization results are shown in the following table.

An excellent specificity and sensitivity were obtained for probes LMO3 and LIS1 respectively at the species and genus level.

TABLE 6

| Taxa tested | n | LIS1 | LMO3 |
|---|---|---|---|
| *Listeria monocytogenes* | 44 | + | + |
| *Listeria ivanovii* | 10 | + | − |
| *Listeria seeligeri* | 11 | + | − |
| *Listeria welshimeri* | 16 | + | − |
| *Listeria innocua* | 23 | + | − |
| *Listeria murrayi* | 3 | + | − |
| *Listeria grayi* | 2 | + | − |
| *Brochotrix thermosphacta* | 1 | − | − |
| *Brochotrix campestris* | 1 | − | − |
| *Bacillus cereus* | 3 | − | − |
| *Bacillus brevis* | 2 | − | − |
| *Bacillus coalgulans* | 1 | − | − |
| *Bacillus pumilis* | 1 | − | − |
| *Bacillus macerans* | 1 | − | − |
| *Bacillus lentus* | 1 | − | − |
| *Bacillus firmus* | 2 | − | − |
| *Bacillus subtilis* | 2 | − | − |
| *Bacillus megantum* | 1 | − | − |
| *Enterococcus faecalis* | 1 | − | − |
| *Enterococcus faecium* | 1 | − | − |
| *Enterococcus durans* | 1 | − | − |
| *Lactococcus lactis* | 3 | − | − |
| *Lactococcus caseï* | 1 | − | − |
| *Escherichia coli* | 1 | − | − |
| *Hafnia halvei* | 1 | − | − |

TABLE 6-continued

| Taxa tested | n | LIS1 | LMO3 |
|---|---|---|---|
| *Agrobacterium tumefaciens* | 2 | – | – |
| *Mycoplasma dimorpha* | 1 | – | – |
| *Clostridium tyrobutyricum* | 1 | – | – |
| *Clostridium perfringens* | 1 | – | – |
| *Clostridium sporogenes* | 1 | – | – |
| *Clostridium acetobutyricum* | 1 | – | – |
| *Brucella abortus* | 1 | – | – |
| *Brucella suis* | 1 | – | – |
| *Brucella melitensis* | 1 | – | – |
| *Staphylococcus aureus* | 1 | – | – |
| *Salmonella typhimurium* | 1 | – | – |
| *Salmonella enteritidis* | 1 | – | – |
| *Yersinia enterocolitica* | 1 | – | – | n: number of strains tested

These two probes can be used for the detection of *Listeria* species and *Listeria monocytogenes* directly on food samples or after enrichment of the samples in liquid broth. In both cases amplification problems can occur with the conserved primerset due to the enormous background flora in these samples.

To circumvent this problem, we designed several sets of primers derived from the 16S-23S rRNA spacer regions of *Listeria* species.

Primers LIS-P1 and LIS-P2 are upper primers, whereas LIS-P3 and LIS-P4 are lower primers. These primersets amplify the smaller 16S-23S rRNA spacer region as well as the larger spacer of *Listeria* species (except *L. grayi* and *L. murrayi*). If needed these primers can be used in a nested PCR assay where LIS-P1/LIS-P4 are the outer primers and LIS-P2/LIS-P3 are the inner primers.

For the specific detection of *Listeria monocytogenes* probe LMO-ICG-3 was designed and derived from the large 16S-23S rRNA spacer region. In order to specifically amplify only this large spacer region for an improved detection of this pathogen directly in samples a set of primers was derived from the part of sequence information from the large 16S-23S rRNA spacer region that is not present in the smaller rRNA spacer. For this aim, primers LIS-P5 and LIS-P6 are used as the upper primers and LIS-P7 is used as the lower primer.

```
LIS-P1:    ACCTGTGAGTTTTCGTTCTTCTC      71

LIS-P2:    CTATTTGTTCAGTTTTGAGAGGTT     72

LIS-P3:    ATTTTCCGTATCAGCGATGATAC      73

LIS-P4:    ACGAAGTAAAGGTTGTTTTCT        74

LIS-P5:    GAGAGGTTACTCTCTTTTATGTCAG    75

LIS-P6:    CTTTTATGTCAGATAAAGTATGCAA    202

LIS-P7:    CGTAAAAGGGTATGATTATTTG       203
```

During the evaluation of the probes for *Listeria* spp. an organism was isolated from cheese that resembled *Listeria* according to the classical determination methods. This isolate (MB 405) showed the following characteristics (similar to *Listeria* spp.): Gram positive growth on Oxford and Tryptic Soy Agar, catalase positive. The only difference with the *Listeria* spp. was the motility, which was negative.

Using the conserved primers as described in example 1 in order to amplify the 16S-23S rRNA spacer region of this isolate MB 405, the same amplicon pattern was obtained with this strain as with *Listeria* spp. Hybridization of the amplicon showed that there was no signal obtained with any of the probes for *Listeria* spp.

Sequencing of the 16S rRNA of isolate MB 405 and subsequent comparison with *Listeria* spp. and relatives showed that the organism was more closely related to *Listeria* spp. than to any other species described in the literature until now. Taxonomical studies will show if this isolate does or does not belong to the genus *Listeria*. This isolate and subsequently isolated organisms from the same type, are referred to in this application as *Listeria* like organisms.

Isolate MB 405 seemed to contain at least 3 different 16S-23S rRNA spacer regions which were cloned and sequenced. Following alignment with *Listeria* spp. an oligonucleotide-probe was chosen te specifically detect *Listeria*-like strains:

```
LISP-ICG-1:    CGTTTTCATAAGCGATCGCACGTT
```

Reverse hybridization reactions of this probe with the 16S-23S rRNA spacer regions of *Listeria* spp. showed that there was no cross-hybridization.

EXAMPLE 4

*Chlamydia trachomatis*

*Chlamydia trachomatis* is a small obligate intracellular gram-negative bacterium, which has 15 serovars (A-K, Ba, L1, L2, and L3) distinguished by the major outer membrane protein (MOMP) and contains a cryptic plasmid required for intracellular growth. The A-K and Ba serovars constitute the trachoma biovar, while the L1, L2, and L3 serovars constitute the LGV biovar.

Serovars A, B, Ba, and C are commonly associated with trachoma, the leading cause of preventable blindness worldwide. The D-K serovars are found mainly in sexually transmitted infections and are the major cause of cervicitis and pelvic inflammatory disease in women, and urethritis and epididymitis in men. Serovars L1, L2 and L3 are involved in lymphogranuloma venereum, a rare sexually transmitted disease.

Cell culture is regarded as the benchmark method for laboratory diagnosis although specimen viability is difficult to maintain during transport and laboratory techniques are time-consuming and technically demanding. Therefore, a number of more rapid test kits were developed, such as an enzyme-linked immunosorbent assay, and direct fluorescent-antibody staining. However, none of these immunoassays have been shown to have high levels of sensitivity or specificity.

A nonisotopic DNA probe assay (Gen-Probe PACE: Woods et al., 1990) that detects chlamydial rRNA is commercially available. Recently, the polymerase chain reaction (PCR) method has been used for detection of *Chlamydia* infections. Detection was targeted at either the cryptic plasmid (Loeffelholz et al., 1992), or the omp1 gene, which encodes for the major outer membrane protein (Taylor-Robinson et al., 1992). Compared with other techniques, PCR has higher sensitivity and specificity (Ossewaarde et al., 1992). None of these assays make use of DNA probes derived from the 16S-23S rRNA gene spacer region.

For a *Chlamydia trachomatis* L2 and a *Chlamydia psittaci* 6BC strain, a part of the ribosomal RNA cistron, containing the 16S-23S rRNA spacer region was amplified using conserved primers (see example 1) and subsequently cloned in a plasmid vector. The 16S-23S rRNA spacer region was sequenced using the dideoxychain terminating chemistry.

The sequence of the spacer region of both Chlamydia species is shown in FIGS. 47 to 48.

Based on this sequence information, following oligonucleotide-probes were chemically synthesized:

```
CHTR-ICG-1:   GGAAGAAGCCTGAGAAGGTTTCTGAC
CHTR-ICG-2:   GCATTTATATGTAAGAGCAAGCATTCTATTTCA
CHTR-ICG-3:   GAGTAGCGTGGTGAGGACGAGA
CHPS-ICG-1:   GGATAACTGTCTTAGGACGGTTTGAC
```

The oligonucleotide-probes were immobilized in a linewise fashion on a membrane strip and subsequently used in a reverse hybridization assay with biotinylated PCR products, containing the 16S-23S rRNA spacer region as target.

Hybridizations were done in a solution of 3× SSC and 20% formamide (FA) at a temperature of 50° C.

The hybridization results with the different probes are shown in the following table.

TABLE 7

| Strains tested | CHTR1 | CHTR2 | CHTR3 | CHPS1 |
|---|---|---|---|---|
| Chlamydia trachomatis L2 | + | + | + | − |
| Chlamydia psittaci 6BC | − | − | − | + |
| Chlamydia psittaci CP | − | − | − | + |
| Chlamydia psittaci TT | − | − | − | + |
| Haemophilus ducreyi CIP 542 | − | − | − | − |
| Haemophilus influenzae NCTC 8143 | − | − | − | − |
| Neisseria gonorrhoeae NCTC 8375 | − | − | − | − |
| Moraxella catarrhalis LMG 5128 | − | − | − | − |
| Escherichia coli B | − | − | − | − |
| Streptococcus pneumoniae S92-2102 | − | − | − | − |

As shown in the table at a hybridization temperature of 50° C. the probes CHTR1. CHTR2 and CHTR3 are specific for Chlamydia trachomatis and probe CHPS1 is specific for Chlamydia psittaci.

Several clinical isolates, obtained from the SSDZ, Delft, Netherlands, identified as Chlamydia trachomatis using conventional methods were tested in a reverse hybridization assay with the different oligonucleotide-probes. All Chlamydia trachomatis specific probes gave a positive hybridization signal and none of the isolates reacted with the Chlamydia psittaci probe. For some clinical isolates the CHTR2 probe reacted significantly weaker than CHTR1 or CHTR3. The spacer region of one of these isolates (94 M 1961) was sequenced (SEQ ID NO 197) and the sequence revealed one mismatch with the spacer sequence of strain L2. An additional probe (CHTR4) was derived from this new spacer sequence:

```
CHTR-ICG-4: GAGTAGCGCGGTGAGGACGAGA (SEQ ID NO 201)
```

This probe gives a stronger hybridization signal than CHTR2 with some clinical isolates from Chlamydia trachomatis. It can be used alone, or in combination with the CHTR2 probe (e.g. both probes applied in one LiPA-line).

In order to develop very sensitive assays for the detection of Chlamydia trachomatis directly in clinical specimens a specific primerset was derived from the 16S-23S rRNA spacer region, CHTR-P1 (upper primer) and CHTR-P2 (lower primer), amplifying specifically the spacer region of Chlamydia species.

```
CHTR-P1:   AAGGTTTCTGACTAGGTTGGGC         69
CHTR-P2:   GGTGAAGTGCTTGCATGGATCT         70
```

EXAMPLE 6

Mycoplasma pneumoniae and Mycoplasma genitalium

Mycoplasmas are a group of the smallest prokaryotes known that are able to grow in cell-free media, lack a cell wall, and have very small genomes with a low G+C content. More than 100 different species have been isolated from humans, animals, plants, and insects.

In humans, mycoplasmas have been recognized either as pathogenic organisms or as commensals. The best known pathogen is Mycoplasma pneumoniae the causative agent of primary atypical pneumonia, especially in children and young adults. The diagnosis of M. pneumoniae has been based on the direct isolation by the culture method or on the detection of specific antibodies against M. pneumoniae in the patient's serum.

Another pathogen, first isolated from urethral specimens from patients with nongonococcal urethritis, has been described as Mycoplasma genitalium. This mycoplasma has several properties in common with M. pneumoniae. Both species are pathogenic and both possess the capability to adhere to erythrocytes, various tissue cells, glass, and plastic surfaces. Furthermore, M. genitalium and M. pneumoniae share antigens, giving rise to extensive cross-reactions in serological tests. The observation that M. genitalium could also be found in respiratory tract specimens from patients with pneumonia and isolated from a mixture with M. pneumoniae has raised questions to the possible pathogenicity of M. genitalium.

Since cultivation of both species is time-consuming and serology lacks specificity more rapid and more specific assays were developed to identify these mycoplasmas. The use of hybridization assays with DNA probes was described for these species, but despite good specificities these tests do not allow the detection of low levels of M. pneumoniae or M. genitalium. So more recently, DNA hybridization techniques were developed using the polymerase chain reaction. M. pneumoniae-specific PCR assays have been reported using the P1 adhesin gene (Buck et al., 1992) and the 16S rRNA gene (Kuppeveld et al. 1992). Specific PCR assays for M. genitalium were described using sequences from the adhesin gene and the 16S rRNA gene.

The spacer sequences of clinical isolates of M. pneumoniae and M. genitalium (obtained from U. Göbel, University of Freiburg, Germany) were determined. They are shown in FIGS. 49 to 50. The sequences show some differences to those from other strains of the same species deposited in the EMBL databank (MPMAC and MGG37 respectively). Based on this information four probes were derived: one general Mycoplasma probe, two M. pneumoniae specific, and one M. genitalium specific probe:

```
Mycoplasma-ICG:   CAAAACTGAAAACGACAATCTTTCTAGTTCC
MPN-ICG-1:        ATCGGTGGTAAATTAAACCCAAATCCCTGT
```

```
-continued
MPN-ICG-2:        CAGTTCTGAAAGAACATTTCCGCTTCTTTC
MGE-ICG-1:        CACCCATTAATTTTTTCGGTGTTAAAACCC
```

The probes were applied to LiPA strips and hybridized under standard conditions (3×SSC, 20% formamide at 50° C.) to amplified spacer material from four *M. pneumoniae* strains, one *M. genitalium* strain and twenty-two non-*Mycoplasma* species strains. The general probe hybridized only to the five *Mycoplasma* strains tested while the specific probes hybridized only to strains of the species for which they were designed.

EXAMPLE 7

Other Mycobacterial Species

With the steady improvement of laboratory techniques the information on the systematics and clinical significance of the so called "potentially pathogenic environmental mycobacteria" increased rapidly. With the emergence of newly recognized diseases, additional syndromes associated with different mycobacterial species have emerged and have assumed major importance.

In order to extend the LiPA test for the simultaneous detection of different mycobacterial species as described in example 2, a new set of DNA probes was designed to specifically identify the following species: *Mycobacterium ulcerans, Mycobacterium genavense, Mycobacterium xenopi, Mycobacterium simiae, Mycobacterium fortuitum, Mycobacterium malmoense, Mycobacterium celatum* and *Mycobacterium haemophilum*.

These probes were derived from the 16S-23S rRNA spacer region sequence. For the above mentioned species this information was obtained through direct sequencing of PCR products or after cloning of the PCR-amplified spacer region. The sequences obtained are represented in FIGS. 80 to 97, and in FIG. 38 for *M. malmoense*.

The sequences of the spacer region of the above-mentioned mycobacterial species were compared and aligned to those already described in example 2 or in publicly available sources. From the regions of divergence, species-specific DNA probes were designed. The probes were selected and designed in such a way that the desired hybridization behaviour (i.e. species-specific hybridization) was obtained under the same conditions as those specified for the other mycobacterial probes mentioned in example 2, i.e. 3× SSC, 20% deionized formamide, 50° C. This allows simultaneous detection of at least two, and possibly all of the mycobacterial species described in the current invention.

The following oligonucleotide probes were designed from the spacer region sequence of respectively *M. ulcerans, M. genavense, M. xenopi, M. simiae, M. fortuitum. M. malmoense, M. celatum* and *M. haemophilum*:

```
MUL-ICG-1:        GGTTTCGGGATGTTGTCCCACC
MGV-ICG-1:        CGACTGAGGTCGACGTGGTGT
MGV-ICG-2:        GGTGTTTGAGCATTGAATAGTGGTTGC
MXE-ICG-1:        GTTGGGCAGCAGGCAGTAACC
MSI-ICG-1:        GCCGGCAACGGTTACGTGTTC
```

```
-continued
MFO-ICG-1:        TCGTTGGATGGCCTCGCACCT
MFO-ICG-2:        ACTTGGCGTGGGATGCGGGAA
MML-ICG-1:        CGGATCGATTGAGTGCTTGTCCC
MML-ICG-2:        TCTAAATGAACGCACTGCCGATGG
MCE-ICG-1:        TGAGGGAGCCCGTGCCTGTA
MHP-ICG-1:        CATGTTGGGCTTGATCGGGTGC
```

The probes were immobilized on a LiPA strip and hybridized with amplified biotinylated material derived from a set of representative mycobacterial species as described in example 2. Amplification of the spacer region was carried out by PCR using a primer set as described in example 2. The different strains used for specificity testing are shown in table 8 together with the hybridization results obtained. The strains were obtained from the collection of the Institute for Tropical Medicine, Antwerp, Belgium.

The probes tested (MSI-ICG1, MXE-ICG-1, MFO-ICG-1, MFO-ICG-2, MML-ICG-1, MML-ICG-2, MCE-ICG-1 and MHP-ICG-1) specifically detected *M. simiae, M. xenopi, M. fortuitum, M. malmoense, M. celatum* and *M. haemophilum* respectively and showed no cross-hybridization with the other mycobacterial species tested. Thus, these probes allow a specific detection of mycobacterial species which were not further identifiable using the set of DNA probes described in example 2. *M. malmoense* was classified in example 2 as a "MIC 4"-type, while the other species mentioned above were only hybridizing to the general probes MYC1/MYC22 for the genus *Mycobacterium* and were thus classified in example 2 as "other mycobacterial species".

All tested *M. genavense* isolates reacted with MGV-ICG1 and MGV-ICG2 and not with MSI-ICG1 designed for *M. simiae*, closely related to *M. genavense*. A group of "intermediate" organisms, situated in between *M. simiae* and *M. genavense*, were received from the Tropical Institute of Medecine, Antwerp, where they were classified as "*M. simiae*-like" (strains 4358, 4824, 4833, 4844, 4849, 4857, 4859, 7375, 7379, 7730, 9745, 94-1228). These strains reacted only with probe MGV-ICG2 and not with probe MSI-ICG1 which specifically detects *M. simiae* strains sensu stricto. Sequencing of the 16S-23S rRNA spacer region of two of these "*M. simiae*-like" isolates (strains 7379 and 9745) (see SEQ ID NO 161 and 162) confirmed that they were more closely related to *M. genavense* than to *M. simiae*. A new probe MGV-ICG3 was designed to specifically detect this group of organisms which possibly belong to a new species.

```
MGV-ICG 3:        TCGGGCCGCGTGTTCGTCAAA
```

This illustrates again that the use of DNA probes derived from the 16S-23S spacer region can be helpful in differentiating different groups of strains, which are also found indeterminate by classical taxonomic criteria. The use of these DNA probes may possilby lead to the description of new (sub)species within mycobacteria. In this case, the MGV-1 probe would react only with *M. genavense* strains sensu stricto. MGV-3 probe would react only with the intermediate "*M. simiae*-like" strains, and MGV-2 probe would detect both types of strains.

The probe MUL-ICG-1 reacted with all *M. ulcerans* strains tested, but also showed cross-hybridization with *M. marinum* strain ITG 7732. Sequencing of the spacer region of this *M. marinum* strain indeed revealed an identical sequence to that of *M. ulcerans* strain 1837 (see FIG. 80). Further differentiation between *M. marinum* and *M. ulcerans* can be done using a probe from the 16S-rRNA gene of *M. ulcerans*, part of which is co-amplified with the spacer region when primers MYC P1-P5 are used for amplification. A species-specific 16S rRNA probe for *M. ulcerans*, which can work under the same hybridization conditions as the spacer probes for *mycobacterium* species differentiation is for example:

```
TGGCCGGTGCAAAGGGCTG        (SEQ ID NO 216)
```

The above paragraph shows that, although it is preferable to use probes derived from the spacer region, it is also possible, and sometimes necessary to combine the spacer probes with probes derived from other gene sequences, e.g. the 16S rRNA gene. Here again these additional probes are selected such that they show the desired hybridization characteristics under the same hybridization and wash conditions as the spacer probes.

For *M. kansasii*, additional strains to the ones mentioned in example 2 have been tested with probes MKA-ICG-1, 2, 3 and 4 described in example 2. Since none of these probes was entirely satisfactory, additional probes were designed for *M. kansasii* detection. Therefor, the spacer region of some of the additional *M. kansasii* strains ITG 6328, 8698 and 8973 was sequenced (see FIGS. 90 to 92). These strains were also obtained from the Institute of Tropical Medecine in Antwerp, Belgium. Apparently, *M. kansasii* strains constitute a quite heterogeneous group, with remarkable differences in the spacer sequence between different strains. Additional probes MKA-ICG-5, 6, 7, 8, 9 and 10 were designed, all hybridizing again under the same conditions as those earlier described, i.e. 3× SSC, 20% deionized formamide, 50° C. The probes were tested with a collection of test strains obtained from the Institute of Tropical Medicine, Antwerp, Belgium, and results are shown in table 8.

None of the *M. kansasii* probes hybridizes with a species other than *M. kansasii*, as far as tested. However, due to the heterogeneous character of this species, none of the *M. kansasii* probes hybridizes with all *M. kansasii* strains. The different *M. kansasii* probes recognize different strains of *M. kansasii*. This differential hybridization may be of clinical significance. On the other hand, if detection of all *M. kansasii* strains is desirable, a combination of different *M. kansasii* probes can be envisaged.

TABLE 8 additional mycobacterial probes

| species/type | strain | MUL ICG-1 | MGV ICG- 1 | MGV ICG- 2 | MGV ICG- 3 | MXE ICG-1 | MFO ICG-2 | MSI ICG-1 | MML ICG-2 | MCE ICG-1 | MHP ICG-1 |
|---|---|---|---|---|---|---|---|---|---|---|---|
| *M. tuberculosis* | 8004 | − | − | − | | − | − | − | − | − | − |
| *M. avium* | 5887 | − | − | − | | − | − | − | − | − | − |
| *M. intracellulare* | 5915 | − | − | − | | − | − | − | | | |
| | 5913 | | | | | | | | | − | − |
| MIC 3.1 strain | 1812 | − | − | − | | − | − | | | | |
| MIC-4 strain | 8724 | | | | | | | − | | | |
| *M. scrophulaceum* | 4979 | − | − | − | | − | − | − | − | − | − |
| *M. kansasii* | 4987 | − | − | − | | − | − | − | − | − | − |
| | 2795 | | | | | | | | | | |
| | 6238 | − | − | − | | − | − | − | − | − | − |
| | 6362 | | | | | | | | | | |
| | 8698 | − | − | − | | − | − | − | − | − | − |
| | 8973 | − | − | − | | − | − | − | − | − | − |
| | 8974 | | | | | | | | | | |
| | 8971 | | | | | | | | | | |
| *M. ulcerans* | 1837 | + | − | − | | − | − | − | − | − | − |
| | 3129 | + | − | − | | − | − | − | − | − | − |
| | 5114 | + | − | − | | − | − | − | | | |
| | 5115 | + | − | − | | − | − | − | | | |
| *M. marinum* | 7732 | + | − | − | | − | − | − | − | − | − |
| *M. malmoense* | 4832 | − | − | − | | − | − | − | + | | |
| | 4842 | − | | | | | | | + | | |
| *M. gordonae* | 7703 | − | − | − | | − | − | − | − | − | − |
| *M. chelonae* | 4975 | − | − | − | | − | − | − | | | |
| | 9855 | − | − | − | | − | − | | | | |
| | 94-330 | − | − | − | | − | − | | | | |
| | 94-379 | − | − | − | | − | − | | | | |
| *M. gordonae* | 94-123 | − | − | − | | − | − | − | − | + | − |
| *M. haemophilum* | 778 | − | | | | | | | | − | + |
| | 3071 | | | | | | | | | − | + |
| *M. genavense* | 8777 | − | + | + | − | − | − | − | | | |
| and *M. simiae*-like | 9745 | − | − | + | + | − | − | − | | | |
| | 92-742 | − | + | + | − | − | − | − | | | |
| | 7379 | − | − | + | + | − | − | − | | | |
| | 9500 | − | + | + | − | − | − | − | | | |
| *M. simiae* | 4484 | − | − | − | | − | + | | | | |
| | 4485 | − | − | − | | − | + | | | | |
| *M. xenopi* | 4986 | − | − | − | | + | − | − | | | |
| *M. fortuitum* | 4304 | − | − | − | | − | + | − | | | |

TABLE 8-continued additional mycobacterial probes

| species/type | strain | MKA ICG-3 | MKA ICG-4 | MKA ICG-5 | MKA ICG-6 | MKA ICG-7 | MKA ICG-8 | MKA ICG-9 | MKA-ICG-10 |
|---|---|---|---|---|---|---|---|---|---|
| M. tuberculosis | 8004 | − | − | − | − | − | − | − | − |
| M. avium | 5887 | − | − | − | − | − | − | − | − |
| M. intracellulare | 5915 | − | − | − | − | | | | |
| | 5913 | | | | | − | − | − | − |
| MIC 3.1 strain | 1812 | − | − | | | | | | |
| MIC-4 strain | 8724 | − | − | − | − | | | | |
| M. scrophulaceum | 4979 | − | − | − | − | − | − | − | − |
| M. kansasii | 4987 | + | + | − | − | − | − | − | + |
| | 2795 | + | + | − | − | − | − | − | + |
| | 6238 | + | − | + | − | − | + | + | + |
| | 6362 | + | − | + | − | − | + | + | + |
| | 8698 | − | − | − | − | + | − | + | w |
| | 8973 | − | − | − | + | − | + | − | − |
| | 8974 | − | − | − | + | − | + | − | − |
| | 8971 | − | − | − | + | − | + | − | − |
| M. ulcerans | 1837 | | | − | − | − | − | − | − |
| | 3129 | | | − | − | − | − | − | − |
| | 5114 | | | − | − | | | | |
| | 5115 | | | − | − | | | | |
| M. marinum | 7732 | − | − | − | − | − | − | − | − |
| M. malmoense | 4832 | − | − | − | − | | | | |
| | 4842 | | | | | | | | |
| M. gordonae | 7703 | − | − | − | − | − | − | − | − |
| M. chelonae | 4975 | | | | | | | | |
| | 9855 | | | | | | | | |
| | 94-330 | | | | | | | | |
| | 94-379 | | | | | | | | |
| M. celatum | 94-123 | | | | | − | − | − | − |
| M. haemophilum | 778 | | | | | − | − | − | − |
| | 3071 | | | | | − | − | − | − |
| M. genavense and M. simiae-like | 8777 | | | | | | | | |
| | 9745 | | | | | | | | |
| | 92-742 | | | | | | | | |
| | 7379 | | | | | | | | |
| | 9500 | | | | | | | | |
| M. simiae | 4484 | | | | | | | | |
| | 4485 | | | | | | | | |
| M. xenopi | 4986 | | | − | − | | | | |
| M. fortuitum | 4304 | | | | | | | | |

− = negative reaction,
+ = positive reaction,
w = weak reaction,
± = variable reaction,
blanc = non tested

EXAMPLE 8

Brucella

Brucellosis is a very widespread and economically important zoonosis which also affects humans.

For the identification of *Brucella* spp., mainly bacteriological and immunological detection techniques are being used. These tests are time-consuming and often give false-positive results. Quick and reliable identification methods are being developed, mainly based on DNA amplification and hybridization.

Specific detection of *Brucella* spp. based on the amplification of a 43 kDa outer membrane protein (Fekete A. et al., 1990) or of a part of the 16S rRNA gene (Herman and De Ridder, 1992) were already described.

In order to develop specific DNA probes and primers for the detection of *Brucella* spp. we analyzed the 16S-23S rRNA gene spacer region. Using conserved primers (sequences are given in example 1) the spacer region was amplified and subsequently cloned into the Bluescript SK+ vector following the same procedures as in example 1. The obtained amplicon of about 1400 bp in length was cloned for the following *Brucella* species: *Brucella abortus* NIDO Tulya biovar 3 (SEQ ID NO 154)
  *Brucella melitensis* NIDO biovar 1 (SEQ ID NO 131)
  *Brucella suis* NIDO biovar 1 (SEQ ID NO 132)

HindIII digestion of the constructs, followed by subcloning of the obtained fragments (n=3) facilitated the sequencing of the spacer region for the three described *Brucella* spp. FIGS. 56, 57 and 79 represent the sequences of the spacer regions obtained for the above-mentioned strains of respectively *Brucella melitensis*, *Brucella suis* and *Brucella abortus*. Due to the high homology of these spacer region sequences between different *Brucella* species, no species-specific DNA probes were deduced from this sequence information, and only genus-specific probes were designed.

For this purpose, the following probes were chemically synthesized:

```
BRU-ICG 1:    CGTGCCGCCTTCGTTTCTCTTT

BRU-ICG 2:    TTCGCTTCGGGGTGGATCTGTG
```

```
BRU-ICG 3:       GCGTAGTAGCGTTTGCGTCGG

BRU-IGG 4:       CGCAAGAAGCTTGCTCAAGCC
```

The oligonucleotides were immobilized on a membrane strip and following reverse hybridization with biotinylated PCR fragments, the hybrids were visualized using a precipitation reaction. The hybridization results of the immobilized probes with different *Brucella* spp. and related organisms are represented in the table 9.

These hybridization results show that probes BRU-ICG 2, BRU-ICG 3 and BRU-ICG 4 are specific for *Brucella* spp. and can be used in a reverse hybridization assay for detection of these pathogens. Probe BRU-ICG 1 cross-hybridizes with *Ochrobactrum antropi* and *Rhizobium loti* strains, which are two taxonomically highly related organisms, but which are not expected to be present in the same sample material as used for *Brucella* detection.

As described in previous examples (e.g. 3 and 4) also for *Brucella* specific primers were chosen from the 16S-23S rRNA spacer region, in order to specifically amplify the spacer region from *Brucella* strains.

BRU-P1 and BRU-P2 are used as upper primers, while BRU-P3 and BRU-P4 are used as lower primers. When used in a nested PCR assay the combination BRU-P1/BRU4 is the outer primerset whereas the combination BRU-P2/BRU-P3 is the inner primerset.

```
BRU-P1:       TCGAGAATTGGAAAGAGGTC        204

BRU-P2:       AAGAGGTCGGATTTATCCG         205

BRU-P3:       TTCGACTGCAAATGCTCG          206

BRU-P4:       TCTTAAAGCCGCATTATGC         207
```

TABLE 9

| TAXA TESTED | n | BRU-ICG 1 | BRU-ICG 2 | BRU-ICG 3 | BRU-ICG 4 |
|---|---|---|---|---|---|
| *Brucella abortus* | 6 | + | + | + | + |
| *Brucella suis* | 3 | + | + | + | + |
| *Brucella melitensis* | 4 | + | + | + | + |
| *Brucella ovis* | 2 | + | + | + | + |
| *Brucella canis* | 2 | + | + | + | + |
| *Brucella neotomae* | 1 | + | + | + | + |
| *Phyllobacterium rubiacearium* | 1 | – | – | NT | NT |
| *Ochrobactrum anthropi* | 8 | + | – | – | – |
| *Agrobacterium tumefaciens* | 2 | – | – | NT | NT |
| *Agrobacterium rhizogenes* | 1 | – | – | NT | NT |
| *Mycoplana dimorpha* | 1 | – | – | NT | NT |
| *Rhizobium loti* | 1 | + | – | – | – |
| *Rhizobium meliloti* | 1 | – | – | NT | NT |
| *Rhizobium leguminosarum* | 1 | – | – | NT | NT |
| *Bradyrhizobium japonicum* | 1 | – | – | NT | NT |
| *Brochothrix thermosphacta* | 1 | – | – | NT | NT |
| *Brochothrix campestris* | 1 | – | – | NT | NT |
| *Bacillus cereus* | 3 | – | – | NT | NT |
| *Bacillus brevis* | 2 | – | – | NT | NT |
| *Bacillus coalgulans* | 1 | – | – | NT | NT |
| *Bacillus pumilis* | 1 | – | – | NT | NT |
| *Bacillus macerans* | 1 | – | – | NT | NT |
| *Bacillus lentus* | 1 | – | – | NT | NT |
| *Bacillus firmus* | 2 | – | – | NT | NT |
| *Bacillus subtilis* | 2 | – | – | NT | NT |
| *Bacillus megantum* | 1 | – | – | NT | NT |
| *Enterococcus faecalis* | 1 | – | – | NT | NT |
| *Enterococcus faecium* | 1 | – | – | NT | NT |
| *Enterococcus durans* | 1 | – | – | NT | NT |
| *Lactobacillus lactis* | 3 | – | – | NT | NT |
| *Lactobacillus caseï* | 1 | – | – | NT | NT |
| *Leuconostoc lactis* | 1 | – | – | NT | NT |
| *Escherichia coli* | 1 | – | – | NT | NT |
| *Hafnia halvei* | 1 | – | – | NT | NT |
| *Clostridium tyrobutyricum* | 1 | – | – | NT | NT |
| *Clostridium perfringens* | 1 | – | – | NT | NT |
| *Clostridium sporogenes* | 1 | – | – | NT | NT |
| *Clostridium acetobutyricum* | 1 | – | – | NT | NT |
| *Staphylococcus aureus* | 1 | – | – | NT | NT |
| *Salmonella enteritidis* | 1 | – | – | NT | NT |
| *Yersinia enterocolitica* | 1 | – | – | NT | NT |
| *Listeria monocytogenes* | 1 | – | – | NT | NT |
| *Listeria ivanovii* | 1 | – | – | NT | NT |
| *Listeria seeligeri* | 1 | – | – | NT | NT |
| *Listeria welshimeri* | 1 | – | – | NT | NT |
| *Listeria innocua* | 1 | – | – | NT | NT |
| *Listeria murrayi* | 1 | – | – | NT | NT |
| *Listeria grayi* | 1 | – | – | NT | NT |

NT = Not tested
n = number of strains tested

EXAMPLE 9

Staphylococcus aureus

*Staphylococcus aureus* is the staphylococcal species most commonly associated with human and animal infections. *Staphylococcus aureus* strains have been identified as important etiologic agents in both community-acquired and nosocomial infections. Recently nosocomial infection with methicillin-resistant *S. aureus* (MRSA) appear to be increasingly prevalent in many countries. The strains belonging to this species are also causative agents of food spoilage and poisoning.

In order to discriminate in a fast and specific way *S. aureus* strains from other staphylococci, the use of molecular techniques based on DNA probes and/or PCR were already described in the literature. Examples of target genes used for the development of these DNA based assays are the 16S rRNA gene (De Buyser at al., 1992; Geha et al, 1994), the mecA gene (Ubukata et al., 1992; Shimaoka et al., 1994 ) and the nuc gene (Brakstad et al., 1992; Chesneau et al., 1993).

As a target for the development of specific DNA probes we chose the 16S-23S rRNA gene spacer region. Amplification using conserved primers derived from the 16S and the 23S rRNA genes (sequences, see example 1) showed that the pattern obtained was not similar in all *S. aureus* strains tested. A lot of variation was seen in either the number of fragments obtained and in the size of these different fragments.

One spacer region from strain UZG 5728 and four spacer regions (differing in length) from strain UZG 6289 were cloned into Bluescript SK+ vector and subsequently sequenced. The sequences are represented in FIG. 64 to FIG. 68 (SEQ ID NO 139 to SEQ ID NO 143). For the development of specific DNA probes these different spacer regions were compared to each other and to the spacer region derived from *Staphylococcus epidermidis* strain UZG CNS41 (SEQ ID NO 144).

The following probes were chemically synthesized:

```
STAU-ICG 1:   TACCAAGCAAAACCGAGTGAATAAAGAGTT
STAU-ICG 2:   CAGAAGATGCGGAATAACGTGAC
STAU-ICG 3:   AACGAAGCCGTATGTGAGCATTTGAC
STAU-ICG 4:   GAACGTAACTTCATGTTAACGTTTGACTTAT
```

The oligonucleotides were immobilized on a membrane strip and following reverse hybridization with biotinylated PCR fragments, the hybrids were visualized using a colorimetric precipitation reaction.

The hybridization results of the immobilized probes with different *Staphylococcus* spp. and non-staphylococcal organisms are represented in Table 10.

These hybridization results show that only probes STAU-ICG 3 and STAU-ICG 4 are specific for *Staphylococcus aureus* strains. Probe STAU-ICG 1 reacts with all *Staphylococcus* spp. tested and probe STAU-ICG 2 cross-hybridizes with the *S. lugdinensis* stain. Neither probe STAU-ICG 3 nor probe STAU-ICG 4 detects all *S. aureus* strains tested, but when both probes are used simultaneously in a LiPA assay, all *S. aureus* stains tested hybridize with one of these probes or with both.

TABLE 10

| Strains tested | n | STAU-ICG 1 | STAU-ICG 2 | STAU-ICG 3 | STAU-ICG 4 |
|---|---|---|---|---|---|
| Staphylococcus aureus | 13 | + | + | + | + |
| Staphylococcus aureus | 10 | + | + | − | + |
| Staphylococcus aureus | 3 | + | + | w | + |
| staphylococcus aureus | 1 | + | + | + | − |
| Staphylococcus epidermidis | 11 | + | − | − | − |
| Staphylococcus saprophyticus | 1 | + | − | − | − |
| Staphylococcus haemolyticus | 1 | + | − | − | − |
| Staphylococcus capitis | 1 | + | − | − | − |
| Staphylococcus lugdinensis | 1 | + | + | − | − |
| Staphylococcus hominis | 1 | + | − | − | − |
| Bordetella pertussis | 1 | + | − | − | − |
| Bordetella parapertussis | 1 | − | − | − | − |
| Bordetella bronchiseptica | 1 | − | − | − | − |
| Mycobacterium tuberculosis | 1 | − | − | − | − |
| Mycobacterium avium | 1 | − | − | − | − |
| Moraxella catarrhalis | 4 | − | − | − | − |
| Haemophilus influenzae | 2 | − | − | − | − |
| Streptococcus pneumoniae | 3 | − | − | − | − |
| Pseudomonas cepacia | 1 | − | − | − | − |
| Pseudomonas aeruginosa | 3 | − | − | − | − |
| Acinetobacter calcoaceticus | 1 | − | − | − | − |

REFERENCES

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297-301.

Barany F (1991). Genetic disease detection and DNA amplification using cloned thermostable ligase. Proc Natl Acad Sci USA 88: 189-193.

Bej A, Mahbubani M, Miller R, Di Cesare J, Haff L, Atlas R (1990) Mutiplex PCR amplification and immobilized capture probes for detection of bacterial pathogens and indicators in water. Mol Cell Probes 4:353-365.

Böddinghaus B, Rogall T, Flohr T, Blöcker H, Böttger E (1990). Detection and identification of Mycobacteria by amplification of rRNA. Journal of Clinical Microbiology, 28: 1751-1759.

Brakstad, O. G., K. Aasbakk, and J. A. Maeland. 1992. Detection of *Staphylococcus aureus* by polymerase chain reaction amplification of the nuc gene. J. Clin. Microbiol. 30:1654-1660.

Bubert A, Köhler S, Goebel W (1992). The homologous and heterologous regions within the iap gene allow genus- and species-specific identification of *Listeria* spp. by polymerase chain reaction. Applied and Environmental Microbiology, 58: 2625-2632.

Buck G, O'Hara L, Summersgill J (1992). Rapid, sensitive detection of *Mycoplasma pneumoniae* in simulated clinical specimens by DNA amplification. Journal of Clinical Microbiology, 30: 3280-3283.

Bukh J, Purcell R, Miller R (1993). At least 12 genotypes ... PNAS 90,8234-8238.

Chesneau, O., J. Allignet and N. El Solh. 1993. Thermonuclease gene as a target nucleotide sequence for specific recognition of *Staphylococcus aureus*. Mol. Cell. Probes. 7:301-310.

Chomczynski P, Sacchi N (1987) Single step method of RNA isolation by acid guanidinium thiocyanate-phenol-chloroform extraction. Anal Biochem 162:156-159.

Compton J (1991). Nucleic acid sequence-based amplification. Nature, 350: 91-92.

Datta A, Moore M, Wentz B, Lane J (1993). Identification and enumeration of *Listeria monocytogenes* by nonradioactive DNA probe colony hybridization. Applid and Environmental Microbiology, 59: 144-149.

De Buyser, M., A. Morvan, S. Aubert, F. Dilasser and N. El Solh. 1992. Evaluation of a ribosomal RNA gene probe for the identification of species and subspecies within the genus *Staphylococcus*. J. Gen. Microbiol. 138:889-899.

Duck P (1990). Probe amplifier system based on chimeric cycling oligonucleotides. Biotechniques 9, 142-147.

Farber J, Peterkin P (1991). *Listeria monocytogenes*, a foodborne pathogen. Microbiological Reviews, 55 : 476-511.

Fekete, A., J. A. Bantle, S. M. Balling and M. R. Sanborn. 1990. Preliminary development of a diagnostic test for *Brucella* using polymerase chain reaction. J. Appl. Bacteriol. 69:216-227.

Frothingham R, Wilson K (1993). Sequence-based differentiation of strains in the *Mycobacterium avium* complex. Journal of Bacteriology, 175.

Frothingham R, Wilson K (1994). Molecular phylogeny of the *Mycobacterium avium* complex demonstrates clinically meaningful divisions. J Infect Diseases, 169: 305-312.

Geha, D. J., J. R. Uhl, C. A. Gustaferro, and D. H. Persing. 1994. Multiplex PCR for identification of methicillin-resistant staphylococci in the clinical laboratory. J. Clin. Microbiol. 32:1768-1772.

Golsteyn Thomas E, King R, Burchak J, Gannon V (1991). Sensitive and specific detection of *Listeria monocytogenes* in milk and ground beef with the polymerase chain reaction. Applied and Environmental Microbiology, 57: 2576-2580.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874-1878.

Herman L, De Ridder H (1993). Evaluation of a DNA-probe assay for the identification of *Listeria monocytogenes*. Milchwissenschaft, 48: 126-128.

Herman, L. and H. De Ridder. 1992. Identification of *Brucella* spp. by using the polymerase chain reaction. Appl. Env. Microbiol. 58:2099-2101.

Jacobs K, Rudersdorf R, Neill S, Dougherty J, Brown E, Fritsch E (1988) The thermal stability of oligonucleotide duplexes is sequence independent in tetraalkylammonium salt solutions: application to identifying recombinant DNA clones. Nucl Acids Res 16:4637-4650.

Jaton K, Sahli R, Bille J (1992). Development of polymerase chain reaction assays for detection of *Listeria monocytogenes* in clinical cerebrospinal fluid samples. Journal of Clinical Microbiology, 30: 1931-1936.

Jonas V, Aldan M, Curry J, Kamisango K, Knott C, Lankford R, Wolfe J, Moore D (1993). Detection and identification of *Mycobacterium tuberculosis* directly from sputum sediments by amplification of rRNA. Journal of Clinical Microbiology, 31: 2410-2416.

Kempsell K et al. (1992). The nucleotide sequence of the promotor, 16S rRNA and spacer region of the ribosomal RNA operon of *Mycobacterium tuberculosis* and comparison with *M. leprae* precursor rRNA. Journal of Gen Microbiol, 138: 1717-1727.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173-1177.

Kwok S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1988). A ligase-mediated gene detection technique. Science 241:1077-1080.

Lizardi P, Guerra C, Lomeli H, Tussie-Luna I, Kramer F (1988) Exponential amplification of recombinant RNA hybridization probes. Bio/Technology 6:1197-1202.

Loeffelholz M, Lewinski C, Silver S, Purohit A, Herman S, Buonagurio D, Dragon E (1992). Detection of *Chlamydia trachomatis* in endocervical specimens by polymerase chain reaction. Journal of Clinical Microbiology, 30: 2847-2851.

Lomeli H, Tyagi S, Printchard C. Lisardi P, Kramer F (1989) Quantitative assays based on the use of replicatable hybridization probes. Clin Chem 35: 1826-1831.

Maniatis T, Fritsch E, Sambrook J (1982) Molecular cloning: a laboratory manual. Cold Spring Harbor Laboratory Press, Cold Spring Harbor, N.Y.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706-10.

McIntosh I, Govan J, Brock D (1992). Detection of *Pseudomonas aeruginosa* in sputum from cystic fibrosis patients by the polymerase chain reaction. Molecular and Cellular Probes, 6: 299-304.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134-43.

Nielsen P, Egholm M, Berg R, Buchardt O (1991) Sequence-selective recognition of DNA by strand displacement with a thymine-substituted polyamide. Science 254(5037):1497-500.

Nielsen P, Egholm M, Berg R, Buchardt O (1993) Sequence specific inhibition of DNA restriction enzyme cleavage by PNA. Nucleic-Acids-Res. 21(2):197-200.

Ninet B, Bannerman E, Bille J (1992). Assessment of the accuprobe *Listeria monocytogenes* culture identification reagent kit for rapid colony confirmation and its application in various enrichment broths. Applied and Environmental Microbiology, 58: 4055-4059.

Ogle J, Janda J, Woods D, Vasil M (1987). Characterization and use of a DNA probe as an epidemiological marker for *Pseudomonas aeruginosa*. The Journal of Infectious Diseases, 155: 119.

Ossewaarde J, Rieffe M, Rozenberg-Arska M, Ossenkoppele P, Nawrocki R, Van Loon A (1992). Development and clinical evaluation of a polymerase chain reaction test for detection of *Chlamydia trachomatis*. Journal of Clinical Microbiology, 30: 2122-2128.

Rogall T, Wolters J, Flohr T, Böttger E (1990). Towards a phylogeny and definition of species at the molecular level within the genus *Mycobacterium*. Int. J. Syst. Bacteriol. 40: 323-330.

Rossau R, Michielsen A, Jannes G, Duhamel M, Kersten K, Van Heuverswyn H. DNA probes for *Bordetella* species and a colorimetric reverse hybridization assay for the detection of *Bordetella pertussis*. Mol. Cell. Probes 6: 281-289, 1992

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239: 487-491.

Saiki R, Walsh P, Levenson C, Erlich H (1989) Genetic analysis of amplified DNA with immobilized sequence-specific oligonucleotide probes (1989) Proc Natl Acad Sci USA 86:6230-6234.

Saito H, Tomioka H, Sato K, Hiromichi T, Tsukamura M, Kuze F, Asano K (1989). Identification and partial characterization of *Mycobacterium avium* and *Mycobacterium intracellulare* by using DNA probes. Journal of Clinical Microbiology, 27: 994-997.

Samadpour M, Moseley S, Lory S (1988). Biotinylated DNA probes for exotoxin A and pilin genes in the differentiation of *Pseudomonas aeruginosa* strains. Journal of Clinical Microbiology, 26: 2319-2323.

Sano T, Smith C, Cantor C (1992) Immuno-PCR: very sensitive antigen detection by means of specific antibody-DNA conjugates. Science 258:120-122.

Shimaoka, M., M. Yoh, A. Segawa, Y. Takarada, K. Yamamoto and T. Honda. 1994. Development of enzyme-labeled oligonucleotide probe for detection of mecA gene in methicillin-resistant *Staphylococcus aureus*. J. Clin. Microbiol. 32:1866-1869.

Stuyver L, Rossau R, Wyseur A, Duhamel M, Vanderborght B, Van Heuverswyn H, Maertens G (1993) Typing of hepatitis C virus (HCV) isolates and characterization of new (sub)types using a Line Probe Assay. J Gen Virology, 74: 1093-1102.

Suzuki Y et al. (1988). Complete nucleotide sequence of the 16S rRNA gene of *Mycobacterium bovis* BCG. J Bacteriol, 170: 2886-2889.

Taylor-Robinson D, Gilroy C, Thomas B, Keat A (1992). Detection of *Chlamydia trachomatis* DNA in joints of reactive arthritis patients by polymerase chain reaction. Lancet 340: 81-82.

Telenti A, Marchesi F, Balz M, Bally F, Böttger E, Bodmer T (1993). Rapid identification of Mycobacteria to the species level by polymerase chain reaction and restriction enzyme analysis. Journal of Clinical Microbiology, 31: 175-178.

Tomioka H, Saito H, Sato K, Tasaka H, Dawson J (1993). Identification of *Mycobacterium avium* complex strains belonging to serovars 21-28 by three commercial DNA probe tests. Tubercle and Lung Disease, 74: 91-95.

Ubukata, K., S. Nakagami, A. Nitta, Y. Yamane, S. Kawakami, M. Suguria and M. Konno. 1992. Rapid detection of the mecA gene in methicillin-resistant staphylococci by enzymatic detection of polymerase chain reaction products. J. Clin. Microbiol. 30:1728-1733.

Van der Giessen, J et al (1994). Comparison of the 23S rRNA genes and the spacer region between the 16S and 23S rRNA genes of the closely related *M. avium* and *M. paratuberculosis* and the fast-growing *M. phlei*. Microbiology, 140: 1103-1108.

Vaneechoutte M, De Beenhouwer H, Claeys G, Verschraegen G, De Rouck A, Paepe N, Elaichouni A, Portaels F (1993). Identification of *Mycobacterium* species by using amplified ribosomal DNA restriction analysis. Journal of Clinical Microbiology, 31: 2061-2065.

Van Kuppeveld F, Van Der Logt J, Angulo A, Van Zoest M, Quint W, Niesters H, Galama J, Melchers W (1992). Genus- and species-specific identification of *mycoplasmas* by 16S rRNA amplification. Applied and Environmental Microbiology, 58: 2606-2615.

Walker G, Little M, Nadeau J, Shank D (1992). Isothermal in vitro amplification of DNA by a restriction enzyme/DNA polymerase system. Proc Natl Acad Sci USA 89:392-396.

Woods G, Young A, Scott J, Blair T, Johnson A (1990). Evaluation of a nonisotopic probe for detection of *Chlamydia trachomatis* in endocervical specimens. Journal of Clinical Microbiology, 28: 370-372.

Wu D, Wallace B (1989). The ligation amplification reaction (LAR)—amplification of specific DNA sequences using sequential rounds of template-dependent ligation. Genomics 4:560-569.

The invention claimed is:

1. A composition comprising a diluent and a sequence selected from the group consisting of: SEQ ID NO:139, SEQ ID NO: 140, SEQ ID NO: 141, SEQ ID NO: 142, SEQ ID NO: 143, a sequence fully complementary to any of the above-recited sequences; and a sequence recited above which contains a U in place of T.

2. A kit for the detection and identification of at least one *Staphylococcus aureus* in a sample comprising a composition according to claim 1.

3. A composition comprising a diluent and at least one probe that specifically hybridizes with a 16S-23S rRNA spacer sequence, said probe being a nucleic acid sequence of at least 10 continuous nucleotides of a sequence selected from the group consisting of: SEQ ID NO:139, SEQ ID NO: 140, SEQ ID NO: 141, SEQ ID NO: 142, SEQ ID NO: 143, a sequence fully complementary to any of the above-recited sequences; and a sequence recited above which contains a U in place of T.

4. A kit for the detection and identification of a *Staphylococcus aureus* in a sample comprising the following components:
(i) optionally, at least one primer pair allowing amplification of a 16S-23S rRNA spacer region, or a part thereof;
(ii) a composition according to claim 3;
(iii) optionally, a buffer, or components necessary to produce the buffer, enabling a hybridization reaction between a probe of (ii) and a nucleic acid present in a sample, or amplified products thereof;
(v) optionally, a solution, or components necessary for producing the solution, enabling washing of hybrids formed under the appropriate wash conditions;
(vi) optionally, a means for detecting the hybrids resulting from hybridization.

5. An isolated 16S-23S rRNA spacer probe nucleic acid sequence of at least 10 continuous nucleotides of a sequence of a nucleic acid sequence selected from the group consisting of: SEQ ID NO:139, SEQ ID NO:139 containing a U in place of/T, a sequence fully complementary to SEQ ID NO:139, a sequence fully complementary to SEQ ID NO:139 containing a U in place of T, SEQ ID NO:140, SEQ ID NO:140 containing a U in place of T, a sequence fully complementary to SEQ ID NO:140, a sequence fully complementary to SEQ ID NO:140 containing a U in place of T, SEQ ID NO:141, SEQ ID NO:141 containing a U in place of T, a sequence fully complementary to SEQ ID NO:141, a sequence fully complementary to SEQ ID NO:141 containing a U in place of T, SEQ ID NO:142, SEQ ID NO:142 containing a U in place of T, a sequence fully complementary to SEQ ID NO:142, a sequence fully complementary to SEQ ID NO:142 containing a U in place of T, SEQ ID NO:143, SEQ ID NO:143 containing a U in place of T, a sequence fully complementary to SEQ ID NO:143, a sequence fully complementary to SEQ ID NO:143 containing a U in place of T; said probe specifically hybridizing with a 16S-23S rRNA spacer sequence.

6. The probe of a claim 5 wherein the probe nucleic acid sequence is 10-50 nucleotides in length.

7. The probe of a claim 5 wherein the probe nucleic acid sequence is 10-25 nucleotides in length.

8. The probe of claim 5 wherein said probe specifically hybridizes to said 16S-23S rRNA spacer sequence in a medium containing 3× SSC and 20% formamide, at a temperature in the range of 45° C. to 55° C.

9. A probe of claim 5 consisting of nucleic acid sequence selected from the group consisting of: SEQ ID NO:139, SEQ ID NO:139 containing a U in place of T, a sequence fully complementary to SEQ ID NO:139, a sequence fully complementary to SEQ ID NO:139 containing a U in place of T, SEQ ID NO:140, SEQ ID NO:140 containing a U in place of T, a sequence fully complementary to SEQ ID NO:140, a sequence fully complementary to SEQ ID NO:140 containing a U in place of T, SEQ ID NO:141, SEQ ID NO:141 containing a U in place of T, a sequence fully complementary to SEQ ID NO:141, a sequence fully complementary to SEQ ID NO:141 containing a U in place of T, SEQ ID NO:142, SEQ ID NO:142 containing a U in place of T, a sequence fully complementary to SEQ ID NO:142, a sequence fully complementary to SEQ ID NO:142 containing a U in place of T, SEQ ID NO:143, SEQ ID NO:143 containing a U in place of T, a sequence fully complementary to SEQ ID NO:143 and a sequence fully complementary to SEQ ID NO:143 containing a U in place of T.

10. A kit for the detection and identification of a *Staphylococcus aureus* in a sample comprising a diluent and a probe of claim 5.

11. Method for the detection and identification of a *Staphylococcus aureus* in a sample, comprising the steps of:
(i) optionally releasing, isolating and/or concentrating the polynucleic acids to be detected in the sample;
(ii) optionally amplifying the 16S-23S rRNA spacer region, or a part thereof, with at least one primer pair;
(iii) detecting the presence of a *Staphylococcus aureus* specific nucleic acid sequence by hybridizing a probe of claim 5 to any *Staphylococcus aureus* specific nucleic acid sequence present in said sample; and
(iv) identifying the *Staphylococcus aureus* present in said sample from the nucleic acid(s) detected in said sample.

12. A kit for the detection and identification of a *Staphylococcus aureus* in a sample comprising the following components:
(i) optionally, at least one primer pair allowing amplification of a 16S-23S rRNA spacer region, or a part thereof;
(ii) a composition comprising a diluent and a probe of claim 5;
(iii) optionally, a buffer, or components necessary to produce the buffer, enabling a hybridization reaction between a probe of (ii) and a nucleic acid present in a sample, or amplified products thereof;
(v) optionally, a solution, or components necessary for producing the solution, enabling washing of hybrids formed under the appropriate wash conditions;
(vi) optionally, a means for detecting the hybrids resulting from hybridization.

13. An isolated polynucleic acid sequence, said polynucleic acid sequence consisting of 10-50 contiguous nucleotides of a nucleic acid sequence selected from the group consisting of: SEQ ID NO:139, SEQ ID NO:139 containing a U in place of T, a sequence fully complementary to SEQ ID NO:139, a sequence fully complementary to SEQ ID NO:139 containing a U in place of T, SEQ ID NO:140, SEQ ID NO:140 containing a U in place of T, a sequence fully complementary to SEQ ID NO:140, a sequence fully complementary to SEQ ID NO:140 containing a U in place of T, SEQ ID NO:141, SEQ ID NO:141 containing a U in place of T, a sequence fully complementary to SEQ ID NO:141, a sequence fully complementary to SEQ ID NO:141 containing a U in place of T, SEQ ID NO:142, SEQ ID NO:142 containing a U in place of T, a sequence fully complementary to SEQ ID NO:142, a sequence fully complementary to SEQ ID NO:142 containing a U in place of T, SEQ ID NO:143, SEQ ID NO:143 containing a U in place of T, a sequence fully complementary to SEQ ID NO:143, a sequence fully complementary to SEQ ID NO:143 containing a U in place of T, SEQ ID NO:144, SEQ ID NO:144 containing a U in place of T, a sequence fully complementary to SEQ ID NO:144, and a sequence fully complementary to SEQ ID NO:144 containing a U in place of T.

14. A probe of claim 5 further comprising a detectable label.

15. A polynucleic acid sequence of claim 13 further comprising a detectable label.

16. A kit for the detection and identification of a *Staphylococcus aureus* in a sample comprising the following components:
(i) optionally, at least one primer pair allowing amplification of a 16S-23S rRNA spacer region, or a part thereof;

(ii) a composition comprising a diluent and a probe selected from the group consisting of SEQ ID NOS: 53, 54, 55 and 56;

(iii) optionally, a buffer, or components necessary to produce the buffer, enabling a hybridization reaction between a probe of (ii) and a nucleic acid present in a sample, or amplified products thereof;

(v) optionally, a solution, or components necessary for producing the solution, enabling washing of hybrids formed under the appropriate wash conditions;

(vi) optionally, a means for detecting the hybrids resulting from hybridization.

17. A probe selected from the group consisting of SEQ ID NOS: 53, 54, 55 and 56.

18. A probe of claim 17 further comprising a detectable label.

19. A kit of claim 16 wherein said probe further comprises a detectable label.

20. A composition comprising a diluent and a sequence selected from the group consisting of: SEQ ID NO: 144, a sequence fully complementary to SEQ ID NO:144; and a sequence recited above which contains a U in place of T.

21. A kit for the detection and identification of at least one *Staphylococcus epidermidis* in a sample comprising a composition according to claim 20.

22. A composition comprising a diluent and at least one probe that specifically hybridizes with a 16S-23S rRNA spacer sequence, said probe being a nucleic acid sequence of at least 10 continuous nucleotides of a sequence selected from the group consisting of: SEQ ID NO: 144, a sequence fully complementary to SEQ ID NO:144; and a sequence recited above which contains a U in place of T.

23. A kit for the detection and identification of a *Staphylococcus epidermidis* in a sample comprising the following components:
(i) optionally, at least one primer pair allowing amplification of a 16S-23S rRNA spacer region, or a part thereof;
(ii) a composition according to claim 22;
(iii) optionally, a buffer, or components necessary to produce the buffer, enabling a hybridization reaction between a probe of (ii) and a nucleic acid present in a sample, or amplified products thereof;
(v) optionally, a solution, or components necessary for producing the solution, enabling washing of hybrids formed under the appropriate wash conditions;
(vi) optionally, a means for detecting the hybrids resulting from hybridization.

24. An isolated 16S-23S rRNA spacer probe nucleic acid sequence of at least 10 continuous nucleotides of a sequence of a nucleic acid sequence selected from the group consisting of: SEQ ID NO:144, SEQ ID NO:144 containing a U in place of T, a sequence complementary to SEQ ID NO:144, and a sequence fully complementary to SEQ ID NO:144 containing a U in place of T; said probe specifically hybridizing with a 16S-23S rRNA spacer sequence.

25. The probe of a claim 24 wherein the probe nucleic acid sequence is 10-50 nucleotides in length.

26. The probe of a claim 24 wherein the probe nucleic acid sequence is 10-25 nucleotides in length.

27. The probe of claim 24 wherein said probe specifically hybridizes to said 16S-23S rRNA spacer sequence in a medium containing 3× SSC and 20% formamide, at a temperature in the range of 45° C. to 55° C.

28. A probe of claim 24 consisting of nucleic acid sequence selected from the group consisting of: SEQ ID NO:144, SEQ ID NO:144 containing a U in place of T, a sequence fully complementary to SEQ ID NO:144, and a sequence fully complementary to SEQ ID NO:144 containing a U in place of T.

29. A kit for the detection and identification of a *Staphylococcus epidermidis* in a sample comprising a diluent and a probe of claim 24.

30. Method for the detection and identification of a *Staphylococcus epidermidis* in a sample, comprising the steps of:
(i) optionally releasing, isolating and/or concentrating the polynucleic acids to be detected in the sample;
(ii) optionally amplifying the 16S-23S rRNA spacer region, or a part thereof, with at least one primer pair;
(iii) detecting the presence of a *Staphylococcus epidermidis* specific nucleic acid sequence by hybridizing a probe of claim 24 to any *Staphylococcus epidermidis* specific nucleic acid sequence present in said sample; and
(iv) identifying the *Staphylococcus epidermidis* present in said sample from the nucleic acid(s) detected in said sample.

31. A kit for the detection and identification of a *Staphylococcus epidermidis* in a sample comprising the following components:
(i) optionally, at least one primer pair allowing amplification of a 16S-23S rRNA spacer region, or a part thereof;
(ii) a composition comprising a diluent and a probe of claim 24;
(iii) optionally, a buffer, or components necessary to produce the buffer, enabling a hybridization reaction between a probe of (ii) and a nucleic acid present in a sample, or amplified products thereof;
(v) optionally, a solution, or components necessary for producing the solution, enabling washing of hybrids formed under the appropriate wash conditions;
(vi) optionally, a means for detecting the hybrids resulting from hybridization.

32. A probe of claim 24 further comprising a detectable label.

* * * * *